(12) United States Patent
McComas et al.

(10) Patent No.: US 9,549,917 B2
(45) Date of Patent: Jan. 24, 2017

(54) HETEROCYCLIC-SUBSTITUTED BENZOFURAN DERIVATIVES AND METHODS OF USE THEREOF FOR THE TREATMENT OF VIRAL DISEASES

(75) Inventors: Casey C. McComas, Phoenixville, PA (US); Nigel J. Liverton, Harleysville, PA (US); Joerg Habermann, Munich (DE); Uwe Koch, Dortmund (DE); Frank Narjes, Kullavik (SE); Peng Li, Shanghai (CN); Xuanjia Peng, Shanghai (CN); Richard Soll, San Diego, CA (US); Hao Wu, Shanghai (CN); Anandan Palani, Bridgewater, NJ (US); Xing Dai, Cranford, NJ (US); Hong Liu, Hillsborough, NJ (US); Shuwen He, Edison, NJ (US); Zhong Lai, East Brunswick, NJ (US); Qun Dang, Westfield, NJ (US); Nicolas Zorn, Fanwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/343,448

(22) PCT Filed: Aug. 16, 2012

(86) PCT No.: PCT/CN2012/080214
§ 371 (c)(1),
(2), (4) Date: Mar. 7, 2014

(87) PCT Pub. No.: WO2013/034047
PCT Pub. Date: Mar. 14, 2013

(65) Prior Publication Data
US 2014/0199263 A1    Jul. 17, 2014

(30) Foreign Application Priority Data
Sep. 8, 2011    (WO) ............... PCT/CN2011/079467

(51) Int. Cl.
| | |
|---|---|
| *A61K 45/06* | (2006.01) |
| *A61K 31/506* | (2006.01) |
| *A61K 31/444* | (2006.01) |
| *A61K 31/443* | (2006.01) |
| *A61K 31/497* | (2006.01) |
| *A61K 31/501* | (2006.01) |
| *A61K 31/695* | (2006.01) |
| *A61K 31/424* | (2006.01) |
| *A61K 31/4245* | (2006.01) |
| *A61K 31/4439* | (2006.01) |
| *C07D 405/14* | (2006.01) |

(Continued)

(52) U.S. Cl.
CPC ......... *A61K 31/4245* (2013.01); *A61K 31/433* (2013.01); *A61K 31/444* (2013.01); *A61K 31/4439* (2013.01); *A61K 31/497* (2013.01); *A61K 31/501* (2013.01); *A61K 31/506* (2013.01); *A61K 31/5365* (2013.01); *A61K 31/5377* (2013.01); *A61K 31/5383* (2013.01); *A61K 31/695* (2013.01); *A61K 45/06* (2013.01); *C07D 405/14* (2013.01); *C07D 409/14* (2013.01); *C07D 413/14* (2013.01); *C07D 417/14* (2013.01); *C07D 471/04* (2013.01); *C07D 498/04* (2013.01); *C07D 513/04* (2013.01); *C07F 7/10* (2013.01)

(58) Field of Classification Search
CPC .... A61K 45/06; A61K 31/506; A61K 31/444; A61K 31/433; A61K 31/497; A61K 31/501; A61K 31/695; A61K 31/424; C07F 7/10; C07D 405/14; C07D 413/14; C07D 409/14; C07D 417/14; C07D 471/04; C07D 498/04; C07D 513/04
See application file for complete search history.

(56) References Cited

U.S. PATENT DOCUMENTS

| | | | |
|---|---|---|---|
| 4,634,697 | A | 1/1987 | Hamashima |
| 4,812,561 | A | 3/1989 | Hamashima et al. |

(Continued)

FOREIGN PATENT DOCUMENTS

| | | |
|---|---|---|
| CN | 1731993 | 2/2006 |
| WO | WO9814181 | 4/1998 |

(Continued)

OTHER PUBLICATIONS

Patani et al., Chem. Rev, 1996, 96, 3147-3176.*

(Continued)

*Primary Examiner* — Sun Jae Yoo
(74) *Attorney, Agent, or Firm* — Alysia A. Finnegan; Gloria M. Fuentes

(57) ABSTRACT

The present invention relates to compounds of formula (I) that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.

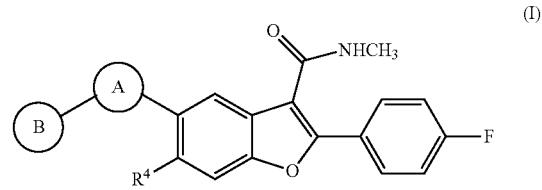

14 Claims, No Drawings

(51) Int. Cl.

| | | |
|---|---|---|
| C07D 413/14 | (2006.01) | |
| C07D 409/14 | (2006.01) | |
| C07D 417/14 | (2006.01) | |
| C07D 471/04 | (2006.01) | |
| C07D 498/04 | (2006.01) | |
| C07D 513/04 | (2006.01) | |
| A61K 31/433 | (2006.01) | |
| A61K 31/5365 | (2006.01) | |
| A61K 31/5377 | (2006.01) | |
| A61K 31/5383 | (2006.01) | |
| C07F 7/10 | (2006.01) | |

(56) References Cited

U.S. PATENT DOCUMENTS

| | | |
|---|---|---|
| 4,933,443 A | 6/1990 | Hamashima et al. |
| 5,017,380 A | 5/1991 | Hamashima et al. |
| 6,767,991 B1 | 7/2004 | Llinas-Brunet et al. |
| 6,800,434 B2 | 10/2004 | Saksena et al. |
| 6,838,475 B2 | 1/2005 | Arasappan et al. |
| 6,846,802 B2 | 1/2005 | Chen et al. |
| 6,894,072 B2 | 5/2005 | Arasappan et al. |
| 6,911,428 B2 | 6/2005 | Zhu et al. |
| 6,914,122 B2 | 7/2005 | Venkatraman et al. |
| 7,012,066 B2 | 3/2006 | Saksena et al. |
| 7,169,760 B2 | 1/2007 | Saksena et al. |
| 7,173,057 B2 | 2/2007 | Chen et al. |
| 7,186,747 B2 | 3/2007 | Arasappan et al. |
| 7,192,957 B2 | 3/2007 | Venkatraman et al. |
| 7,205,330 B2 | 4/2007 | Bogen et al. |
| 7,244,271 B2 | 7/2007 | Lentz et al. |
| 7,253,160 B2 | 8/2007 | Njoroge et al. |
| 7,342,041 B2 | 3/2008 | Njoroge et al. |
| 7,425,576 B2 | 9/2008 | Arasappan et al. |
| 7,442,695 B2 | 10/2008 | Njoroge et al. |
| 7,449,447 B2 | 11/2008 | Chen et al. |
| 7,485,625 B2 | 2/2009 | Velazquez et al. |
| 7,494,988 B2 | 2/2009 | Perni et al. |
| 7,666,863 B2 | 2/2010 | Saha et al. |
| 2002/0068702 A1 | 6/2002 | Lim-Wilby et al. |
| 2002/0160962 A1 | 10/2002 | Saksena et al. |
| 2005/0119168 A1 | 6/2005 | Venkatraman et al. |
| 2005/0176648 A1 | 8/2005 | Saksena et al. |
| 2005/0209164 A1 | 9/2005 | Bogen et al. |
| 2005/0249702 A1 | 11/2005 | Njoroge et al. |
| 2007/0042968 A1 | 2/2007 | Bennett et al. |
| 2007/0274951 A1 | 11/2007 | Tong et al. |

FOREIGN PATENT DOCUMENTS

| | | |
|---|---|---|
| WO | WO9817679 | 4/1998 |
| WO | WO9822496 | 5/1998 |
| WO | WO9907734 | 2/1999 |
| WO | WO03006490 | 1/2003 |
| WO | WO03087092 | 10/2003 |
| WO | WO2004041201 | 5/2004 |
| WO | WO2004092161 | 10/2004 |
| WO | WO2005087731 | 9/2005 |
| WO | WO2008082484 | 7/2008 |
| WO | WO2008082488 | 7/2008 |
| WO | WO2008124148 | 10/2008 |
| WO | WO2008136815 | 11/2008 |
| WO | WO2009032116 | 3/2009 |
| WO | WO2009032123 | 3/2009 |
| WO | WO2009032124 | 3/2009 |
| WO | WO2009032125 | 3/2009 |
| WO | WO2009101022 | 8/2009 |
| WO | WO2010030592 | 3/2010 |
| WO | WO2011103063 | 8/2011 |
| WO | WO2011106340 | 9/2011 |
| WO | WO2011106992 | * 9/2011 |
| WO | WO2012142075 | 10/2012 |
| WO | WO2012142085 | 10/2012 |
| WO | WO2012142093 | 10/2012 |
| WO | WO2013033899 | 3/2013 |
| WO | WO2013033900 | 3/2013 |
| WO | WO2013033971 | 3/2013 |
| WO | WO2013034048 | 3/2013 |

OTHER PUBLICATIONS

Beaulieu et al., Inhibitors of the HCV NS5B polymerase: New hope for the treatment of hepatitis C infections, Current Opinions in Investigational Drugs, 2004, 838:5.

Behrens, Identification and properties of the RNA-dependnt RNA polymerase of hepatitis C virus, EMBO. J., 1996, 15(1):12-22.

Bioworld Today, The Daily Biotechnology Newspaper, 1998, vol. 9(217):1-5.

Carroll, Inhibition of Hepatitis C Virus RNA Replication by 2'-Modified Nucleoside Analogs, 2003, 278(14):11979-84.

Elzouki et al., Serine protease inhibitors in patients with chronic viral hepatitis, Journal of Hepatology, 1997, 27:42-48.

Ingallinella et al., Potent Peptide Inhibitors of Human Hepatitis C Virus NS3 Protease Are Obtained by Optimizing the Cleavage Products, Biochemistry, 1998, 37:8906-8914.

Landro et al., Mechanistic Role of an NS4A Peptide Cofactor with the Truncated NS3 Protease of Hepatitis C Virus: Elucidation of the NS4A Stimulatory Effect Via Kinetic Analysis and Inhibitor Mapping, Biochemistry, 1997, 31:9340-9348.

Llinas-Brunet et al., Peptide-based Inhibitors of the Hepatitis C Virus Serine Protease, Bioorganic & Medicinal Chemistry Letters, 1998, 8:1713-1718.

Martin et al., Affinity selection of a camelized VH domain antibody inhibitor of hepatitis C virus NS3 protease, Protein Engineering, 1997, 10(5):607-614.

Ni et al., Progress and Development of Small Molecule HCV Antivirals, Current Opinion in Drug Discovery and Development, 2004, 7(4):446.

Tan et al., Hepatits C Therapeutics: Current Status and Emerging Strategies, Nature Reviews, 2002, 1:867-881.

Extended European search report for EP2753618, dated Feb. 18, 2015.

* cited by examiner

HETEROCYCLIC-SUBSTITUTED BENZOFURAN DERIVATIVES AND METHODS OF USE THEREOF FOR THE TREATMENT OF VIRAL DISEASES

FIELD OF THE INVENTION

The present invention relates to novel Heterocyclic-Substituted Benzofuran Derivatives, compositions comprising at least one Heterocyclic-Substituted Benzofuran Derivative, and methods of using the Heterocyclic-Substituted Benzofuran Derivatives for treating or preventing HCV infection in a patient.

CROSS-REFERENCE TO RELATED APPLICATIONS

This application is a §371 National Stage Application of PCT/CN2012/080214, international filing date of Aug. 16, 2012, which claims the benefit of PCT/CN2011/079467, filed Sep. 8, 2011.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

HCV NS5B polymerase is described, for example, in Behrens et al., *EMBO J.* 15(1) 12-22 (1996). Antagonists of NS5B activity are known to be inhibitors of HCV replication. See Carroll et al., *J. Biol. Chem.* 278(14) 11979-84 (2003).

There is a clear and long-felt need to develop effective therapeutics for treatment of HCV infection. Specifically, there is a need to develop compounds that selectively inhibit HCV viral replication and that would be useful for treating HCV-infected patients.

SUMMARY OF THE INVENTION

In one aspect, the present invention provides Compounds of Formula (I):

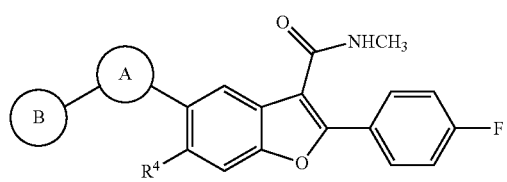

(I)

or a pharmaceutically acceptable salt thereof, wherein:

A is 5 or 6-membered monocyclic heteroarylene, which is optionally substituted with up to 4 groups, which can be the same or different, and are selected from halo, hydroxy, $C_1$-$C_6$ alkyl, —O—($C_1$-$C_6$ alkyl), $C_1$-$C_6$ haloalkyl, —S(O)$_2$—($C_1$-$C_6$ alkyl), 5 or 6-membered monocyclic heterocycloalkyl, 9 or 10-membered bicyclic heteroaryl, —N(R$^5$)$_2$, —NO$_2$, —O—($C_1$-$C_6$ alkylene)-C(O)OR$^5$, and —CN, wherein said 5 or 6-membered monocyclic heteroarylene group can optionally have one of its ring carbon atoms derivatized as a ring carbonyl group;

B is 8 to 10-membered bicyclic heteroaryl having from 1 to 4 ring heteroatoms, each independently selected from N, O and S, wherein said 8 to 10-membered bicyclic heteroaryl group is optionally substituted with up to 4 R$^c$ groups, which can be the same or different, and are selected from:
  a) halogen,
  b) OH
  c) $C_1$-$C_6$ alkyl,
  d) O($C_1$-$C_6$ alkyl),
  e) CN,
  f) (CH$_2$)$_{0-3}$—ArB, wherein each ArB is an independently selected aromatic ring system selected from the group consisting of:
    i) 5- or 6-membered monocyclic rings with 0, 1, 2, 3 or 4 heteroatom ring atoms independently selected from the group consisting of N, O or S, and
    ii) 8-, 9- or 10-membered bicyclic rings with 0, 1, 2, 3 or 4 heteroatom ring atoms independently selected from the group consisting of N, O or S,
  g) (CH$_2$)$_{0-3}$NR$^d$C(O)R$^e$,
  h) (CH$_2$)$_{0-3}$NR$^d$SO$_2$R$^e$,
  i) (CH$_2$)$_{0-3}$C(O)NR$^d$R$^e$,
  j) (CH$_2$)$_{0-3}$SO$_2$R$^e$,
  k) —OSO$_2$($C_1$-$C_6$ alkyl),
  l) —C(O)OR$^5$; and
  m) —($C_1$-$C_6$ alkylene)-O—($C_1$-$C_6$ alkylene)-Si(R$^8$)$_3$, wherein the following R$^e$ groups: c) $C_1$-$C_6$ alkyl, d) O($C_1$-$C_6$ alkyl), and f) (CH$_2$)$_{0-3}$—ArB, can each be optionally substituted with up to 4 substituents R$^f$;

each R$^d$ is independently selected from the group consisting of hydrogen and $C_{1-6}$alkyl;

each R$^e$ is independently selected from the group consisting of hydrogen, $C_{1-6}$alkyl, O$C_{1-6}$alkyl and 5- or 6-membered monocyclic rings with 0, 1, 2, 3 or 4 heteroatom ring atoms independently selected from the group consisting of N, O or S, wherein each R$^e$$C_{1-6}$alkyl, O$C_{1-6}$alkyl and 5- or 6-membered monocyclic rings is substituted by 0, 1, 2, 3 or 4 substituents independently selected from the group consisting of $C_1$-$C_6$ alkyl, O($C_1$-$C_6$ alkyl), halogen and OH;

each R$^f$ is independently selected from the group consisting of:
  a) halogen,
  b) $C_1$-$C_6$ alkyl,
  c) O($C_1$-$C_6$ alkyl),
  d) CN,
  e) N(R$^q$)$_2$,
  f) OH,
  g) C(O)H,
  h) NHC(O)R$^s$,
  i) NHS(O)$_2$R$^s$,
  j) C(O)NHR$^q$,
  k) C(O)OR$^q$,
  l) OS(O)$_2$($C_1$-$C_6$ alkyl),
  m) (CH$_2$)$_{0-3}$—ArC, wherein each ArC is an independently selected aromatic ring system selected from the group consisting of:
    i) 5- or 6-membered monocyclic rings with 0, 1, 2, 3 or 4 heteroatom ring atoms independently selected from the group consisting of N, O or S, and ii) 8-, 9- or 10-membered bicyclic rings with 0, 1, 2, 3 or 4 heteroatom ring atoms independently selected from the group consisting of N, O or S, wherein the following $R^f$ groups: b) $C_1$-$C_6$ alkyl, c) $O(C_1$-$C_6$ alkyl), and m) $(CH_2)_{0-3}$—ArC can be optionally substituted with up to 4 substituents $R^g$;

each $R^g$ is independently selected from the group consisting of halogen, —OH, —N$(R^q)_2$, —CN, $C_{1-6}$alkyl, —O—$(C_1$-$C_6$ alkyl), —$CF_3$ and —C(O)OH;

each $R^q$ is independently selected from the group consisting of H and $C_{1-6}$alkyl; each $R^s$ is independently selected from the group consisting of $C_{1-6}$alkyl, heterocyclyl and $C_{6-10}$aryl, wherein said heterocyclyl group can be optionally substituted on a ring nitrogen or ring carbon atom with a —C(O)O—$(C_1$-$C_6$ alkyl) group;

$R^4$ is H, —N$(R^6)SO_2R^7$ or

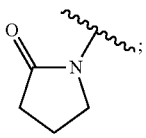 [SMILES: *N1CCCC1=O]

each occurrence of $R^5$ is independently H or $C_1$-$C_6$ alkyl;
$R^6$ is $C_1$-$C_6$ alkyl or $C_1$-$C_6$ haloalkyl;
$R^7$ is independently $C_1$-$C_6$ alkyl; and
each occurrence of $R^8$ is independently $C_1$-$C_6$ alkyl.

The Compounds of Formula (I) (also referred to herein as the "Heterocyclic-Substituted Benzofuran Derivatives") and pharmaceutically acceptable salts thereof can be useful, for example, for inhibiting HCV viral replication or replicon activity, and for treating or preventing HCV infection in a patient. Without being bound by any specific theory, it is believed that the Heterocyclic-Substituted Benzofuran Derivatives inhibit HCV viral replication by inhibiting HCV NS5B.

Accordingly, the present invention provides methods for treating or preventing HCV infection in a patient, comprising administering to the patient an effective amount of at least one Heterocyclic-Substituted Benzofuran Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Heterocyclic-Substituted Benzofuran Derivatives, compositions comprising at least one Heterocyclic-Substituted Benzofuran Derivative, and methods of using the Heterocyclic-Substituted Benzofuran Derivatives for treating or preventing HCV infection in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring.

Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

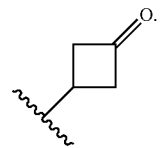 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "halo," as used herein, means —F, —Cl, —Br or —I. In one embodiment, halo is —Cl. In another embodiment, halo is —F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH₂CH₂CH₂OH and —CH₂CH(OH)CH₃. The term "C₁-C₆ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring and a 5 membered aromatic heterocycle group fused to a cyclohexyl group. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "5 or 6-membered monocyclic heteroarylene," as used herein, refers to an aromatic monocyclic ring system comprising 5 or 6 ring atoms, wherein from 1 to 4 of the ring atoms is independently O, N or S and the remaining ring atoms are carbon atoms. In one embodiment, a 5 or 6-membered monocyclic heteroarylene group has 5 ring atoms. In another embodiment, a 5 or 6-membered monocyclic heteroarylene group is monocyclic and has 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "5 or 6-membered monocyclic heteroarylene" also encompasses a 5 or 6-membered monocyclic heteroarylene group, as defined above, which is fused to a benzene ring. Non-limiting examples of 5 or 6-membered monocyclic heteroarylenes include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "5 or 6-membered monocyclic heteroarylene" also refers to partially saturated heteroaryl moieties such as, for example, tetrahydroisoquinolyl, tetrahydroquinolyl and the like. In one embodiment, a 5 or 6-membered monocyclic heteroarylene group is a 5-membered monocyclic heteroarylene. In another embodiment, a 5 or 6-membered monocyclic heteroarylene group is a 6-membered monocyclic heteroarylene. In another embodiment, a 5 or 6-membered monocyclic heteroarylene group comprises a 5 or 6-membered heteroarylene group fused to a benzene ring. Unless otherwise indicated, a 5 or 6-membered monocyclic heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is monocyclic has from about 5 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

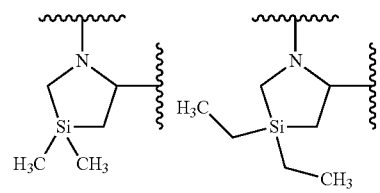

-continued

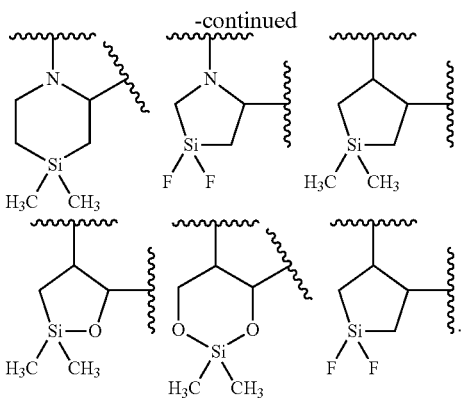

A ring carbon atom of a heterocycloalkyl group may be functionalized as a carbonyl group. An illustrative example of such a heterocycloalkyl group is:

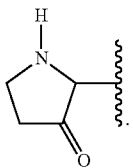

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "5 to 7-membered monocyclic cycloalkyl" refers to a monocyclic heterocycloalkyl group having from 5 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

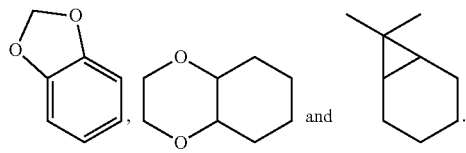

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3- to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^6$, $R^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Heterocyclic-Substituted Benzofuran Derivative or a pharmaceutically acceptable salt or solvate of the compound. The transformation may occur by various mechanisms (e.g., by metabolic or chemical processes), such as, for example, through hydrolysis in blood.

For example, if a Heterocyclic-Substituted Benzofuran Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (3-dimethylaminoethyl), carbamoyl-$(C_1-C_2)$alkyl, N,N-di $(C_1-C_2)$ alkylcarbamoyl-$(C_1-C_2)$alkyl and piperidino-, pyrrolidino- or morpholino$(C_2-C_3)$alkyl, and the like.

Similarly, if a Heterocyclic-Substituted Benzofuran Derivative contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a Heterocyclic-Substituted Benzofuran Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino $(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Heterocyclic-Substituted Benzofuran Derivatives can form salts which are also within the scope of this invention. Reference to a Heterocyclic-Substituted Benzofuran Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Heterocyclic-Substituted Benzofuran Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Heterocyclic-Substituted Benzofuran Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In one embodiment, a compound of formula (I) is present as its dihydrochloride salt. In another embodiment, a compound of formula (I) is present as its dimesylate salt. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Heterocyclic-Substituted Benzofuran Derivatives may be atropisomers (e.g., substituted biaryls) and are considered as part of this invention. Enantiomers can also be directly separated using chiral chromatographic techniques.

It is also possible that the Heterocyclic-Substituted Benzofuran Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Heterocyclic-Substituted Benzofuran Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Heterocyclic-Substituted Benzofuran Derivatives, and of the salts, solvates, hydrates, esters and prodrugs of the Heterocyclic-Substituted Benzofuran Derivatives, are intended to be included in the present invention.

The following abbreviations are used below and have the following meanings: Ac is acyl; AcOH is acetic acid; $BF_3 \cdot OEt_2$ is boron trifluoride etherate; BOC or Boc is tert-butyloxycarbonyl; $Boc_2O$ is Boc anhydride; Boc-Pro-OH is Boc protected proline; L-Boc-Val-OH is Boc protected L-valine; n-BuLi is n-butyllithium; dba is dibenzylideneacetone; DCM is dichloromethane; DIPEA is diisopropylethylamine; DME is dimethoxyethane; DMF is N,N-dimethylformamide; dppf is diphenylphosphinoferrocene; DMSO is dimethylsulfoxide; EtOAc is ethyl acetate; $Et_2O$ is diethyl ether; $Et_3N$ is triethylamine; HATU is O-(7-azabenzotriazol-1-yl)-N,N,N',N'-tetramethyluronium hexafluorophosphate; $Hg(OAc)_2$ is mercuric acetate; HPLC is high performance liquid chromatography; HRMS is high resolution mass spectrometry; KOAc is potassium acetate; Lawesson's Reagent is 2,4-Bis(4-methoxyphenyl)-1,3-dithiadiphosphetane-2,4-disulfide; LCMS is liquid chromatography/mass spectrometry; LRMS is low resolution mass spectrometry; mCPBA is m-chloroperbenzoic acid; MeOH is methanol; Ms is —$SO_2CH_3$ (or "mesyl"); MTBE is tert-butylmethyl ether; NBS is N-bromosuccinimide; $NH_4OAc$ is ammonium acetate; $Pd(PPh_3)_4$ is tetrakis(triphenylphosphine) palladium(0); $PdCl_2(dppf)_2$ is [1,1'-Bis(diphenylphosphino)ferrocene]dichloro palladium(II); $PdCl_2(dppf)_2\text{-}CH_2Cl_2$ is [1,1'-Bis(diphenylphosphino)ferrocene]dichloro palladium(II) complex with dichloromethane; $pinacol_2B_2$ is bis(pinacolato)diboron; PPTS is pyridinium p-toluene sulfonate; RPLC is reverse-phase liquid chromatography; SEM-Cl is 2-(trimethylsilyl)ethoxymethyl chloride; TBAF is tetrabutylammonium fluoride; TBAI is tetrabutylammonium iodide; TBDMSCl is tert-butyldimethylsilyl chloride; TFA is trifluoroacetic acid; THF is tetrahydrofuran; TLC is thin-layer chromatography; XPhos is 2-dicyclohexylphosphino-2',4',6'-triisopropylbiphenyl; and Z-Pro-OH is N-Benzyloxycarbonyl-L-proline.

The Compounds of Formula (I)

The present invention provides Heterocyclic-Substituted Benzofuran Derivatives of Formula (I):

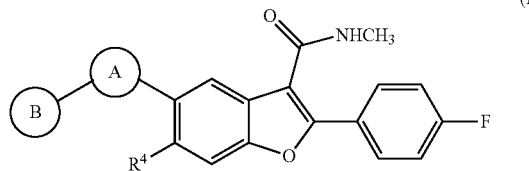

(I)

wherein A, B and $R^4$ are as defined above for the compounds of formula (I).

In one embodiment, $R^4$ is —$N(CH_3)SO_2CH_3$.

In one embodiment, A is pyridyl, pyridazinyl, thiophenyl, pyrimidinyl or pyrazinyl, each of which can be optionally substituted as defined above for the compounds of formula (I).

In another embodiment, A is pyridyl, which can be optionally substituted as defined above for the compounds of formula (I).

In another embodiment, A is pyrazinyl, which can be optionally substituted as defined above for the compounds of formula (I).

In still another embodiment, A is pyridazinyl, which can be optionally substituted as defined above for the compounds of formula (I).

In another embodiment, A is pyrimidinyl which can be optionally substituted as defined above for the compounds of formula (I).

In yet another embodiment, A is thiophenyl, which can be optionally substituted as defined above for the compounds of formula (I).

In one embodiment, B is an 8-membered bicyclic heteroaryl group, which can be optionally substituted as defined above for the compounds of formula (I).

In another embodiment, B is a 9-membered bicyclic heteroaryl group, which can be optionally substituted as defined above for the compounds of formula (I).

In another embodiment, B is a 10-membered bicyclic heteroaryl group, which can be optionally substituted as defined above for the compounds of formula (I).

In one embodiment, A is pyridyl or pyrazinyl, each of which can be optionally substituted with halo or a —O—($C_1$-$C_6$ alkyl) group, and B is selected from indolyl, benzoxazolyl or oxazolo[4,5-b]pyridinyl, each of which can be optionally substituted as defined above for the compounds of formula (I).

In one embodiment, the group:

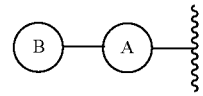

is selected from:

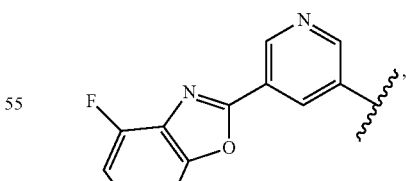

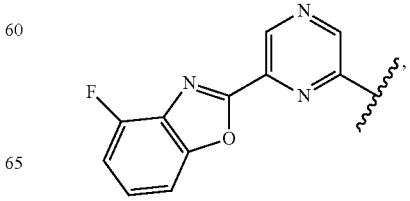

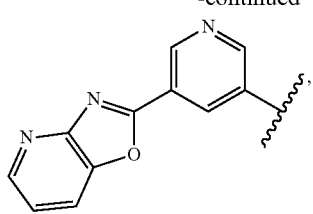
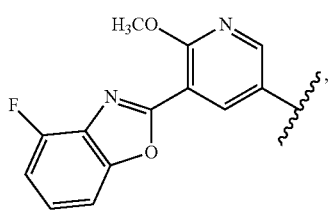
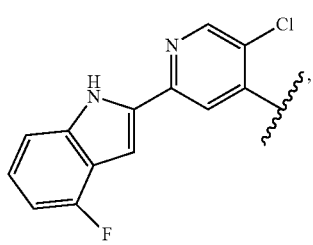
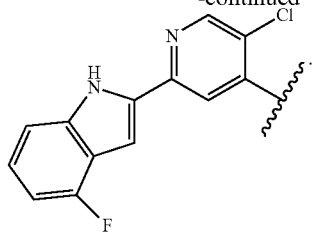
In another embodiment, the group:
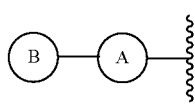
is selected from:
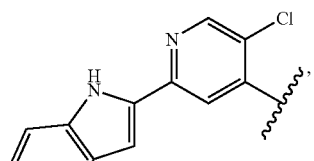
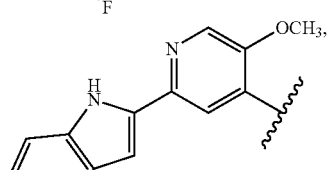
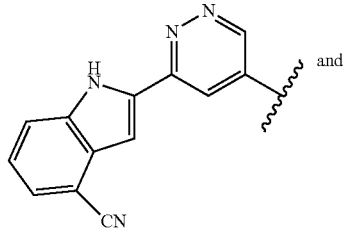
and
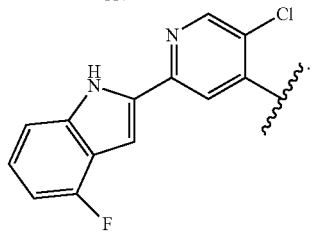
In still another embodiment, the group:
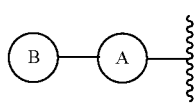

is selected from:

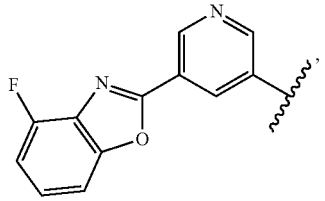

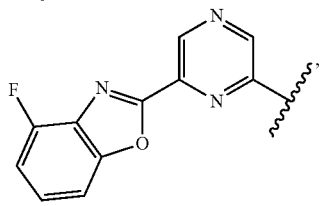

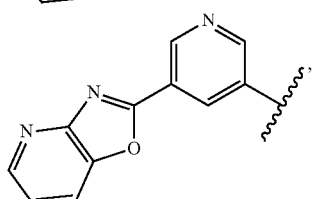

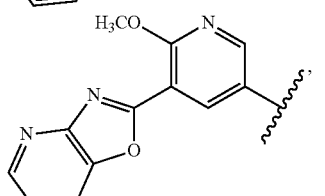

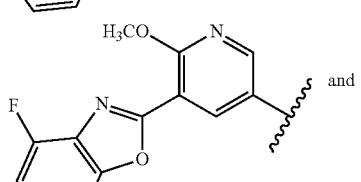 and

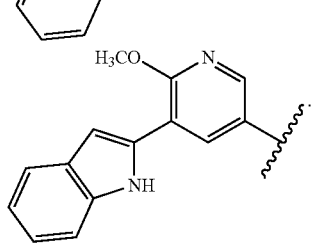

In one embodiment, R⁴ is —N(CH₃)SO₂CH₃ and A is pyridyl, pyridazinyl, pyrimidinyl or pyrazinyl, each of which can be optionally substituted as defined above for the compounds of formula (I).

In another embodiment, R⁴ is —N(CH₃)SO₂CH₃; A is pyridyl, pyridazinyl, pyrimidinyl or pyrazinyl, each of which can be optionally substituted as defined above for the compounds of formula (I); and B is 9-membered heteroaryl.

In another embodiment, R⁴ is —N(CH₃)SO₂CH₃; A is pyridyl, pyridazinyl, pyrimidinyl or pyrazinyl, each of which can be optionally substituted as defined above for the compounds of formula (I); and B is 10-membered heteroaryl.

In one embodiment, R⁴ is —N(CH₃)SO₂CH₃ and the group:

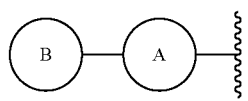

is selected from:

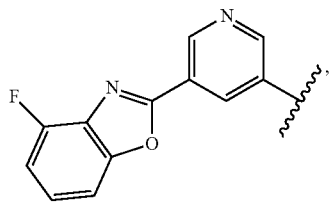

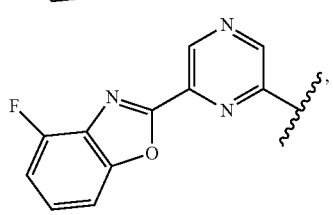

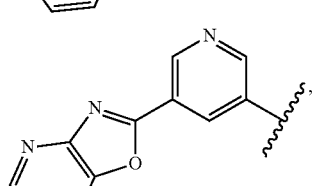

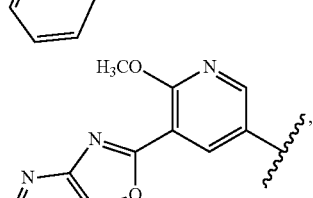

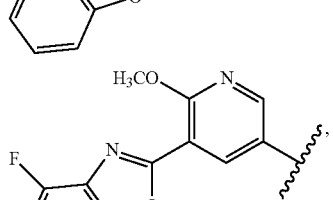

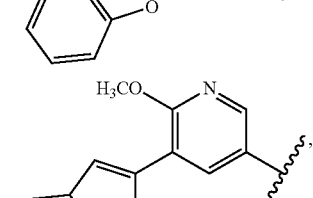

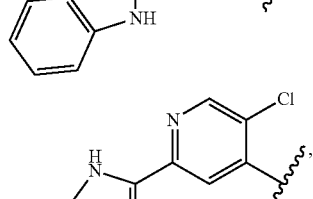

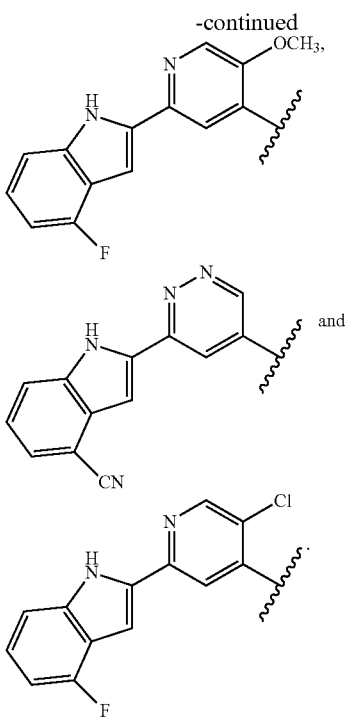

In another embodiment of the invention, the compound of the invention is one of compounds 1-297, as depicted in the Examples below, or a pharmaceutically acceptable salt thereof.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula (I) in the preparation of a medicament for inhibiting HCV NS5B activity in a subject in need thereof.

(g) A use of a compound of formula (I) in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula (I).

(i) The method of (h), wherein the compound of formula (I) is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula (I) in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis. All stereoisomers and tautomeric forms of the compounds are contemplated.

Scheme 1 shows a method useful for making compounds of formula K, which correspond to the Compounds of Formula (I), wherein $R^4$ is —$N(CH_3)SO_2CH_3$.

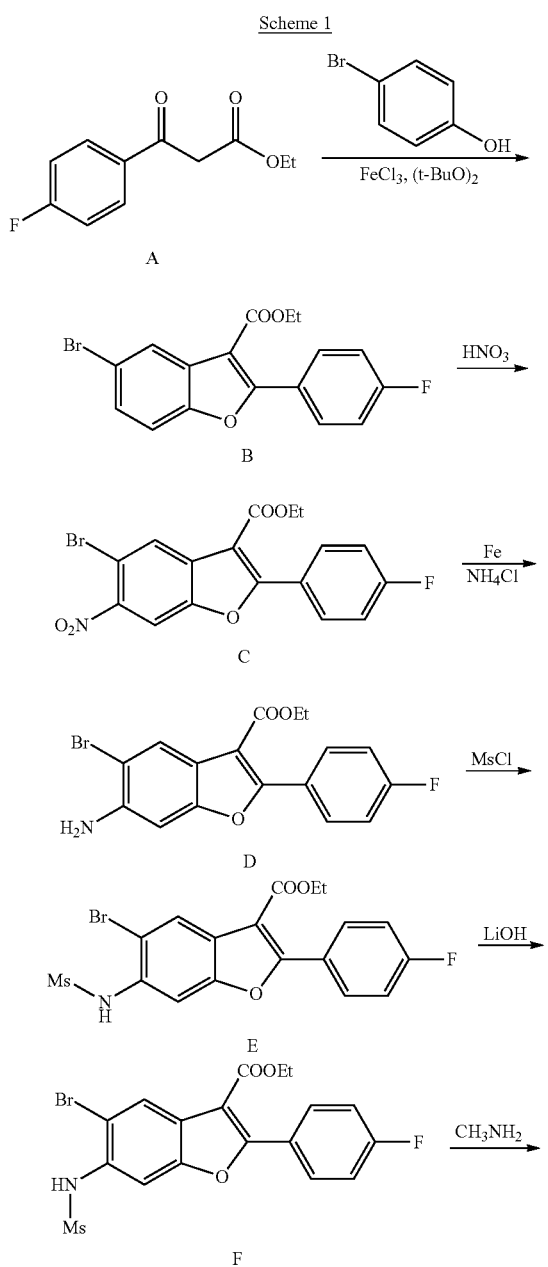

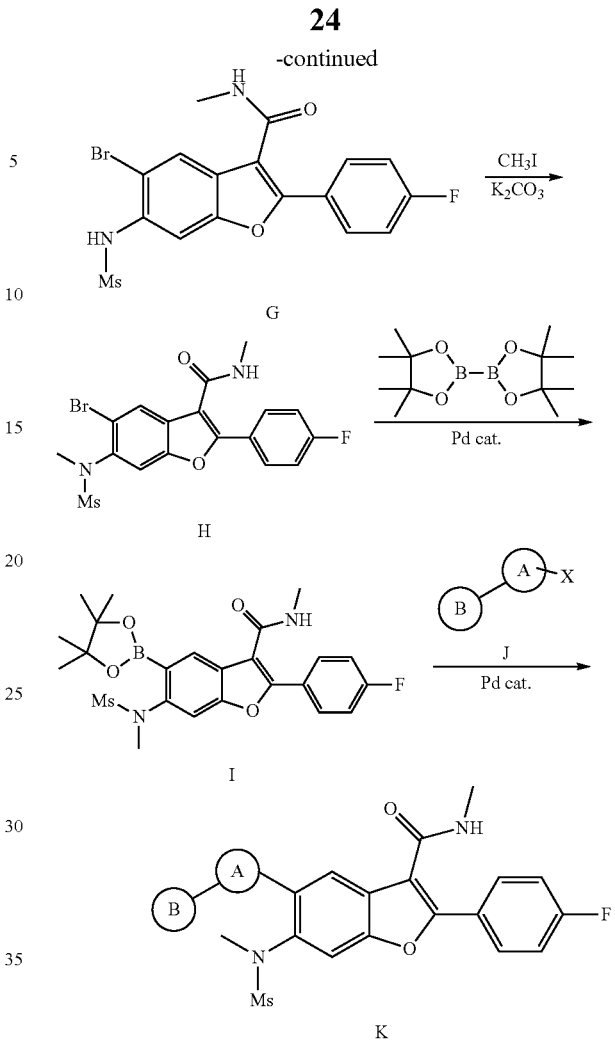

Wherein Ms is —$SO_2CH_3$ ("mesyl"); X is Cl, Br, I, OTs or OMs; and A and B are each defined above for the Compounds of Formula (I).

Commercially available compound A can be cyclized with 4-bromophenol to provide benzofuran compound B. Nitration of compound B provides nitrocompound C, which can be reduced to provide amine compound D. Mesylation of the amino group of D provides compound E, which can then be hydrolyzed using LiOH, for example, to provide the carboxylic acid compound F. is generated by reduction of the nitro group in compound C, and the amino group in compound D is then sulfonylated with MsCl to furnish compound E. The ester functionality in compound E is readily hydrolyzed by aqueous base to afford compound F. The carboxylic acid of compound F is then condensed with methanamine using common amide forming reagents such as EDCI and HOBT to provide compound G. The sulfonamide group of G can be coupled with MeI in the presence of potassium carbonate to provide compound H. Compound H can be converted to corresponding boronic ester I using bis(pinacolato)diboron in the presence of a palladium catalyst. Finally, compound I can be reacted with substituted bicyclic heteroaryl halides of formula J to provide the compounds of formula K.

Scheme 2 shows an alternate method useful for making compounds of formula K, which correspond to the Compounds of Formula (I), wherein $R^4$ is —$N(CH_3)SO_2CH_3$.

Scheme 2

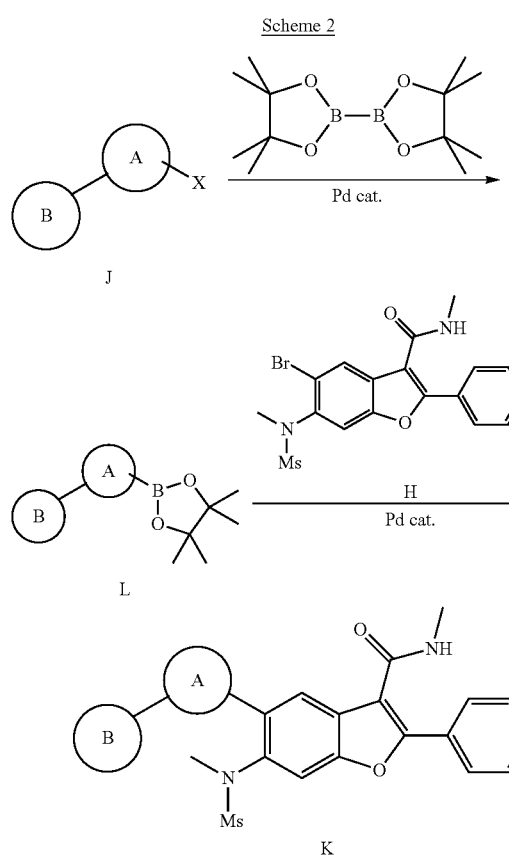

Wherein Ms is —SO$_2$CH$_3$ ("mesyl"); X is Cl, Br, I, OTs or OMs; and A and B are each defined above for the Compounds of Formula (I).

A bicyclic heteroaryl halides of formula J (X could be Cl, Br, I, OTs or OMs) can be converted to the corresponding boronic esters of formula L using bis(pinacolato)diboron in the presence of a palladium catalyst. A palladium-catalyzed coupling reaction (e.g. Suzuki coupling) could then be performed to couple a compound of formula L with compound H to provide the compounds of formula K.

Scheme 3 shows methods useful for making compounds of formula J, which are intermediates useful for making the Compounds of Formula (I).

Scheme 3

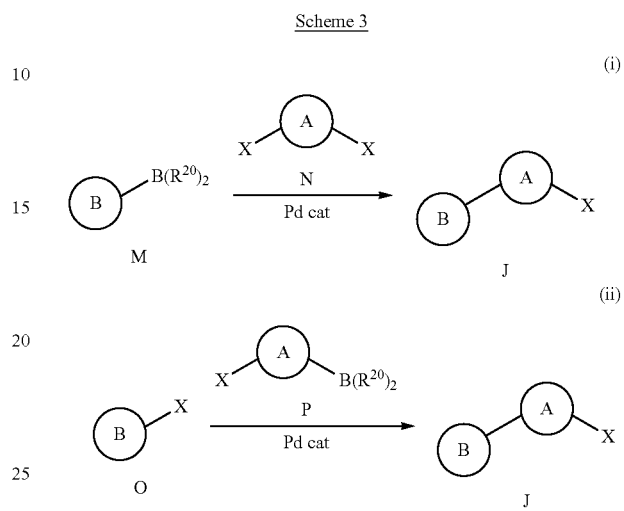

Wherein —B(R$^{20}$)$_2$ is —B(OH)$_2$ or pinacolato borane; X is Cl, Br, I, OTs or OMs; and A and B are each defined above for the Compounds of Formula (I).

A bicyclic heteroaryl boronate compound of formula M can be coupled in the presence of a palladium catalyst with a monocyclic heteroaryl derivative of formula N or to provide compounds of formula J (as shown in reaction (i)). Alternatively, a bicyclic heteroaryl derivative of formula O can be coupled in the presence of a palladium catalyst with a monocyclic heteroaryl boronate compound of formula P or to provide compounds of formula J (as shown in reaction (ii)).

Scheme 4 shows a method useful for making compounds of formula T, which correspond to the Compounds of Formula (I), wherein R$^4$ is pyrrolidinone.

Scheme 4

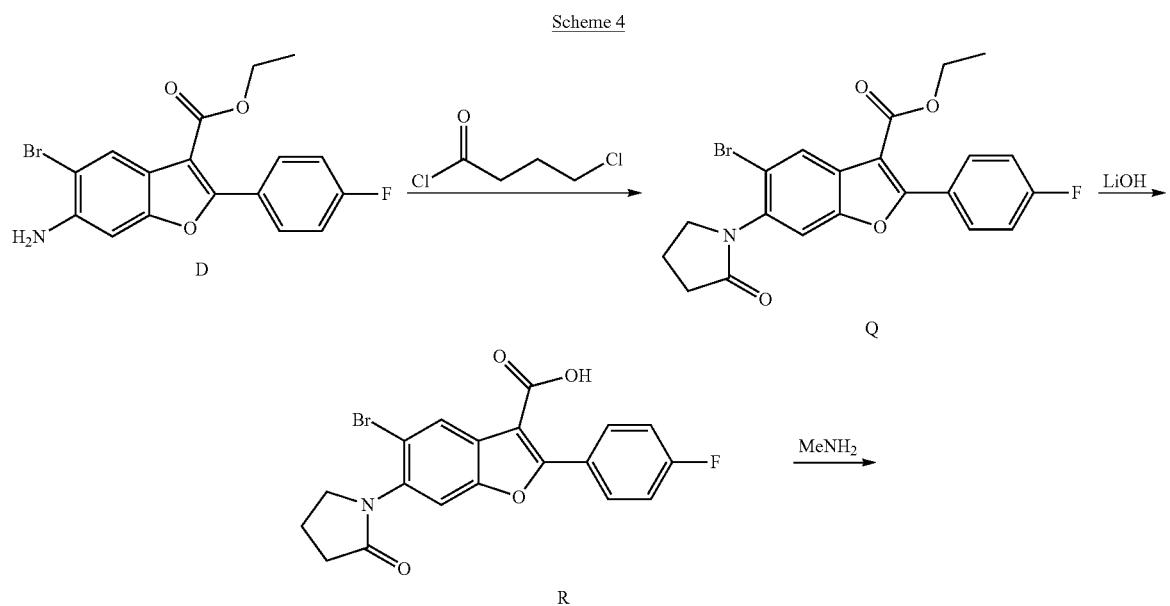

-continued

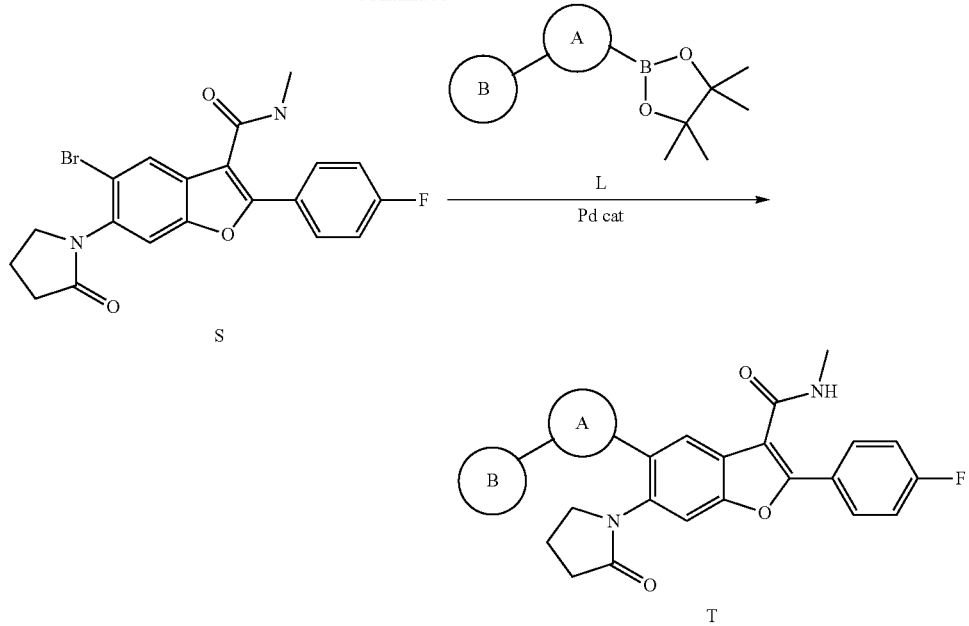

Compound D can be reacted with 4-chlorobutanoyl chloride to provide the pyrrolidinone compound of formula Q. The ester moiety of Q can be hydrolyzed using base to provide the carboxylic acid compound of formula R. Methylation of the amino group of R using iodomethane, for example, provides compound S. A palladium-catalyzed coupling reaction (e.g., Suzuki coupling) could then be performed to couple a boronate compound of formula L with bromo compound S to provide the compounds of formula T.

One skilled in the art of organic synthesis will recognize that the synthesis of compounds with multiple reactive functional groups, such as —OH and NH$_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, 3$^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula K and T may be further elaborated using methods that would be well-known to those skilled in the art of organic synthesis or, for example, the methods described in the Examples below, to make the full scope of the Compounds of Formula (I).

The starting materials used and the intermediates prepared using the methods set forth above in Schemes 1-4 may be isolated and purified if desired using conventional techniques, including but not limited to filtration, distillation, crystallization, chromatography and alike. Such materials can be characterized using conventional means, including physical constants and spectral data.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESI). $^1$H NMR spectra were recorded at 400-500 MHz. Compounds described herein were synthesized as a racemic mixture unless otherwise stated in the experimental procedures.

Example 1

Preparation of Compound 1

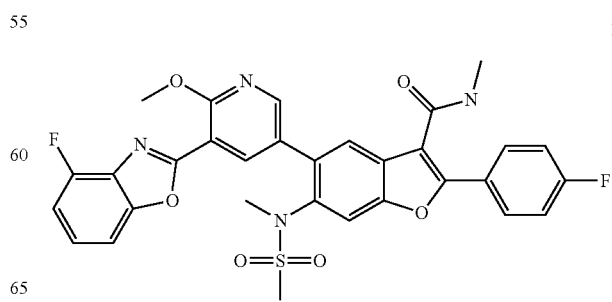

Step 1—Synthesis of 5-bromo-N-(2-fluoro-6-hydroxyphenyl)-2-methoxynicotinamide

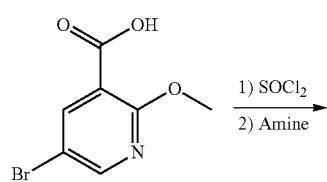

Step B—Synthesis of 2-(5-bromo-2-methoxypyridin-3-yl)-4-fluorobenzo[d]oxazole

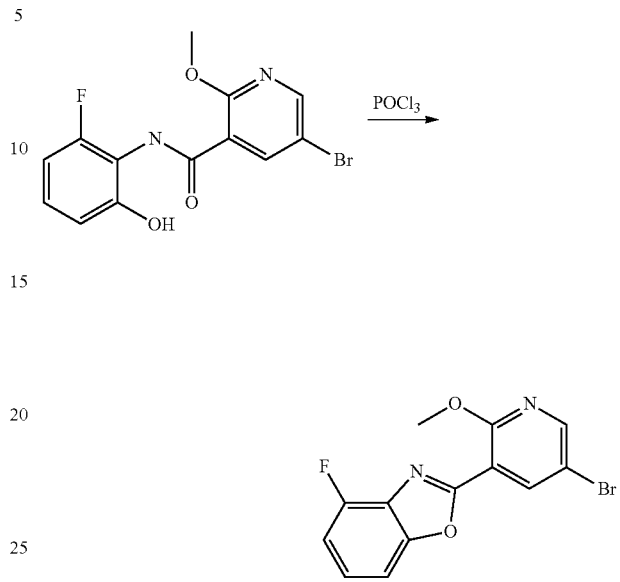

To a solution of 5-bromo-2-methoxynicotinic acid (650 mg, 2.8 mmol) in anhydrous DCM (15 mL), SOCl$_2$ (1 mL) was added dropwise and the mixture was heated to reflux and allowed to stir at this temperature for 2 hours. The reaction mixture was concentrated in vacuo, then anhydrous DCM (10 mL) was added and the solvent was evaporated again. The crude product was dissolved in anhydrous DCM (3 mL), and added dropwise to a solution of the 2-amino-3-fluorophenol (256 mg, 2.8 mmol) and Et$_3$N (1 mL) in DCM (10 mL) at ice-bath. The mixture was allowed to stir at room temperature for 3 hours, then was poured into water, extracted with DCM. The organic phase was washed with brine, dried over Na$_2$SO$_4$, and concentrated in vacuo. The resulting residue was purified using column chromatography (eluted with PE:EtOAc=10:1) to provide 5-bromo-N-(2-fluoro-6-hydroxyphenyl)-2-methoxynicotinamide (820 mg, yield: 75.0%). $^1$H-NMR (CDCl$_3$, 400 MHz) δ 10.39 (s, 1H), 9.89 (s, 1H), 8.61 (d, J=2.0 Hz, 1H), 8.34 (d, J=4.0 Hz, 1H), 7.00~7.06 (m, 1H), 6.77~6.79 (m, 1H), 6.62~6.66 (m, 1H), 4.14 (s, 3H). MS (M+H)$^+$: 341/343.

A solution of 5-bromo-N-(2-fluoro-6-hydroxyphenyl)-2-methoxynicotinamide (350 mg, 1.0 mmol) in POCl$_3$ (5 mL) and toluene (5 mL) was heated to reflux for 8 hours. After being cooled to room temperature, the reaction mixture was poured into ice-water, and extracted with DCM. The organic phase was washed with H$_2$O and brine, concentrated in vacuo. The resulting residue was purified using column chromatography (eluted with PE:EtOAc=20:1) to provide 2-(5-bromo-2-methoxypyridin-3-yl)-4-fluorobenzo[d]oxazole (200 mg, yield: 62.3%) as a white solid. $^1$H-NMR (CDCl$_3$, 400 MHz) δ 8.59 (d, J=4.0 Hz, 1H), 8.36 (d, J=4.0 Hz, 1H), 7.04~7.08 (m, 1H), 6.76~6.79 (m, 1H), 6.68~6.70 (m, 1H), 4.18 (s, 3H). MS (M+H)$^+$: 323/325.

Step C—Synthesis of 5-(5-(4-fluorobenzo[d]oxazol-2-yl)-6-methoxypyridin-3-yl)-2-(4-fluorophenyl)-N-methyl-6-(N-methylmethylsulfonamido)benzofuran-3-carboxamide (Compound 1)

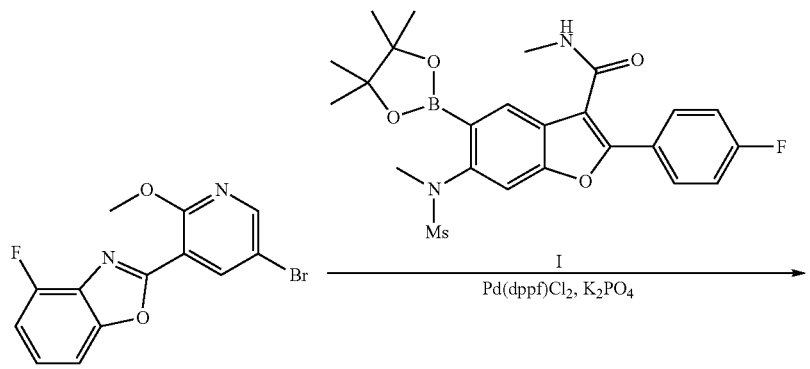

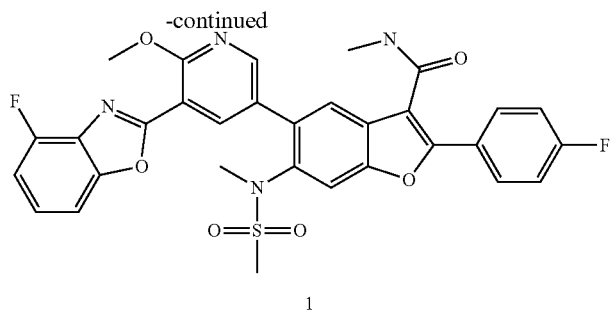

1

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 100 mg, 0.2 mmol) and 2-(5-bromo-2-methoxypyridin-3-yl)-4-fluorobenzo[d]oxazole (65 mg, 0.2 mmol) in dry DMF (3 mL) was added Pd(dppf)Cl$_2$ (10 mg) and K$_3$PO$_4$ (120 mg, 0.4 mmol) under N$_2$ protection. The mixture was heated to 100° C. and allowed to stir at this temperature for about 15 hours and then was to room temperature and filtered. The filtrate was washed with H$_2$O, brine, dried over Na$_2$SO$_4$. After being concentrated in vacuo, the resulting residue was purified using prep-HPLC to provide Compound 1 (68 mg, yield: 57.6%). $^1$H-NMR (CDCl$_3$, 400 MHz) δ 8.57 (d, J=2.0 Hz, 1H), 8.41 (d, J=1.6 Hz, 1H), 7.90~7.93 (m, 2H), 7.86 (s, 1H), 7.63 (s, 1H), 7.40~7.42 (m, 1H), 7.30~7.34 (m, 1H), 7.18 (t, J=4.8 Hz, 2H), 7.05~7.09 (m, 1H), 5.98 (d, J=3.2 Hz, 1H), 3.20 (s, 3H), 3.00 (d, J=4.4 Hz, 3H), 2.83 (s, 3H). MS (M+H)$^+$: 619.

Compounds 2-22, depicted in the table below, were prepared using the method described in Example 1 and substituting the appropriate reactants and/or reagents.

| No. | Structure | NMR | MS (M + H)$^+$ |
|---|---|---|---|
| 2 | 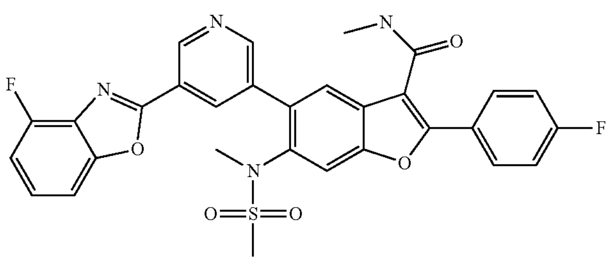 [SMILES: CNC(=O)c1c(-c2ccc(F)cc2)oc2cc(N(C)S(C)(=O)=O)c(-c3cncc(-c4nc5c(F)cccc5o4)c3)cc12] | $^1$H-NMR (CDCl$_3$, 400 MHz) δ 9.42 (s, 1H), 8.77 (s, 1H), 8.58 (s, 1H), 7.85~7.89 (m, 3H), 7.61 (s, 1H), 7.38 (d, J = 8.0 Hz, 1H), 7.27~7.33 (m, 1H), 7.15 (t, J = 8.0 Hz, 2H), 7.06 (t, J = 8.0 Hz, 1H), 5.89 (s, 1H), 3.18 (s, 3H), 2.95 (d, J = 4.0 Hz, 3H), 2.72 (s, 3H). | 589 |
| 3 | 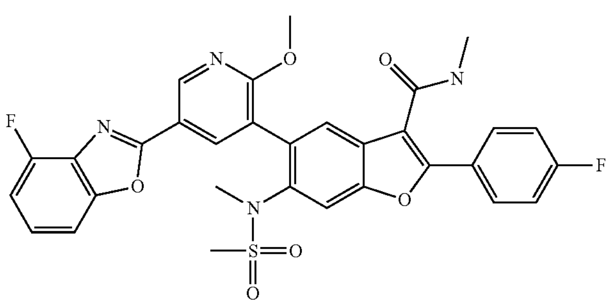 [SMILES: CNC(=O)c1c(-c2ccc(F)cc2)oc2cc(N(C)S(C)(=O)=O)c(-c3cc(-c4nc5c(F)cccc5o4)cnc3OC)cc12] | $^1$H-NMR (CDCl$_3$, 400 MHz) δ 9.04 (s, 1H), 8.37 (d, J = 4.4 Hz, 1H), 7.88~7.92 (m, 2H), 7.75 (s, 1H), 7.57 (s, 1H), 7.33 (d, J = 8.0 Hz, 1H), 7.22~7.26 (m, 1H), 7.13~7.17 (m, 2H), 7.02 (t, J = 8.8 Hz, 1H), 5.80 (d, J = 3.6 Hz, 1H), 3.95 (s, 3H), 3.21 (s, 3H), 2.94 (d, J = 4.8 Hz, 3H), 4.06 (s, 3H). | 619 |
| 4 | 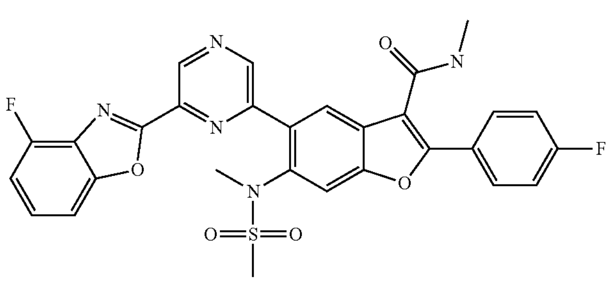 | $^1$H-NMR (CDCl$_3$, 400 MHz) δ 9.27 (s, 1H), 8.60 (s, 1H), 7.90~7.93 (m, 2H), 7.79 (s, 1H), 7.65 (s, 1H), 7.30~7.36 (m, 2H), 7.13~7.17 (m, 2H), 7.05 (t, J = 8.4 Hz, 1H), 5.96 (d, J = 4.4 Hz, 1H), 3.22 (s, 3H), 2.91 (s, 3H), 2.88 (d, J = 4.8 Hz, 3H). | 590 |

| No. | Structure | NMR | MS (M + H)+ |
|---|---|---|---|
| 5 | 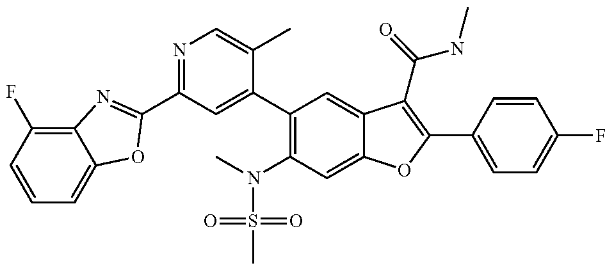 [SMILES: CNC(=O)c1c(-c2ccc(F)cc2)oc2cc(N(C)S(C)(=O)=O)c(-c3cc(-c4nc5c(F)cccc5o4)ncc3C)cc12] | ¹H-NMR (CDCl₃, 400 MHz) δ 8.75 (s, 1H), 8.30 (s, 1H), 7.90~7.93 (m, 2H), 7.75 (s, 1H), 7.64 (s, 1H), 7.43~7.46 (m, 1H), 7.32~7.38 (m, 1H), 7.20~7.25 (m, 2H), 7.07~7.12 (m, 1H), 6.05~6.09 (br s, 1H), 3.25 (s, 3H), 2.98 (d, J = 5.2 Hz, 3H), 2.68 (s, 3H), 2.32 (s, 3H). | 603 |
| 6 | 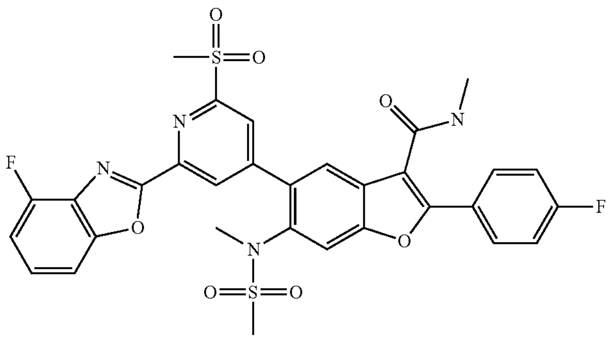 [SMILES: CNC(=O)c1c(-c2ccc(F)cc2)oc2cc(N(C)S(C)(=O)=O)c(-c3cc(-c4nc5c(F)cccc5o4)nc(S(C)(=O)=O)c3)cc12] | ¹H-NMR (DMSO-d6, 400 MHz) δ 8.58 (d, J = 8.0 Hz, 3H), 8.26 (s, 1H), 7.99~8.02 (m, 2H), 7.77 (d, J = 8.0 Hz, 1H), 7.54~7.59 (m, 1H), 7.35~7.42 (m, 3H), 3.37 (s, 3H), 3.34 (s, 3H), 2.94 (s, 3H), 2.79 (d, J = 8.0 Hz, 3H). | 667 |
| 7 | 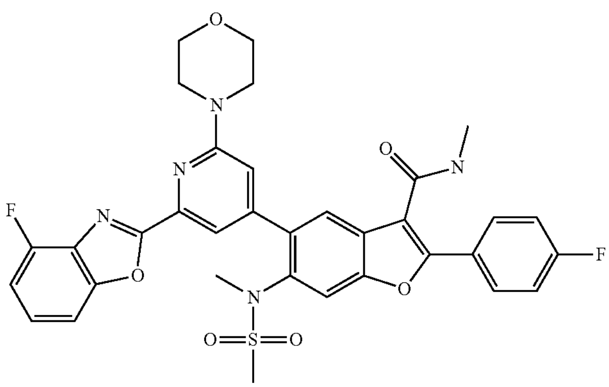 [SMILES: CNC(=O)c1c(-c2ccc(F)cc2)oc2cc(N(C)S(C)(=O)=O)c(-c3cc(-c4nc5c(F)cccc5o4)nc(N4CCOCC4)c3)cc12] | ¹H-NMR (DMSO-d6, 400 MHz) δ 8.55 (d, J = 4.0 Hz, 1H), 7.97~8.00 (m, 3H), 7.79 (s, 1H), 7.68 (d, J = 8.0 Hz, 1H), 7.59 (s, 1H), 7.47~7.52 (m, 2H), 7.34~7.41 (m, 2H), 7.29~7.32 (m, 1H), 3.71 (s, 4H), 3.60 (s, 4H), 3.22 (s, 3H), 2.92 (s, 3H), 2.79 (d, J = 4.0 Hz, 3H). | 674 |
| 8 | 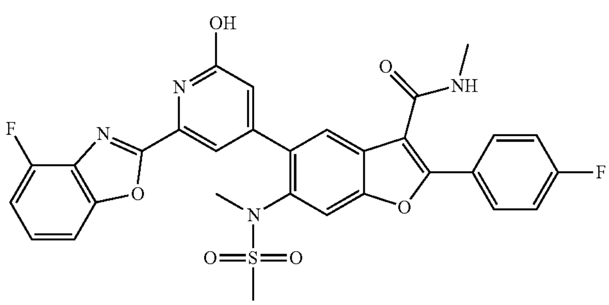 [SMILES: CNC(=O)c1c(-c2ccc(F)cc2)oc2cc(N(C)S(C)(=O)=O)c(-c3cc(O)nc(-c4nc5c(F)cccc5o4)c3)cc12] | ¹H-NMR (CDCl₃, 400 MHz) δ 7.98~8.03 (m, 3H), 7.58 (s, 1H), 7.30~7.37 (m, 4H), 7.08~7.12 (m, 3H), 6.99-7.09 (m, 1H), 3.29 (s, 3H), 3.03 (d, J = 8.0 Hz, 3H), 2.95 (s, 3H). | 605 |
| 9 | 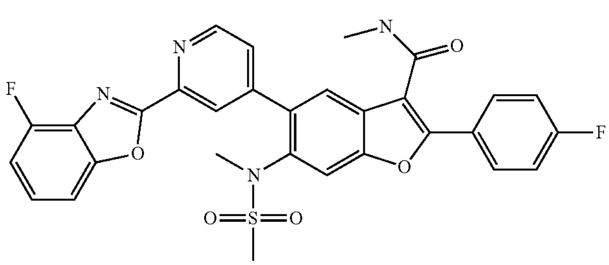 [SMILES: CNC(=O)c1c(-c2ccc(F)cc2)oc2cc(N(C)S(C)(=O)=O)c(-c3ccnc(-c4nc5c(F)cccc5o4)c3)cc12] | ¹H-NMR (CDCl₃, 400 MHz) δ 8.80 (d, J = 5.2 Hz, 1H), 8.43 (d, J = 0.8 Hz, 1H), 7.85~7.88 (m, 3H), 7.56~7.58 (m, 2H), 7.42 (d, J = 8.0 Hz, 1H), 7.28~7.34 (m, 1H), 7.03~7.16 (m, 2H), 6.01 (d, J = 4.0 Hz, 1H), 5.95 (s, 1H), 3.16 (s, 3H), 2.97 (d, J = 4.0 Hz, 3H), 2.79 (s, 3H). | 589 |

| No. | Structure | NMR | MS (M + H)+ |
|---|---|---|---|
| 10 | 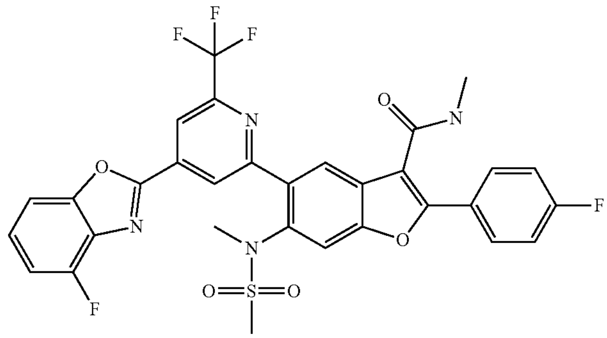 | ¹H-NMR (DMSO-d6, 400 MHz) δ 8.58 (s, 2H), 8.46 (s, 1H), 8.15 (s, 1H), 7.98~8.02 (m, 2H), 7.95 (s, 1H), 7.76 (d, J = 8.8 Hz, 1H), 7.52~7.61 (m, 1H), 7.38~7.45 (m, 3H), 2.94 (s, 3H), 2.80 (d, J = 4.0 Hz, 3H), 2.64 (s, 3H). | 657 |
| 11 | 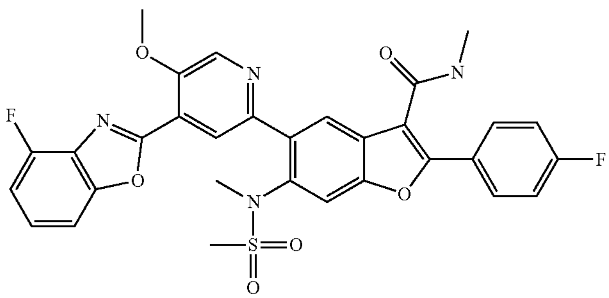 [SMILES: CNC(=O)c1c(-c2ccc(F)cc2)oc2cc(N(C)S(C)(=O)=O)c(-c3cc(-c4nc5c(F)cccc5o4)c(OC)cn3)cc12] | ¹H-NMR (DMSO-d6, 400 MHz) δ 8.78 (s, 1H), 8.56~8.57 (m, 1H), 8.23 (s, 1H), 8.02 (s, 1H), 7.96~7.99 (m, 2H), 7.83 (d, J = 3.6 Hz, 1H), 7.69 (d, J = 8.0 Hz, 1H), 7.46~7.56 (m, 1H), 7.29~7.41 (m, 3H), 4.12 (s, 3H), 3.23 (s, 3H), 2.79 (d, J = 4.0 Hz, 3H), 2.63 (s, 3H). | 619 |
| 12 | 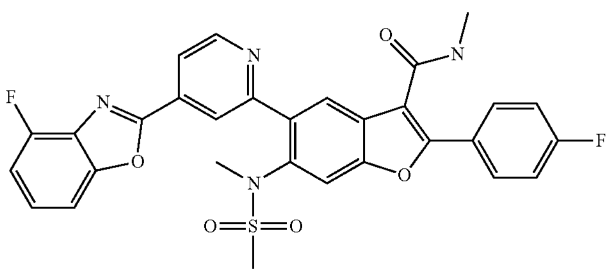 | ¹H-NMR (CDCl₃, 400 MHz) δ 8.83~8.85 (m, 1H), 8.34 (t, J = 0.8 Hz, 1H), 8.06~8.08 (m, 1H), 8.01 (s, 1H), 7.91~7.95 (m, 2H), 7.66 (s, 1H), 7.38~7.41 (m, 1H), 7.31~7.36 (m, 1H), 7.15 (t, J = 8.0 Hz, 2H), 7.05~7.10 (m, 1H), 5.92 (s, 1H), 3.22 (s, 3H), 2.95 (d, J = 4.8 Hz, 3H), 2.75 (s, 3H). | 589 |
| 13 | 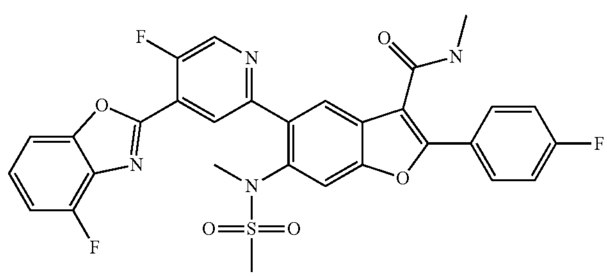 [SMILES: CNC(=O)c1c(-c2ccc(F)cc2)oc2cc(N(C)S(C)(=O)=O)c(-c3cc(-c4nc5c(F)cccc5o4)c(F)cn3)cc12] | ¹H-NMR (DMSO-d6, 400 MHz) δ 8.96 (d, J = 1.6 Hz, 1H), 8.55 (d, J = 4.8 Hz, 1H), 8.36 (d, J = 5.6 Hz, 1H), 8.06 (s, 1H), 7.96~8.00 (m, 2H), 7.88 (s, 1H), 7.74~7.76 (m, 1H), 7.52~7.57 (m, 1H), 7.34~7.41 (m, 3H), 3.26 (s, 3H), 2.97 (s, 3H), 2.80 (d, J = 4.4 Hz, 3H). | 607 |
| 14 | 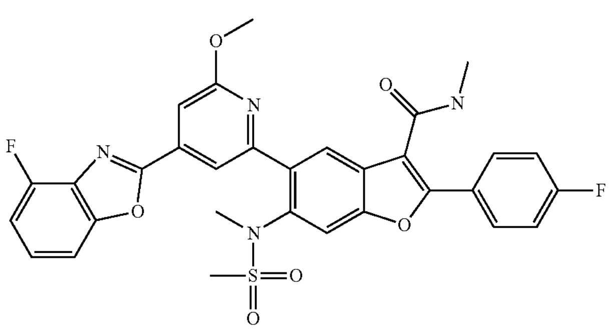 [SMILES: CNC(=O)c1c(-c2ccc(F)cc2)oc2cc(N(C)S(C)(=O)=O)c(-c3cc(-c4nc5c(F)cccc5o4)cc(OC)n3)cc12] | ¹H-NMR (CDCl₃, 400 MHz) δ 8.01 (s, 1H), 7.88~7.90 (m, 3H), 7.63 (s, 1H), 7.51 (s, 1H), 7.36~7.39 (m, 1H), 7.29~7.34 (m, 1H), 7.15 (t, J = 8.8 Hz, 2H), 7.08 (t, J = 8.4 Hz, 1H), 5.92 (d, J = 4.4 Hz, 1H), 3.99 (s, 3H), 3.31 (s, 3H), 2.95 (d, J = 4.8 Hz, 3H), 2.68 (s, 3H). | 619 |

| No. | Structure | NMR | MS (M + H)+ |
|---|---|---|---|
| 15 | 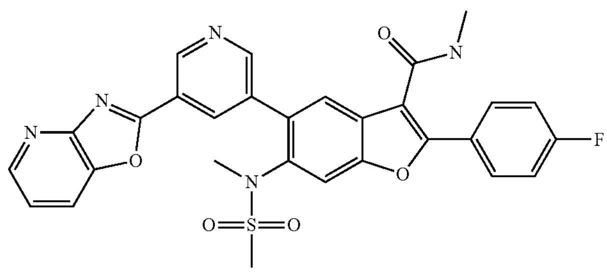 [SMILES: CNC(=O)c1c(-c2ccc(F)cc2)oc2cc(N(C)S(C)(=O)=O)c(-c3cncc(-c4nc5ncccc5o4)c3)cc12] | ¹H-NMR (CDCl₃, 400 MHz) δ 9.52 (s, 1H), 8.92 (s, 1H), 8.83 (s, 1H), 8.66 (s, 1H), 7.92~7.99 (m, 4H), 7.68 (s, 1H), 7.39~7.43 (m, 1H), 7.20~7.24 (m, 2H), 6.02 (d, J = 2.0 Hz, 1H), 3.29 (s, 3H), 3.01 (d, J = 8.0 Hz, 3H), 2.83 (s, 3H). | 572 |
| 16 | 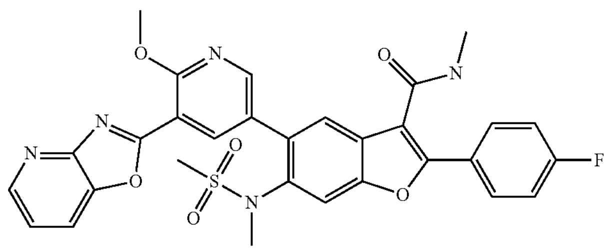 [SMILES: CNC(=O)c1c(-c2ccc(F)cc2)oc2cc(N(C)S(C)(=O)=O)c(-c3cnc(OC)c(-c4nc5ncccc5o4)c3)cc12] | ¹H-NMR (CDCl₃, 400 MHz) δ 8.61 (d, J = 2.4 Hz, 1H), 8.54 (d, J = 3.6 Hz, 1H), 8.40 (s, 1H), 7.87~7.90 (m, 3H), 7.84 (d, J = 4.0 Hz, 1H), 7.60 (s, 1H), 7.25~7.28 (m, 1H), 7.15 (t, J = 8.8 Hz, 2H), 5.82 (d, J = 4.8 Hz, 1H), 4.16 (s, 3H), 3.18 (s, 3H), 2.95 (d, J = 4.8 Hz, 3H), 2.79 (s, 3H). | 602 |
| 17 | 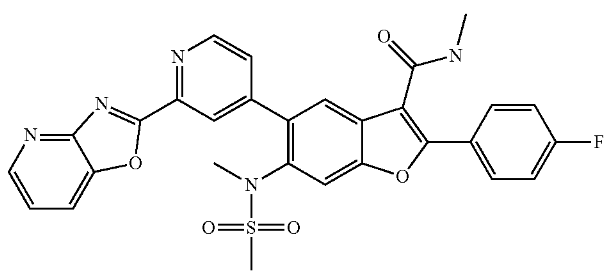 [SMILES: CNC(=O)c1c(-c2ccc(F)cc2)oc2cc(N(C)S(C)(=O)=O)c(-c3ccnc(-c4nc5ncccc5o4)c3)cc12] | ¹H-NMR (CDCl₃, 400 MHz) δ 8.65 (s, 1H), 8.52 (d, J = 4.0 Hz, 1H), 8.26 (s, 1H), 7.88~7.91 (m, 2H), 7.81 (d, J = 8.0 Hz, 1H), 7.62 (s, 1H), 7.50 (s, 1H), 7.25~7.28 (m, 2H), 7.13~7.20 (m, 2H), 6.36~6.37 (br s, 1H), 3.20 (s, 3H), 2.96 (d, J = 4.8 Hz, 3H), 2.60 (s, 3H), 2.24 (s, 3H). | 572 |
| 18 | 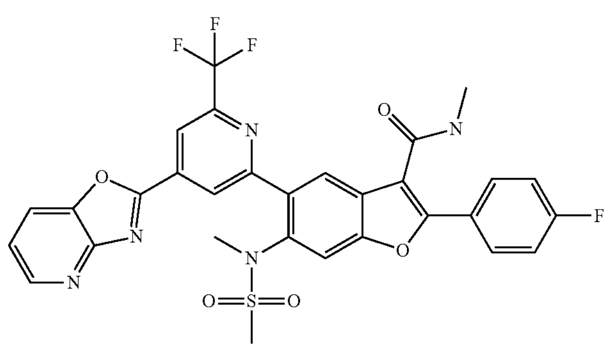 [SMILES: CNC(=O)c1c(-c2ccc(F)cc2)oc2cc(N(C)S(C)(=O)=O)c(-c3cc(-c4nc5ncccc5o4)cc(C(F)(F)F)n3)cc12] | ¹H-NMR (CDCl₃, 400 MHz) δ 8.69 (d, J = 3.2 Hz, 1H), 8.63 (s, 1H), 8.54 (s, 1H), 8.14 (s, 1H), 7.93~8.00 (m, 3H), 7.70 (s, 1H), 7.42~7.45 (m, 1H), 7.20~7.24 (m, 2H), 5.90~5.94 (br s, 1H), 3.38 (s, 3H), 3.00 (d, J = 4.8 Hz, 3H), 2.76 (s, 3H). | 640 |
| 19 | 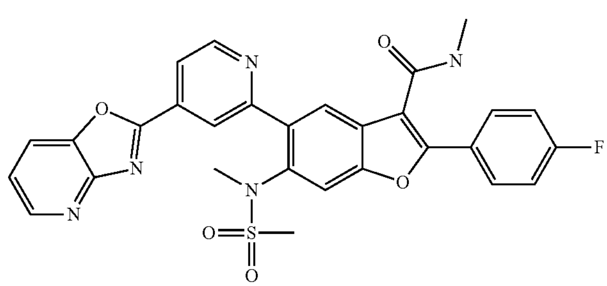 [SMILES: CNC(=O)c1c(-c2ccc(F)cc2)oc2cc(N(C)S(C)(=O)=O)c(-c3cc(-c4nc5ncccc5o4)ccn3)cc12] | ¹H-NMR (DMSO-d6, 400 MHz) δ 8.95 (d, J = 2.8 Hz, 1H), 8.56~8.61 (m, 2H), 8.31~8.37 (m, 2H), 8.11 (d, J = 5.2 Hz, 1H), 8.07 (s, 1H), 7.98~8.00 (m, 2H), 7.90 (s, 1H), 7.51~7.55 (m, 1H), 7.37~7.42 (m, 2H), 3.28 (s, 3H), 2.95 (s, 3H), 2.97 (d, J = 4.8 Hz, 3H). | 572 |

| No. | Structure | NMR | MS (M + H)+ |
|---|---|---|---|
| 20 | 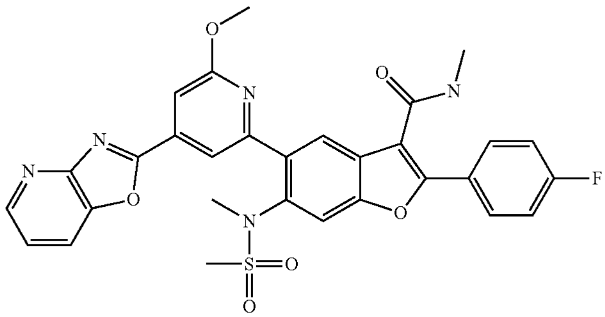 [SMILES: CNC(=O)c1c(-c2ccc(F)cc2)oc2cc(N(C)S(C)(=O)=O)c(-c3cc(-c4nc5ncccc5o4)cc(OC)n3)cc12] | ¹H-NMR (CDCl₃, 400 MHz) δ 8.59 (d, J = 4.8 Hz, 1H), 8.03 (s, 1H), 7.96 (s, 1H), 7.88~7.93 (m, 3H), 7.63 (s, 1H), 7.55 (s, 1H), 7.32~7.35 (m, 1H), 7.15 (t, J = 8.4 Hz, 2H), 5.91 (s, 1H), 4.00 (s, 3H), 3.32 (s, 3H), 2.95 (d, J = 4.8 Hz, 3H), 2.71 (s, 3H). | 600 |
| 21 | 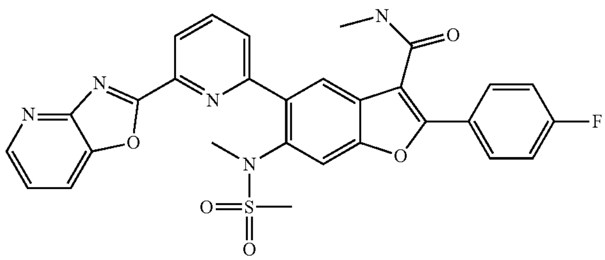 [SMILES: CNC(=O)c1c(-c2ccc(F)cc2)oc2cc(N(C)S(C)(=O)=O)c(-c3cccc(-c4nc5ncccc5o4)n3)cc12] | ¹H-NMR (CDCl₃, 400 MHz) δ 8.61 (d, J = 3.2 Hz, 1H), 8.46 (d, J = 7.6 Hz, 1H), 7.97~8.03 (m, 2H), 7.89~7.93 (m, 3H), 7.80 (d, J = 6.8 Hz, 1H), 7.62 (s, 1H), 7.31~7.35 (m, 1H), 7.13~7.16 (m, 2H), 5.87~5.89 (m, 1H), 3.26 (s, 3H), 2.94 (d, J = 4.8 Hz, 3H), 2.78 (s, 3H). | 572 |
| 22 | 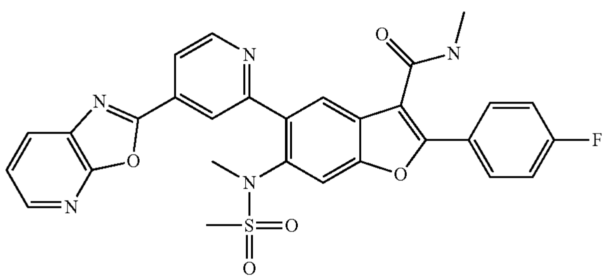 | ¹H-NMR (CDCl₃, 400 MHz) δ 8.63 (d, J = 5.2 Hz, 1H), 8.52 (s, 1H), 8.44 (d, J = 1.2 Hz, 1H), 8.28 (d, J = 1.2 Hz, 1H), 8.14 (d, J = 1.2 Hz, 1H), 8.06 (s, 1H), 7.99 (d, J = 5.6 Hz, 2H), 7.63 (s, 1H), 7.41 (d, J = 4.8 Hz, 1H), 7.13 (t, J = 8.8 Hz, 2H), 6.54 (d, J = 4.4 Hz, 1H), 3.34 (s, 3H), 2.97 (d, J = 4.4 Hz, 3H), 2.78 (s, 3H). | 572 |

Compounds 157-170, depicted in the table below, were prepared using the method described in Example 1 and substituting the appropriate reactants and/or reagents.

| No. | Structure | NMR | MS (M + H)+ |
|---|---|---|---|
| 157 | 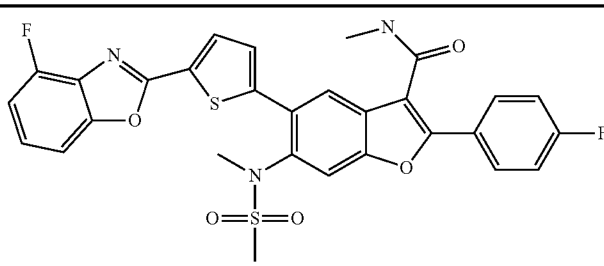 | ¹H-NMR (CDCl3, 400 MHz) δ 8.04 (s, 1H), 7.86~7.89 (m, 3H), 7.82 (s, 1H), 7.69 (s, 1H), 7.54 (s, 1H), 7.28~7.34 (m, 2H), 7.13 (d, J = 8.0 Hz, 2H), 7.03 (d, J = 8.8 Hz, 1H), 3.17 (s, 3H), 2.93 (s, 3H), 2.82 (s, 3H). | 594 |
| 158 | 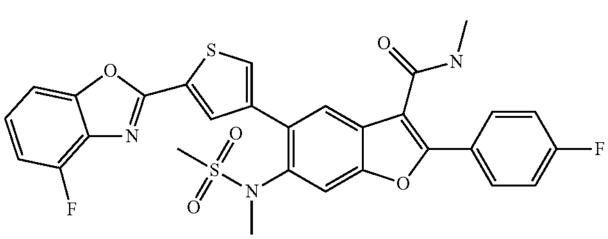 [SMILES: CNC(=O)c1c(-c2ccc(F)cc2)oc2cc(N(C)S(C)(=O)=O)c(-c3csc(-c4nc5c(F)cccc5o4)c3)cc12] | ¹H-NMR (CDCl3, 400 MHz) δ 8.12 (s, 1H), 7.94~7.98 (m, 3H), 7.76 (s, 1H), 7.64 (s, 1H), 7.41 (d, J = 8.4 Hz, 1H), 7.32~7.34 (m, 1H), 7.24 (t, J = 8.4 Hz, 2H), 7.12 (t, J = 8.8 Hz, 1H), 5.96 (br s, 1H), 3.26 (s, 3H), 3.05 (d, J = 4.8 Hz, 3H), 2.89 (s, 3H). | 594 |

| No. | Structure | NMR | MS (M + H)+ |
|---|---|---|---|
| 159 | 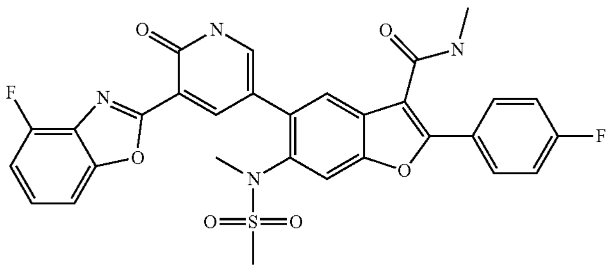 [SMILES: CNC(=O)c1c(-c2ccc(F)cc2)oc2cc(N(C)S(C)(=O)=O)c(-c3c[nH]c(=O)c(-c4nc5c(F)cccc5o4)c3)cc12] | ¹H-NMR (DMSO-d₆, 400 MHz) δ 8.50 (d, J = 4.8 Hz, 1H), 8.45 (d, J = 2.4 Hz, 1H), 8.03 (s, 1H), 7.96~8.00 (m, 2H), 7.79 (d, J = 6.4 Hz, 1H), 7.71 (s, 1H), 7.61~7.62 (m, 1H), 7.37~7.43 (m, 3H), 7.22~7.27 (m, 1H), 3.18 (s, 3H), 3.08 (s, 3H), 2.80 (d, J = 4.4 Hz, 3H). | 605 |
| 160 | 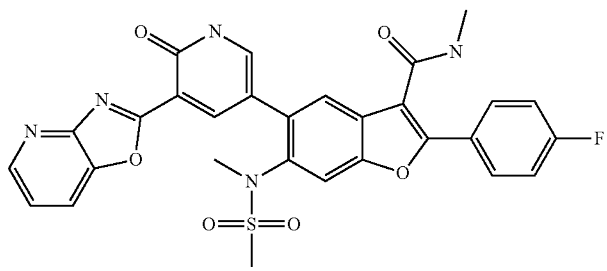 [SMILES: CNC(=O)c1c(-c2ccc(F)cc2)oc2cc(N(C)S(C)(=O)=O)c(-c3c[nH]c(=O)c(-c4nc5ncccc5o4)c3)cc12] | ¹H-NMR (CDCl₃, 400 MHz) δ 9.04 (s, 1H), 8.37 (d, J = 4.4 Hz, 1H), 7.88~7.92 (m, 2H), 7.75 (s, 1H), 7.57 (s, 1H), 7.33 (d, J = 8.0 Hz, 1H), 7.22~7.26 (m, 1H), 7.13~7.17 (m, 2H), 7.02 (t, J = 8.8 Hz, 1H), 5.80 (d, J = 3.6 Hz, 1H), 3.95 (s, 3H), 3.21 (s, 3H), 2.94 (d, J = 4.8 Hz, 3H), 4.06 (s, 3H). | 588 |
| 161 | 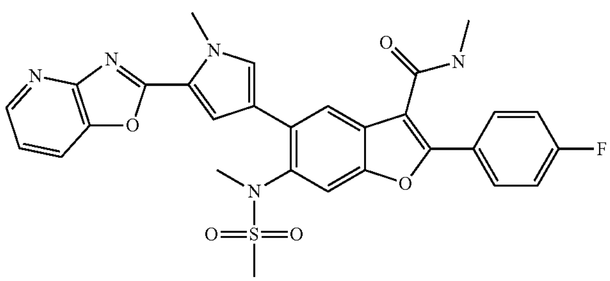 [SMILES: CNC(=O)c1c(-c2ccc(F)cc2)oc2cc(N(C)S(C)(=O)=O)c(-c3cc(-c4nc5ncccc5o4)n(C)c3)cc12] | ¹HNMR (CDCl₃, 400 MHz) δ 8.56 (d, J = 4.0 Hz, 1H), 8.02 (s, 1H), 7.90~7.95 (m, 3H), 7.58 (s, 1H), 7.53 (s, 1H), 7.45 (s, 1H), 7.34~7.35 (m, 1H), 7.20~7.24 (m, 2H), 5.87 (br, 1H), 4.26 (s, 3H), 3.25 (s, 3H), 3.00~3.04 (m, 6H). | 574 |
| 162 | 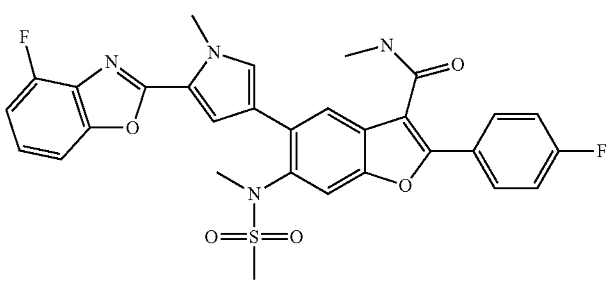 [SMILES: CNC(=O)c1c(-c2ccc(F)cc2)oc2cc(N(C)S(C)(=O)=O)c(-c3cc(-c4nc5c(F)cccc5o4)n(C)c3)cc12] | ¹H-NMR (CDCl₃, 300 MHz) δ 8.00 (s, 1H), 7.91~7.96 (m, 2H), 7.58 (s, 1H), 7.34~7.39 (m, 3H), 7.18~7.21 (m, 2H), 7.00~7.09 (m, 2H), 5.84 (br, 1H), 4.23 (s, 3H), 3.26 (s, 3H), 3.02~3.04 (d, J = 6.0 Hz, 3H), 2.96 (s, 3H). | 591 |
| 163 | 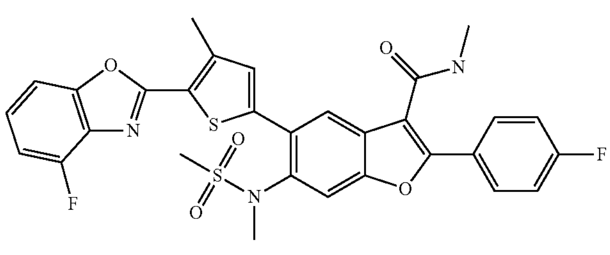 [SMILES: CNC(=O)c1c(-c2ccc(F)cc2)oc2cc(N(C)S(C)(=O)=O)c(-c3cc(C)c(-c4nc5c(F)cccc5o4)s3)cc12] | ¹H-NMR (CDCl₃, 400 MHz) δ 7.84~7.87 (m, 3H), 7.75 (s, 1H), 7.61 (s, 1H), 7.30 (d, J = 7.8 Hz, 1H), 7.22~7.26 (m, 1H), 7.04~7.18 (m, 2H), 7.02 (t, J = 9.2 Hz, 1H), 5.74 (d, J = 4.0 Hz, 1H), 3.23 (s, 3H), 2.93 (d, J = 4.8 Hz, 3H), 2.61 (s, 3H), 2.18 (s, 3H). | 608 |
| 164 | 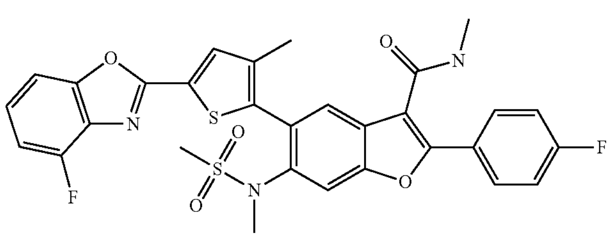 [SMILES: CNC(=O)c1c(-c2ccc(F)cc2)oc2cc(N(C)S(C)(=O)=O)c(-c3sc(-c4nc5c(F)cccc5o4)cc3C)cc12] | ¹H-NMR (CDCl₃, 400 MHz) δ 7.88~7.92 (m, 3H), 7.80 (s, 1H), 7.66 (s, 1H), 7.35 (d, J = 8.0 Hz, 1H), 7.21~7.29 (m, 3H), 7.07 (t, J = 8.4 Hz, 1H), 5.85 (d, J = 4.0 Hz, 1H), 3.31 (s, 3H), 2.96 (d, J = 4.8 Hz, 3H), 2.60 (s, 3H), 2.15 (s, 3H). | 608 |

| No. | Structure | NMR | MS (M + H)+ |
|---|---|---|---|
| 165 | | ¹H-NMR (CDCl₃, 400 MHz) δ 8.93 (s, 1H), 8.08 (s, 1H), 7.94~7.97 (m, 2H), 7.56 (s, 1H), 7.23~7.30 (m, 1H), 7.18~7.22 (m, 1H), 7.08~7.12 (m, 2H), 6.91~6.96 (m, 1H), 6.38~6.39 (br s, 1H), 3.07 (s, 3H), 2.87 (d, J = 4.8 Hz, 3H), 2.70 (s, 3H). | 595 |
| 165 | | ¹H-NMR (CDCl₃, 400 MHz) δ 8.04 (s, 1H), 7.81~7.85 (m, 2H), 7.60 (s, 1H), 7.34 (d, J = 8.0 Hz, 1H), 7.24~7.27 (m, 2H), 7.10~7.14 (m, 2H), 6.99~7.04 (m, 1H), 6.62 (s, 1H), 3.27 (s, 3H), 2.96~2.98 (m, 6H). | 612 |
| 167 | 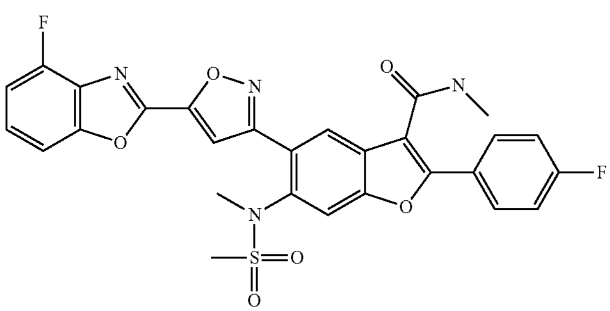 [SMILES: CNC(=O)c1c(-c2ccc(F)cc2)oc2cc(N(C)S(C)(=O)=O)c(-c3cc(-c4nc5c(F)cccc5o4)on3)cc12] | ¹H-NMR (CDCl₃, 400 MHz) δ 9.33 (s, 1H), 8.27 (s, 1H), 8.12~8.15 (m, 2H), 7.75 (s, 1H), 7.32~7.36 (m, 2H), 7.22~7.26 (m, 2H), 7.07~7.10 (m, 1H), 6.42 (br s, 1H), 3.27 (s, 3H), 3.02 (d, J = 4.8 Hz, 3H), 2.85 (s, 3H). | 579 |
| 168 | 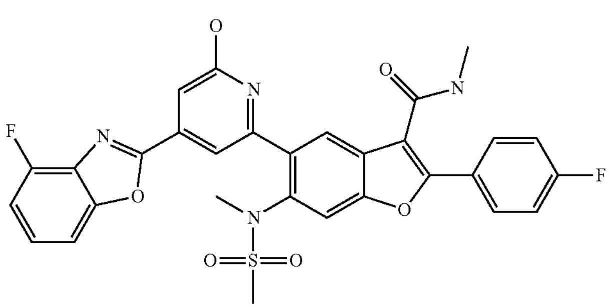 [SMILES: CNC(=O)c1c(-c2ccc(F)cc2)oc2cc(N(C)S(C)(=O)=O)c(-c3cc(-c4nc5c(F)cccc5o4)cc(O)n3)cc12] | ¹H-NMR (DMSO-d₆, 400 MHz) δ 8.51 (d, J = 4.8 Hz, 1H), 7.96~7.99 (m, 3H), 7.76 (s, 1H), 7.67 (d, J = 8.0 Hz, 1H), 7.45~7.50 (m, 1H), 7.39 (t, J = 8.8 Hz, 2H), 7.29 (t, J = 8.8 Hz, 1H), 6.99 (s, 1H), 6.95 (s, 1H), 3.24 (s, 3H), 2.97 (s, 3H), 2.80 (d, J = 4.8 Hz, 3H). | 605 |
| 169 | 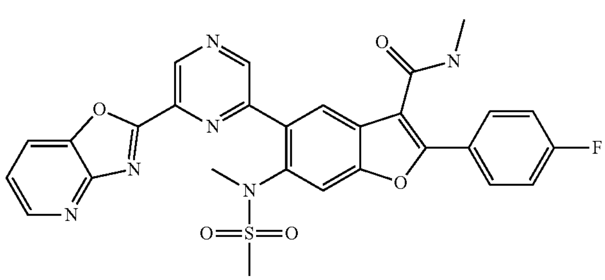 [SMILES: CNC(=O)c1c(-c2ccc(F)cc2)oc2cc(N(C)S(C)(=O)=O)c(-c3cncc(-c4nc5ncccc5o4)n3)cc12] | ¹H-NMR (CDCl3, 400 MHz) δ 9.57 (s, 1H), 8.98 (s, 1H), 8.62 (d, J = 8.0 Hz, 1H), 8.13 (s, 1H), 7.92~7.89 (m, 3H), 7.63 (s, 1H), 7.36~7.33 (m, 1H), 7.14 (t, J = 8.0 Hz, 2H), 6.01 (s, 1H), 3.33 (s, 3H), 2.94 (d, J = 4.0 Hz, 3H), 2.81 (s, 3H) | 573 |

| No. | Structure | NMR | MS (M + H)+ |
|---|---|---|---|
| 170 | 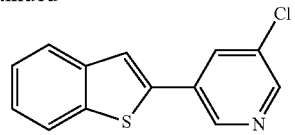 | ¹H-NMR (CDCl₃, 400 MHz) δ 8.94 (d, J = 5.2 Hz, 1H), 8.67 (d, J = 3.6 Hz, 1H), 8.63 (s, 1H), 8.30 (d, J = 4.4 Hz, 1H), 8.06 (s, 1H), 7.93~7.99 (m, 3H), 7.68 (s, 1H), 7.41~7.45 (m, 1H), 7.16 (t, J = 8.8 Hz, 2H), 6.38 (s, 1H), 5.86~6.13 (m, 1H), 3.82~4.05 (m, 2H), 2.97 (d, J = 4.4 Hz, 3H), 2.92 (s, 3H). | 622 |

Example 2

Preparation of Compound 23

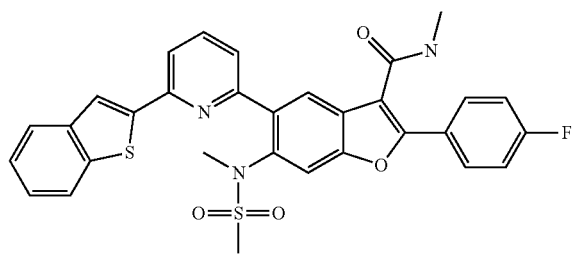

Step 1—Synthesis of 3-(benzo[b]thiophen-2-yl)-5-chloropyridine

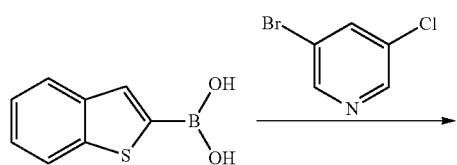

To a degassed solution of benzo[b]thiophen-2-ylboronic acid (300 mg, 1.69 mmol) and 3-bromo-5-chloropyridine (270 mg, 1.40 mmol) in 1,4-Dioxane (20 mL) was added K₃PO₄·3H₂O (900 mg, 3.37 mmol) under N₂. Then Pd(dppf)Cl₂ (10 mg) was added. After being allowed to stir at 100° C. and allowed to stir at this temperature for about 15 hours, the reaction mixture was cooled to room temperature and concentrated and extracted with EtOAc. The organic layers were washed with brine, dried over Na₂SO₄. After being concentrated in vacuo, the resulting residue was purified using column chromatography (eluted with PE:EtOAc=5:1) to provide 3-(benzo[b]thiophen-2-yl)-5-chloropyridine as white solid (160 mg, yield: 38.6%). ¹H-NMR (CDCl₃, 400 MHz) δ 8.43~8.45 (m, 1H), 7.71~7.78 (m, 4H), 7.27~7.32 (m, 2H), 7.13~7.14 (m, 1H). MS (M+H)⁺: 246.

Step B—Synthesis of 5-(6-(benzo[b]thiophen-2-yl)pyridin-2-yl)-2-(4-fluorophenyl)-N-methyl-6-(N-methylmethylsulfonamido)benzofuran-3-carboxamide (Compound 23)

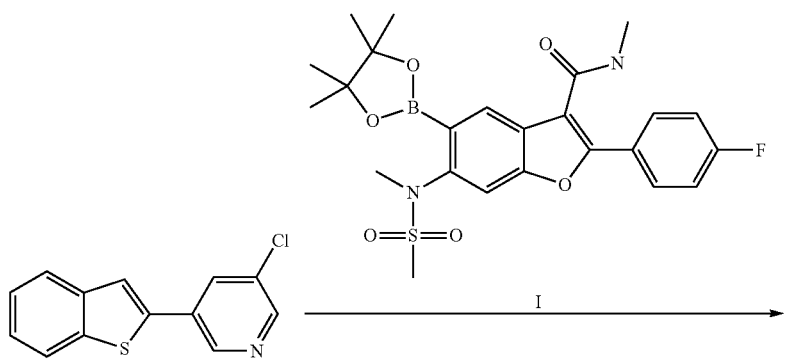

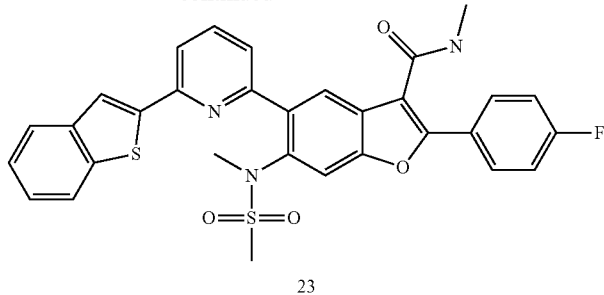

23

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 100 mg, 0.2 mmol) and 3-(benzo[b]thiophen-2-yl)-5-chloropyridine (50 mg, 0.2 mmol) in 1,4-Dioxane/H$_2$O (5:1, 3 mL) were added Pd$_2$(dba)$_3$ (10 mg), X-Phos (5 mg) and K$_3$PO$_4$ (120 mg, 0.4 mmol) under N$_2$ protection. The mixture was heated to 100° C. and allowed to stir at this temperature for about 15 hours and then was to room temperature and filtered. The filtrate was washed with H$_2$O, brine, dried over Na$_2$SO$_4$. After being concentrated in vacuo, the resulting residue was purified using prep-HPLC to provide Compound 23 (35 mg, yield: 42.8%). $^1$H-NMR (CDCl$_3$, 400 MHz) δ 8.70~8.78 (m, 1H), 8.05 (s, 1H), 8.01 (s, 1H), 7.87~7.93 (m, 3H), 7.84~7.86 (m, 2H), 7.64 (s, 1H), 7.41~7.42 (m, 1H), 7.35~7.39 (m, 2H), 7.20~7.24 (m, 2H), 5.91 (d, J=4.8 Hz, 1H), 3.18 (s, 3H), 2.99 (d, J=4.8 Hz, 3H), 2.87 (s, 3H). MS (M+H)$^+$: 586.

Compounds 24-58, depicted in the table below, were prepared using the method described in Example 2 and substituting the appropriate reactants and/or reagents.

| No. | Structure | NMR | MS (M + H)$^+$ |
|---|---|---|---|
| 24 | ![structure] | $^1$H-NMR (DMSO-d6, 400 MHz) δ 9.71 (s, 1H), 8.57 (d, J = 4.4 Hz, 1H), 8.38 (s, 1H), 8.15 (s, 1H), 8.11 (s, 1H), 8.06 (d, J = 5.2 Hz, 1H), 7.90~8.02 (m, 4H), 7.35~7.52 (m, 4H), 3.27 (s, 3H), 3.02 (s, 3H), 2.80 (d, J = 4.0 Hz, 3H). | 587 |
| 25 | ![structure] | $^1$H-NMR (CDCl$_3$, 400 MHz) δ 8.64 (s, 1H), 7.94~7.98 (m, 3H), 7.79~7.82 (m, 3H), 7.72 (s, 1H), 7.30~7.37 (m, 2H), 7.20 (t, J = 8.8 Hz, 2H), 5.94 (s, 1H), 3.99 (s, 3H), 3.33 (s, 3H), 2.97 (d, J = 5.2 Hz, 3H), 2.71 (s, 3H). | 617 |
| 26 | ![structure] | $^1$H-NMR (CDCl$_3$, 400 MHz) δ 8.20 (s, 1H), 8.15 (s, 1H), 7.86~7.96 (m, 3H), 7.80~7.84 (m, 3H), 7.66 (s, 1H), 7.31~7.38 (m, 2H), 7.20~7.24 (m, 2H), 5.86 (s, 1H), 4.06 (s, 3H), 3.20 (s, 3H), 3.00 (d, J = 4.2 Hz, 3H), 2.82 (s, 3H). | 616 |

-continued

| No. | Structure | NMR | MS (M + H)+ |
|---|---|---|---|
| 27 | 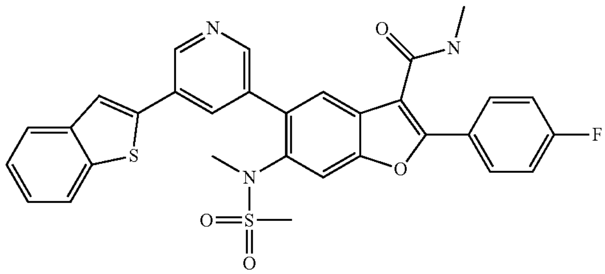 [SMILES: CNC(=O)c1c(-c2ccc(F)cc2)oc2cc(N(C)S(C)(=O)=O)c(-c3cncc(-c4cc5ccccc5s4)c3)cc12] | ¹H-NMR (CDCl₃, 400 MHz) δ 8.99 (s, 1H), 8.63 (s, 1H), 8.26 (s, 1H), 7.85~7.94 (m, 3H), 7.81~7.86 (m, 2H), 7.72 (s, 1H), 7.64 (s, 1H), 7.34~7.40 (m, 2H), 7.18~7.23 (m, 2H), 5.89 (d, J = 2.8 Hz, 1H), 3.18 (s, 3H), 2.99 (d, J = 4.8 Hz, 3H), 2.82 (s, 3H). | 586 |
| 28 | 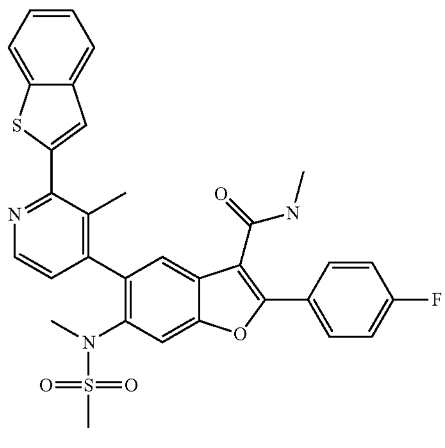 [SMILES: CNC(=O)c1c(-c2ccc(F)cc2)oc2cc(N(C)S(C)(=O)=O)c(-c3ccnc(-c4cc5ccccc5s4)c3C)cc12] | ¹H-NMR (CDCl₃, 400 MHz) δ 8.68 (s, 1H), 7.82~7.85 (m, 4H), 7.77 (s, 2H), 7.61 (s, 1H), 7.49 (s, 1H), 7.37 (t, J = 4.4 Hz, 2H), 7.15 (d, J = 8.4 Hz, 2H), 5.96~6.02 (br s, 1H), 3.19 (s, 3H), 2.90 (d, J = 4.4 Hz, 3H), 2.74 (s, 3H), 2.40 (s, 3H). | 600 |
| 29 | 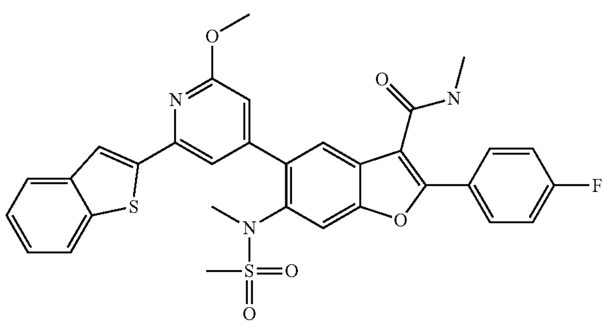 | ¹H-NMR (CDCl₃, 400 MHz) δ 7.83~7.89 (m, 2H), 7.80 (s, 1H), 7.78 (d, J = 2.8 Hz, 1H), 7.73~7.76 (m, 2H), 7.58 (s, 1H), 7.49 (d, J = 0.8 Hz, 1H), 7.26~7.31 (m, 2H), 7.15 (t, J = 8.4 Hz, 2H), 6.70 (d, J = 1.2 Hz, 1H), 5.78 (d, J = 4.4 Hz, 1H), 4.04 (s, 3H), 3.10 (s, 3H), 2.93 (d, J = 5.2 Hz, 3H), 2.79 (s, 3H). | 616 |
| 30 | 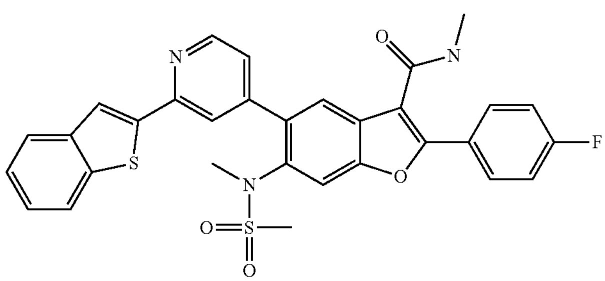 [SMILES: CNC(=O)c1c(-c2ccc(F)cc2)oc2cc(N(C)S(C)(=O)=O)c(-c3ccnc(-c4cc5ccccc5s4)c3)cc12] | ¹H-NMR (CDCl₃, 400 MHz) δ 8.70~8.78 (m, 1H), 8.05 (s, 1H), 8.01 (s, 1H), 7.87~7.93 (m, 3H), 7.84~7.86 (m, 2H), 7.64 (s, 1H), 7.41~7.42 (m, 1H), 7.35~7.39 (m, 2H), 7.20~7.24 (m, 2H), 5.91 (d, J = 4.8 Hz, 1H), 3.18 (s, 3H), 2.99 (d, J = 4.8 Hz, 3H), 2.87 (s, 3H). | 586 |

| No. | Structure | NMR | MS (M + H)+ |
|---|---|---|---|
| 31 | 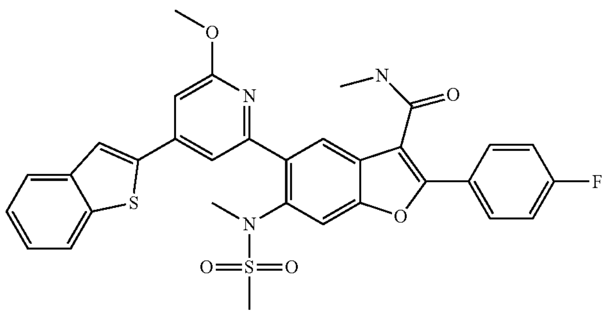 [SMILES: CNC(=O)c1c(-c2ccc(F)cc2)oc2cc(N(C)S(C)(=O)=O)c(-c3cc(-c4cc5ccccc5s4)cc(OC)n3)cc12] | ¹H-NMR (CDCl₃, 400 MHz) δ 8.04 (s, 1H), 7.95~7.99 (m, 2H), 7.80~7.86 (m, 3H), 7.66 (s, 1H), 7.56 (d, J = 1.2 Hz, 1H), 7.36~7.39 (m, 2H), 7.18~7.23 (m, 2H), 7.05 (d, J = 1.2 Hz, 1H), 6.02 (d, J = 5.6 Hz, 1H), 4.03 (s, 3H), 3.32 (s, 3H), 3.00 (d, J = 4.8 Hz, 3H), 2.77 (s, 3H). | 616 |
| 32 | 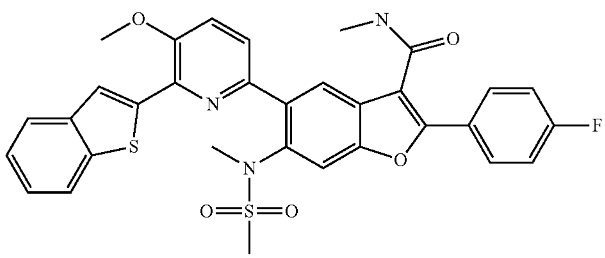 [SMILES: CNC(=O)c1c(-c2ccc(F)cc2)oc2cc(N(C)S(C)(=O)=O)c(-c3ccc(OC)c(-c4cc5ccccc5s4)n3)cc12] | ¹H-NMR (CDCl₃, 400 MHz) δ 8.26 (s, 1H), 8.00 (s, 1H), 7.97~7.99 (m, 2H), 7.81 (t, J = 4.0 Hz, 2H), 7.64 (s, 1H), 7.53 (d, J = 8.4 Hz, 1H), 7.41 (d, J = 8.4 Hz, 1H), 7.22~7.34 (m, 2H), 7.17 (t, J = 8.0 Hz, 2H), 5.94 (d, J = 4.0 Hz, 1H), 4.10 (s, 3H), 3.41 (s, 3H), 3.00 (d, J = 1.2 Hz, 3H), 2.61 (s, 3H). | 616 |
| 33 | 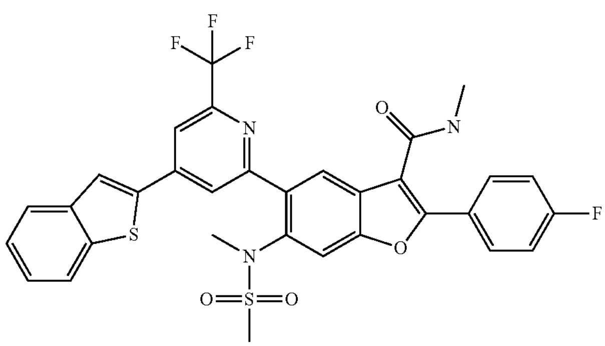 [SMILES: CNC(=O)c1c(-c2ccc(F)cc2)oc2cc(N(C)S(C)(=O)=O)c(-c3cc(-c4cc5ccccc5s4)cc(C(F)(F)F)n3)cc12] | ¹H-NMR (CDCl₃, 400 MHz) δ 8.11 (s, 1H), 8.09 (s, 1H), 7.92~7.97 (m, 4H), 7.84~7.88 (m, 2H), 7.68 (s, 1H), 7.40~7.42 (m, 2H), 7.18~7.23 (m, 2H), 5.90 (d, J = 4.4 Hz, 1H), 3.29 (s, 3H), 2.99 (d, J = 5.2 Hz, 3H), 2.78 (s, 3H). | 654 |
| 34 | 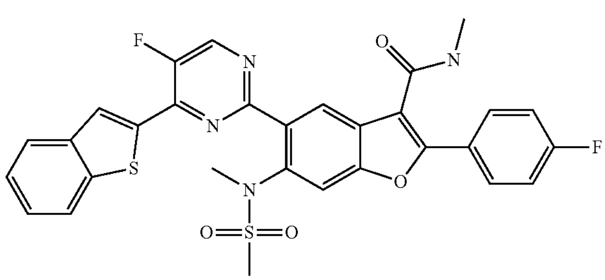 [SMILES: CNC(=O)c1c(-c2ccc(F)cc2)oc2cc(N(C)S(C)(=O)=O)c(-c3ncc(F)c(-c4cc5ccccc5s4)n3)cc12] | ¹H-NMR (CDCl₃, 400 MHz) δ 8.79 (s, 1H), 8.32 (d, J = 3.6 Hz, 2H), 8.04 (dd, J₁ = 8.8 Hz, J₂ = 5.2 Hz, 2H), 7.91~7.95 (m, 2H), 7.73 (s, 1H), 7.43~7.50 (m, 2H), 7.23 (t, J = 8.8 Hz, 2H), 6.13~6.19 (br s, 1H), 3.56 (s, 3H), 3.06 (d, J = 4.4 Hz, 3H), 2.82 (s, 3H). | 605 |
| 35 | 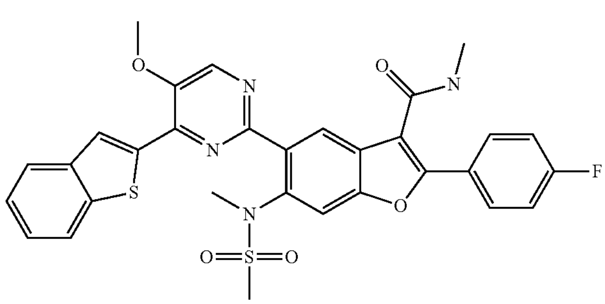 [SMILES: CNC(=O)c1c(-c2ccc(F)cc2)oc2cc(N(C)S(C)(=O)=O)c(-c3ncc(OC)c(-c4cc5ccccc5s4)n3)cc12] | ¹H-NMR (CDCl₃, 400 MHz) δ 8.53 (s, 1H), 8.38 (s, 1H), 8.21 (s, 1H), 7.98 (dd, J₁ = 8.8 Hz, J₂ = 5.6 Hz, 2H), 7.79~7.82 (m, 2H), 7.66 (s, 1H), 7.32 (dd, J₁ = 6.4 Hz, J₂ = 3.2 Hz, 2H), 7.13 (t, J = 8.4 Hz, 2H), 5.96~6.02 (br s, 1H), 4.15 (s, 3H), 3.43 (s, 3H), 2.97 (d, J = 5.2 Hz, 3H), 2.69 (s, 3H). | 617 |

| No. | Structure | NMR | MS (M + H)+ |
|---|---|---|---|
| 36 | 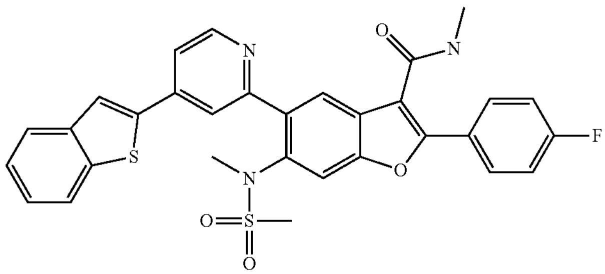 [SMILES: CNC(=O)c1c(-c2ccc(F)cc2)oc2cc(N(C)S(C)(=O)=O)c(-c3cc(-c4cc5ccccc5s4)ccn3)cc12] | ¹H-NMR (CDCl₃, 400 MHz) δ 8.79 (d, J = 5.6 Hz, 1H), 8.14 (s, 1H), 8.09 (s, 1H), 8.02~8.06 (m, 2H), 7.93 (s, 1H), 7.85~7.88 (m, 2H), 7.71 (d, J = 4.4 Hz, 1H), 7.66 (s, 1H), 7.39~7.42 (m, 2H), 7.16~7.21 (m, 2H), 6.44 (d, J = 2.8 Hz, 1H), 3.24 (s, 3H), 3.01 (d, J = 4.8 Hz, 3H), 2.91 (s, 3H). | 586 |
| 37 | 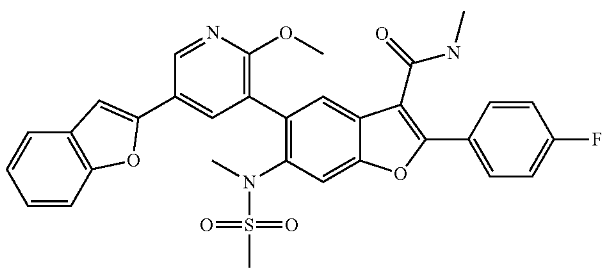 [SMILES: CNC(=O)c1c(-c2ccc(F)cc2)oc2cc(N(C)S(C)(=O)=O)c(-c3cc(-c4cc5ccccc5o4)cnc3OC)cc12] | ¹H-NMR (CDCl₃, 400 MHz) δ 8.72 (d, J = 2.4 Hz, 1H), 8.06 (d, J = 2.8 Hz, 1H), 7.93~7.97 (m, 2H), 7.82 (s, 1H), 7.64 (s, 1H), 7.57 (d, J = 8.0 Hz, 1H), 7.51 (d, J = 8.0 Hz, 1H), 7.28~7.30 (m, 1H), 7.19~7.23 (m, 3H), 6.99 (s, 1H), 5.83~5.87 (br s, 1H), 3.97 (s, 3H), 3.23 (s, 3H), 2.98 (d, J = 4.0 Hz, 3H), 2.63 (s, 3H). | 600 |
| 38 | 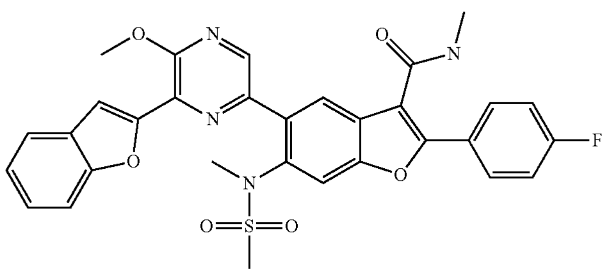 [SMILES: CNC(=O)c1c(-c2ccc(F)cc2)oc2cc(N(C)S(C)(=O)=O)c(-c3cnc(OC)c(-c4cc5ccccc5o4)n3)cc12] | ¹H-NMR (CDCl₃, 400 MHz) δ 8.72 (s, 1H), 7.94~8.04 (m, 3H), 7.54~7.70 (m, 3H), 7.18~7.35 (m, 5H), 5.95~6.01 (br s, 1H), 4.00 (s, 3H), 3.32 (s, 3H), 2.98 (d, J = 4.8 Hz, 3H), 2.73 (s, 3H). | 601 |
| 39 | 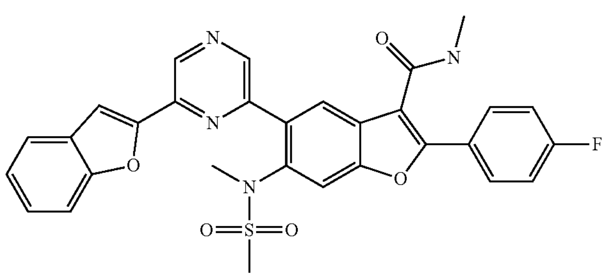 [SMILES: CNC(=O)c1c(-c2ccc(F)cc2)oc2cc(N(C)S(C)(=O)=O)c(-c3cncc(-c4cc5ccccc5o4)n3)cc12] | ¹H-NMR (CDCl₃, 400 MHz) δ 9.15 (s, 1H), 8.76 (s, 1H), 8.12 (s, 1H), 7.93~7.97 (m, 2H), 7.70 (s, 1H), 7.56 (d, J = 7.6 Hz, 1H), 7.55~7.60 (m, 2H), 7.36~7.40 (m, 1H), 7.26~7.30 (m, 1H), 7.19~7.23 (m, 2H), 5.90~5.97 (br s, 1H), 3.36 (s, 3H), 2.99 (d, J = 4.8 Hz, 3H), 2.76 (s, 3H). | 571 |
| 40 | 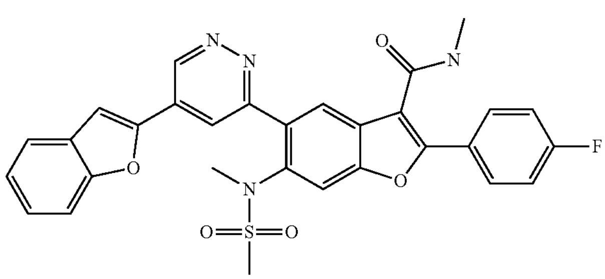 [SMILES: CNC(=O)c1c(-c2ccc(F)cc2)oc2cc(N(C)S(C)(=O)=O)c(-c3cc(-c4cc5ccccc5o4)cnn3)cc12] | ¹H-NMR (CDCl₃, 400 MHz) δ 9.61 (s, 1H), 8.24 (s, 1H), 8.15 (s, 1H), 7.95~8.03 (m, 2H), 7.67~7.70 (m, 2H), 7.58 (d, J = 8.4 Hz, 1H), 7.49 (s, 1H), 7.39~7.43 (m, 1H), 7.28~7.32 (m, 1H), 7.20 (t, J = 8.8 Hz, 2H), 3.21 (s, 3H), 3.01 (d, J = 4.8 Hz, 3H) 2.93 (s, 3H). | 571 |

| No. | Structure | NMR | MS (M + H)+ |
|---|---|---|---|
| 41 | 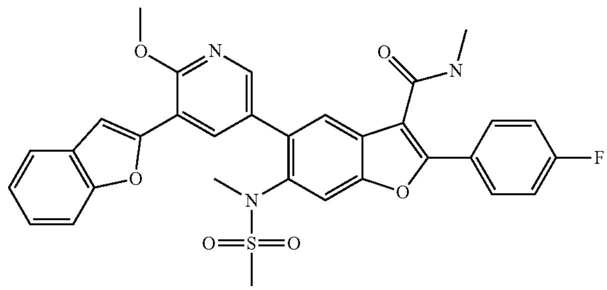 [SMILES: CNC(=O)c1c(-c2ccc(F)cc2)oc2cc(N(C)S(C)(=O)=O)c(-c3cnc(OC)c(-c4cc5ccccc5o4)c3)cc12] | ¹H-NMR (CDCl₃, 400 MHz) δ 8.33 (d, J = 2.0 Hz, 1H), 8.15 (d, J = 4.0 Hz, 1H), 7.87~7.90 (m, 2H), 7.80 (s, 1H), 7.61 (s, 1H), 7.55~7.57 (m, 1H), 7.41 (d, J = 8.0 Hz, 2H), 7.21~7.24 (m, 1H), 7.12~7.17 (m, 3H), 5.80 (d, J = 4.0 Hz, 1H), 4.14 (s, 3H), 3.14 (s, 3H), 2.92 (d, J = 4.0 Hz, 3H), 2.71 (s, 3H). | 600 |
| 42 | 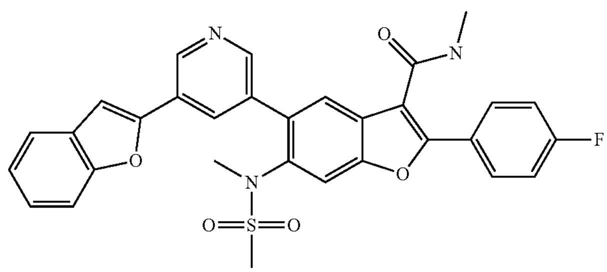 [SMILES: CNC(=O)c1c(-c2ccc(F)cc2)oc2cc(N(C)S(C)(=O)=O)c(-c3cncc(-c4cc5ccccc5o4)c3)cc12] | ¹H-NMR (CDCl₃, 400 MHz) δ 8.62 (s, 1H), 7.90 (d, J = 4.0 Hz, 1H), 7.85~7.86 (m, 3H), 7.80 (s, 1H), 7.58~7.60 (m, 1H), 7.57 (s, 1H), 7.52 (d, J = 8.0 Hz, 1H), 7.40 (s, 1H), 7.30 (t, J = 4.0 Hz, 1H), 7.28 (d, J = 8.0 Hz, 1H), 7.12~7.23 (m, 2H), 5.83 (d, J = 4.0 Hz, 1H), 3.13 (s, 3H), 2.92 (d, J = 4.0 Hz, 3H), 2.69 (s, 3H). | 570 |
| 43 | 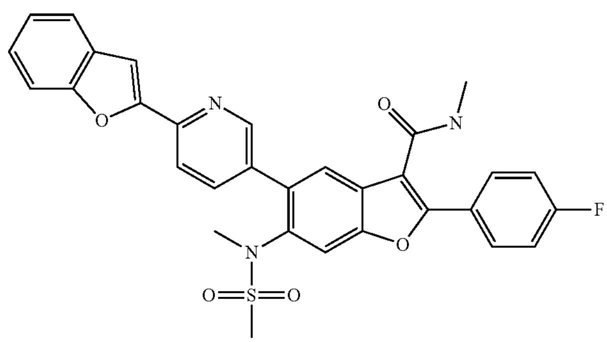 [SMILES: CNC(=O)c1c(-c2ccc(F)cc2)oc2cc(N(C)S(C)(=O)=O)c(-c3ccc(-c4cc5ccccc5o4)nc3)cc12] | ¹H-NMR (CDCl₃, 400 MHz) δ 9.04 (s, 1H), 8.55 (d, J = 1.6 Hz, 1H), 8.23 (t, J = 2.0 Hz, 1H), 7.85~7.89 (m, 3H), 7.59 (s, 1H), 7.55 (d, J = 4.0 Hz, 1H), 7.47 (d, J = 4.4 Hz, 1H), 7.21~7.28 (m, 1H), 7.18~7.19 (m, 1H), 7.12~7.17 (m, 3H), 5.85 (d, J = 4.0 Hz, 1H), 3.11 (s, 3H), 2.92 (s, 3H), 2.72 (s, 3H). | 570 |
| 44 | 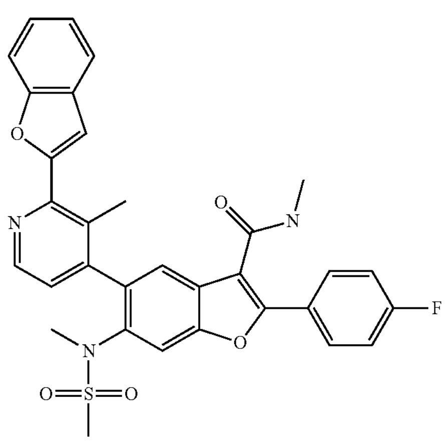 [SMILES: CNC(=O)c1c(-c2ccc(F)cc2)oc2cc(N(C)S(C)(=O)=O)c(-c3ccnc(-c4cc5ccccc5o4)c3C)cc12] | ¹H-NMR (CDCl₃, 400 MHz) δ 8.58 (d, J = 4.4 Hz, 1H), 7.85~7.88 (m, 2H), 7.69 (s, 1H), 7.54~7.69 (m, 3H), 7.13~7.31 (m, 6H), 5.80 (s, 1H), 3.10 (s, 3H), 2.91 (d, J = 5.2 Hz, 3H), 2.57 (s, 3H), 2.39 (s, 3H). | 584 |

-continued

| No. | Structure | NMR | MS (M + H)+ |
|---|---|---|---|
| 45 | 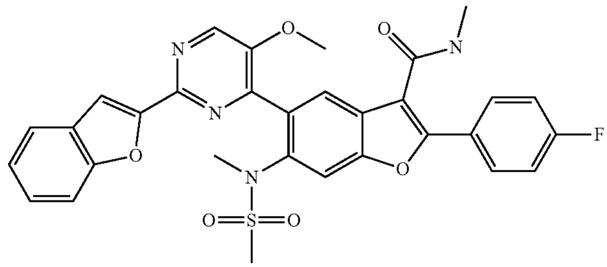 [SMILES: CNC(=O)c1c(-c2ccc(F)cc2)oc2cc(N(C)S(C)(=O)=O)c(-c3nc(-c4cc5ccccc5o4)ncc3OC)cc12] | $^1$H-NMR (CDCl$_3$, 400 MHz) δ 8.68 (s, 1H), 8.21 (s, 1H), 7.99~8.03 (m, 2H), 7.86 (s, 1H), 7.69 (s, 1H), 7.66 (d, J = 8.0 Hz, 1H), 7.53 (d, J = 8.0 Hz, 1H), 7.37 (t, J = 7.2 Hz, 1H), 7.25 (t, J = 7.2 Hz, 1H), 7.14 (t, J = 8.4 Hz, 2H), 6.26 (d, J = 4.4 Hz, 1H), 4.18 (s, 3H), 3.44 (s, 3H), 2.98 (d, J = 4.8 Hz, 3H), 2.81 (s, 3H). | 601 |
| 46 | 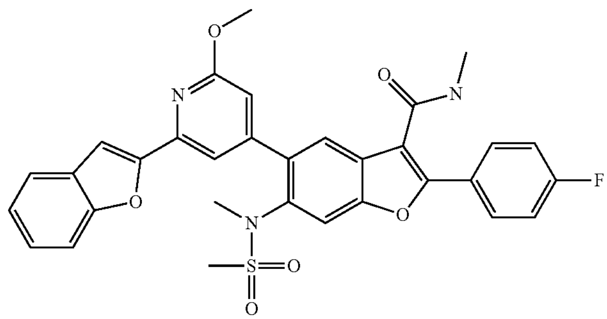 [SMILES: CNC(=O)c1c(-c2ccc(F)cc2)oc2cc(N(C)S(C)(=O)=O)c(-c3cc(OC)nc(-c4cc5ccccc5o4)c3)cc12] | $^1$H-NMR (CDCl$_3$, 400 MHz) δ 7.92~7.95 (m, 2H), 7.86 (s, 1H), 7.62~7.66 (m, 2H), 7.60 (s, 1H), 7.49 (t, J = 8.8 Hz, 2H), 7.31 (t, J = 10.8 Hz, 1H), 7.25 (d, J = 6.8 Hz, 1H), 7.20 (t, J = 8.4 Hz, 2H), 6.82 (s, 1H), 5.88 (d, J = 3.6 Hz, 1H), 4.07 (s, 3H), 3.19 (s, 3H), 2.98 (d, J = 4.8 Hz, 3H), 2.81 (s, 3H). | 600 |
| 47 | 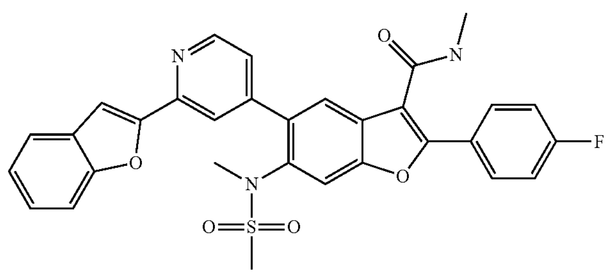 [SMILES: CNC(=O)c1c(-c2ccc(F)cc2)oc2cc(N(C)S(C)(=O)=O)c(-c3ccnc(-c4cc5ccccc5o4)c3)cc12] | $^1$H-NMR (CDCl$_3$, 400 MHz) δ 8.89 (d, J = 5.6 Hz, 1H), 8.19 (s, 1H), 7.96 (s, 1H), 7.83~7.86 (m, 3H), 7.67 (d, J = 7.6 Hz, 1H), 7.61 (s, 1H), 7.55 (d, J = 4.4 Hz, 1H), 7.49 (d, J = 8.4 Hz, 1H), 7.35 (t, J = 8.0 Hz, 1H), 7.25 (t, J = 7.6 Hz, 1H), 7.16 (d, J = 8.4 Hz, 2H), 5.88 (d, J = 4.0 Hz, 1H), 3.19 (s, 3H), 2.94 (d, J = 4.8 Hz, 3H), 2.84 (s, 3H). | 570 |
| 48 | 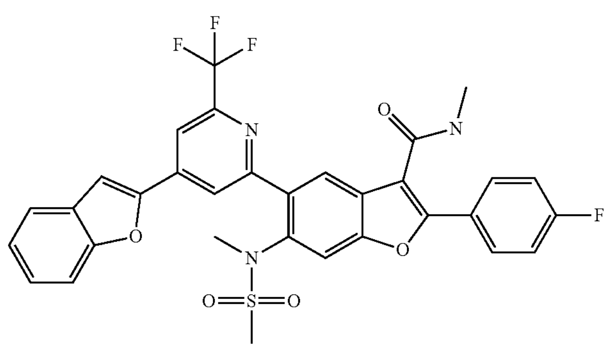 [SMILES: CNC(=O)c1c(-c2ccc(F)cc2)oc2cc(N(C)S(C)(=O)=O)c(-c3cc(-c4cc5ccccc5o4)cc(C(F)(F)F)n3)cc12] | $^1$H-NMR (CDCl$_3$, 400 MHz) δ 8.17 (s, 1H), 8.04 (d, J = 3.6 Hz, 2H), 7.88~7.91 (m, 2H), 7.60~7.64 (m, 2H), 7.52 (d, J = 8.4 Hz, 1H), 7.33~7.38 (m, 2H), 7.14~7.24 (m, 3H), 5.83~5.88 (br s, 1H), 3.24 (s, 3H), 2.93 (d, J = 4.8 Hz, 3H), 2.70 (s, 3H). | 638 |
| 49 | 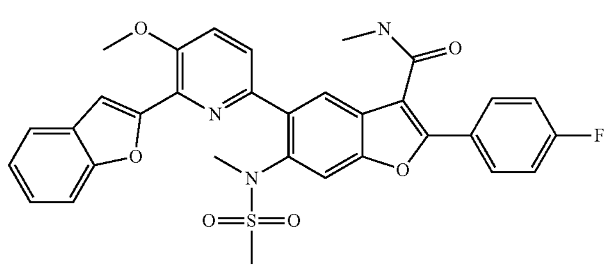 [SMILES: CNC(=O)c1c(-c2ccc(F)cc2)oc2cc(N(C)S(C)(=O)=O)c(-c3ccc(OC)c(-c4cc5ccccc5o4)n3)cc12] | $^1$H-NMR (CDCl$_3$, 400 MHz) δ 7.98~8.02 (m, 3H), 7.61~7.66 (m, 4H), 7.48~7.53 (m, 2H), 7.32 (t, J = 7.2 Hz, 1H), 7.15~7.30 (m, 3H), 6.21 (s, 1H), 4.11 (s, 3H), 3.31 (s, 3H), 2.98 (d, J = 4.8 Hz, 3H), 2.80 (s, 3H). | 600 |

| No. | Structure | NMR | MS (M + H)+ |
|---|---|---|---|
| 50 | 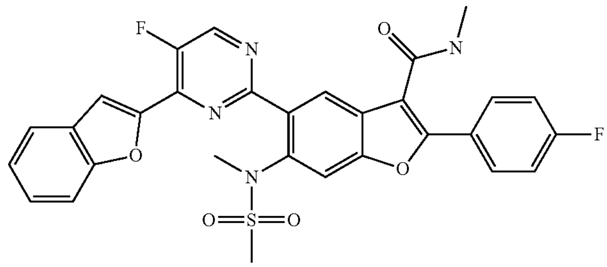 [SMILES: CNC(=O)c1c(-c2ccc(F)cc2)oc2cc(N(C)S(C)(=O)=O)c(-c3ncc(F)c(-c4cc5ccccc5o4)n3)cc12] | ¹H-NMR (CDCl₃, 400 MHz) δ 8.73 (d, J = 2.8 Hz, 1H), 8.28 (s, 1H), 7.93~7.97 (m, 2H), 7.66~7.71 (m, 3H), 7.56 (d, J = 8.4 Hz, 1H), 7.33~7.41 (m, 1H), 7.21~7.29 (m, 1H), 7.12~7.19 (m, 2H), 6.03~6.07 (br s, 1H), 3.04 (s, 3H), 2.97 (d, J = 5.2 Hz, 3H), 2.80 (s, 3H). | 589 |
| 51 | 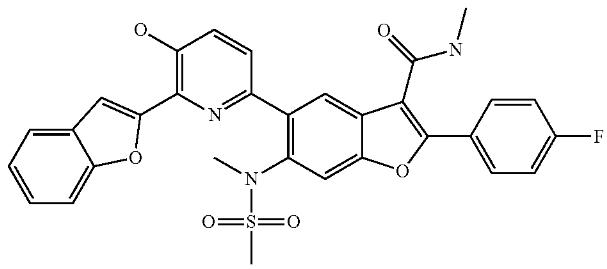 [SMILES: CNC(=O)c1c(-c2ccc(F)cc2)oc2cc(N(C)S(C)(=O)=O)c(-c3ccc(O)c(-c4cc5ccccc5o4)n3)cc12] | ¹H-NMR (CDCl₃, 400 MHz) δ 7.89~7.94 (m, 3H), 7.59 (d, J = 8.0 Hz, 2H), 7.51 (d, J = 2.8 Hz, 1H), 7.42~7.45 (m, 3H), 7.29~7.33 (m, 1H), 7.24~7.26 (m, 1H), 7.13~7.19 (m, 2H), 5.85~5.89 (br s, 1H), 3.26 (s, 3H), 2.94 (d, J = 4.0 Hz, 3H), 2.63 (s, 3H). | 586 |
| 52 | 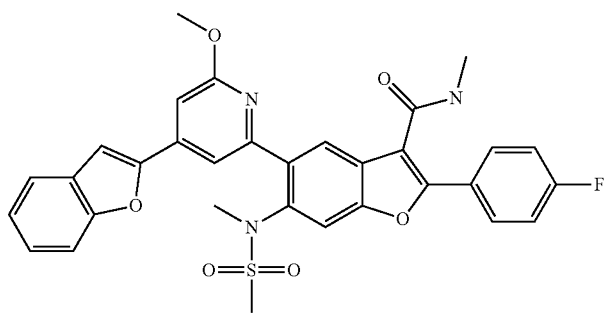 [SMILES: CNC(=O)c1c(-c2ccc(F)cc2)oc2cc(N(C)S(C)(=O)=O)c(-c3cc(-c4cc5ccccc5o4)cc(OC)n3)cc12] | ¹H-NMR (CDCl₃, 400 MHz) δ 7.98 (s, 1H), 7.88~7.91 (m, 2H), 7.59 (s, 1H), 7.56 (d, J = 4.0 Hz, 2H), 7.47 (d, J = 8.0 Hz, 1H), 7.27~7.30 (m, 1H), 7.16~7.21 (m, 2H), 7.11~7.18 (m, 3H), 5.87 (d, J = 4.0 Hz, 1H), 3.96 (s, 3H), 3.25 (s, 3H), 2.92 (d, J = 4.0 Hz, 3H), 2.67 (s, 3H). | 600 |
| 53 | 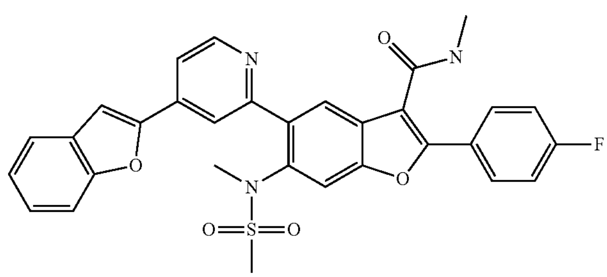 [SMILES: CNC(=O)c1c(-c2ccc(F)cc2)oc2cc(N(C)S(C)(=O)=O)c(-c3cc(-c4cc5ccccc5o4)ccn3)cc12] | ¹H-NMR (CDCl₃, 400 MHz) δ 8.70 (d, J = 4.0 Hz, 1H), 8.00 (d, J = 4.0 Hz, 1H), 7.97~7.99 (m, 2H), 7.96 (s, 1H), 7.84~7.86 (m, 1H), 7.61~7.63 (m, 2H), 7.50~7.52 (m, 1H), 7.43 (d, J = 2.0 Hz, 1H), 7.33~7.37 (m, 1H), 7.22~7.26 (m, 1H), 7.12~7.15 (m, 2H), 3.21 (s, 3H), 2.95 (s, 3H), 2.85 (s, 3H). | 570 |
| 54 | 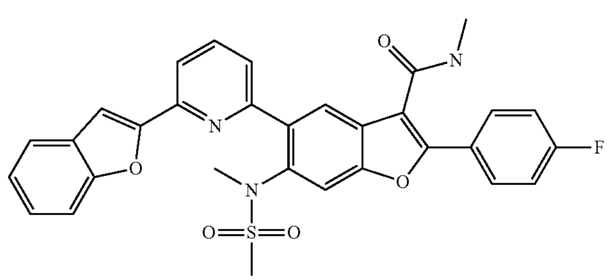 [SMILES: CNC(=O)c1c(-c2ccc(F)cc2)oc2cc(N(C)S(C)(=O)=O)c(-c3cccc(-c4cc5ccccc5o4)n3)cc12] | ¹H-NMR (CDCl₃, 400 MHz) δ 7.87~7.96 (m, 5H), 7.62 (s, 1H), 7.58 (d, J = 8.0 Hz, 1H), 7.52 (t, J = 6.4 Hz, 2H), 7.46 (s, 1H), 7.30 (t, J = 7.2 Hz, 1H), 7.23 (s, 1H), 7.15 (t, J = 8.8 Hz, 2H), 6.04 (d, J = 3.6 Hz, 1H), 3.28 (s, 3H), 2.94 (d, J = 4.8 Hz, 3H), 2.62 (s, 3H). | 570 |

| No. | Structure | NMR | MS (M + H)+ |
|---|---|---|---|
| 55 | 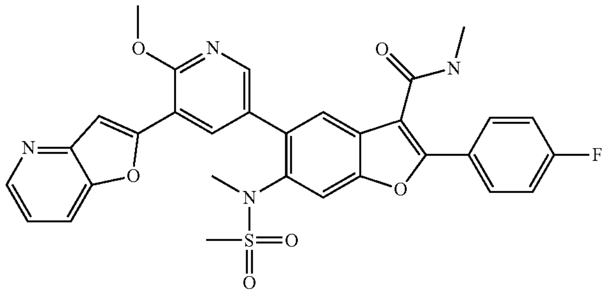 [SMILES: CNC(=O)c1c(-c2ccc(F)cc2)oc2cc(N(C)S(C)(=O)=O)c(-c3cnc(OC)c(-c4cc5ncccc5o4)c3)cc12] | ¹H-NMR (CDCl₃, 400 MHz) δ 8.48 (d, J = 4.8 Hz, 1H), 8.37 (d, J = 2.4 Hz, 1H), 8.21 (d, J = 2.0 Hz, 1H), 7.89~7.85 (m, 2H), 7.83 (s, 1H), 7.69 (d, J = 4.0 Hz, 1H), 7.59 (s, 2H), 7.17~7.18 (m, 3H), 5.89 (d, J = 4.4 Hz, 1H), 4.14 (s, 3H), 3.15 (s, 3H), 2.94 (d, J = 4.8 Hz, 3H), 2.74 (s, 3H). | 601 |
| 56 | 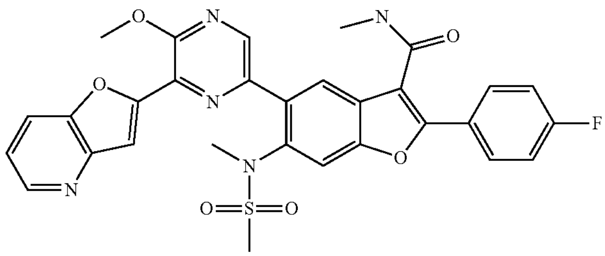 [SMILES: CNC(=O)c1c(-c2ccc(F)cc2)oc2cc(N(C)S(C)(=O)=O)c(-c3cnc(OC)c(-c4cc5ncccc5o4)n3)cc12] | ¹H-NMR (Methanol-d4, 400 MHz) δ 8.80 (s, 1H), 8.55 (d, J = 4.4 Hz, 1H), 8.14 (s, 1H), 8.06 (d, J = 8.0 Hz, 1H), 7.98~7.94 (m, 2H), 7.89 (s, 1H), 7.83 (s, 1H), 7.46~7.42 (m, 1H), 7.27~7.22 (m, 2H), 4.22 (s, 3H), 3.50 (s, 3H), 2.96 (s, 3H), 2.86 (s, 3H). | 602 |
| 57 | 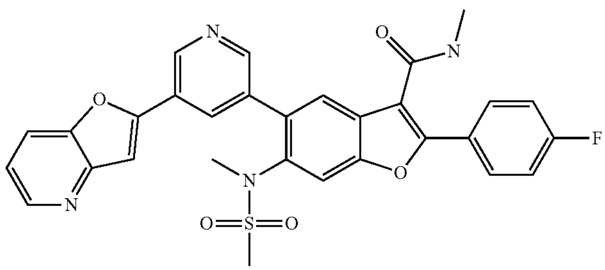 [SMILES: CNC(=O)c1c(-c2ccc(F)cc2)oc2cc(N(C)S(C)(=O)=O)c(-c3cncc(-c4cc5ncccc5o4)c3)cc12] | ¹H-NMR (CDCl₃, 400 MHz) δ 9.17 (s, 1H), 8.75 (s, 1H), 8.61 (d, J = 2.4 Hz, 1H), 8.50 (s, 1H), 8.11 (d, J = 8.0 Hz, 1H), 7.93 (s, 1H), 7.83~7.86 (m, 2H), 7.72 (s, 1H), 7.59 (s, 1H), 7.48~7.51 (m, 1H), 7.14~7.16 (m, 2H), 5.89 (d, J = 4.0 Hz, 1H), 3.19 (s, 3H), 2.93 (d, J = 4.8 Hz, 3H), 2.81 (s, 3H). | 571 |
| 58 | 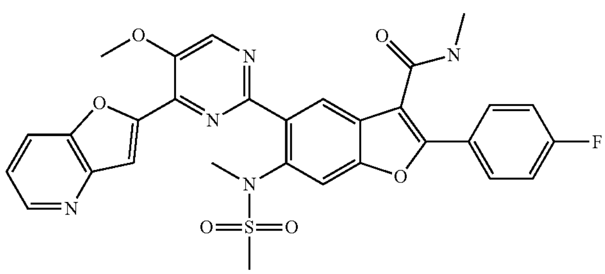 [SMILES: CNC(=O)c1c(-c2ccc(F)cc2)oc2cc(N(C)S(C)(=O)=O)c(-c3ncc(OC)c(-c4cc5ncccc5o4)n3)cc12] | ¹H-NMR (CDCl₃, 400 MHz) δ 8.55 (s, 1H), 8.40 (s, 1H), 7.99 (s, 1H), 7.92~7.96 (m, 2H), 7.83~7.86 (m, 2H), 7.63 (s, 1H), 7.29 (d, J = 3.2 Hz, 1H), 7.17~7.12 (m, 2H), 6.83 (s, 1H), 4.20 (s, 3H), 3.30 (s, 3H), 2.93 (s, 3H), 2.83 (s, 3H). | 602 |

Compounds 171-181, depicted in the table below, were prepared using the method described in Example 2 and substituting the appropriate reactants and/or reagents.

| No. | Structure | NMR | MS (M + H)+ |
|---|---|---|---|
| 171 | 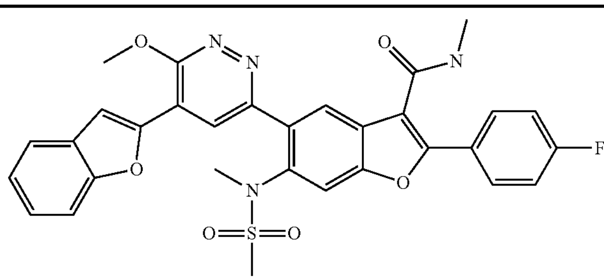 | ¹H-NMR (CDCl₃, 400 MHz) 8.24 (s, 1H), 8.07 (s, 1H), 7.95~7.99 (m, 2H), 7.67~7.71 (m, 3H), 7.53 (t, J = 4.0 Hz, 1H), 7.36~7.41 (m, 1H), 2.80 (t, J = 7.2 Hz, 1H), 7.19 (t, J = 8.4 Hz, 2H), 6.10 (d, J = 4.4 Hz, 1H), 4.39 (s, 3H), 3.27 (s, 3H), 3.00 (d, J = 4.8 Hz, 3H), 2.87 (s, 3H). | 601 |

| No. | Structure | NMR | MS (M + H)+ |
|---|---|---|---|
| 172 | 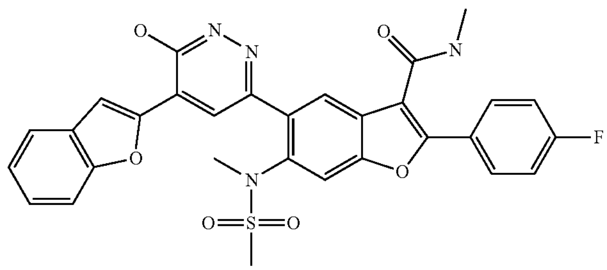 [SMILES: CNC(=O)c1c(-c2ccc(F)cc2)oc2cc(N(C)S(C)(=O)=O)c(-c3cc(-c4cc5ccccc5o4)c(O)nn3)cc12] | ¹H-NMR (CDCl₃, 400 MHz) δ 8.07 (s, 1H), 7.99 (s, 1H), 7.88~7.94 (m, 3H), 7.60~7.634 (m, 2H), 7.42 (d, J = 8.4 Hz, 1H), 7.31 (t, J = 7.20 Hz, 1H), 7.12~7.24 (m, 3H), 6.78~6.79 (m, 1H), 3.25 (s, 3H), 2.94 (d, J = 4.4 Hz, 3H), 2.89 (s, 3H). | 587 |
| 173 | 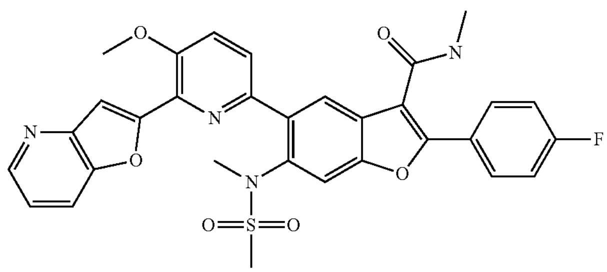 [SMILES: CNC(=O)c1c(-c2ccc(F)cc2)oc2cc(N(C)S(C)(=O)=O)c(-c3ccc(OC)c(-c4cc5ncccc5o4)n3)cc12] | ¹H-NMR (Methanol-d₄, 400 MHz) δ 8.57 (d, J = 4.4 Hz, 1H), 8.05 (s, 1H), 7.97~8.00 (m, 2H), 7.84 (t, J = 4 4 Hz, 2H), 7.70 (t, J = 8.0 Hz, 2H), 7.50 (d, J = 8.8 Hz, 1H), 7.18~7.22 (m, 2H), 6.01 (s, 1H), 4.11 (s, 3H), 3.31 (s, 3H), 2.99 (d, J = 8.8 Hz, 3H), 2.81 (s, 3H). | 601 |
| 174 | 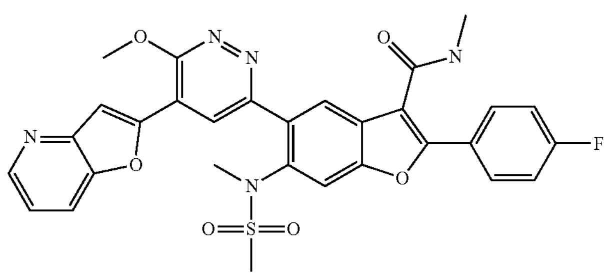 [SMILES: CNC(=O)c1c(-c2ccc(F)cc2)oc2cc(N(C)S(C)(=O)=O)c(-c3cc(-c4cc5ncccc5o4)c(OC)nn3)cc12] | ¹H-NMR (CDCl₃, 400 MHz) δ 8.55 (s, 1H), 8.25 (s, 1H), 8.04 (s, 1H), 7.91 (dd, J₁ = 8.8 Hz, J₂ = 5.2 Hz, 2H), 7.82 (s, 1H), 7.76 (d, J = 8.4 Hz, 1H), 7.64 (s, 1H), 7.23~7.27 (m, 1H), 7.14 (t, J = 8.4 Hz, 2H), 5.97 (brs, 1H), 4.35 (s, 3H), 3.22 (s, 3H), 2.93 (d, J = 4.8 Hz, 3H), 2.82 (s, 3H). | 605 |
| 175 | 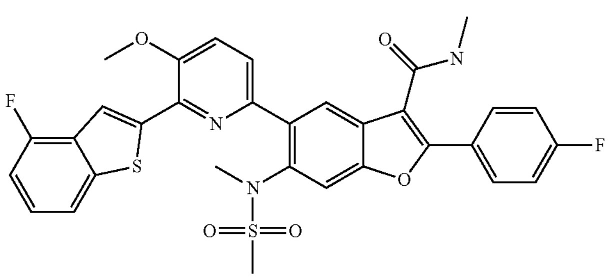 [SMILES: CNC(=O)c1c(-c2ccc(F)cc2)oc2cc(N(C)S(C)(=O)=O)c(-c3ccc(OC)c(-c4cc5c(F)cccc5s4)n3)cc12] | ¹H-NMR (CDCl₃, 400 MHz) δ 8.32 (s, 1H), 7.96~7.99 (m, 3H), 7.62 (s, 1H), 7.53~7.57 (m, 2H), 7.43 (d, J = 8.8 Hz, 1H), 7.23~7.28 (m, 1H), 7.16~7.21 (m, 2H), 6.97~7.01 (m, 1H), 6.19 (br s, 1H), 4.10 (s, 3H), 3.39 (s, 3H), 2.99 (d, J = 4.8 Hz, 3H), 2.63 (s, 3H). | 634 |
| 176 | 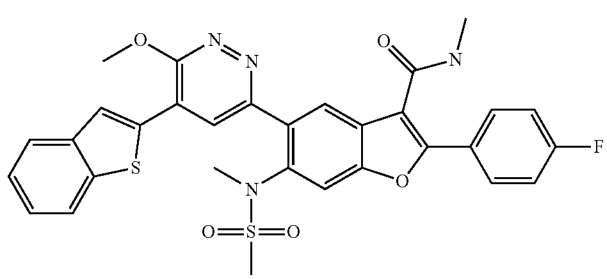 | ¹H-NMR (CDCl₃, 400 MHz) 8.21 (s, 1H), 8.09 (d, J = 3.6 Hz, 2H), 7.99 (dd, J = 8.8, 5.2 Hz, 2H), 7.85~7.88 (m, 2H), 7.65 (s, 1H), 7.39 (dd, J = 6.0, 3.2 Hz, 2H), 7.18 (t, J = 8.4 Hz, 2H), 6.13 (d, J = 4.4 Hz, 1H), 4.37 (s, 3H), 3.22 (s, 3H), 3.01 (d, J = 4.8 Hz, 3H), 2.96 (s, 3H). | 617 |

| No. | Structure | NMR | MS (M + H)+ |
|---|---|---|---|
| 177 | 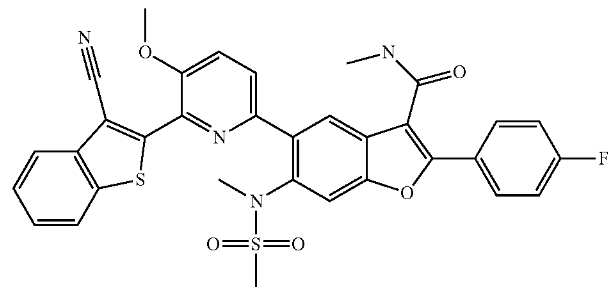 [SMILES: CNC(=O)c1c(-c2ccc(F)cc2)oc2cc(N(C)S(C)(=O)=O)c(-c3ccc(OC)c(-c4sc5ccccc5c4C#N)n3)cc12] | ¹H-NMR (DMSO-d₆, 400 MHz) δ 8.41 (s, 1H), 8.17 (d, J = 8.4 Hz, 1H), 8.15 (s, 1H), 8.06 (s, 1H), 8.00~8.03 (m, 2H), 7.95 (d, J = 7.6 Hz, 1H), 7.84~7.89 (m, 2H), 7.54~7.62 (m, 2H), 7.38~7.42 (m, 2H), 4.08 (s, 3H), 3.28 (s, 3H), 2.99 (s, 3H), 2.82 (d, J = 4.4 Hz, 3H). | 641 |
| 178 | 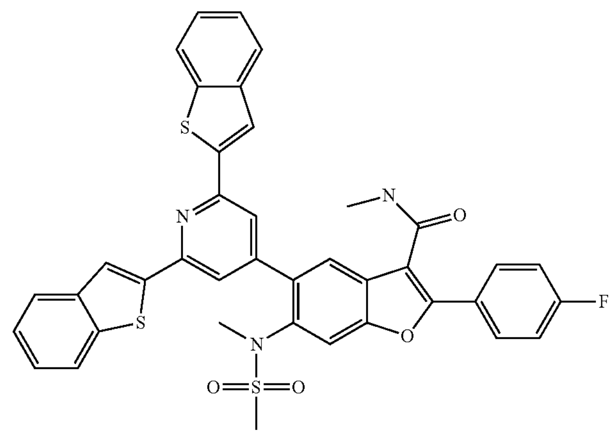 [SMILES: CNC(=O)c1c(-c2ccc(F)cc2)oc2cc(N(C)S(C)(=O)=O)c(-c3cc(-c4cc5ccccc5s4)nc(-c4cc5ccccc5s4)c3)cc12] | ¹H-NMR (CDCl₃, 400 MHz) δ 7.92 (s, 3H), 7.84~7.89 (m, 4H), 7.80~7.83 (m, 2H), 7.76~7.79 (m, 2H), 7.61 (s, 1H), 7.29~7.33 (m, 4H), 7.19 (t, J = 8.8 Hz, 2H), 5.82 (brs, 1H), 3.08 (s, 3H), 2.94 (d, J = 5.2 Hz, 3H), 2.86 (s, 3H). | 718 |
| 179 | 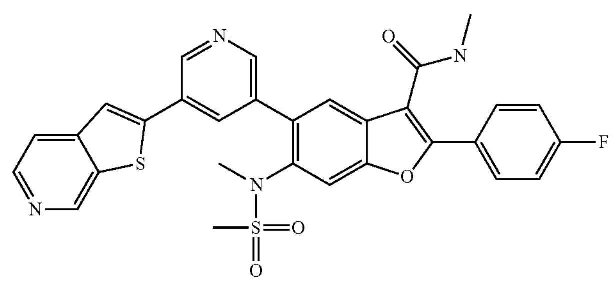 [SMILES: CNC(=O)c1c(-c2ccc(F)cc2)oc2cc(N(C)S(C)(=O)=O)c(-c3cncc(-c4cc5ccncc5s4)c3)cc12] | ¹H-NMR (CDCl₃, 400 MHz) δ 9.50 (s, 1H), 9.07 (d, J = 2.0 Hz, 1H), 8.09 (d, J = 2.0 Hz, 1H), 8.61 (t, J = 6.4 Hz, 1H), 8.51 (s, 1H), 8.09 (d, J = 6.8 Hz, 1H), 7.98~8.02 (m, 2H), 7.88~7.91 (m, 2H), 7.61 (s, 1H), 7.20~7.23 (m, 2H), 5.85 (brs, 1H), 3.14 (s, 3H), 3.00 (s, 3H), 2.97 (d, J = 4.8 Hz, 3H). | 587 |
| 180 | 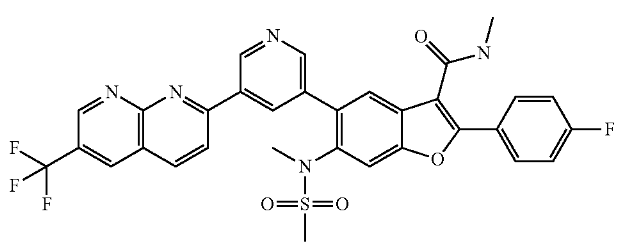 [SMILES: CNC(=O)c1c(-c2ccc(F)cc2)oc2cc(N(C)S(C)(=O)=O)c(-c3cncc(-c4ccc5cc(C(F)(F)F)cnc5n4)c3)cc12] | ¹H-NMR (CDCl₃, 400 MHz) δ 9.55 (s, 1H), 9.29 (s, 1H), 8.76~8.97 (m, 2H), 8.51 (s, 1H), 8.44 (s, 1H), 8.21~8.28 (m, 1H), 7.80~8.05 (m, 3H), 7.59 (s, 1H), 7.12~7.16 (m, 2H), 6.09 (brs, 1H), 3.15 (s, 3H), 2.98 (s, 3H), 2.86 (s, 3H). | 650 |
| 181 | 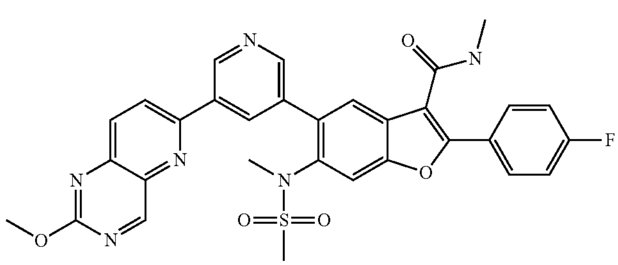 [SMILES: CNC(=O)c1c(-c2ccc(F)cc2)oc2cc(N(C)S(C)(=O)=O)c(-c3cncc(-c4ccc5nc(OC)ncc5n4)c3)cc12] | ¹H-NMR (CDCl₃, 400 MHz) δ 9.41 (s, 1H), 9.31 (d, J = 2.0 Hz, 1H), 8.69 (d, J = 2.0 Hz, 1H), 8.59 (t, J = 2.0 Hz, 1H), 8.24 (d, J = 8.8 Hz, 1H), 8.17 (d, J = 8.8 Hz, 1H), 7.89 (s, 1H), 7.84~7.88 (m, 2H), 7.59 (s, 1H), 7.15 (t, J = 8.4 Hz, 2H), 5.92 (brs, 1H), 4.11 (s, 3H), 3.10 (s, 3H), 2.92 (d, J = 4.8 Hz, 3H), 2.80 (s, 3H). | 613 |

Example 3

Preparation of Compound 59

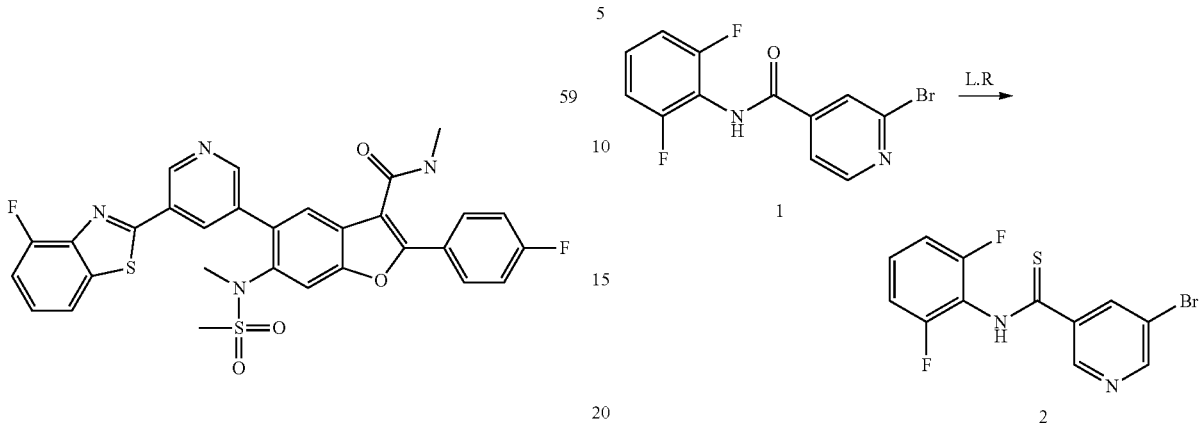

Step 1—Synthesis of 2-bromo-N-(2,6-difluorophenyl)isonicotinamide

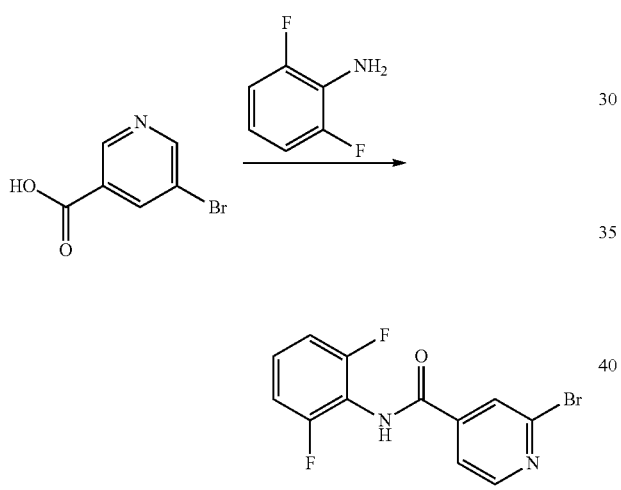

5-bromonicotinic acid (2.0 g, 10 mmol) was dissolved in DCM (5 mL), then SOCl₂ (1 mL) was added dropwise to this mixture. The reaction mixture was heated to reflux and allowed to stir at this temperature for 2 hours. The reaction mixture was concentrated in vacuo, then DCM (2 mL) was added and the resulting solution was concentrated in vacuo again. The resulting residue was diluted with DCM (30 mL) and the resulting solution was added to a solution of 2,6-difluoro aniline (1.05 g, 9.48 mmol) and TEA (1.05 g, 10.34 mmol) in DCM (20 mL) at 0 dropwise. The mixture was allowed to stir at room temperature for 2 hours, and then diluted with DCM. The diluted mixture was washed with water and brine, dried over Na₂SO₄, filtered and concentrated in vacuo. The resulting residue was purified using column chromatography (eluted with PE:EtOAc=10:1) to provide 2-bromo-N-2,6-difluorophenyl)isonicotinamide (1.4 g, yield: 64.0%) as a white solid. $^1$H-NMR (CDCl₃, 400 MHz) δ 9.07 (s, 1H), 8.89 (s, 1H), 8.80~8.84 (m, 1H), 8.40~8.42 (m, 1H), 7.62~7.64 (m, 2H), 7.02~7.06 (m, 1H). MS (M+H)$^+$: 313/315.

Step B—Synthesis of 5-bromo-N-(2,6-difluorophenyl)pyridine-3-carbothioamide

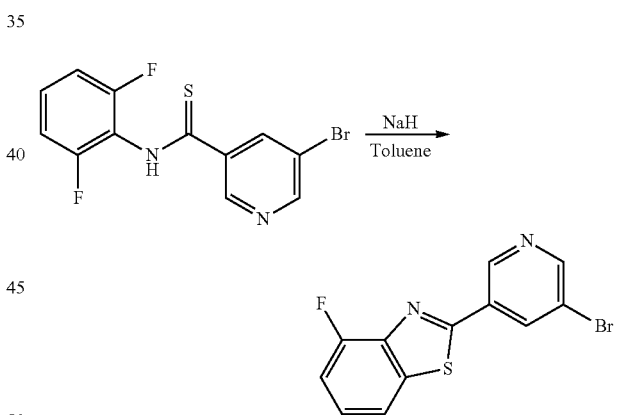

A mixture of 2-bromo-N-(2,6-difluorophenyl)isonicotinamide (300 mg, 0.96 mmol) and L.R (387 mg, 0.96 mmol) in anhydrous toluene (10 mL) was heated to reflux with stirring for about 15 hours. After the reaction mixture was concentrated in vacuo, the resulting residue was purified using column chromatography (eluted with PE:EtOAc=10:1) to provide 5-bromo-N-(2,6-difluorophenyl)pyridine-3-carbothioamide (200 mg, yield: 63.3%) as yellow solid, which was used in the next step without purification.

Step C—Synthesis of 2-(5-bromopyridin-3-yl)-4-fluorobenzo[d]thiazole

To a solution of sodium hydride (140 mg, 0.17 mmol) in anhydrous toluene (2 mL) at 0° C., 5-bromo-N-(2,6-difluorophenyl)pyridine-3-carbothioamide (100 mg, 0.15 mmol) in one portion was added. The solution was warmed to room temperature over 1 hour and then heated to a gentle reflux. After 30 minutes, DMF (0.2 mL) was carefully added and the mixture was allowed to stir for an addition 2 hours. The solution was quenched with ice-water. The solution was extracted with EtOAc, the organic phase was dried (Na₂SO₄) and concentrated and the resulting residue was purified using prep-TLC (eluted with PE:EtOAc=3:1) to provide 2-(5-bromopyridin-3-yl)-4-fluorobenzo[d]thiazole (30 mg, yield: 31.3%). $^1$H-NMR (CDCl₃, 400 MHz) δ 9.09 (s, 1H), 8.72 (s, 1H), 8.56 (s, 1H), 7.64~7.66 (m, 1H), 7.32~7.38 (m, 1H), 7.16~7.20 (m, 1H). MS (M+H)$^+$: 309/311.

Step D—Synthesis of 5-(5-(4-fluorobenzo[d]thi-azol-2-yl)pyridin-3-yl)-2-(4-fluorophenyl)-N-methyl-6-(N-methylmethylsulfonamido)benzofuran-3-carboxamide

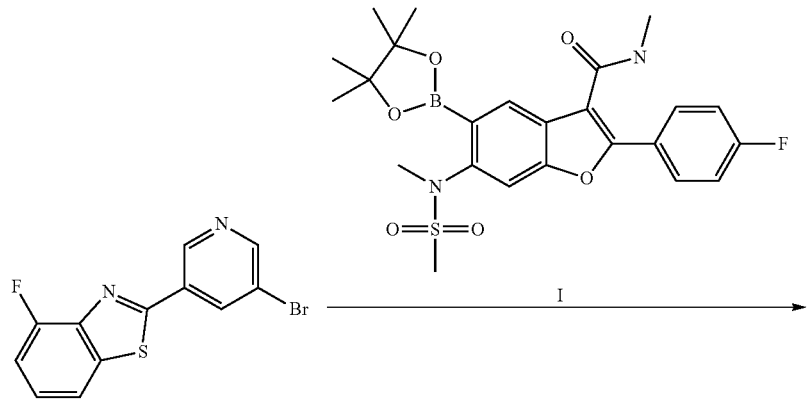

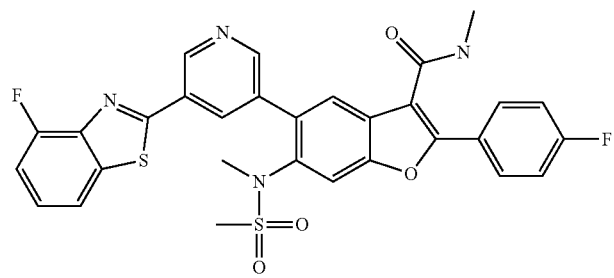

59

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 100 mg, 0.2 mmol) and 3-(benzo[b]thiophen-2-yl)-5-chloropyridine (62 mg, 0.2 mmol) in 1,4-Dioxane/$H_2O$ (5:1, 3 mL) were added Pd(dppf)$Cl_2$ (10 mg) and $K_3PO_4$ (120 mg, 0.4 mmol) under $N_2$ protection. The mixture was heated to 100° C. and allowed to stir at this temperature for about 15 hours and then cooled to room temperature and filtered. The filtrate was washed with $H_2O$, brine, dried over $Na_2SO_4$. After being concentrated in vacuo, the resulting residue was purified using prep-HPLC to provide 5-(5-(4-fluorobenzo[d]thiazol-2-yl)pyridin-3-yl)-2-(4-fluorophenyl)-N-methyl-6-(N-methylmethylsulfonamido)benzofuran-3-carboxamide (35 mg, yield: 29.1%). $^1$H-NMR (CDCl$_3$, 400 MHz) δ 9.33 (s, 1H), 8.83 (s, 1H), 8.71 (s, 1H), 7.91~7.95 (m, 3H), 7.72 (d, J=8.0 Hz, 1H), 7.53 (s, 1H), 7.39~7.44 (m, 1H), 7.19~7.23 (m, 3H), 5.96 (d, J=4.8 Hz, 1H), 3.22 (s, 3H), 3.01 (d, J=4.8 Hz, 3H), 2.89 (s, 3H). MS (M+H)$^+$: 605.

Compounds 60-67, depicted in the table below, were prepared using the method described in Example 3 and substituting the appropriate reactants and/or reagents.

| No. | Structure | NMR | MS (M + H)$^+$ |
|---|---|---|---|
| 60 | 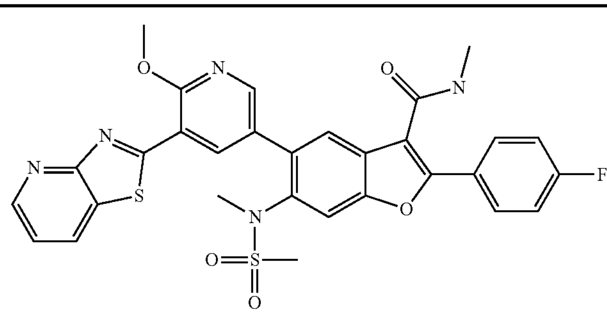 | $^1$H-NMR (CDCl$_3$, 400 MHz) δ 8.93 (d, J = 1.6 Hz, 1H), 8.65 (d, J = 5.6 Hz, 1H), 8.35 (d, J = 2.0 Hz, 1H), 8.22 (d, J = 8.0 Hz, 1H), 7.84~7.88 (m, 2H), 7.76 (s, 1H), 7.56 (s, 1H), 7.22~7.26 (m, 1H), 7.06~7.10 (m, 2H), 5.80 (d, J = 4.4 Hz, 1H), 4.17 (s, 3H), 3.15 (s, 3H), 2.90 (d, J = 4.8 Hz, 3H), 2.72 (s, 3H). | 618 |

| No. | Structure | NMR | MS (M + H)+ |
|---|---|---|---|
| 61 | 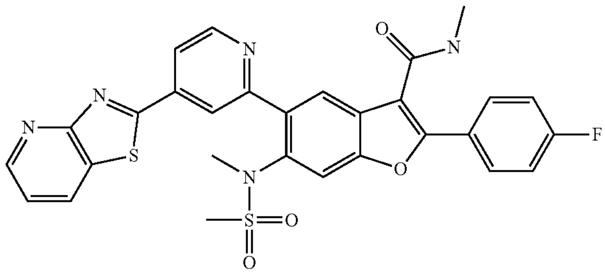 [SMILES: CNC(=O)c1c(-c2ccc(F)cc2)oc2cc(N(C)S(C)(=O)=O)c(-c3cc(-c4nc5ncccc5s4)ccn3)cc12] | ¹H-NMR (CDCl₃, 400 MHz) δ 8.75 (d, J = 3.2 Hz, 1H), 8.74 (s, 1H), 8.26~8.31 (m, 2H), 8.02~8.05 (m, 2H), 7.92~7.96 (m, 2H), 7.62 (s, 1H), 7.34~7.36 (m, 1H), 7.11~7.16 (m, 2H), 6.00 (d, J = 4.8 Hz, 1H), 3.18 (s, 3H), 2.96 (d, J = 4.8 Hz, 3H), 2.83 (s, 3H). | 588 |
| 62 | 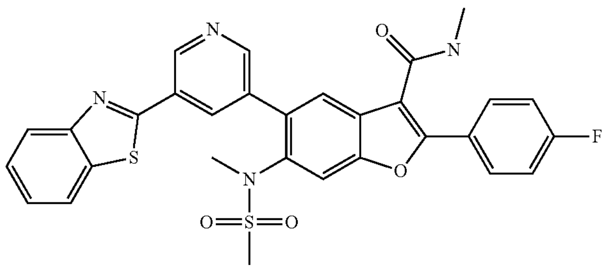 [SMILES: CNC(=O)c1c(-c2ccc(F)cc2)oc2cc(N(C)S(C)(=O)=O)c(-c3cncc(-c4nc5ccccc5s4)c3)cc12] | ¹H-NMR (CDCl₃, 400 MHz) δ 9.30 (s, 1H), 8.76 (d, J = 2.0 Hz, 1H), 8.59 (d, J = 2.0 Hz, 1H), 8.05 (d, J = 8.4 Hz, 1H), 7.86~7.91 (m, 4H), 7.62 (s, 1H), 7.48 (t, J = 6.8 Hz, 1H), 7.39 (t, J = 7.2 Hz, 1H), 7.15 (t, J = 8.4 Hz, 2H), 5.82 (d, J = 4.4 Hz, 1H), 3.16 (s, 3H), 2.95 (d, J = 4.8 Hz, 3H), 2.79 (s, 3H). | 587 |
| 63 | 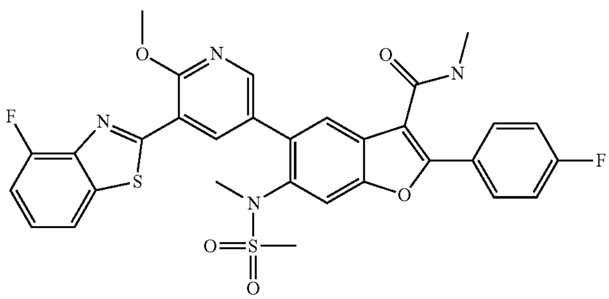 [SMILES: CNC(=O)c1c(-c2ccc(F)cc2)oc2cc(N(C)S(C)(=O)=O)c(-c3cnc(OC)c(-c4nc5c(F)cccc5s4)c3)cc12] | ¹H-NMR (CDCl₃, 400 MHz) δ 8.91 (d, J = 2.0 Hz, 1H), 8.36 (d, J = 2.0 Hz, 1H), 7.88~7.92 (m, 2H), 7.82 (s, 1H), 7.63~7.67 (m, 2H), 7.26~7.31 (m, 1H), 7.11~7.16 (m, 3H), 5.86 (s, 1H), 4.20 (s, 3H), 3.13 (s, 3H), 2.95 (d, J = 4.8 Hz, 3H), 2.87 (s, 3H). | 635 |
| 64 | 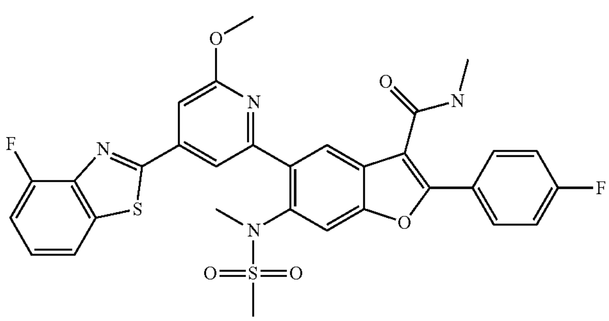 [SMILES: CNC(=O)c1c(-c2ccc(F)cc2)oc2cc(N(C)S(C)(=O)=O)c(-c3cc(-c4nc5c(F)cccc5s4)cc(OC)n3)cc12] | ¹H-NMR (CDCl₃, 400 MHz) δ 8.10 (s, 1H), 7.98 (dd, J = 8.8, 5.2 Hz, 2H), 7.92 (s 1H), 7.66~7.70 (m, 2H), 7.39~7.45 (m, 2H), 7.24~7.19 (m, 3H), 5.93~5.90 (m, 1H), 4.06 (s, 3H), 3.33 (s, 3H), 3.03 (d, J = 4.8 Hz, 3H), 2.83 (s, 3H). | 635 |
| 65 | 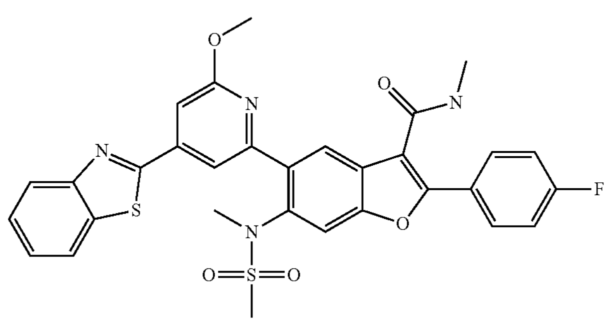 [SMILES: CNC(=O)c1c(-c2ccc(F)cc2)oc2cc(N(C)S(C)(=O)=O)c(-c3cc(-c4nc5ccccc5s4)cc(OC)n3)cc12] | ¹H-NMR (CDCl₃, 400 MHz) δ 8.11 (d, J = 8.0 Hz, 1H), 8.08 (s, 1H), 7.96~8.80 (m, 2H), 7.94 (s, 1H), 7.86 (s, 1H), 7.69 (s, 1H), 7.52~7.56 (m, 1H), 7.42~7.48 (m, 2H), 7.21 (t, J = 8.8 Hz, 2H), 5.91~5.96 (br s, 1H), 4.05 (s, 3H), 3.34 (s, 3H), 3.01 (d, J = 4.8 Hz, 3H), 2.78 (s, 3H). | 617 |

| No. | Structure | NMR | MS (M + H)+ |
|---|---|---|---|
| 66 | 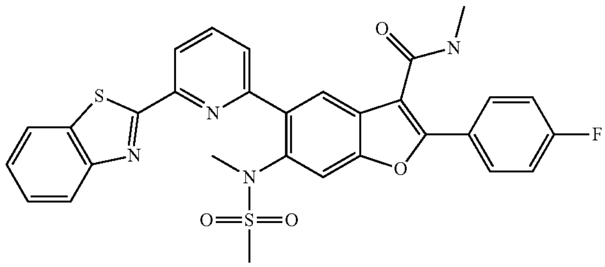 [SMILES: CNC(=O)c1c(-c2ccc(F)cc2)oc2cc(N(C)S(C)(=O)=O)c(-c3cccc(-c4nc5ccccc5s4)n3)cc12] | ¹H-NMR (CDCl₃, 400 MHz) δ 8.33 (d, J = 7.2 Hz, 1H), 8.05 (d, J = 8.0 Hz, 1H), 7.98 (s, 1H), 7.86~7.93 (m, 4H), 7.62~7.64 (m, 2H), 7.34~7.48 (m, 2H), 7.15 (t, J = 8.8 Hz, 2H), 5.87 (d, J = 4.0 Hz, 1H), 3.39 (s, 3H), 2.93 (d, J = 4.8 Hz, 3H), 2.53 (s, 3H). | 587 |
| 67 | 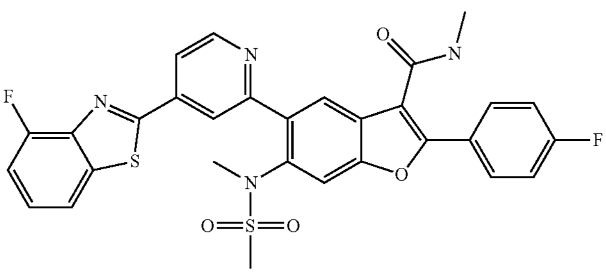 [SMILES: CNC(=O)c1c(-c2ccc(F)cc2)oc2cc(N(C)S(C)(=O)=O)c(-c3cc(-c4nc5c(F)cccc5s4)ccn3)cc12] | ¹H-NMR (CDCl₃, 400 MHz) δ 8.80 (d, J = 5.2 Hz, 1H), 8.26 (s, 1H), 8.04 (s, 1H), 7.93~7.98 (m, 3H), 7.65~7.66 (m, 2H), 7.36~7.40 (m, 1H), 7.15 (t, J = 8.4 Hz, 3H), 5.80~5.84 (br s, 1H), 3.16 (s, 3H), 2.95 (d, J = 4.8 Hz, 3H), 2.85 (s, 3H). | 605 |

Example 4

Preparation of Compound 68

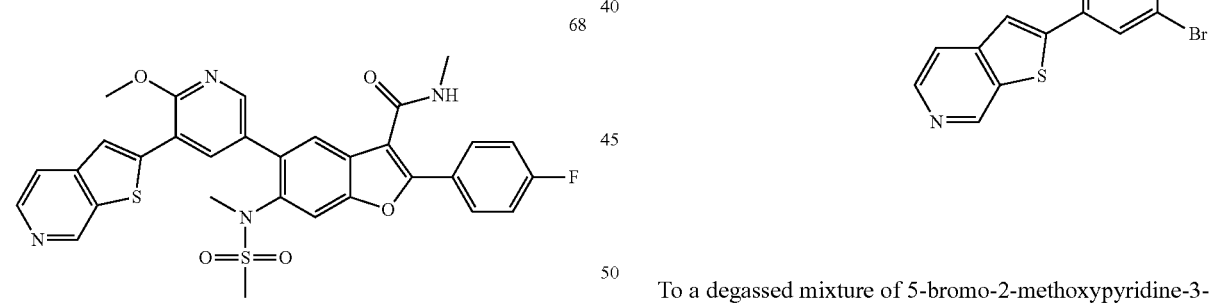

Step 1—Synthesis of 2-(5-bromo-2-methoxypyridin-3-yl)thieno[2,3-c]pyridine

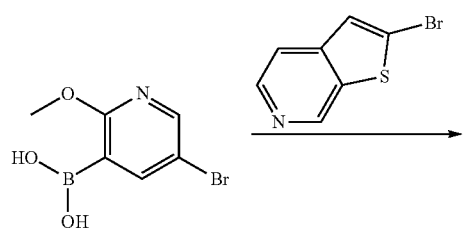

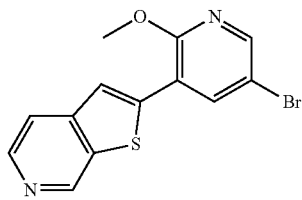

To a degassed mixture of 5-bromo-2-methoxypyridine-3-boronic acid (232 mg, 1 mmol) and 2-bromo-thieno[2,3-C]pyridine (214 mg, 1 mmol) in 1,4-dioxane (10 mL) was added Pd(dppf)Cl₂ (73 mg) and K₃PO₄ (800 mg, 3 mmol) under N₂. The mixture was heated to 90° C. and allowed to stir at this temperature for about 15 hours. After being cooled to room temperature and filtered, the filtrate was concentrated in vacuo, and the resulting residue was purified using flash chromatography on silica gel (eluted with PE:EtOAc=2:1) to provide 2-(5-bromo-2-methoxypyridin-3-yl)thieno[2,3-c]pyridine (120 mg, yield: 37.4%). ¹H-NMR (CDCl₃, 400 MHz) δ 9.17 (s, 1H), 8.55 (d, J=5.6 Hz, 1H), 8.41 (s, 1H), 7.72 (d, J=4.8 Hz, 1H), 7.66 (s, 1H), 6.97 (s, 1H), 3.97 (s, 3H). MS (M+H)⁺: 321/323.

Step B—Synthesis of 2-(4-fluorophenyl)-5-(6-methoxy-5-(thieno[2,3-c]pyridin-2-yl)pyridin-3-yl)-N-methyl-6-(N-methylmethylsulfonamido)benzofuran-3-carboxamide (Compound 68)

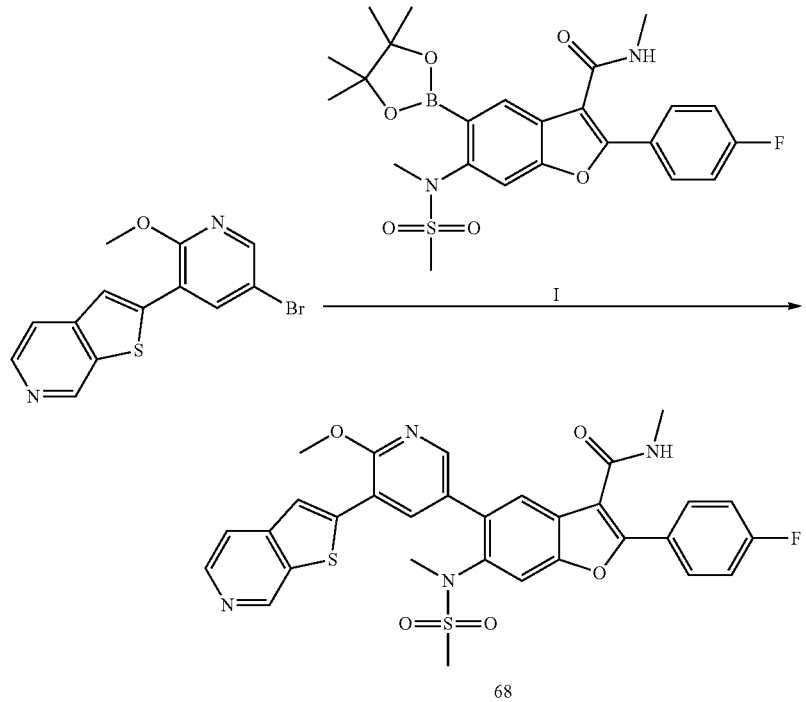

Compound 68 was made from the indicated starting material using the methods described in Example 1. ¹H-NMR (CDCl₃, 400 MHz) δ 9.39 (s, 1H), 8.48 (s, 1H), 8.31 (s, 1H), 7.88~7.92 (m, 4H), 7.53 (s, 1H), 7.49 (s, 1H), 7.21~7.26 (m, 2H), 7.10 (s, 1H), 5.85 (s, 1H), 4.07 (s, 3H), 2.95 (d, J=4.4 Hz, 3H), 2.70 (s, 6H). MS (M+H)⁺: 617.

Compounds 69-78, depicted in the table below, were prepared using the method described in Example 4 and substituting the appropriate reactants and/or reagents.

| No. | Structure | NMR | MS (M + H)⁺ |
|---|---|---|---|
| 69 | 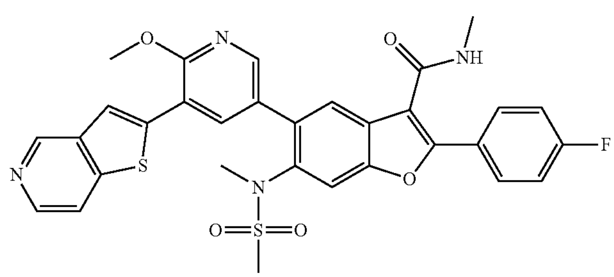 [SMILES: CNC(=O)c1c(-c2ccc(F)cc2)oc2cc(N(C)S(C)(=O)=O)c(-c3cnc(OC)c(-c4cc5cnccc5s4)c3)cc12] | ¹H-NMR (CDCl₃, 400 MHz) δ 9.24 (s, 1H), 8.44 (d, J = 6.0 Hz, 1H), 8.26 (s, 1H), 8.09 (d, J = 6.0 Hz, 1H), 7.88~7.91 (m, 3H), 7.50 (s, 1H), 7.40 (s, 1H), 7.20~7.24 (t, J = 8.0 Hz, 2H), 7.05 (s, 1H), 5.91 (s, 1H), 4.06 (s, 3H), 2.94 (d, J = 4.0 Hz, 3H), 2.76 (s, 3H), 2.70 (s, 3H). | 617 |
| 70 | 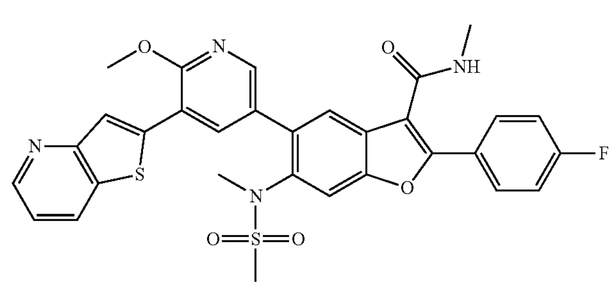 [SMILES: CNC(=O)c1c(-c2ccc(F)cc2)oc2cc(N(C)S(C)(=O)=O)c(-c3cnc(OC)c(-c4cc5ncccc5s4)c3)cc12] | ¹H-NMR (CDCl₃, 400 MHz) δ 8.58 (d, J = 5.2 Hz, 1H), 8.52 (d, J = 8.0 Hz, 1H), 8.26 (s, 1H), 7.98~8.02 (m, 2H), 7.88 (s, 1H), 7.69 (s, 1H), 7.52~7.55 (m, 1H), 7.41 (s, 1H), 7.16~7.21 (m, 2H), 7.06 (s, 1H), 4.07 (s, 3H), 3.01 (d, J = 4.8 Hz, 3H), 2.69 (s, 6H). | 617 |

| No. | Structure | NMR | MS (M + H)+ |
|---|---|---|---|
| 71 | 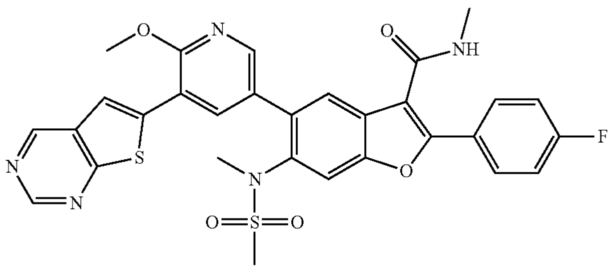 [SMILES: CNC(=O)c1c(-c2ccc(F)cc2)oc2cc(N(C)S(C)(=O)=O)c(-c3cnc(OC)c(-c4cc5cncnc5s4)c3)cc12] | ¹H-NMR (DMSO-d6, 400 MHz) δ 8.48 (d, J = 4.8 Hz, 1H), 7.95~7.99 (m, 2H), 7.93 (s, 1H), 7.70~7.73 (m, 1H), 7.50~7.56 (m, 2H), 7.35~7.47 (m, 4H), 7.28 (d, J = 6.8 Hz, 1H), 3.09 (s, 3H), 2.79 (d, J = 4.8 Hz, 3H), 2.71 (s, 3H), 1.91 (s, 3H). | 618 |
| 72 | 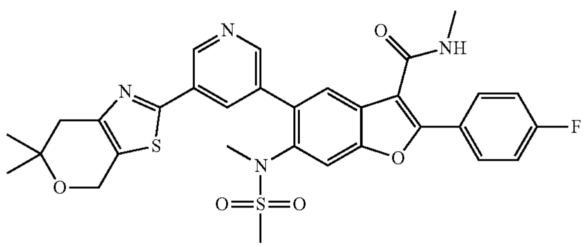 [SMILES: CNC(=O)c1c(-c2ccc(F)cc2)oc2cc(N(C)S(C)(=O)=O)c(-c3cncc(-c4nc5c(s4)COC(C)(C)C5)c3)cc12] | ¹H-NMR (CDCl₃, 400 MHz) δ 9.21 (s, 1H), 8.79 (s, 1H), 8.60 (s, 1H), 7.97 (s, 1H), 7.92~7.96 (m, 2H), 7.67 (s, 1H), 7.22~7.24 (m, 2H), 5.92 (d, J = 4.0 Hz, 1H), 4.90 (s, 2H), 3.24 (s, 3H), 3.01 (d, J = 8.0 Hz, 3H), 2.87 (s, 3H), 2.20 (s, 2H), 1.38 (s, 6H). | 621 |
| 73 | 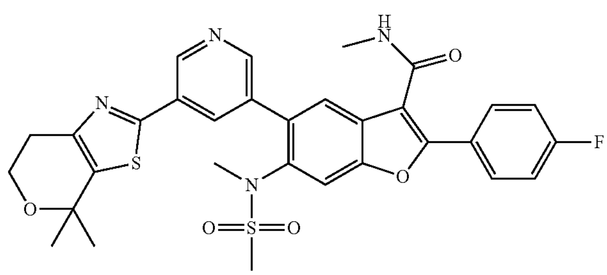 [SMILES: CNC(=O)c1c(-c2ccc(F)cc2)oc2cc(N(C)S(C)(=O)=O)c(-c3cncc(-c4nc5c(s4)C(C)(C)OCC5)c3)cc12] | ¹H-NMR (CDCl₃, 400 MHz) δ 9.87 (d, J = 1.6 Hz, 1H), 9.77 (d, J = 1.6 Hz, 1H), 8.56 (s, 1H), 7.92~7.95 (m, 3H), 7.67 (s, 1H), 7.21~7.26 (m, 2H), 5.93 (d, J = 4.0 Hz, 1H), 4.07~4.10 (m, 2H), 3.26 (s, 3H), 3.02 (d, J = 5.2 Hz, 3H), 2.93~2.96 (m, 2H), 2.84 (s, 3H), 1.62 (s, 6H). | 621 |
| 74 | 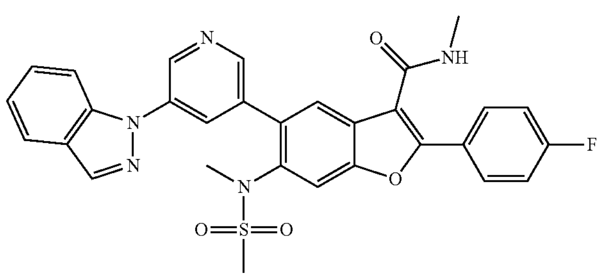 [SMILES: CNC(=O)c1c(-c2ccc(F)cc2)oc2cc(N(C)S(C)(=O)=O)c(-c3cncc(-n4ncc5ccccc54)c3)cc12] | ¹H-NMR (CDCl₃, 400 MHz) δ 9.01 (d, J = 4.0 Hz, 1H), 8.58 (d, J = 4.0 Hz, 1H), 8.19~8.20 (m, 2H), 7.85~7.89 (m, 3H), 7.82 (d, J = 8.0 Hz, 1H), 7.76 (d, J = 8.0 Hz, 1H), 7.61 (s, 1H), 7.42~7.46 (m, 1H), 7.20~7.23 (m, 1H), 7.12~7.19 (m, 2H), 5.82 (d, J = 3.6 Hz, 1H), 3.19 (s, 3H), 2.92 (d, J = 4.0 Hz, 3H), 2.76 (s, 3H). | 570 |
| 75 | 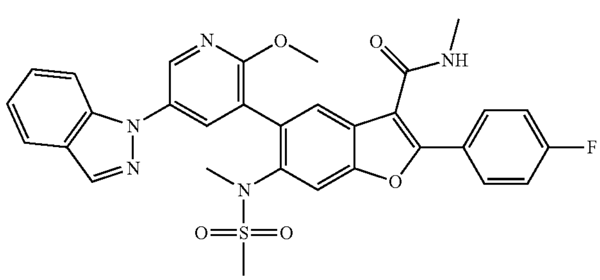 [SMILES: CNC(=O)c1c(-c2ccc(F)cc2)oc2cc(N(C)S(C)(=O)=O)c(-c3cc(-n4ncc5ccccc54)cnc3OC)cc12] | ¹H-NMR (CDCl₃, 400 MHz) δ 8.50 (s, 1H), 8.13 (s, 1H), 7.86~7.92 (m, 3H), 7.67~7.74 (m, 3H), 7.58 (s, 1H), 7.33~7.40 (m, 1H), 7.10~7.17 (m, 3H), 5.78~5.88 (br, 1H), 3.91 (s, 3H), 3.22 (s, 3H), 2.90 (d, J = 8.0 Hz, 3H), 2.64 (s, 3H). | 600 |

| No. | Structure | NMR | MS (M + H)+ |
|---|---|---|---|
| 76 | 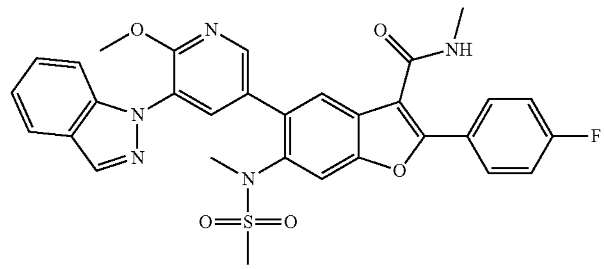 [SMILES: CNC(=O)c1c(-c2ccc(F)cc2)oc2cc(N(C)S(C)(=O)=O)c(-c3cnc(OC)c(-n4ncc5ccccc54)c3)cc12] | ¹H-NMR (CDCl₃, 400 MHz) δ 8.31 (d, J = 4.0 Hz, 1H), 8.21 (s, 1H), 7.89~7.94 (m, 3H), 7.84 (s, 1H), 7.78 (d, J = 8.0 Hz, 1H), 7.63 (s, 1H), 7.36~7.41 (m, 2H), 7.16~7.24 (m, 3H), 5.84~5.90 (br, 1H), 4.03 (s, 3H), 3.20 (s, 3H), 2.97 (d, J = 8.0 Hz, 3H), 2.88 (s, 3H). | 600 |
| 77 | 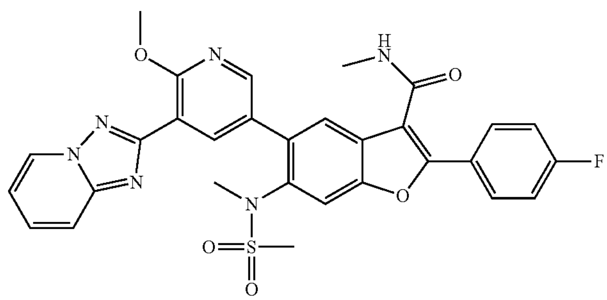 [SMILES: CNC(=O)c1c(-c2ccc(F)cc2)oc2cc(N(C)S(C)(=O)=O)c(-c3cnc(OC)c(-c4nc5ccccn5n4)c3)cc12] | ¹H-NMR (CDCl₃, 400 MHz) δ 8.26~8.31 (m, 2H), 7.95~7.98 (m, 2H), 7.70 (s, 1H), 7.50~7.59 (m, 1H), 7.46 (s, 1H), 7.43~7.45 (m, 2H), 7.10~7.16 (m, 2H), 6.89~6.93 (m, 1H), 6.21~6.26 (br s, 1H), 4.02 (s, 3H), 2.93 (d, J = 4.8 Hz, 3H), 2.65 (s, 3H), 2.57 (s, 3H). | 601 |
| 78 | 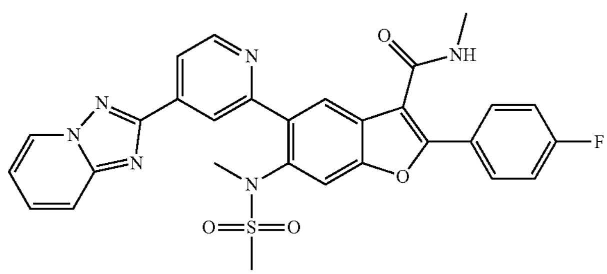 [SMILES: CNC(=O)c1c(-c2ccc(F)cc2)oc2cc(N(C)S(C)(=O)=O)c(-c3cc(-c4nc5ccccn5n4)ccn3)cc12] | ¹H-NMR (CDCl₃, 400 MHz) δ 8.75 (s, 1H), 8.53 (s, 1H), 8.34 (s, 1H), 8.05~8.07 (m, 1H), 7.92 (s, 1H), 7.86~7.90 (m, 2H), 7.69~7.71 (m, 1H), 7.62 (s, 1H), 7.47~7.51 (m, 1H), 7.06~7.11 (m, 2H), 7.00~7.03 (m, 1H), 6.29 (s, 1H), 3.16 (s, 3H), 2.90 (d, J = 4.8 Hz, 3H), 2.70 (s, 3H). | 571 |

Example 5

Preparation of Compound 79

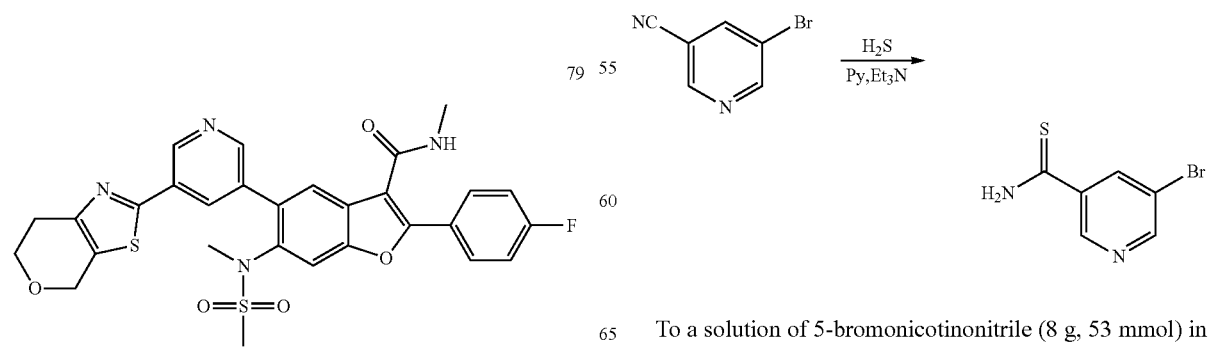

Step 1—Synthesis of 5-bromopyridine-3-carbothioamide

To a solution of 5-bromonicotinonitrile (8 g, 53 mmol) in 34 mL of pyridine was added Et₃N at 15° C., and then H₂S was passed through this solution for 1 hour. After being allowed to stir at 15° C. for 12 hours, the mixture was poured into ice water and the resulting residue was washed by water to provide 5-bromopyridine-3-carbothioamide (6.5 g, yield: 66.3%). ¹H-NMR (DMSO-d6, 300 MHz) δ 10.19 (s, 1H), 9.78 (s, 1H), 8.93 (d, J=8.0 Hz, 1H), 8.77 (d, J=8.0 Hz, 1H), 8.34 (s, 1H).

Step B—Synthesis of 2-(5-bromopyridin-3-yl)-6,7-dihydro-4H-pyrano[4,3-d]thiazole

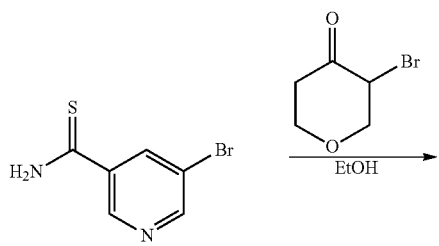

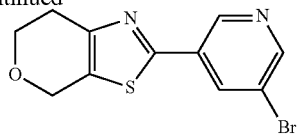

A solution of 5-bromopyridine-3-carbothioamide (570 mg, 2.6 mmol), 3-bromodihydro-2H-pyran-4(3H)-one (470 mg, 2.6 mmol) in 20 mL of EtOH was heated to reflux and allowed to stir at this temperature for 12 hours The reaction mixture was concentrated in vacuo, and the resulting residue was purified using silica gel chromatograph (eluted with PE:EtOAc=10:1) to provide 2-(5-bromopyridin-3-yl)-6,7-dihydro-4H-pyrano[4,3-d]thiazole (50 mg, yield: 6.4%). ¹H-NMR (CDCl₃, 300 MHz) δ 8.98 (d, J=3.0 Hz, 1H), 8.67 (s, 1H), 8.36~8.36 (m, 1H), 4.88 (s, 2H), 3.65~3.67 (m, 2H), 2.68~2.70 (m, 2H).

Step C—Synthesis of 5-(5-(6,7-dihydro-4H-pyrano[4,3-d]thiazol-2-yl)pyridin-3-yl)-2-(4-fluorophenyl)-N-methyl-6-(N-methylmethylsulfonamido)benzofuran-3-carboxamide (Compound 79)

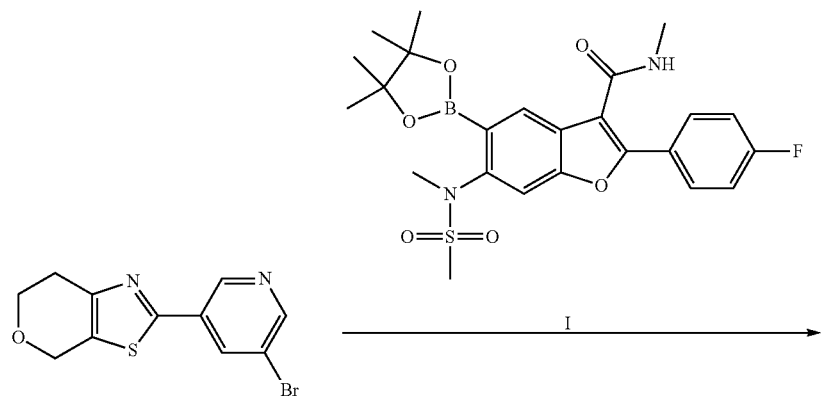

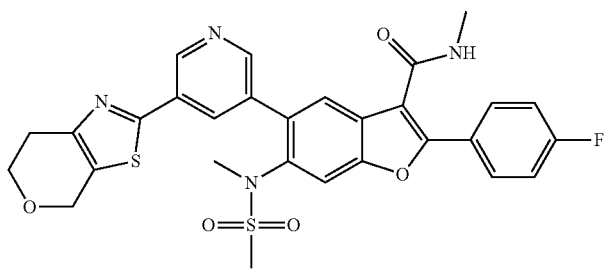

Compound 79 was made from the indicated starting material using methods described in Example 1. ¹H-NMR (CDCl₃, 300 MHz) δ 9.23 (s, 1H), 8.84 (s, 1H), 8.73 (s, 1H), 7.98 (s, 1H), 7.90~7.94 (m, 2H), 7.65 (s, 1H), 7.23 (s, 1H), 7.20 (s, 1H), 6.00~6.01 (m, 1H), 4.91 (s, 2H), 4.07~4.10 (m, 2H), 3.25 (s, 3H), 3.01 (s, 3H), 3.00 (s, 2H), 2.90 (s, 3H). MS (M+H)⁺: 593.

Compounds 80-84, depicted in the table below, were prepared using the method described in Example 5 and substituting the appropriate reactants and/or reagents.

| No. | Structure | NMR | MS (M + H)⁺ |
|---|---|---|---|
| 80 | 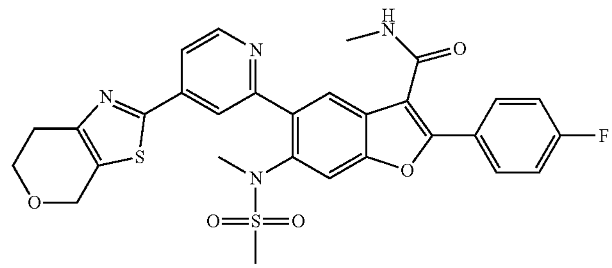 [SMILES: CNC(=O)c1c(-c2ccc(F)cc2)oc2cc(N(C)S(C)(=O)=O)c(-c3cc(-c4nc5c(s4)COCC5)ccn3)cc12] | ¹H-NMR (CDCl₃, 400 MHz) δ 9.02 (d, J = 4.0 Hz, 1H), 8.53 (s, 1H), 8.16 (d, J = 8.0 Hz, 1H), 8.13 (s, 1H), 8.13 (s, 1H), 8.11 (s, 1H), 7.66 (s, 1H), 7.18~7.22 (m, 2H), 6.60~6.70 (m, 1H), 4.95 (s, 2H), 4.11 (t, J = 4.0 Hz, 2H), 3.34 (s, 3H), 3.06 (s, 3H), 3.05 (s, 2H), 2.99 (s, 3H). | 593 |
| 81 | 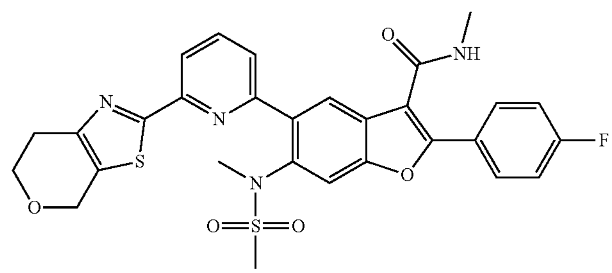 [SMILES: CNC(=O)c1c(-c2ccc(F)cc2)oc2cc(N(C)S(C)(=O)=O)c(-c3cccc(-c4nc5c(s4)COCC5)n3)cc12] | ¹H-NMR (CDCl₃, 300 MHz) δ 8.15 (d, J = 9.0 Hz, 1H), 7.99 (s, 1H), 7.89~7.96 (m, 3H), 7.66 (s, 1H), 7.61 (d, J = 6.0 Hz, 1H), 7.73 (d, J = 6.0 Hz, 2H), 5.99 (d, J = 6.0 Hz, 1H), 4.87 (s, 2H), 4.06~4.09 (m, 2H), 3.38 (s, 3H), 3.00 (s, 3H), 2.99 (s, 2H), 2.59 (s, 3H). | 593 |
| 82 | 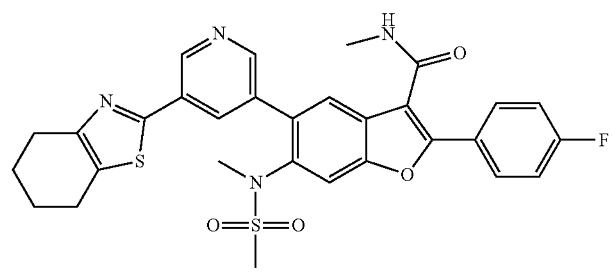 [SMILES: CNC(=O)c1c(-c2ccc(F)cc2)oc2cc(N(C)S(C)(=O)=O)c(-c3cncc(-c4nc5c(s4)CCCC5)c3)cc12] | ¹H-NMR (CDCl₃, 400 MHz) δ 9.17 (s, 1H), 8.78 (s, 1H), 8.63 (s, 1H), 7.92~7.95 (m, 3H), 7.66 (s, 1H), 7.23 (t, J = 8.0 Hz, 2H), 6.05 (s, 1H), 3.24 (s, 3H), 3.02 (d, J = 4.0 Hz, 3H), 2.87 (s, 7H), 1.91 (s, 4H). | 590 |
| 83 | 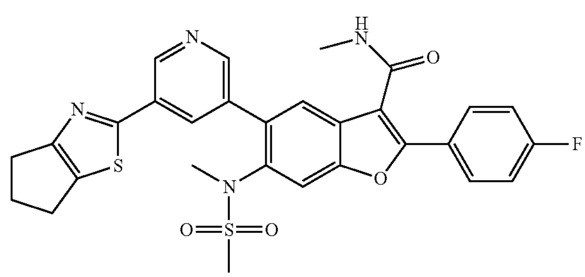 [SMILES: CNC(=O)c1c(-c2ccc(F)cc2)oc2cc(N(C)S(C)(=O)=O)c(-c3cncc(-c4nc5c(s4)CCC5)c3)cc12] | ¹H-NMR (CDCl₃, 400 MHz) δ 9.19 (s, 1H), 8.78 (s, 1H), 8.64 (s, 1H), 7.93 (t, J = 6.0 Hz, 3H), 7.66 (s, 1H), 7.23 (t, J = 8.0 Hz, 2H), 5.97 (s, 1H), 3.25 (s, 3H), 3.01~3.02 (m, 5H), 2.93 (d, J = 8.0 Hz, 2H), 2.87 (s, 3H), 2.58 (t, J = 8.0 Hz, 2H). | 576 |
| 84 | 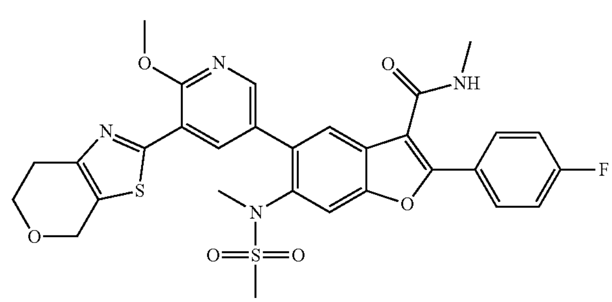 [SMILES: CNC(=O)c1c(-c2ccc(F)cc2)oc2cc(N(C)S(C)(=O)=O)c(-c3cnc(OC)c(-c4nc5c(s4)COCC5)c3)cc12] | ¹H-NMR (CDCl₃, 400 MHz) δ 8.71 (s, 1H), 8.33 (d, J = 2.0 Hz, 1H), 7.95~7.98 (m, 2H), 7.86 (s, 1H), 7.66 (s, 1H), 7.21 (t, J = 8.0 Hz, 2H), 6.00 (s, 1H), 4.92 (s, 2H), 4.21 (s, 3H), 4.07 (t, J = 5.2 Hz, 2H), 3.19 (s, 3H), 2.98~3.01 (m, 5H), 2.83 (s, 3H). | 623 |

Compound 182, depicted in the table below, was prepared using the method described in Example 5 and substituting the appropriate reactants and/or reagents.

(yield: 44.3%) as white solid. $^1$H-NMR (CDCl$_3$, 400 MHz) δ 8.34 (s, 1H), 4.64 (t, J=3.6 Hz, 1H), 2.91~3.00 (m, 1H), 2.66~2.73 (m, 1H), 2.28~2.47 (m, 2H).

| No. | Structure | NMR | MS (M + H)$^+$ |
|---|---|---|---|
| 182 | 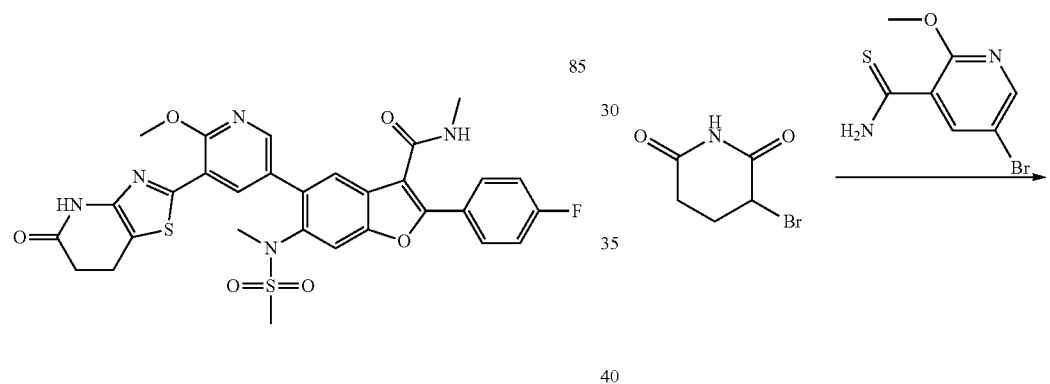 | $^1$HNMR (CDCl$_3$, 400 MHz) δ 9.18 (s, 1H), 8.80 (s, 1H), 8.71 (s, 1H), 7.92~7.96 (m, 3H), 7.66 (s, 1H), 7.21~7.25 (m, 2H), 6.02 (br, 1H), 3.72 (s, 1H), 3.65 (s, 1H), 3.27 (s, 3H), 3.01 (d, J = 4.8 Hz, 3H), 2.89 (s, 3H), 2.09~2.11 (d, J = 8.8 Hz, 1H), 2.01 (m, 2H), 1.72~1.74 (d, J = 8.8 Hz, 1H), 1.14~1.25 (m, 2H). | 603 |

Example 6

Preparation of Compound 85

85

Step 1—Synthesis of 5-bromopyridine-3-carbothioamide

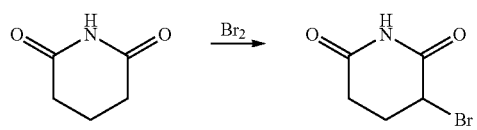

Bromine (6.4 g, 0.04 mol) was added to a solution of piperidine-2,6-dione (4.5 g, 0.04 mol) in 14 mL of 1,1,2-trichloroethane at room temperature. The mixture was allowed to stir for 2 hours at 110° C. and then for 1 hour at room temperature. The reaction mixture was concentrated in vacuo and the resulting residue was purified using flash chromatography on silica gel (eluted with PE:EtOAc=5:1~2:1) to provide 3.4 g of 3-bromopiperidine-2,6-dione

Step B—Synthesis of 2-(5-bromo-2-methoxypyridin-3-yl)-6,7-dihydrothiazolo[4,5-b]pyridin-5(4H)-one

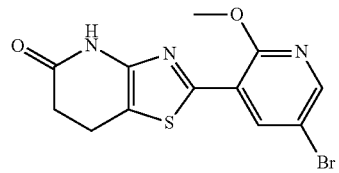

A mixture of 3-bromopiperidine-2,6-dione (3.84 g, 20 mmol) and 5-bromo-2-methoxypyridine-3-carbothioamide (3.71 g, 15 mmol) in 100 mL of dry ethanol was heated to reflux and allowed to stir at this temperature for 48 hours After being cooled to room temperature, the precipitate was collected by filtration, washed with cooled ethanol, and dried to provide 2-(5-bromo-2-methoxypyridin-3-yl)-6,7-dihydrothiazolo[4,5-b]pyridin-5(4H)-one (2.6 g, yield: 51%). $^1$H-NMR (DMSO-d6, 300 MHz) δ 10.75 (s, 1H), 8.47 (d, J=2.4 Hz, 1H), 8.38 (d, J=2.4 Hz, 1H), 4.09 (s, 3H), 3.02 (t, J=7.6 Hz, 2H), 2.62 (t, J=7.6 Hz, 2H). MS (M+H)$^+$: 340/342.

Step C—Synthesis of 2-(4-fluorophenyl)-5-(6-methoxy-5-(5-oxo-4,5,6,7-tetrahydrothiazolo[4,5-b]pyridin-2-yl)pyridin-3-yl)-N-methyl-6-(N-methylmethylsulfonamido)benzofuran-3-carboxamide (Compound 85)

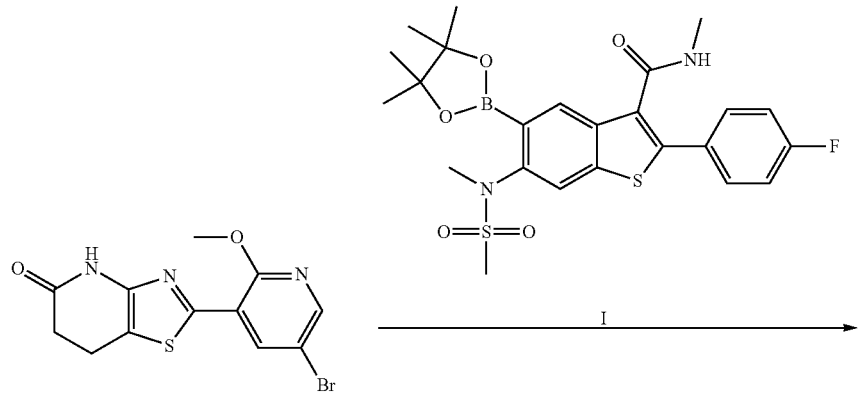

A mixture of 2-(5-bromo-2-methoxypyridin-3-yl)-6,7-dihydrothiazolo[4,5-b]pyridin-5(4H)-one (68 mg, 0.2 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 101 mg, 0.2 mmol), K$_3$PO$_4$·3H$_2$O (160 mg, 0.6 mmol) and Pd(dppf)Cl$_2$ (15 mg, 0.02 mmol) in 4 mL of dry dioxane was allowed to stir at 90° C. under N$_2$ for about 15 hours. The reaction mixture was concentrated in vacuo and the resulting residue was purified using prep-HPLC to provide Compound 85 (12 mg, yield: 9.4%). $^1$H-NMR (CDCl$_3$, 400 MHz) δ 8.54 (s, 1H), 8.22 (s, 1H), 8.06 (s, 1H), 7.86~7.89 (m, 2H), 7.80 (s, 1H), 7.59 (s, 1H), 7.13~7.17 (m, 2H), 5.84 (s, 1H), 4.15 (s, 3H), 3.13 (s, 3H), 3.01 (t, J=7.6 Hz, 2H), 2.93 (t, J=4.4 Hz, 3H), 2.72~2.78 (m, 5H). MS (M+H)$^+$: 636.

Compounds 86-87, depicted in the table below, were prepared using the method described in Example 6 and substituting the appropriate reactants and/or reagents.

| No. | Structure | NMR | MS (M + H)$^+$ |
|---|---|---|---|
| 86 | 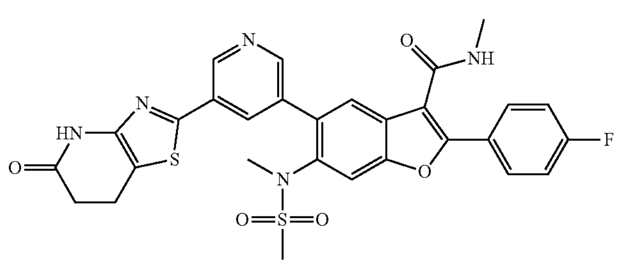 [SMILES: CNC(=O)c1c(-c2ccc(F)cc2)oc2cc(N(C)S(C)(=O)=O)c(-c3cncc(-c4nc5c(s4)CCC(=O)N5)c3)cc12] | $^1$H-NMR (DMSO-d6, 400 MHz) δ 9.02 (s, 1H), 8.69 (s, 1H), 8.52 (d, J = 4.8 Hz, 1H), 8.23 (s, 1H), 8.12 (s, 1H), 7.99~8.03 (m, 2H), 7.74 (s, 1H), 7.41 (t, J = 8.8 Hz, 2H), 3.18 (s, 3H), 2.99~3.03 (m, 5H), 2.81 (d, J = 4.4 Hz, 3H), 2.62 (t, J = 8.0 Hz, 2H). | 606 |

| No. | Structure | NMR | MS (M + H)+ |
|---|---|---|---|
| 87 | 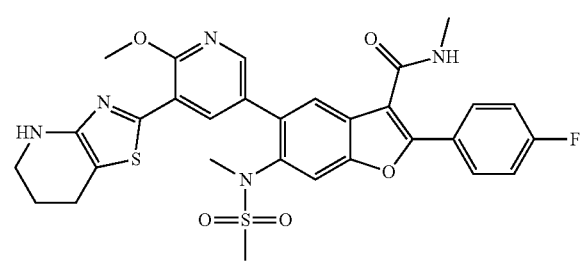 [SMILES: CNC(=O)c1c(-c2ccc(F)cc2)oc2cc(N(C)S(C)(=O)=O)c(-c3cncc(-c4nc5c(s4)CCCN5)c3)cc12] | ¹H-NMR (DMSO-d6, 300 MHz) δ 8.54 (d, J = 6.0 Hz, 2H), 7.95~8.00 (m, 3H), 7.84 (s, 1H), 7.79 (s, 1H), 7.56 (d, J = 9.0 Hz, 1H), 7.36~7.42 (m, 2H), 7.02 (s, 1H), 6.97 (s, 1H), 3.18 (s, 3H), 3.13 (s, 2H), 2.90 (s, 3H), 2.80 (s, 3H), 2.79 (s, 2H). | 588 |

Example 7

Preparation of Compound 88

88

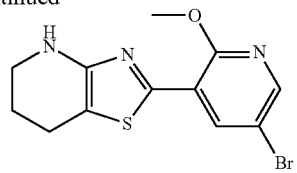

To a solution of 2-(5-bromo-2-methoxypyridin-3-yl)-6,7-dihydrothiazolo[4,5-b]pyridin-5(4H)-one (2.04 g, 6 mmol) in 60 mL of dry THF was added BH₃—SMe₂ (912 mg, 12 mmol) at 0° C. The reaction mixture was allowed to stir at room temperature for about 15 hours, and then quenched with water and aqueous H₂SO₄ (5 M). The resulting solution was filtered, aqueous NaOH was added to the filtrate until pH to 14 and this aqueous layer was extracted with EtOAc. The organic layer was washed with brine, dried over Na₂SO₄, concentrated and purified using flash chromatography on silica gel (eluted with PE:EtOAc=:1) to provide 2-(5-bromo-2-methoxypyridin-3-yl)-4,5,6,7-tetrahydrothiazolo[4,5-b]pyridine (1.6 g, yield: 81.6%) as yellow solid. ¹H-NMR (CDCl₃, 300 MHz) δ 8.63 (s, 1H), 8.17 (s, 1H), 4.12 (s, 3H), 3.39 (t, J=5.2 Hz, 2H), 2.84 (t, J=6.4 Hz, 2H), 2.01~2.07 (m, 2H). MS (M+H)⁺: 326/328.

Step 1—Synthesis of 2-(5-bromo-2-methoxypyridin-3-yl)-4,5,6,7-tetrahydrothiazolo[4,5-b]pyridine

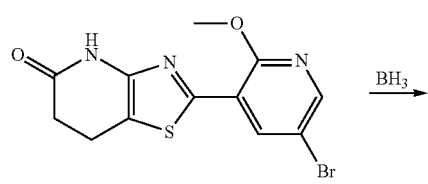

Step B—Synthesis of 2-(4-fluorophenyl)-5-(6-methoxy-5-(4,5,6,7-tetrahydrothiazolo[4,5-b]pyridin-2-yl)pyridin-3-yl)-N-methyl-6-(N-methylmethylsulfonamido)benzofuran-3-carboxamide (Compound 88)

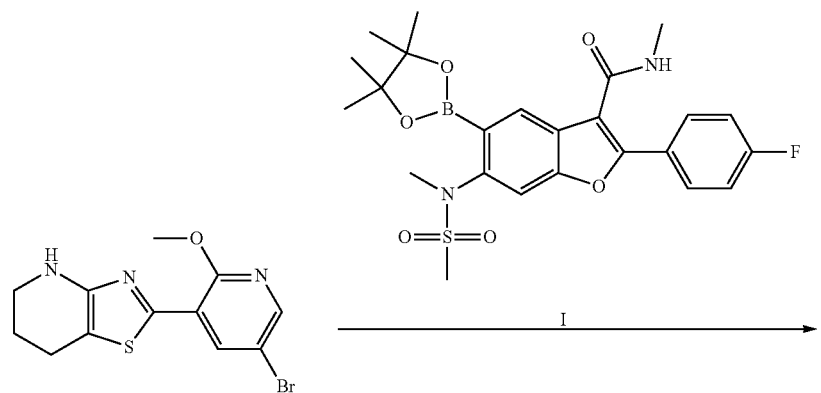

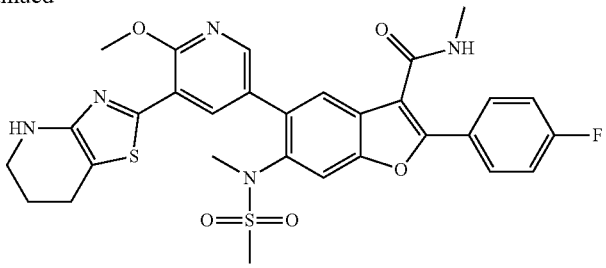

88

A mixture of 2-(5-bromo-2-methoxypyridin-3-yl)-4,5,6,7-tetrahydrothiazolo[4,5-b]pyridine (66 mg, 0.2 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 101 mg, 0.2 mmol), $K_3PO_4 \cdot 3H_2O$ (160 mg, 0.6 mmol) and Pd(dppf)Cl$_2$ (15 mg, 0.02 mmol) in 4 mL of dry dioxane was allowed to stir at 90° C. under N$_2$ for about 15 hours. The reaction mixture was concentrated in vacuo and the resulting residue was purified using prep-HPLC to provide Compound 88 (39 mg, yield: 31.4%). $^1$H-NMR (CDCl$_3$, 400 MHz) δ 8.62 (s, 1H), 8.25 (s, 1H), 7.98~8.01 (m, 2H), 7.84 (s, 1H), 7.69 (s, 1H), 7.20~7.25 (m, 2H), 5.90 (s, 1H), 4.21 (s, 3H), 3.38 (t, J=5.2 Hz, 2H), 3.19 (s, 3H), 3.03 (t, J=5.2 Hz, 3H), 2.85 (t, J=6.4 Hz, 2H), 2.81 (s, 3H), 2.02~2.08 (m, 2H). MS (M+H)$^+$: 622.

Compound 89, depicted in the table below, was prepared using the method described in Example 7 and substituting the appropriate reactants and/or reagents.

Step 1—Synthesis of 1-(2-(5-bromo-2-methoxypyridin-3-yl)-6,7-dihydrothiazolo[4,5-b]pyridin-4(5H)-yl)ethanone

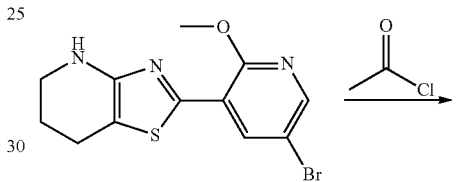

| No. | Structure | NMR | MS (M + H)$^+$ |
|---|---|---|---|
| 89 | 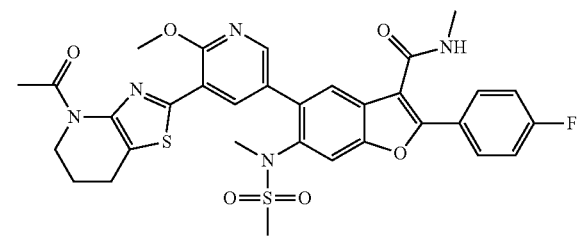 | $^1$H-NMR (CDCl$_3$, 400 MHz) δ 9.08 (d, J = 4.0 Hz, 1H), 8.64 (d, J = 4.0 Hz, 1H), 8.25 (t, J = 2.0 Hz, 1H), 7.94~7.98 (m, 3H), 7.88 (s, 1H), 7.67 (s, 1H), 7.20~7.24 (m, 2H), 5.85 (s, 1H), 3.38 (t, J = 7.6 Hz, 2H), 3.17 (s, 3H), 3.01 (d, J = 8.0 Hz, 3H), 2.82 (t, J = 4.0 Hz, 2H), 2.75 (s, 3H), 2.01~2.05 (m, 2H). | 592 |

Example 8

Preparation of Compound 90

90

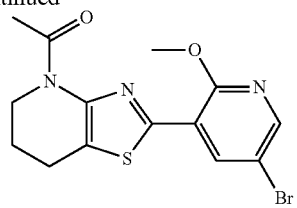

To a mixture of 2-(5-bromo-2-methoxypyridin-3-yl)-4,5,6,7-tetrahydrothiazolo[4,5-b]pyridine (326 mg, 1.0 mmol) in 6 mL of dry DCM was added Et$_3$N (202 mg, 2 mmol), after stirred for 20 minutes, acetyl chloride (118 mg, 1.5 mmol) was added at 0° C. The reaction mixture was allowed to stir at room temperature for about 15 hours, and then partitioned between DCM and water. The organic layer was washed with brine, dried over Na$_2$SO$_4$, concentrated and purified using flash chromatography on silica gel (eluted with PE:EtOAc=2:1) to provide 1-(2-(5-bromo-2-methoxypyridin-3-yl)-6,7-dihydrothiazolo[4,5-b]pyridin-4(5H)-yl)ethanone (340 mg, yield: 92.4%). ¹H-NMR (CDCl₃, 400 MHz) δ 8.56 (d, J=2.4 Hz, 1H), 8.22 (d, J=2.4 Hz, 1H), 4.13 (s, 3H), 3.97 (t, J=5.2 Hz, 2H), 2.91 (t, J=6.4 Hz, 2H), 2.64 (s, 3H), 2.01~2.07 (m, 2H).

Step B—Synthesis of 5-(5-(4-acetyl-4,5,6,7-tetrahydrothiazolo[4,5-b]pyridin-2-yl)-6-methoxypyridin-3-yl)-2-(4-fluorophenyl)-N-methyl-6-(N-methylmethylsulfonamido)benzofuran-3-carboxamide (Compound 90)

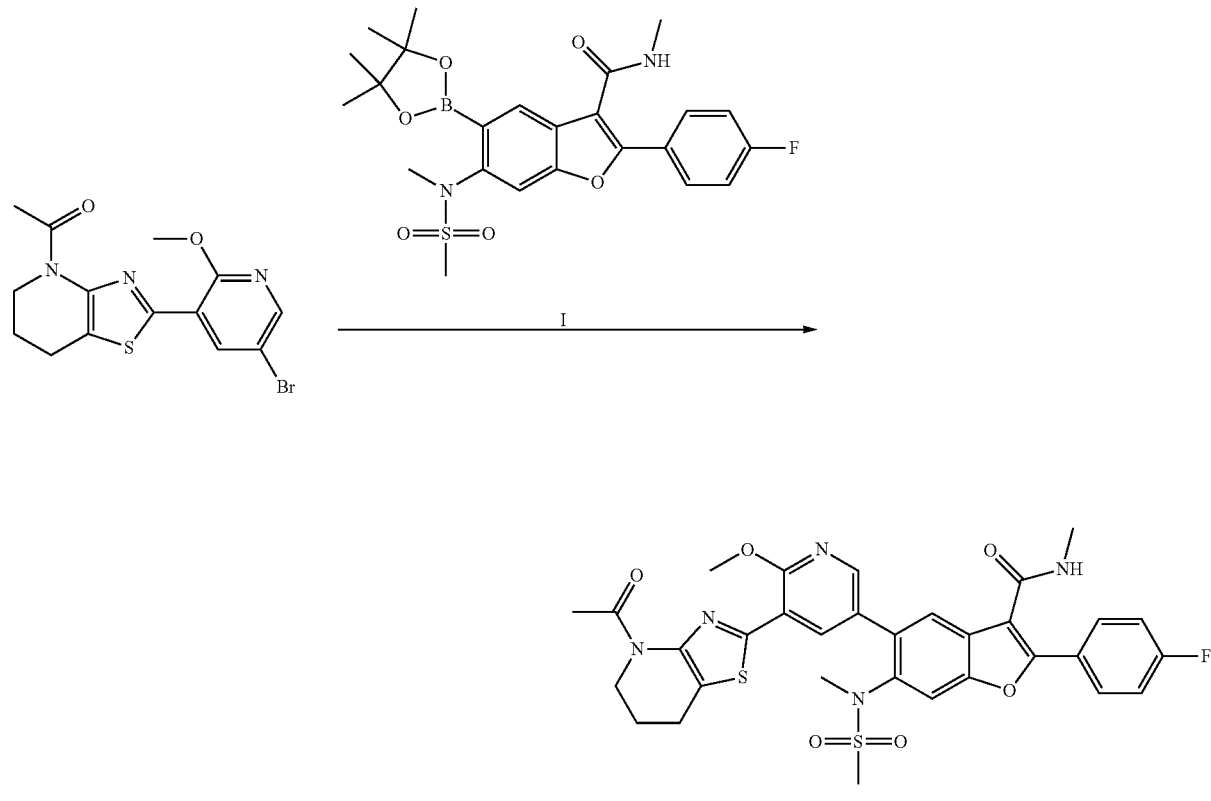

Compound 90 was made from the indicated starting material using methods described in Example 1. ¹H-NMR (CDCl₃, 400 MHz) δ 8.64 (s, 1H), 8.26 (s, 1H), 7.92~7.96 (m, 2H), 7.86 (s, 1H), 7.65 (s, 1H), 7.19~7.24 (m, 2H), 5.85 (d, J=5.2 Hz, 1H), 4.22 (s, 3H), 3.92~3.98 (m, 2H), 3.18 (s, 3H), 2.99 (t, J=4.8 Hz, 3H), 2.92 (t, J=6.4 Hz, 2H), 2.82 (s, 3H), 2.60 (s, 3H), 2.02~2.08 (m, 2H). MS (M+H)⁺: 664.

Compound 91, depicted in the table below, was prepared using the method described in Example 8 and substituting the appropriate reactants and/or reagents.

| No. | Structure | NMR | MS (M + H)⁺ |
|---|---|---|---|
| 91 | 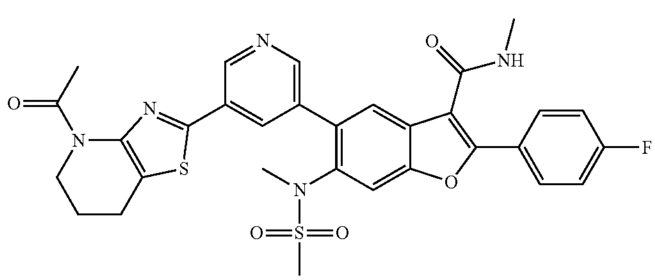 [SMILES: CNC(=O)c1c(-c2ccc(F)cc2)oc2cc(N(C)S(C)(=O)=O)c(-c3cncc(-c4nc5c(s4)CCCN5C(C)=O)c3)cc12] | ¹H-NMR (CDCl₃, 400 MHz) δ 9.13 (d, J = 2.4 Hz, 1H), 8.67 (d, J = 2.0 Hz, 1H), 8.34 (t, J = 4.0 Hz, 1H), 7.92~7.95 (m, 3H), 7.65 (s, 1H), 7.21~7.25 (m, 2H), 5.85 (d, J = 2.0 Hz, 1H), 3.97~4.00 (m, 2H), 3.16 (s, 3H), 3.00 (d, J = 8.0 Hz, 3H), 2.92 (t, J = 4.0 Hz, 2H), 2.83 (s, 3H), 2.63 (s, 3H), 2.02~2.07 (m, 2H). | 634 |

Example 9

Preparation of Compound 92

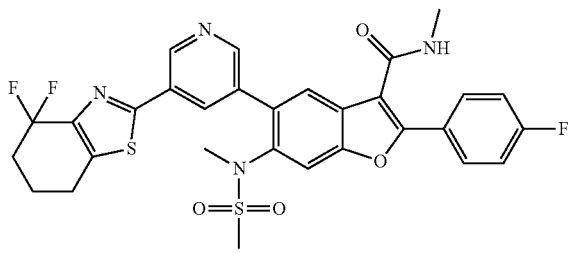

Step 1—Synthesis of 2-(5-bromopyridin-3-yl)-6,7-dihydrobenzo[d]thiazol-4(5H)-one

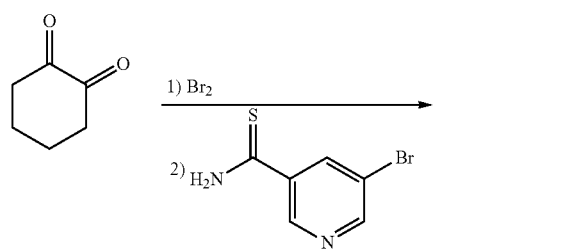

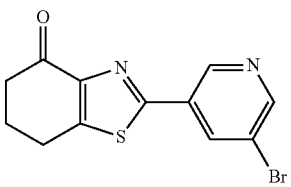

To a solution of cyclohexane-1,2-dione (1.5 g, 13.5 mmol) in THF (20 mL) was added Br₂ (2.5 g, 13.5 mmol) dropwise at 0° C. The mixture was allowed to stir for 1 hour at room temperature, then 5-bromopyridine-3-carbothioamide (2.5 g, 13.5 mmol) was added and the mixture was allowed to stir at 50° C. for about 15 hours. The reaction mixture was concentrated in vacuo and the resulting residue was purified using column chromatography on silica gel (eluted with PE:EtOAc=1:1) to provide 2-(5-bromopyridin-3-yl)-6,7-dihydrobenzo[d]thiazol-4(5H)-one as yellow solid (1 g, yield: 24.0%). ¹H-NMR (CDCl₃, 400 MHz) δ 9.02 (s, 1H), 8.73 (s, 1H), 8.57 (s, 1H), 3.20 (t, J=6.0 Hz, 2H), 2.75 (t, J=6.0 Hz, 2H), 2.29~2.36 (m, 2H).

Step B—Synthesis of 2-(5-bromopyridin-3-yl)-4,4-difluoro-4,5,6,7-tetrahydrobenzo[d]thiazole

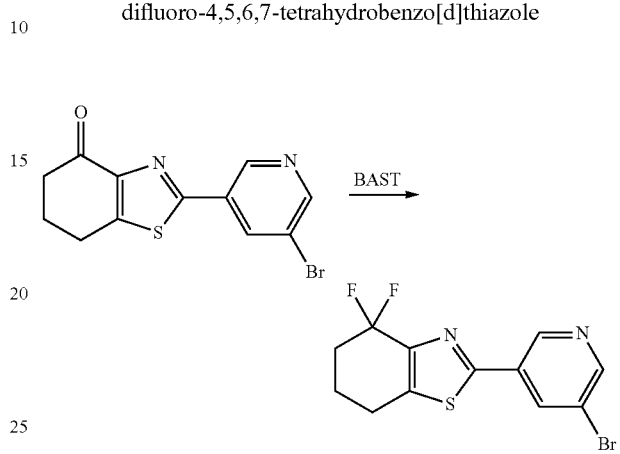

A solution of 2-(5-bromopyridin-3-yl)-6,7-dihydrobenzo[d]thiazol-4(5H)-one (0.6 g, 1.94 mmol) and BAST (2 mL) in THF (5 mL) was added to a sealed tube under N₂. The resulting mixture was allowed to stir at 80° C. for 10 hours, then was cooled to room temperature. The reaction mixture was poured into NaHCO₃ (saturated aqueous, 10 mL) slowly and extracted with EtOAc (20 mL*3). The combined organic extracts were washed with brine, dried over Na₂SO₄, and concentrated in vacuo. The resulting residue was purified using column chromatography on silica gel (eluted with PE:EtOAc=15:1~10:1) to provide 2-(5-bromopyridin-3-yl)-4,4-difluoro-4,5,6,7-tetrahydrobenzo[d]thiazole as yellow oil (0.47 g, yield: 74.7%). ¹H-NMR (400 MHz, CDCl₃) δ 9.00 (s, 1H), 8.72 (s, 1H), 8.49 (s, 1H), 2.94~2.99 (m, 2H), 2.33~2.44 (m, 2H), 2.06~2.19 (m, 2H).

Step C—Synthesis of 5-(5-(4,4-difluoro-4,5,6,7-tetrahydrobenzo[d]thiazol-2-yl)pyridin-3-yl)-2-(4-fluorophenyl)-N-methyl-6-(N-methylmethylsulfonamido)benzofuran-3-carboxamide (Compound 92)

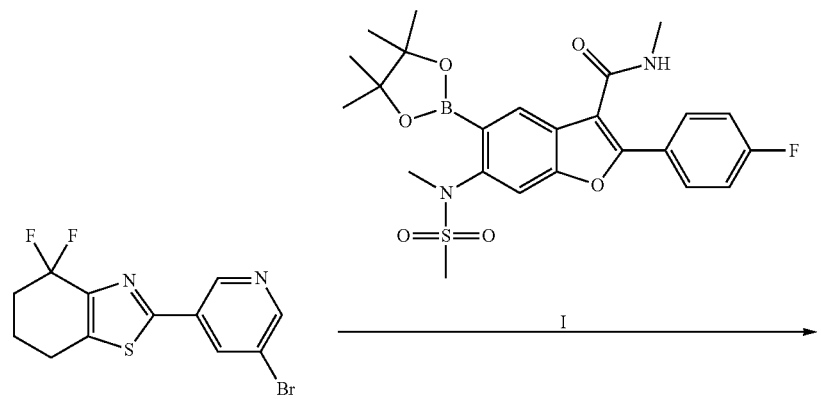

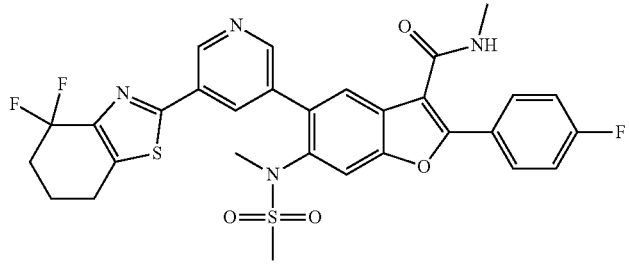 [SMILES: CNC(=O)c1c(-c2ccc(F)cc2)oc2cc(N(C)S(C)(=O)=O)c(-c3cc(-c4nc5c(s4)CCCC5(F)F)ccn3)cc12]

92

Compound 92 was made from the indicated starting material using methods described in Example 1. ¹H-NMR (CDCl₃, 400 MHz) δ 9.23 (s, 1H), 8.87 (s, 1H), 8.80 (s, 1H), 7.91~7.95 (m, 3H), 7.66 (s, 1H), 7.23 (t, J=8.8 Hz, 2H), 6.12 (d, J=4.4 Hz, 1H), 3.24 (s, 3H), 2.99~3.05 (m, 5H), 2.93 (s, 3H), 2.34~2.43 (m, 2H), 2.16~2.20 (m, 2H). MS (M+H)⁺: 627.

Compounds 93~95, depicted in the table below, were prepared using the method described in Example 9 and substituting the appropriate reactants and/or reagents.

| No. | Structure | NMR | MS (M + H)⁺ |
|---|---|---|---|
| 93 | 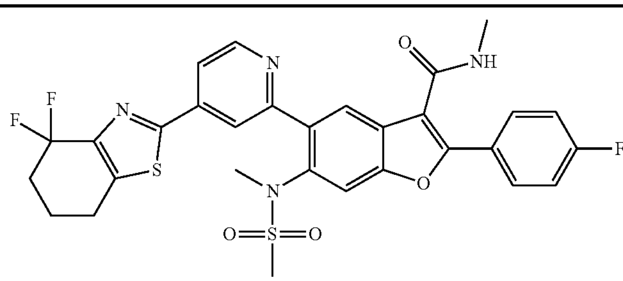 | ¹H-NMR (CDCl₃, 400 MHz) δ 9.04 (d, J = 6.0 Hz, 1H), 8.58 (s, 1H), 8.36 (d, J = 6.0 Hz, 1H), 8.10~8.16 (m, 3H), 7.67 (s, 1H), 7.17~7.27 (s, 2H), 3.31 (s, 3H), 3.00~3.07 (m, 8H), 2.36~2.44 (m, 2H), 2.17~2.23 (m, 2H), | 627 |
| 94 | 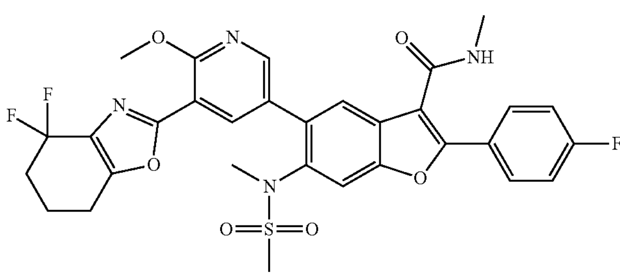 [SMILES: CNC(=O)c1c(-c2ccc(F)cc2)oc2cc(N(C)S(C)(=O)=O)c(-c3cnc(OC)c(-c4nc5c(o4)CCCC5(F)F)c3)cc12] | ¹H-NMR (CDCl₃, 400 MHz) δ 8.38 (d, J = 9.2 Hz, 2H), 7.92~7.96 (m, 2H), 7.83 (s, 1H), 7.64 (s, 1H), 7.21 (t, J = 8.4 Hz, 2H), 5.98 (s, 1H), 4.14 (s, 3H), 3.20 (s, 3H), 3.03 (d, J = 4.8 Hz, 3H), 2.84~2.86 (m, 2H), 2.82 (s, 3H), 2.26~2.34 (m, 2H), 2.13~2.17 (m, 2H). | 641 |
| 95 | 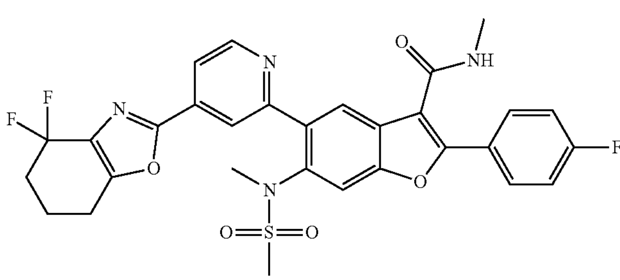 [SMILES: CNC(=O)c1c(-c2ccc(F)cc2)oc2cc(N(C)S(C)(=O)=O)c(-c3cc(-c4nc5c(o4)CCCC5(F)F)ccn3)cc12] | ¹H-NMR (CDCl₃, 400 MHz) δ 9.05 (d, J = 5.2 Hz, 1H), 8.47 (s, 1H), 8.24 (d, J = 5.6 Hz, 1H), 8.06~8.10 (m, 2H), 7.68 (s, 1H), 7.18~7.23 (m, 2H), 6.87 (s, 1H), 3.39 (s, 3H), 3.04 (d, J = 4.8 Hz, 3H), 2.90~2.92 (m, 2H), 2.86 (s, 3H), 2.34~2.38 (m, 2H), 2.17~2.23 (m, 2H). | 611 |

Example 10

Preparation of Compound 96

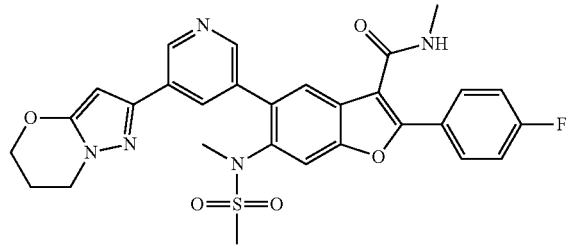 [SMILES: CNC(=O)c1c(-c2ccc(F)cc2)oc2cc(N(C)S(C)(=O)=O)c(-c3cnc(OC)c(-c4cc5n(n4)CCCO5)c3)cc12]

96

Step 1—Synthesis of methyl 3-(5-bromopyridin-3-yl)-3-oxopropanoate

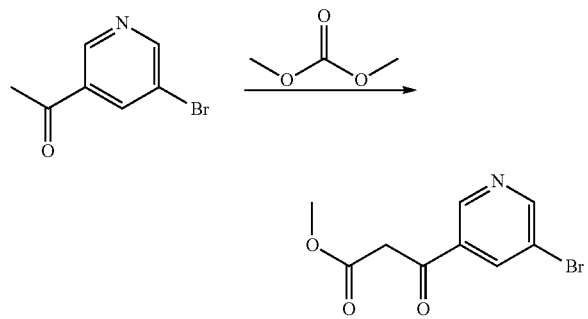

A solution of dimethyl carbonate (2 g, 10 mmol) and NaH (720 mg, 30 mmol) in 50 mL of THF was allowed to stir at 70° C. for 2 hours. Then, 1-(5-bromopyridin-3-yl)ethanone (2.36 g, 20 mmol) was added slowly and the reaction mixture was allowed to stir at 70° C. for 12 hours. The mixture was concentrated in vacuo, and the resulting residue was purified using flash silica gel column chromatography (eluted with PE:EtOAc=3:1) to provide methyl 3-(5-bromopyridin-3-yl)-3-oxopropanoate (1.6 g, yield: 62%). $^1$H-NMR (CDCl$_3$, 400 MHz) δ 12.45 (s, 0.5H), 9.04 (d, J=2.0 Hz, 0.5H), 8.88 (s, 1H), 8.74 (d, J=2.0 Hz, 0.5H), 8.37 (s, 0.5H), 8.20 (t, J=2.0 Hz, 0.5H), 5.71 (s, 0.5H), 4.01 (s, 1H), 3.83 (s, 1.5H), 3.77 (s, 1.5H).

Step B—Synthesis of 3-(5-bromopyridin-3-yl)-1H-pyrazol-5-ol

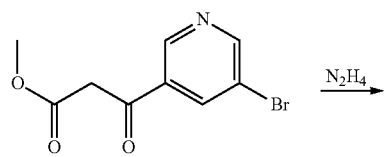

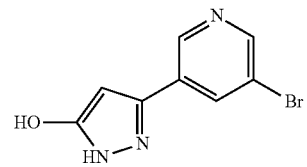

A mixture of methyl 3-(5-bromopyridin-3-yl)-3-oxopropanoate (0.8 g, 3.1 mmol) and N$_2$H$_4$ (0.497 g, 15.5 mmol) in 12 mL of MeOH was heated under reflux for 12 hours. The resulting solution was filtered and concentrated in vacuo and the resulting residue was washed with hexane, dissolved in EtOAc, dried over Na$_2$SO$_4$, filtered and concentrated in vacuo to provide 3-(5-bromopyridin-3-yl)-1H-pyrazol-5-ol (0.4 g, 53.8%), which was used without further purification.

Step C—Synthesis of 2-(5-bromopyridin-3-yl)-6,7-dihydro-5H-pyrazolo[5,1-b][1,3]oxazine

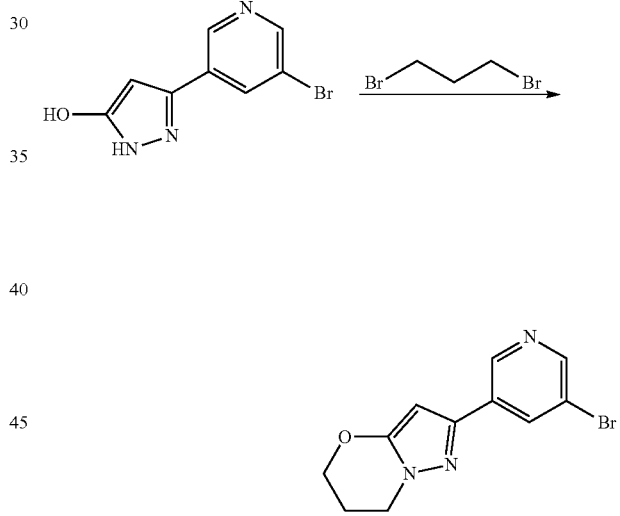

A mixture of 3-(5-bromopyridin-3-yl)-1H-pyrazol-5-ol (0.2 g, 0.833 mmol), 1,3-dibromopropane (0.2 g, 1 mmol) and K$_2$CO$_3$ (0.3452 g, 2.5 mmol) in 5 mL of CH$_3$CN was heated under reflux for 12 hours. The reaction mixture was then cooled to room temperature and concentrated in vacuo. The resulting residue was partitioned between EtOAc and water, the organic layer was washed with brine, dried over Na$_2$SO$_4$, concentrated in vacuo to provide a residue which was purified using silica gel column chromatography (eluted with PE:EtOAc=3:1) to provide 2-(5-bromopyridin-3-yl)-6,7-dihydro-5H-pyrazolo[5,1-b][1,3]oxazine (0.13 g, yield: 55.8%).

Step D—Synthesis of 5-(5-(6,7-dihydro-5H-pyrazolo[5,1-b][1,3]oxazin-2-yl)pyridin-3-yl)-2-(4-fluorophenyl)-N-methyl-6-(N-methylmethylsulfonamido)benzofuran-3-carboxamide (Compound 96)

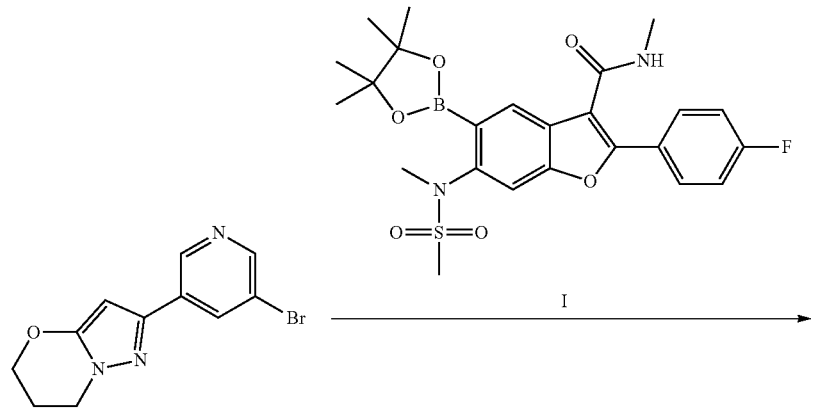

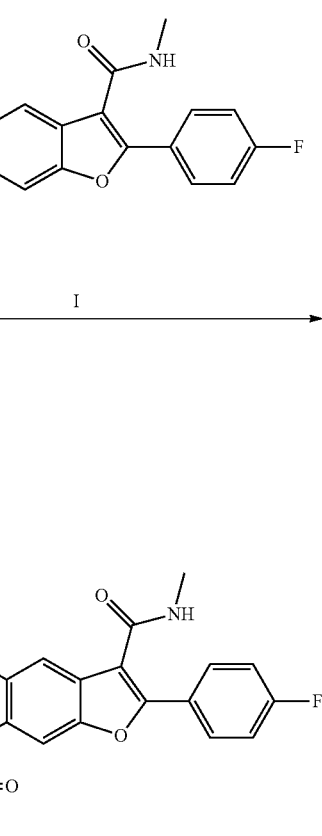

Compound 96 was made from the indicated starting material using methods described in Example 1. $^1$H-NMR (CDCl$_3$, 400 MHz) δ 9.04 (s, 1H), 8.75 (s, 1H), 8.63 (s, 1H), 7.92~7.96 (m, 3H), 7.65 (s, 1H), 7.20~7.25 (m, 2H), 6.09 (s, 1H), 5.96 (s, 1H), 4.35 (t, J=4.0 Hz, 2H), 4.23 (t, J=4.0 Hz, 2H), 3.24 (s, 3H), 3.02 (d, J=4.0 Hz, 3H), 2.87 (s, 3H), 2.33 (t, J=8.0 Hz, 2H). MS (M+H)$^+$: 576.

Compound 97, depicted in the table below, was prepared using the method described in Example 10 and substituting the appropriate reactants and/or reagents.

| No. | Structure | NMR | MS (M + H)$^+$ |
|---|---|---|---|
| 97 | (structure) | $^1$H-NMR (CDCl$_3$, 400 MHz) δ 9.12 (s, 1H), 8.77 (s, 1H). 8.73 (s, 1H), 7.92~7.97 (m, 3H), 7.66 (s, 1H), 7.23 (t, J = 8.4 Hz, 2H), 6.50 (s, 1H), 6.00~6.06 (br, 1H), 4.90 (s, 2H), 4.27 (t, J = 5.2 Hz, 2H), 4.17 (t, J = 5.2 Hz, 2H), 3.23 (s, 3H), 3.01 (d, J = 4.8 Hz, 3H), 2.90 (s, 3H). | 576 |

Compounds 183-184, depicted in the table below, was prepared using the method described in Example 10 and substituting the appropriate reactants and/or reagents.

| No. | Structure | NMR | MS (M + H)+ |
|---|---|---|---|
| 183 | 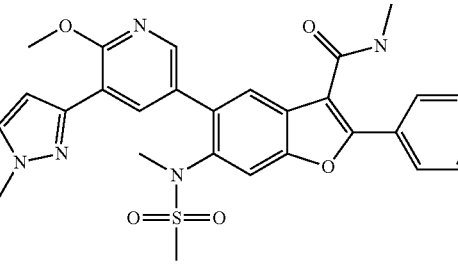 | ¹HNMR (CDCl₃, 400 MHz): δ 8.28 (s, 1H), 8.26 (s, 1H), 7.98~8.00 (m, 2H), 7.81 (s, 1H), 7.64 (s, 1H), 7.18~7.22 (m, 2H), 6.23 (s, 1H), 6.22 (s, 1H), 4.25~4.37 (m, 4H), 4.11 (s, 3H), 3.18 (s, 3H), 3.01 (s, 3H), 2.79 (s, 3H), 2.32~2.34 (m, 2H). | 606 |
| 184 | 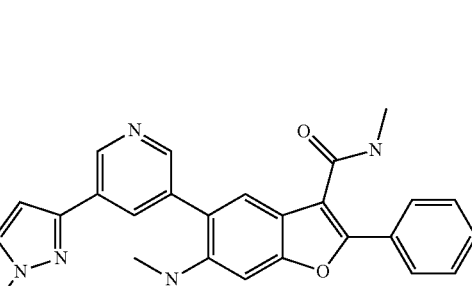 | ¹H-NMR (Methanol-d₄, 400 MHz) δ 8.89 (d, J = 4.0 Hz, 1H), 8.56 (d, J = 4.0 Hz, 1H), 8.26~8.27 (m, 1H), 7.96~8.00 (m, 2H), 7.91 (s, 1H), 7.74 (s, 1H), 7.27 (t, J = 8.0 Hz, 2H), 5.94 (s, 1H), 5.11 (t, J = 8.0 Hz, 2H), 4.35 (t, J = 8.0 Hz, 2H), 3.20 (s, 3H), 2.95 (s, 3H), 2.94 (s, 3H). | 562 |

Example 11

Preparation of Compound 98

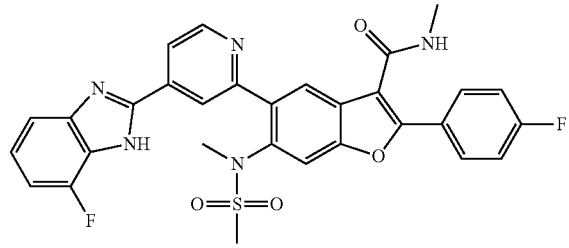

Step 1—Synthesis of 2-(2-chloropyridin-4-yl)-7-fluoro-1H-benzo[d]imidazole

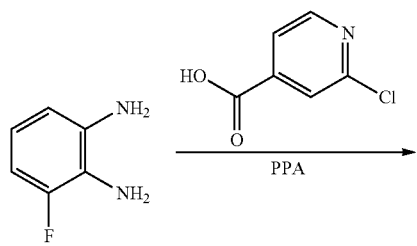

-continued

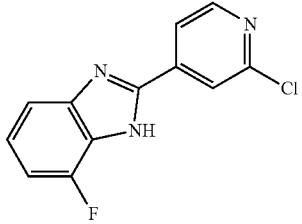

A mixture of 3-fluorobenzene-1,2-diamine (0.50 g, 3.96 mmol), 2-chloroisonicotinic acid (0.63 g, 4.00 mmol) and PPA (5 mL) was heated to 160° C. and allowed to stir at this temperature for 3 hours. The reaction mixture was added to water and basified with NaOH until pH~7. The solution was extracted with EtOAc, the organic extract was washed with brine, dried over Na₂SO₄ and concentrated in vacuo. The resulting residue was purified using column chromatography (eluted with PE:EtOAc=1:1) to provide 2-(2-chloropyridin-4-yl)-7-fluoro-1H-benzo[d]imidazole (600 mg, yield: 61%). ¹H-NMR (CDCl₃, 400 MHz) δ 8.56 (d, J=5.2 Hz, 1H), 8.01 (s, 1H), 7.86~7.88 (m, 1H), 7.42~7.46 (br s, 1H), 7.27~7.32 (m, 1H), 7.04~7.09 (m, 1H), 6.52~6.65 (m, 1H).

Step B—Synthesis of 5-(4-(7-fluoro-1H-benzo[d]imidazol-2-yl)-2-(4-fluorophenyl)-N-methyl-6-(N-methylmethylsulfonamido)benzofuran-3-carboxamide (Compound 98)

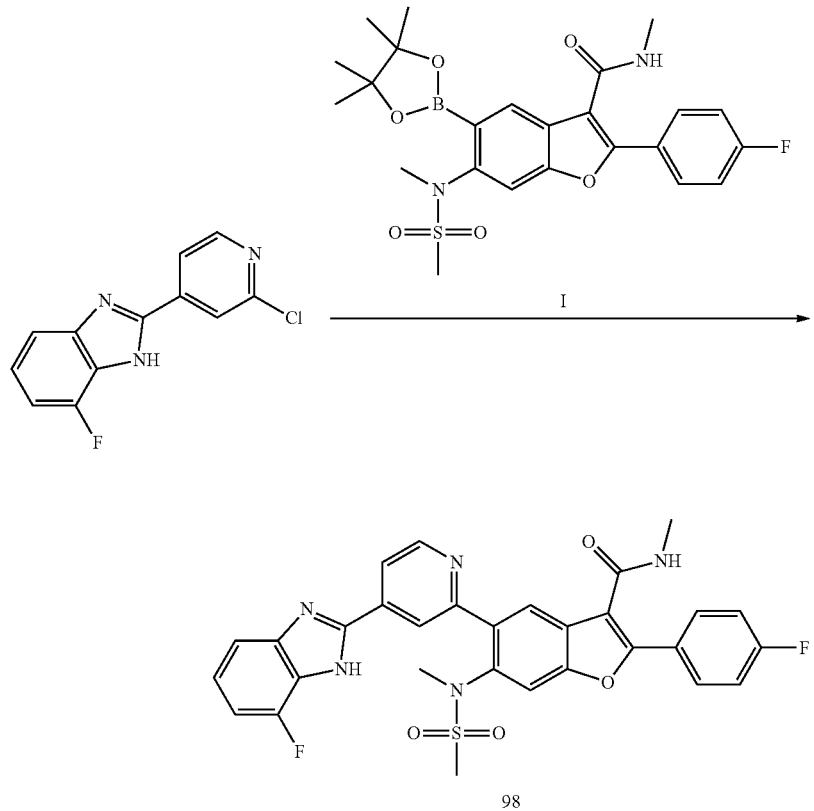

To a solution of 2-(2-chloropyridin-4-yl)-7-fluoro-1H-benzo[d]imidazole (40 mg, 0.16 mmol), K$_3$PO$_4$—H$_2$O (70 mg, 0.26 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 60 mg, 0.12 mmol) in DMF (5 mL) were added Pd$_2$(dba)$_3$ (5 mg) and X-Phos (10 mg) under N$_2$ protection. The mixture was allowed to stir at 100° C. for about 15 hours, then the reaction mixture was concentrated in vacuo and the resulting residue was suspended in water and extracted with EtOAc. The organic layer was washed with brine, dried over Na$_2$SO$_4$ and concentrated in vacuo. The resulting residue was purified using prep-TLC (eluted with PE:EtOAc=1:1) to provide Compound 98 (50 mg, yield: 71%). $^1$H-NMR (CDCl$_3$, 400 MHz) δ 8.58~8.63 (br s, 1H), 8.35~8.39 (br s, 1H), 8.04~8.12 (m, 2H), 7.83~7.87 (br s, 2H), 7.49 (s, 1H), 7.33~7.35 (m, 1H), 7.18~7.24 (m, 1H), 6.93~7.04 (m, 3H), 3.25 (s, 3H), 3.07 (d, J=4.8 Hz, 3H), 2.89 (s, 3H). MS (M+H)$^+$: 588.

Compounds 99~102, depicted in the table below, were prepared using the method described in Example 11 and substituting the appropriate reactants and/or reagents.

| No. | Structure | NMR | MS (M + H)$^+$ |
|---|---|---|---|
| 99 | (structure) | $^1$H-NMR (DMSO-d6, 400 MHz) δ 13.54 (s, 1H), 9.35 (s, 1H), 8.75 (s, 1H), 7.50~7.60 (m, 2H), 8.11 (s, 1H), 7.96~7.98 (m, 2H), 7.74 (s, 1H), 7.37~7.41 (m, 3H), 7.15~7.25 (m, 1H), 6.99~7.01 (m, 1H), 3.22 (s, 3H), 2.95 (s, 3H), 2.79 (d, J = 8.0 Hz, 3H). | 588 |

-continued

| No. | Structure | NMR | MS (M + H)+ |
|---|---|---|---|
| 100 | 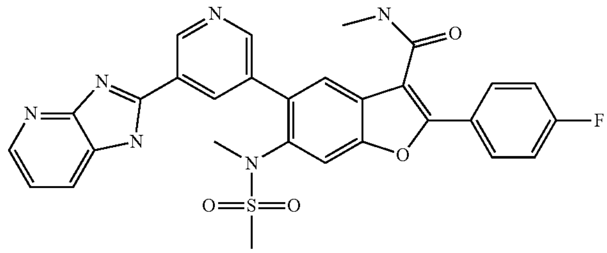 [SMILES: CNC(=O)c1c(-c2ccc(F)cc2)oc2cc(N(C)S(C)(=O)=O)c(-c3cncc(-c4nc5ncccc5[nH]4)c3)cc12] | 1H-NMR (Methanol-d4, 400 MHz) δ 9.39 (s, 1H), 8.88 (s, 1H), 8.75 (s, 1H), 8.55 (d, J = 5.2 Hz, 1H), 8.38 (d, J = 8.0 Hz, 1H), 7.96~8.04 (m, 3H), 7.86 (s, 1H), 7.56~7.62 (m, 1H), 7.30 (t, J = 8.8 Hz, 2H), 3.34 (s, 3H), 2.98 (s, 3H), 2.96 (s, 3H). | 571 |
| 101 | 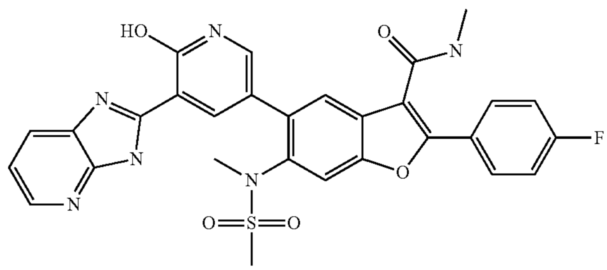 [SMILES: CNC(=O)c1c(-c2ccc(F)cc2)oc2cc(N(C)S(C)(=O)=O)c(-c3cnc(O)c(-c4nc5cccnc5[nH]4)c3)cc12] | 1H-NMR (Methanol-d4, 400 MHz) δ 8.97 (s, 1H), 8.50~8.60 (br, 2H), 7.92~7.98 (br, 4H), 7.81 (s, 1H), 7.62~7.70 (br, 1H), 7.28 (t, J = 8.0 Hz, 2H), 3.08 (s, 3H), 2.97 (s, 3H), 2.90 (s, 3H). | 587 |
| 102 | 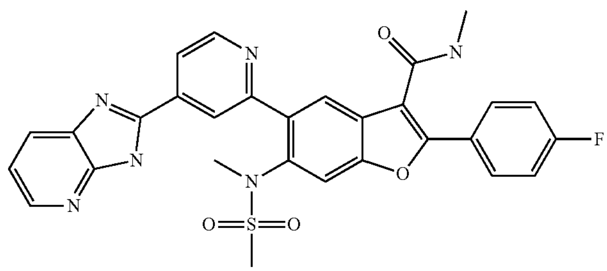 [SMILES: CNC(=O)c1c(-c2ccc(F)cc2)oc2cc(N(C)S(C)(=O)=O)c(-c3cc(-c4nc5cccnc5[nH]4)ccn3)cc12] | 1H-NMR (Methanol-d4, 400 MHz) δ 8.94 (d, J = 5.6 Hz, 1H), 8.61 (s, 2H), 8.45 (d, J = 8.0 Hz, 1H), 8.35~8.41 (m, 1H), 8.04 (s, 1H), 7.99 (s, 1H), 7.92~7.98 (m, 2H), 7.61~7.67 (m, 1H), 7.27 (t, J = 8.8 Hz, 2H), 3.45 (s, 3H), 2.96 (s, 3H), 2.94 (s, 3H). | 571 |

Compounds 185-186, depicted in the table below, were prepared using the method described in Example 11 and substituting the appropriate reactants and/or reagents.

| No. | Structure | NMR | MS (M + H)+ |
|---|---|---|---|
| 185 | 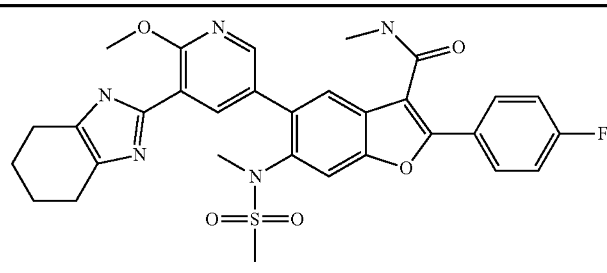 | 1HNMR (CDCl3, 400MHz): δ = 13.72 (br, 1H), 8.78 (s, 1H), 8.47 (s, 1H), 8.12 (d, J = 3.2 Hz, 1H), 8.00~8.04 (m, 2H), 7.86 (s, 1H), 7.56 (s, 1H), 7.13~7.17 (m, 2H), 4.15 (s, 3H), 3.24 (s, 3H), 3.04 (d, J = 4 Hz, 3H), 2.96 (s, 3H), 2.69 (s, 4H), 1.88 (s, 4H). | 604 |
| 186 | 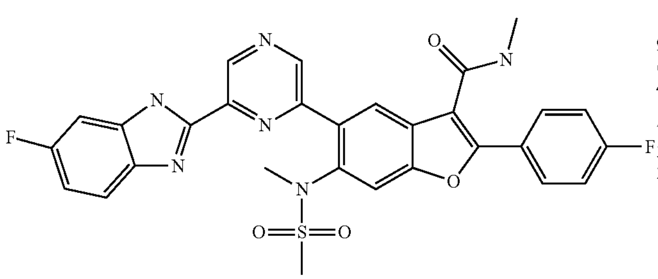 [SMILES: CNC(=O)c1c(-c2ccc(F)cc2)oc2cc(N(C)S(C)(=O)=O)c(-c3cncc(-c4nc5ccc(F)cc5[nH]4)n3)cc12] | 1HNMR (DMSO-d6, 300 Hz): δ = 9.40 (s, 1H), 8.92 (s, 1H), 8.51 (d, J = 4.8 Hz, 1H), 8.18 (s, 1H), 8.06 (s, 1H), 7.98 (m, 2H), 7.67 (m, 1H), 7.41 (m, 3H), 7.10 (m, 1H), 3.35 (s, 3H), 2.97 (s, 3H), 2.80 (d, J = 4.5 Hz, 3H). | 589 |

Example 12

Preparation of Compound 103

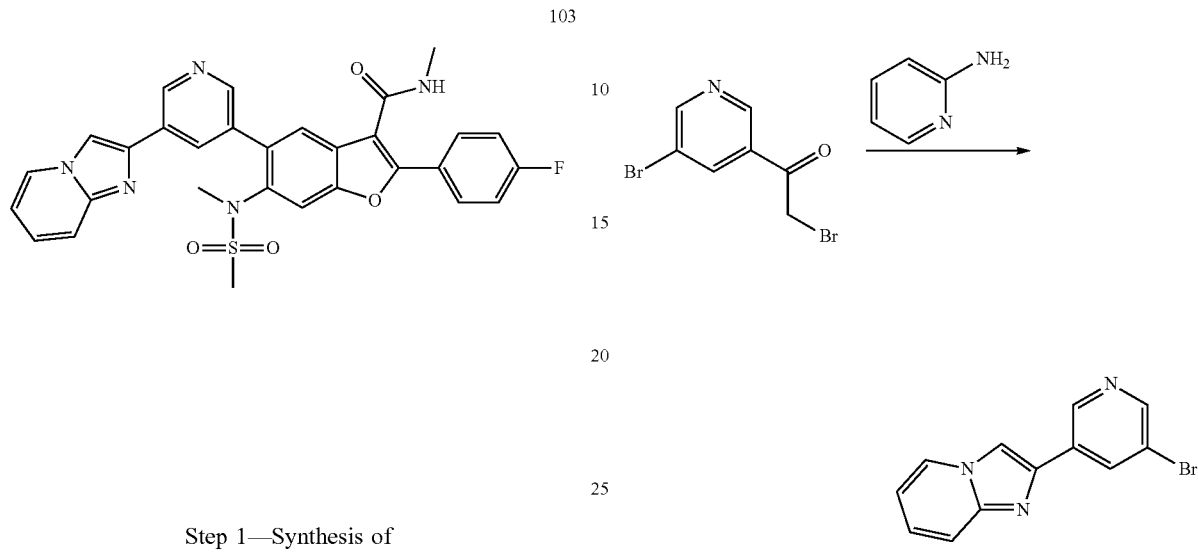

Step 1—Synthesis of 2-bromo-1-(5-bromopyridin-3-yl)ethanone

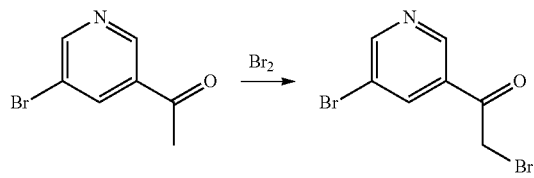

To a solution of 3-acetyl-5-bromopyridine (1.0 g, 5.0 mmol) in HBr (10 mL, HOAc solution), Br$_2$ (800 mg, 5.01 mmol) was added dropwise at room temperature. The reaction mixture was allowed to stir at room temperature for 3 hours. Then the reaction mixture was filtered and the collected solid was suspended with Na$_2$CO$_3$ solution and extracted with EtOAc. The combined organic extracts were washed with brine, dried over Na$_2$SO$_4$, filtered and concentrated in vacuo to provide pure 2-bromo-1-(5-bromopyridin-3-yl)ethanone (1.2 g, yield: 86.0%). $^1$H-NMR (CDCl$_3$, 400 MHz) δ 9.09 (d, J=1.6 Hz, 1H), 8.88 (d, J=2.4 Hz, 1H), 8.40 (t, J=2.0 Hz, 1H), 4.40 (s, 2H).

Step B—Synthesis of 2-(5-bromopyridin-3-yl)imidazo[1,2-a]pyridine

A mixture of 2-bromo-1-(5-bromopyridin-3-yl)ethanone (300 mg, 1.08 mmol) and 2-aminopyridine (110 mg, 1.17 mmol) in EtOH (10 mL) was allowed to stir at reflux for about 15 hours. The reaction mixture was concentrated in vacuo and the resulting residue was diluted with H$_2$O. The resulting solution was extracted with EtOAc and the organic extract was washed with brine, dried over Na$_2$SO$_4$, filtered and concentrated in vacuo. The resulting residue was purified using column chromatography (eluted with DCM:MeOH=50:1) to provide 2-(5-bromopyridin-3-yl)imidazo[1,2-a]pyridine (200 mg, yield: 68.0%). $^1$H-NMR (CDCl$_3$, 400 MHz) δ 9.03 (d, J=2.0 Hz, 1H), 8.61 (d, J=2.0 Hz, 1H), 8.47 (t, J=2.0 Hz, 1H), 8.15 (d, J=6.8 Hz, 1H), 7.94 (s, 1H), 7.62~7.65 (m, 1H), 7.21~7.25 (m, 1H), 6.82~6.86 (m, 1H). (M+H)$^+$: 274/276.

Step C—Synthesis of 2-(4-fluorophenyl)-5-(5-(imidazo[1,2-a]pyridin-2-yl)pyridin-3-yl)-N-methyl-6-(N-methylmethylsulfonamido)benzofuran-3-carboxamide (Compound 103)

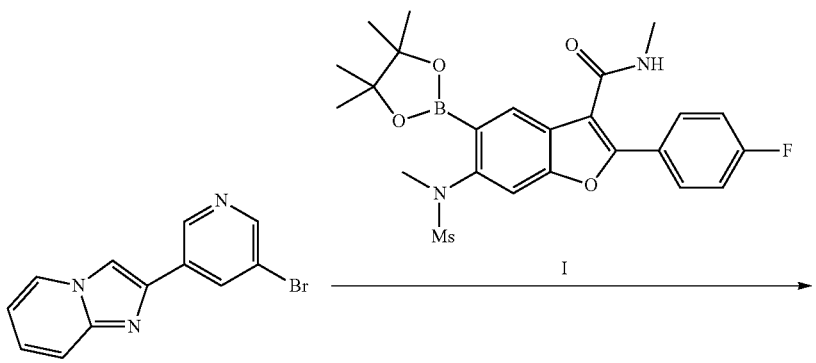

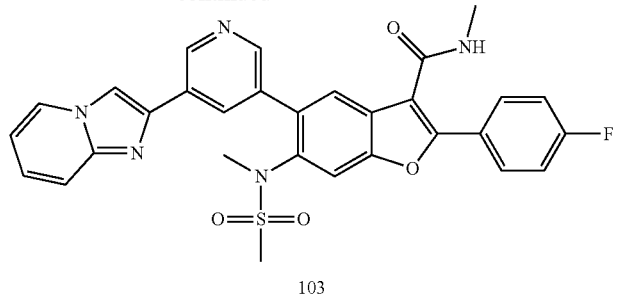

103

To a degassed solution of 2-(5-bromopyridin-3-yl)imidazo[1,2-a]pyridine (50 mg, 0.18 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 80 mg, 0.15 mmol) in 1,4-dioxane (2 mL) was added Pd(dppf)Cl$_2$ (10 mg) and K$_3$PO$_4$ (90 mg, 0.33 mmol) under N$_2$. The mixture was heated to 80° C. and allowed to stir at this temperature for about 15 hours. The reaction mixture was cooled to room temperature, filtered and washed with EtOAc. The filtrate was washed with H$_2$O, brine, dried over Na$_2$SO$_4$, filtered and concentrated in vacuo. The resulting residue was purified using prep-TLC (eluted with PE:EtOAc=1:1) to provide Compound 103 (31 mg, yield: 34.1%). $^1$H-NMR (CDCl$_3$, 400 MHz) δ 9.16 (s, 1H), 8.57 (s, 1H), 8.39 (s, 1H), 8.14 (d, J=6.8 Hz, 1H), 7.92~7.99 (m, 3H), 7.83 (d, J=1.2 Hz, 1H), 7.56~7.60 (m, 2H), 7.16~7.20 (m, 3H), 6.79~6.83 (m, 1H), 6.35~6.40 (br s, 1H), 3.12 (s, 3H), 3.02 (d, J=4.8 Hz, 3H), 2.79 (s, 3H). (M+H)$^+$: 570.

Compounds 104-107, depicted in the table below, were prepared using the method described in Example 12 and substituting the appropriate reactants and/or reagents.

| No. | Structure | NMR | MS (M + H)$^+$ |
|---|---|---|---|
| 104 | 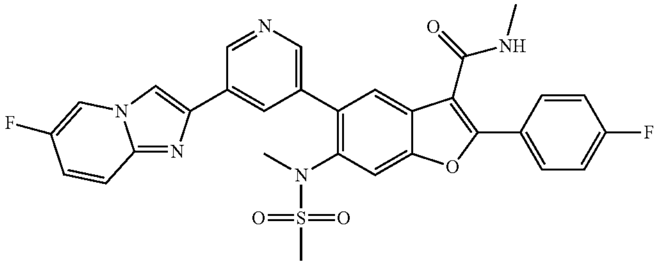 [SMILES: CNC(=O)c1c(-c2ccc(F)cc2)oc2cc(N(C)S(C)(=O)=O)c(-c3cncc(-c4cn5cc(F)ccc5n4)c3)cc12] | $^1$H-NMR (CDCl$_3$, 400 MHz) δ 9.15 (s, 1H), 8.59 (s, 1H), 8.38 (d, J = 2.0 Hz, 1H), 8.09~8.11 (m, 1H), 8.00 (s, 1H), 7.92~7.97 (m, 2H), 7.85 (s, 1H), 7.60 (s, 1H), 7.54~7.58 (m, 1H), 7.17~7.22 (m, 2H), 7.09~7.15 (m, 1H), 6.22~6.28 (br s, 1H), 3.11 (s, 3H), 3.01 (d J = 4.8 Hz, 3H), 2.82 (s, 3H). | 588 |
| 105 | 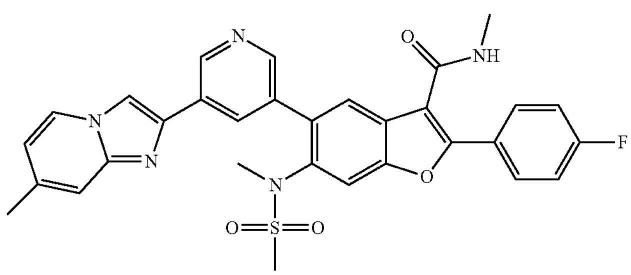 [SMILES: CNC(=O)c1c(-c2ccc(F)cc2)oc2cc(N(C)S(C)(=O)=O)c(-c3cncc(-c4cn5ccc(C)cc5n4)c3)cc12] | $^1$H-NMR (CDCl$_3$, 400 MHz) δ 9.32 (s, 1H), 9.07 (s, 1H), 8.75 (s, 1H), 8.42 (s, 1H), 8.27 (d, J = 6.4 Hz, 1H), 7.94~7.97 (m, 2H), 7.90 (s, 1H), 7.80 (s, 1H), 7.55 (s, 1H), 7.41~7.44 (m, 1H), 7.09~7.15 (m, 2H), 3.24 (s, 3H), 2.96 (d, J = 4.4 Hz, 3H), 2.85 (s, 3H), 2.55 (s, 3H), | 584 |
| 106 | 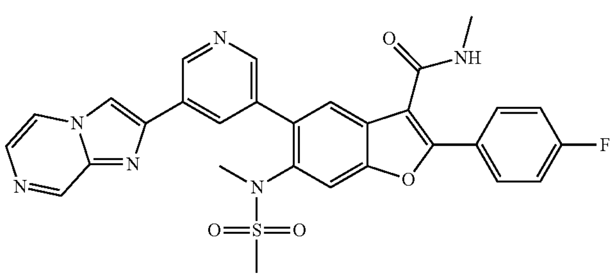 [SMILES: CNC(=O)c1c(-c2ccc(F)cc2)oc2cc(N(C)S(C)(=O)=O)c(-c3cncc(-c4cn5ccncc5n4)c3)cc12] | $^1$H-NMR (CDCl$_3$, 400 MHz) δ 9.28 (s, 1H), 9.10 (s, 1H), 8.85 (s, 1H), 8.76 (s, 1H), 8.26 (s, 1H), 8.15 (s, 1H), 7.93 (s, 1H), 7.91~7.87 (m, 2H), 7.61 (s, 1H), 7.20~7.16 (m, 2H), 7.05 (s, 1H), 6.33~6.39 (br s, 1H), 3.19 (s, 3H), 3.0 (d, J = 4.8 Hz, 3H), 2.96 (s, 3H), | 571 |

| No. | Structure | NMR | MS (M + H)+ |
|---|---|---|---|
| 107 | 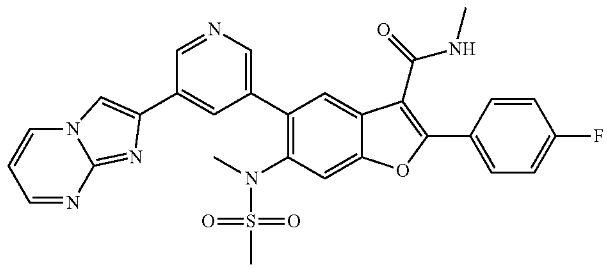 [SMILES: CNC(=O)c1c(-c2ccc(F)cc2)oc2cc(N(C)S(C)(=O)=O)c(-c3cncc(-c4cn5cccnc5n4)c3)cc12] | 1H-NMR (CDCl3, 400 MHz) δ 9.18 (s, 1H), 8.96 (d, J = 4.0 Hz, 1H), 8.68~8.74 (m, 2H), 8.69 (d, J = 4.0 Hz, 1H), 8.49 (s, 1H), 7.90~7.96 (m, 3H), 7.86 (s, 1H), 7.29~7.21 (m, 2H), 7.18 (t, J = 4.0 Hz, 1H), 3.30 (s, 3H), 2.99 (d, J = 4.8 Hz, 3H), 2.94 (s, 3H). | 571 |

Compounds 187 and 188, depicted in the table below, were prepared using the method described in Example 12 and substituting the appropriate reactants and/or reagents.

| No. | Structure | NMR | MS (M + H)+ |
|---|---|---|---|
| 187 | 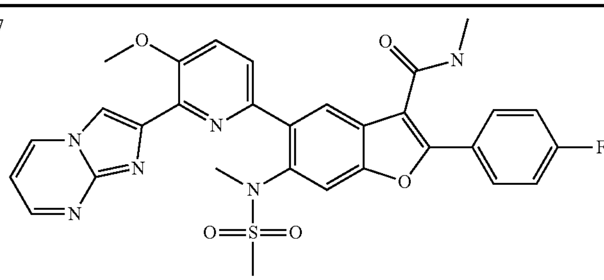 | 1H-NMR (CDCl3, 400 MHz) δ 8.21 (s, 1H), 8.00~8.09 (m, 2H), 7.96~7.99 (m, 2H), 7.60 (d, J = 8.4 Hz, 1H), 7.44~7.49 (m, 2H), 7.35 (d, J = 8.8 Hz, 1H), 7.27 (s, 1H), 7.08~7.12 (m, 2H), 7.03~7.07 (m, 1H), 6.74 (t, J = 6.0 Hz, 1H), 4.04 (s, 3H), 3.14 (s, 3H), 2.91 (d, J = 4.8 Hz, 3H), 2.85 (s, 3H). | 600 |
| 188 | 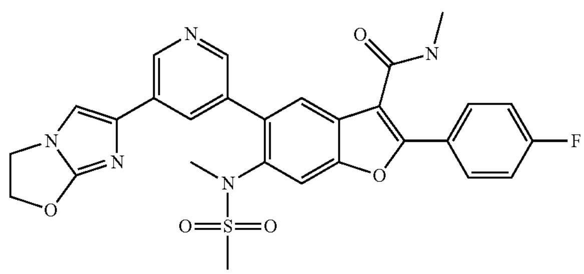 [SMILES: CNC(=O)c1c(-c2ccc(F)cc2)oc2cc(N(C)S(C)(=O)=O)c(-c3cncc(-c4cn5c(n4)OCC5)c3)cc12] | 1H-NMR (Methanol-d4, 400 MHz) δ 8.74 (d, J = 2.0 Hz, 1H), 8.40 (d, J = 2.0 Hz, 1H), 8.09 (t, J = 2.0 Hz, 1H), 7.91~7.95 (m, 2H), 7.83 (s, 1H), 7.68 (s, 1H), 7.30 (s, 1H), 7.23 (t, J = 8.8 Hz, 2H), 5.02 (t, J = 8.0 Hz, 2H), 4.22 (t, J = 8.0 Hz, 2H), 3.17 (s, 3H), 2.92 (s, 3H), 2.91 (s, 3H). | 562 |

Example 13

Preparation of Compound 108

Step A—Synthesis of tert-butyl 2-(6-chloropyrimidin-4-yl)-1H-indole-1-carboxylate

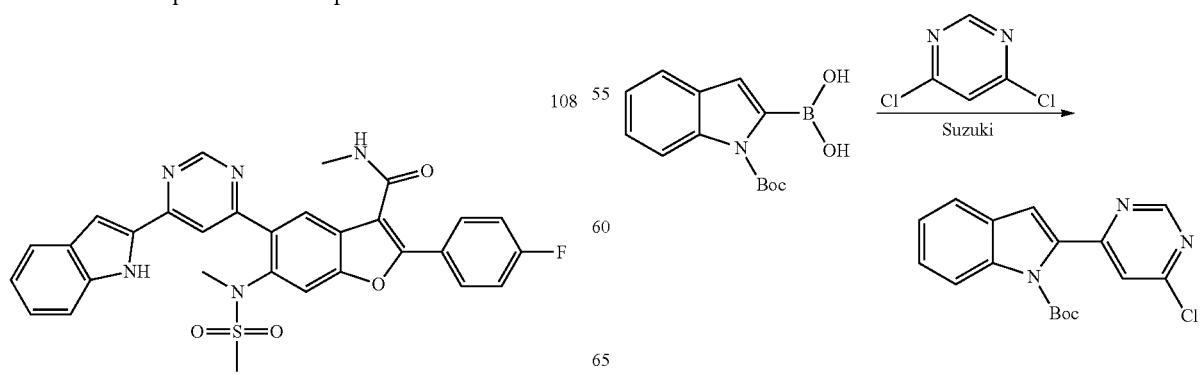

To a mixture of 1-(tert-butoxycarbonyl)-1H-indol-2-ylboronic acid (100 mg, 0.39 mmol), 4,6-dichloropyrimidine (290 mg, 1.9 mmol) and K₃PO₄·3H₂O (310 mg, 1.2 mmol) in DMF (2 mL), Pd(dppf)Cl₂ (28 mg, 0.04 mmol) was added under N₂ atmosphere. The mixture was allowed to stir at 25° C. for 12 hours. Water was added, and then extracted with EtOAc. The combined organic layers were washed with brine, dried over Na₂SO₄. After being concentrated in vacuo, the resulting residue was purified using prep-TLC (eluted with PE:EtOAc=4:1) to provide 2-(6-chloropyrimidin-4-yl)-1H-indole-1-carboxylate (100 mg, yield: 80%). ¹H-NMR (CDCl₃, 400 MHz) δ 9.01 (s, 1H), 8.16 (d, J=4.8 Hz, 1H), 7.63 (d, J=7.6 Hz, 1H), 7.53 (s, 1H), 7.41~7.45 (m, 1H), 7.29~7.31 (m, 1H), 7.02 (s, 1H), 1.54 (s, 9H).

Step B—Synthesis of 2-(6-chloropyrimidin-4-yl)-1H-indole

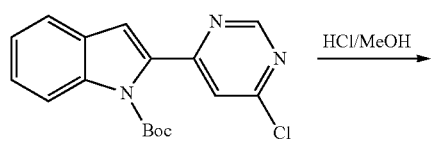

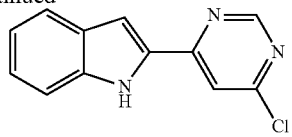

To a mixture of 2-(6-chloropyrimidin-4-yl)-1H-indole-1-carboxylate (91 mg, 0.28 mmol) in MeOH (1 mL), 4 N HCl in MeOH (2 mL) was added at 0° C. The mixture was allowed to stir at 25° C. for 1 hour, then the reaction mixture was concentrated in vacuo. The resulting residue was purified using prep-TLC (eluted with PE:EtOAc=4:1) to provide 2-(6-chloropyrimidin-4-yl)-1H-indole (60 mg, yield: 90%).

Step C—Synthesis of 5-(6-(1H-indol-2-yl)pyrimidin-4-yl)-2-(4-fluorophenyl)-N-methyl-6-(N-methylmethylsulfonamido)benzofuran-3-carboxamide (Compound 108)

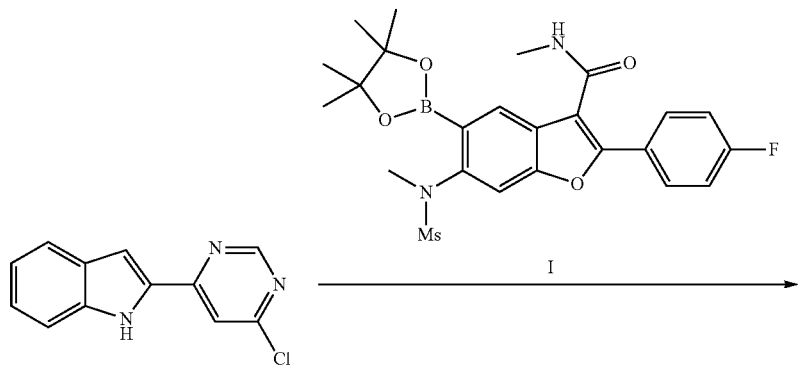

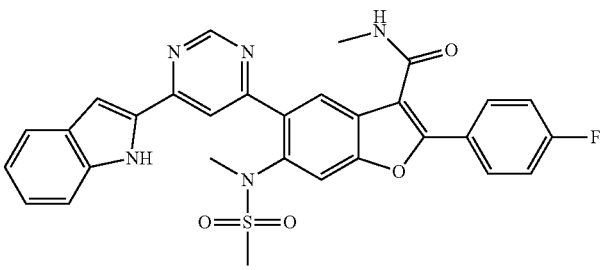

108

A mixture of 2-(6-chloropyrimidin-4-yl)-1H-indole (72 mg, 0.3 mmol), 2-(4-fluorophenyl)-N-methyl-6-(N-methyl-methylsulfonamido)-5-(4,4,5,5-tetramethyl-1,3,2-dioxa-borolan-2-yl)benzofuran-3-carboxamide (Compound I, 174 mg, 0.3 mmol), $K_3PO_4 \cdot 3H_2O$ (250 mg, 0.9 mmol), $Pd_2(dba)_3$ (14 mg, 0.016 mmol), X-Phos (15 mg, 0.032 mmol) was allowed to stir in dioxane/$H_2O$ (5 mL, 4/1) at 110° C. for 12 hours. The reaction mixture was cooled to 25° C., diluted with water and extracted with ethyl acetate. The organic extract was washed with brine, dried over $Na_2SO_4$, filtered and concentrated in vacuo. The resulting residue was purified using prep-HPLC to provide Compound 108 (35 mg, yield: 18%). $^1$H-NMR (CDCl$_3$, 400 MHz) δ 9.65 (s, 1H), 9.25 (s, 1H), 8.25 (s, 1H), 8.13 (s, 1H), 7.95~7.99 (m, 2H), 7.60~7.65 (m, 2H), 7.38~7.45 (m, 2H), 7.28 (m, 1H), 7.09~7.16 (m, 3H), 6.35 (s, 1H), 3.23 (s, 3H), 2.97 (d, J=4.8 Hz, 3H), 2.95 (s, 3H). MS (M+H)$^+$: 570.

Compounds 109-149, depicted in the table below, were prepared using the method described in Example 13 and substituting the appropriate reactants and/or reagents.

| No. | Structure | NMR | MS (M + H)$^+$ |
|---|---|---|---|
| 109 | 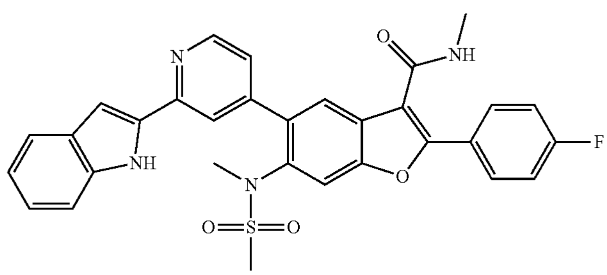 [SMILES: CNC(=O)c1c(-c2ccc(F)cc2)oc2cc(N(C)S(C)(=O)=O)c(-c3ccnc(-c4cc5ccccc5[nH]4)c3)cc12] | $^1$H-NMR (Methanol-d4, 400 MHz) δ 8.70 (d, J = 6.0 Hz, 1H), 8.41 (s, 1H), 8.12 (s, 1H), 8.00~8.03 (m, 3H), 7.88 (d, J = 5.6 Hz, 1H), 7.73 (d, J = 8.0 Hz, 1H), 7.50~7.55 (m, 2H), 7.32~7.36 (m, 3H), 7.18 (d, J = 1.6 Hz, 1H), 3.46 (s, 3H), 3.03 (s, 3H), 2.98 (s, 3H). | 569 |
| 110 | 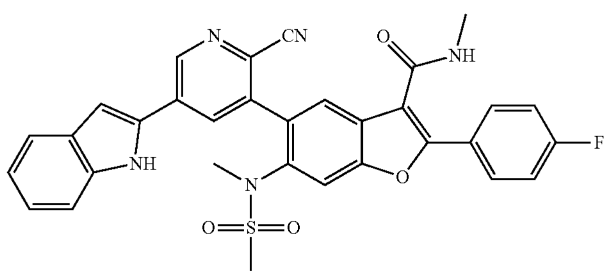 [SMILES: CNC(=O)c1c(-c2ccc(F)cc2)oc2cc(N(C)S(C)(=O)=O)c(-c3cc(-c4cc5ccccc5[nH]4)cnc3C#N)cc12] | $^1$H-NMR (CDCl$_3$, 400 MHz) 9.00 (s, 1H), 8.92 (d, J = 2.0 Hz, 1H), 8.15 (d, J = 2.0 Hz, 1H), 7.86~7.89 (m, 3H), 7.56 (d, J = 8.0 Hz, 2H), 7.31 (d, J = 8.0 Hz, 1H), 7.05~7.18 (m, 4H), 6.87 (s, 1H), 5.87 (d, J = 4.4 Hz, 1H), 3.18 (s, 3H), 2.91 (d, J = 4.8 Hz, 3H), 2.90 (s, 3H). | 594 |
| 111 | 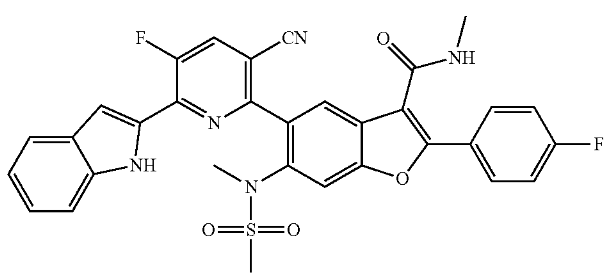 [SMILES: CNC(=O)c1c(-c2ccc(F)cc2)oc2cc(N(C)S(C)(=O)=O)c(-c3nc(-c4cc5ccccc5[nH]4)c(F)cc3C#N)cc12] | $^1$H-NMR (Methanol-d4, 400 MHz) δ 8.03 (d, J = 11.2 Hz, 1H), 7.89~7.93 (m, 4H), 7.55 (d, J = 8.0 Hz, 1H), 7.34 (d, J = 8.0 Hz, 1H), 7.28 (d, J = 4.0 Hz, 1H), 7.21 (t, J = 8.4 Hz, 2H), 7.12 (t, J = 7.2 Hz, 1H), 6.96 (t, J = 7.6 Hz, 1H), 3.36 (s, 3H), 2.85 (s, 3H), 2.80 (s, 3H). | 612 |
| 112 | 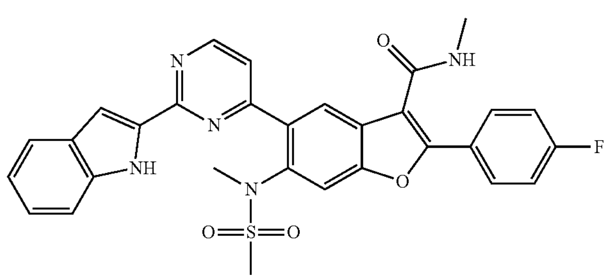 [SMILES: CNC(=O)c1c(-c2ccc(F)cc2)oc2cc(N(C)S(C)(=O)=O)c(-c3ccnc(-c4cc5ccccc5[nH]4)n3)cc12] | $^1$H-NMR (CDCl$_3$, 400 MHz) δ 9.64 (s, 1H), 8.71 (d, J = 5.2 Hz, 1H), 8.07 (s, 1H), 7.85~7.89 (m, 2H), 7.61 (d, J = 7.6 Hz, 1H), 7.56 (s, 1H), 7.35~7.38 (m, 3H), 7.12~7.21 (m, 3H), 7.04~7.07 (m, 1H), 5.91 (d, J = 4.8 Hz, 1H), 3.23 (s, 3H), 2.91 (d, J = 4.8 Hz, 3H), 2.81 (s, 3H). | 570 |

| No. | Structure | NMR | MS (M + H)+ |
|---|---|---|---|
| 113 | 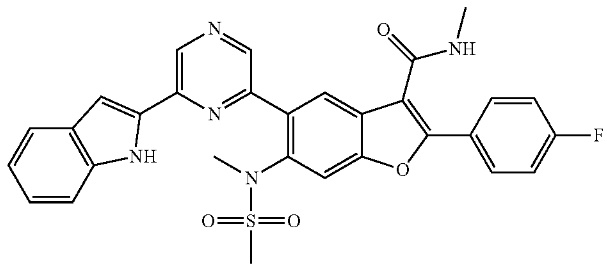 [SMILES: CNC(=O)c1c(-c2ccc(F)cc2)oc2cc(N(C)S(C)(=O)=O)c(-c3cncc(-c4cc5ccccc5[nH]4)n3)cc12] | ¹H-NMR (CDCl₃, 400 MHz) δ 9.82 (s, 1H), 9.00 (s, 1H), 8.60 (s, 1H), 8.09 (s, 1H), 7.87~7.91 (m, 2H), 7.61(t, J = 9.6 Hz, 2H), 7.38 (d, J = 8.0 Hz, 1H), 7.50~7.18 (m, 5H), 5.83 (d, J = 4.8 Hz, 1H), 3.13 (s, 3H), 2.92 (d, J = 5.2 Hz, 3H), 2.88 (s, 3H). | 570 |
| 114 | 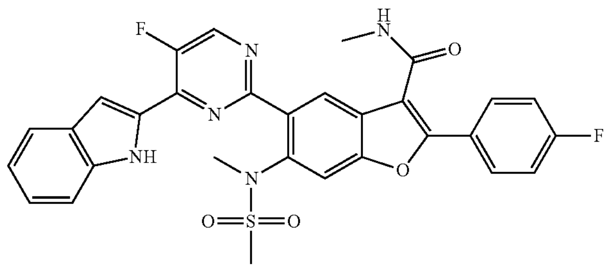 [SMILES: CNC(=O)c1c(-c2ccc(F)cc2)oc2cc(N(C)S(C)(=O)=O)c(-c3ncc(F)c(-c4cc5ccccc5[nH]4)n3)cc12] | ¹H-NMR (CDCl₃, 400 MHz) δ 10.52 (s, 1H), 8.65 (s, 1H), 8.56 (s, 1H), 7.93~7.97 (m, 2H), 7.71~7.73 (m, 1H), 7.61 (s, 1H), 7.46~7.50 (m, 2H), 7.20~7.32 (m, 1H), 7.12~7.18 (m, 3H), 6.04~6.09 (br, 1H), 3.26 (s, 3H), 3.09 (s, 3H), 2.99 (d, J = 4.8 Hz, 3H). | 588 |
| 115 | 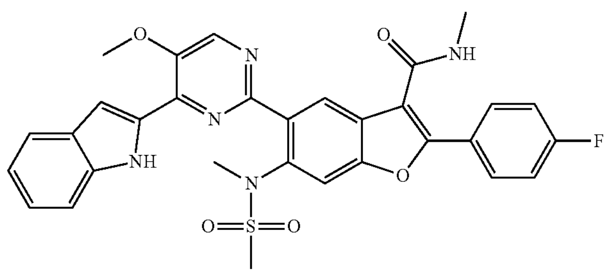 [SMILES: CNC(=O)c1c(-c2ccc(F)cc2)oc2cc(N(C)S(C)(=O)=O)c(-c3ncc(OC)c(-c4cc5ccccc5[nH]4)n3)cc12] | ¹H-NMR (CDCl₃, 400 MHz) δ 10.24 (s, 1H), 8.46 (s, 1H), 8.38 (s, 1H), 7.93~7.97 (m, 2H), 7.63 (d, J = 8.0 Hz, 1H), 7.60 (s, 1H), 7.52 (d, J = 1.2 Hz, 1H), 7.43 (d, J = 8.0 Hz, 1H), 7.21~7.23 (m, 1H), 7.07~7.16 (m, 2H), 7.06 (d, J = 1.2 Hz, 1H), 5.95 (d, J = 4.0 Hz, 1H), 4.12 (s, 3H), 3.19 (s, 3H), 2.96 (d, J = 4.4 Hz, 6H). | 600 |
| 116 | 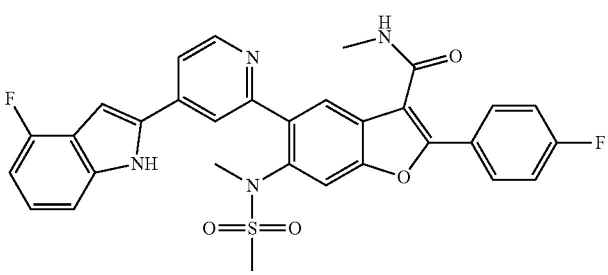 | ¹H-NMR (Methanol-d4, 400 MHz) δ 8.65~8.70 (m, 1H), 8.31~8.35 (m, 1H), 8.09~8.19 (m, 2H), 7.92~8.02 (m, 3H), 7.52~7.56 (m, 1H), 7.20~7.30 (m, 4H), 6.75~6.79 (m, 1H), 3.45 (s, 3H), 2.95 (s, 3H), 2.93 (s, 3H). | 587 |
| 117 | 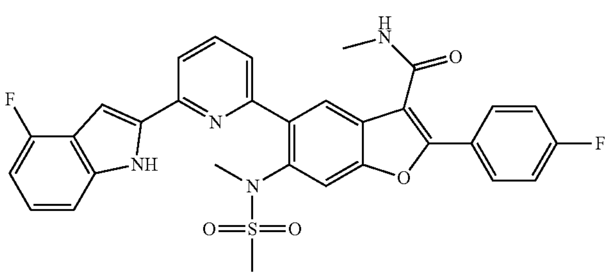 [SMILES: CNC(=O)c1c(-c2ccc(F)cc2)oc2cc(N(C)S(C)(=O)=O)c(-c3cccc(-c4cc5c(F)cccc5[nH]4)n3)cc12] | ¹H-NMR (CDCl₃, 400 MHz) δ 11.87 (s, 1H), 8.05~8.18 (m, 5H), 7.62~7.66 (m, 3H). 7.42~7.43 (m, 1H), 7.18~7.24 (m, 4H), 6.79~6.83 (m, 1H), 3.31 (s, 3H), 3.03 (d, J = 4.8 Hz, 3H), 2.92 (s, 3H). | 587 |

| No. | Structure | NMR | MS (M + H)+ |
|---|---|---|---|
| 118 | 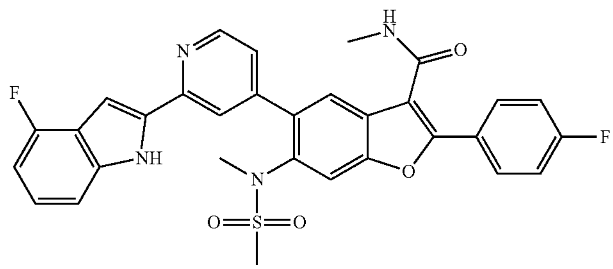 [SMILES: CNC(=O)c1c(-c2ccc(F)cc2)oc2cc(N(C)S(C)(=O)=O)c(-c3ccnc(-c4cc5c(F)cccc5[nH]4)c3)cc12] | ¹H-NMR (CDCl₃, 400 MHz) δ 8.80 (s, 1H), 8.54 (s, 1H), 8.09 (s, 1H), 7.86~7.99 (m, 5H), 7.73~7.75 (m, 1H), 7.66~7.68 (m, 1H), 7.37~7.42 (m, 2H), 7.20~7.25 (m, 1H), 6.96~7.00 (m, 1H), 6.86~6.87 (m, 1H), 3.28 (s, 3H), 3.04 (s, 3H), 2.79 (d, J = 4.4 Hz, 3H). | 587 |
| 119 | 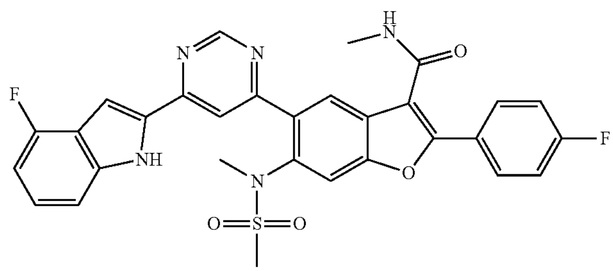 [SMILES: CNC(=O)c1c(-c2ccc(F)cc2)oc2cc(N(C)S(C)(=O)=O)c(-c3cc(-c4cc5c(F)cccc5[nH]4)ncn3)cc12] | ¹H-NMR (CDCl₃, 400 MHz) δ 9.90 (s, 1H), 9.21 (s, 1H), 8.26 (s, 1H), 8.17 (s, 1H), 7.94~7.98 (m, 2H), 7.59 (s, 1H), 7.46 (s, 1H), 7.12~7.20 (m, 3H), 6.71~6.78 (m, 2H), 5.13 (s, 1H), 3.29 (s, 3H), 3.00 (s, 3H), 2.92 (s, 3H). | 588 |
| 120 | 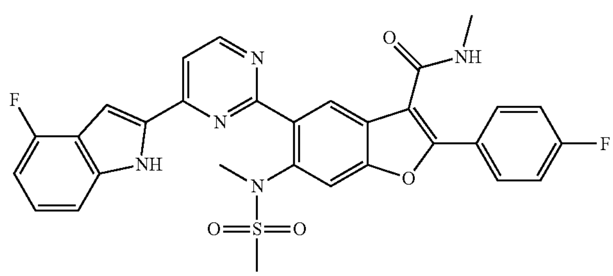 [SMILES: CNC(=O)c1c(-c2ccc(F)cc2)oc2cc(N(C)S(C)(=O)=O)c(-c3nccc(-c4cc5c(F)cccc5[nH]4)n3)cc12] | ¹H-NMR (CDCl₃, 400 MHz) δ 10.79 (s, 1H), 8.83 (d, J = 5.2 Hz, 1H), 8.67 (s, 1H), 7.99~8.02 (m, 2H), 7.68 (d, J = 5.2 Hz, 1H), 7.64 (s, 1H), 7.29~7.32 (m, 3H), 7.22~7.24 (m, 2H), 6.81 (t, J = 8.8 Hz, 1H), 6.08 (s, 1H), 3.27 (s, 3H), 3.16 (s, 3H), 3.03 (d, J = 4.8 Hz, 3H). | 588 |
| 121 | 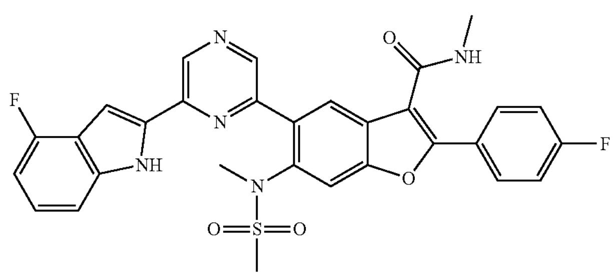 [SMILES: CNC(=O)c1c(-c2ccc(F)cc2)oc2cc(N(C)S(C)(=O)=O)c(-c3cncc(-c4cc5c(F)cccc5[nH]4)n3)cc12] | ¹H-NMR (DMSO-d6, 400 MHz) δ 12.03 (s, 1H), 9.29 (s, 1H), 8.72 (s, 1H), 8.52 (d, J = 4.4 Hz, 1H), 8.16 (s, 1H), 7.98~8.03 (m, 3H), 7.38~7.46 (m, 3H), 7.32 (d, J = 8.4 Hz, 1H), 7.09~7.14 (m, 1H), 6.78~6.82 (m, 1H), 3.33 (s, 3H), 2.97 (s, 3H), 2.80 (d, J = 5.2 Hz, 3H). | 588 |
| 122 | 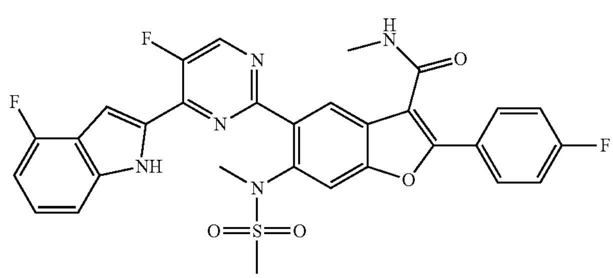 [SMILES: CNC(=O)c1c(-c2ccc(F)cc2)oc2cc(N(C)S(C)(=O)=O)c(-c3ncc(F)c(-c4cc5c(F)cccc5[nH]4)n3)cc12] | ¹H-NMR (CDCl₃, 400 MHz) δ 10.73 (s, 1H), 8.72 (s, 1H), 8.63 (s, 1H), 7.98~8.01 (m, 2H), 7.62 (s, 1H), 7.54 (s, 1H), 7.30~7.32 (m, 1H), 7.19~7.23 (m, 3H), 6.78~6.82 (m, 1H), 5.98~6.03 (br, 1H), 3.26 (s, 3H), 3.15 (s, 3H), 3.04 (d, J = 4.8 Hz, 3H). | 606 |

-continued

| No. | Structure | NMR | MS (M + H)+ |
|---|---|---|---|
| 123 | 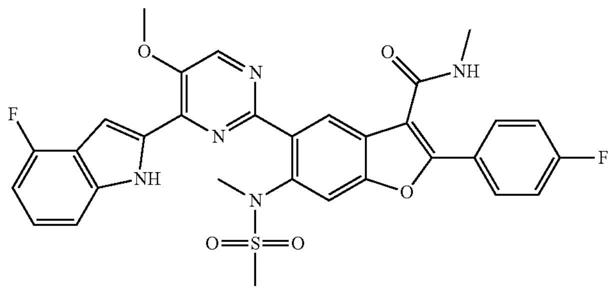 [SMILES: CNC(=O)c1c(-c2ccc(F)cc2)oc2cc(N(C)S(C)(=O)=O)c(-c3ncc(OC)c(-c4cc5c(F)cccc5[nH]4)n3)cc12] | 1H-NMR (CDCl3, 400 MHz) δ 10.66 (s, 1H), 8.57 (s, 1H), 8.31 (s, 1H), 8.03~8.06 (m, 2H), 7.76 (d, J = 3.2 Hz, 1H), 7.61 (s, 1H), 7.29~7.32 (m, 2H), 7.16 (t, J = 8.8 Hz, 2H), 6.80~6.85 (m, 2H), 4.08 (s, 3H), 3.19 (s, 3H), 3.17 (s, 3H), 3.08 (d, J = 4.8 Hz, 3H). | 618 |
| 124 | 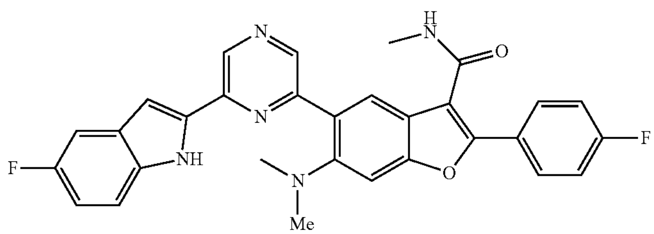 [SMILES: CNC(=O)c1c(-c2ccc(F)cc2)oc2cc(N(C)C)c(-c3cncc(-c4cc5cc(F)ccc5[nH]4)n3)cc12] | 1H-NMR (CDCl3, 400 MHz) δ 9.98 (s, 1H), 9.04 (s, 1H), 8.68 (s, 1H), 8.17 (s, 1H), 7.91~7.95 (m, 2H), 7.64 (s, 1H), 7.34~7.37 (m, 1H), 7.29~7.31 (m, 1H), 7.20 (s, 2H), 7.12 (d, J = 1.2 Hz, 1H), 6.96~7.01 (m, 1H), 5.86 (d, J = 4.8 Hz, 1H), 3.18 (s, 3H), 2.96~3.04 (m, 6H). | 588 |
| 125 | 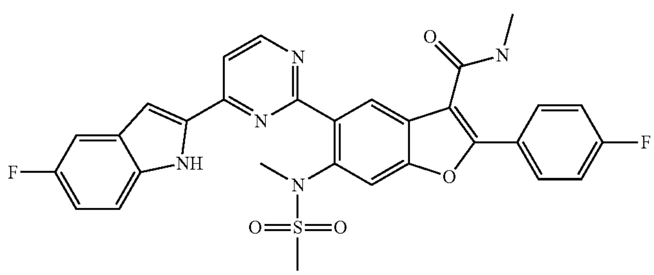 [SMILES: CNC(=O)c1c(-c2ccc(F)cc2)oc2cc(N(C)S(C)(=O)=O)c(-c3nccc(-c4cc5cc(F)ccc5[nH]4)n3)cc12] | 1H-NMR (CDCl3, 400 MHz) δ 10.62 (s, 1H), 8.81 (d, J = 5.2 Hz, 1H), 8.65 (s, 1H), 7.97~8.01 (m, 2H), 7.63 (d, J = 6.4 Hz, 2H), 7.40~7.44 (m, 1H), 7.00~7.31 (m, 5H), 5.98 (d, J = 3.6 Hz, 1H), 3.24 (s, 3H), 3.13 (s, 3H), 3.02 (d, J = 4.8 Hz, 3H). | 588 |
| 126 | 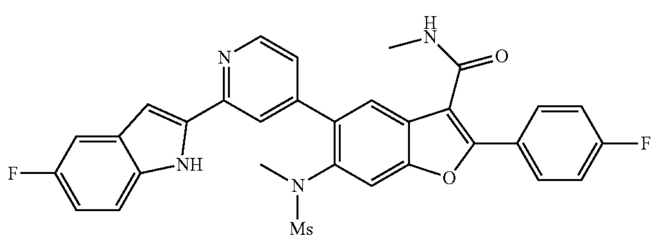 [SMILES: CNC(=O)c1c(-c2ccc(F)cc2)oc2cc(N(C)S(C)(=O)=O)c(-c3ccnc(-c4cc5cc(F)ccc5[nH]4)c3)cc12] | 1H-NMR (CDCl3, 400 MHz) δ 9.45 (s, 1H), 8.65 (s, 1H), 8.10 (s, 1H), 8.05 (s, 1H), 7.94~7.98 (m, 2H), 7.52 (t, J = 2.0 Hz, 2H), 7.32~7.36 (m, 1H), 7.25~7.28 (m, 1H), 7.14~7.19 (m, 2H), 6.92 (d, J = 12 Hz, 1H), 6.95~6.99 (m, 1H), 6.11 (d, J = 4.4 Hz, 1H), 3.16 (s, 3H), 3.01 (s, 3H), 2.99 (d, J = 4.8 Hz, 3H). | 587 |
| 127 | 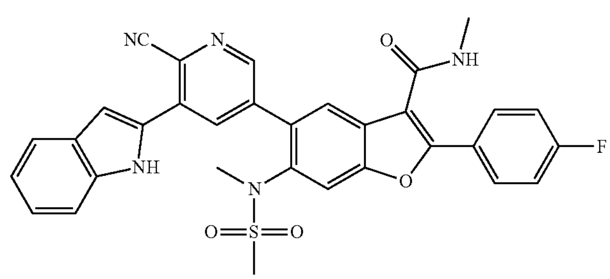 [SMILES: CNC(=O)c1c(-c2ccc(F)cc2)oc2cc(N(C)S(C)(=O)=O)c(-c3cnc(C#N)c(-c4cc5ccccc5[nH]4)c3)cc12] | 1H-NMR (CDCl3, 400 MHz) δ 9.42 (s, 1H), 8.49 (d, J = 1.6 Hz, 1H), 8.26 (d, J = 2.0 Hz, 1H), 7.90 (s, 1H), 7.77~7.81 (m, 2H), 7.59 (d, J = 7.6 Hz, 1H), 7.45 (s, 1H), 7.34 (d, J = 8.4 Hz, 1H), 7.24 (d, J = 1.2 Hz, 1H), 7.04~7.16 (m, 4H), 5.91 (d, J = 4.4 Hz, 1H), 3.06 (s, 3H), 2.93 (s, 3H), 2.91 (s, 3H). | 594 |
| 128 | 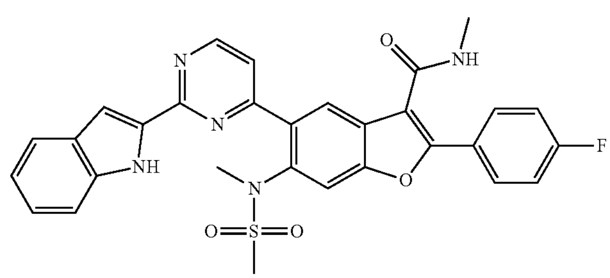 [SMILES: CNC(=O)c1c(-c2ccc(F)cc2)oc2cc(N(C)S(C)(=O)=O)c(-c3ccnc(-c4cc5ccccc5[nH]4)n3)cc12] | 1H-NMR (CDCl3, 400 MHz) δ 9.64 (s, 1H), 8.71 (d, J = 5.2 Hz, 1H), 8.07 (s, 1H), 7.85~7.89 (m, 2H), 7.61 (d, J = 7.6 Hz, 1H), 7.56 (s, 1H), 7.35~7.38 (m, 3H), 7.12~7.21 (m, 3H), 7.04~7.07 (m, 1H), 5.91 (d, J = 4.8 Hz, 1H), 3.23 (s, 3H), 2.91 (d, J = 4.8 Hz, 3H), 2.81 (s, 3H). | 570 |

| No. | Structure | NMR | MS (M + H)+ |
|---|---|---|---|
| 129 | 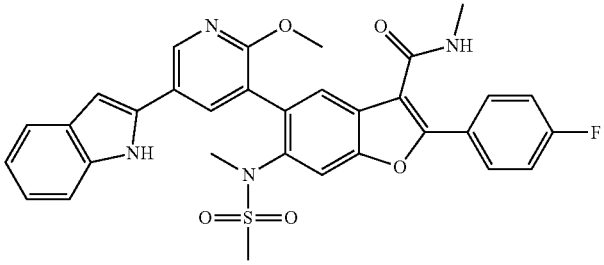 [SMILES: CNC(=O)c1c(-c2ccc(F)cc2)oc2cc(N(C)S(C)(=O)=O)c(-c3cc(-c4cc5ccccc5[nH]4)cnc3OC)cc12] | ¹H-NMR (CDCl₃, 400 MHz) δ 8.93 (s, 1H), 8.53 (d, J = 2.4 Hz, 1H), 7.91~7.96 (m, 3H), 7.80 (s, 1H), 7.60 (d, J = 8.0 Hz, 1H), 7.55 (s, 1H), 7.37 (t, J = 7.6 Hz, 1H), 7.65~7.22 (m, 3H), 7.09~7.12 (m, 1H), 6.73 (d, J = 1.2 Hz, 1H), 5.96 (d, J = 4.8 Hz, 1H), 3.95 (s, 3H), 3.12 (s, 3H), 2.95 (d, J = 4.8 Hz, 3H), 2.75 (s, 3H). | 599 |
| 130 | 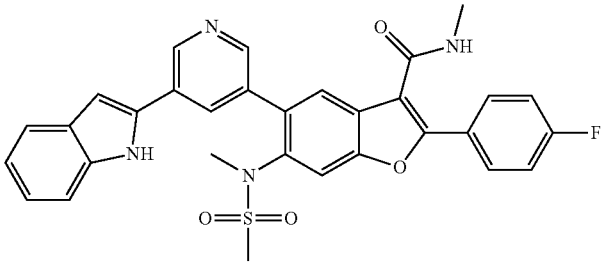 [SMILES: CNC(=O)c1c(-c2ccc(F)cc2)oc2cc(N(C)S(C)(=O)=O)c(-c3cncc(-c4cc5ccccc5[nH]4)c3)cc12] | ¹H-NMR (CDCl₃, 400 MHz) δ 9.43 (s, 1H), 8.94 (d, J = 1.6 Hz, 1H), 8.51 (d, J = 1.6 Hz, 1H), 8.22 (s, 1H), 7.86~7.91 (m, 3H), 7.62 (d, J = 7.6 Hz, 1H), 7.52 (s, 1H), 7.43 (d, J = 8.0 Hz, 1H), 7.09~7.22 (m, 4H), 6.88 (s, 1H), 6.08 (d, J = 4.8 Hz, 1H), 2.98 (s, 6H), 2.93 (d, J = 4.8 Hz, 3H). | 569 |
| 131 | 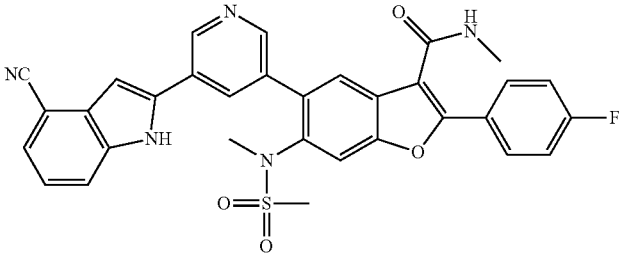 [SMILES: CNC(=O)c1c(-c2ccc(F)cc2)oc2cc(N(C)S(C)(=O)=O)c(-c3cncc(-c4cc5c(C#N)cccc5[nH]4)c3)cc12] | ¹H-NMR (CDCl₃, 400 MHz) δ 10.31 (s, 1H), 8.81 (s, 1H), 8.50 (s, 1H), 8.15 (s, 1H), 7.81~7.85 (m, 2H), 7.77 (s, 1H), 7.59 (d, J = 8.4 Hz, 1H), 7.51 (s, 1H), 7.41 (d, J = 7.2 Hz, 1H), 7.12~7.20 (m, 3H), 6.85 (s, 1H), 6.47 (d, J = 4.4 Hz, 1H), 3.06 (s, 3H), 3.92 (s, 3H), 2.93 (d, J = 4.4 Hz, 3H). | 594 |
| 132 | 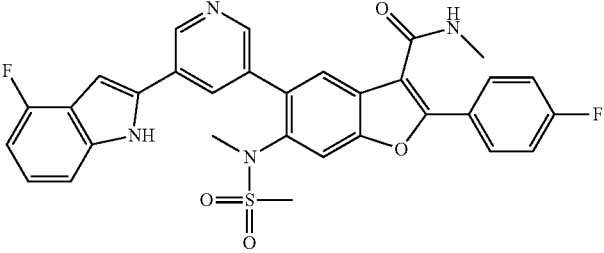 [SMILES: CNC(=O)c1c(-c2ccc(F)cc2)oc2cc(N(C)S(C)(=O)=O)c(-c3cncc(-c4cc5c(F)cccc5[nH]4)c3)cc12] | ¹H-NMR (Methanol-d4, 400 MHz) δ 8.97 (d, J = 0.12 Hz, 1H), 8.56 (s, 1H), 8.35 (s, 1H), 7.95~7.99 (m, 2H), 7.93 (s, 1H), 7.79 (s, 1H), 7.23~7.28 (m, 3H), 7.05~7.11 (m, 2H), 6.68~6.73 (m, 1H), 3.23 (s, 3H), 2.97 (s, 3H), 2.93 (s, 3H). | 587 |
| 133 | 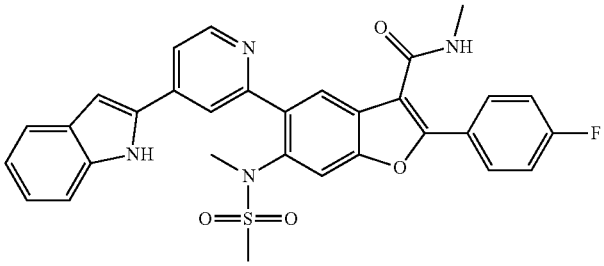 | ¹H-NMR (CDCl₃, 400 MHz) δ 9.48 (s, 1H), 8.64 (d, J = 5.2 Hz, 1H), 8.09 (d, J = 2.0 Hz, 1H), 8.05 (s, 1H), 7.94~7.97 (m, 2H), 7.64 (d, J = 8.0 Hz, 1H), 7.55 (d, J = 5.2 Hz, 1H), 7.53 (s, 1H), 7.43 (d, J = 8.0 Hz, 1H), 7.11~7.25 (m, 4H), 7.01 (s, 1H), 6.16 (s, 1H), 3.09 (d, J = 0.8 Hz, 3H), 3.03 (s, 3H), 2.98 (d, J = 4.8 Hz, 3H). | 569 |

| No. | Structure | NMR | MS (M + H)+ |
|---|---|---|---|
| 134 | 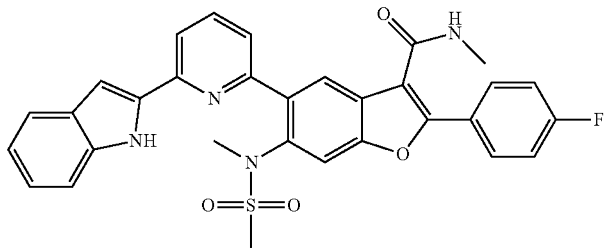 [SMILES: CNC(=O)c1c(-c2ccc(F)cc2)oc2cc(N(C)S(C)(=O)=O)c(-c3cccc(-c4cc5ccccc5[nH]4)n3)cc12] | ¹H-NMR (CDCl₃, 400 MHz) δ 9.76 (s, 1H), 7.94 (s, 1H), 7.87~7.89 (m, 2H), 7.71 (d, J = 0.28 Hz, 2H), 7.58 (d, J = 7.6 Hz, 1H), 7.54 (s, 1H), 7.33~7.37 (m, 2H), 7.13 (t, J = 8.4 Hz, 3H), 7.03 (t, J = 7.4 Hz, 1H), 6.97 (s, 1H), 5.93 (s, 1H), 3.08 (s, 3H), 2.88 (d, J = 4.8 Hz, 3H), 2.75 (s, 3H). | 569 |
| 135 | 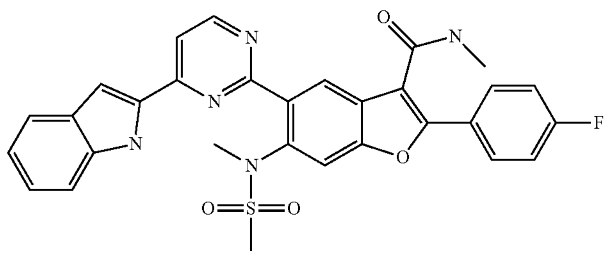 [SMILES: CNC(=O)c1c(-c2ccc(F)cc2)oc2cc(N(C)S(C)(=O)=O)c(-c3nccc(-c4cc5ccccc5[nH]4)n3)cc12] | ¹H-NMR (CDCl₃, 400 MHz) δ 9.76 (s, 1H), 7.94 (s, 1H), 7.87~7.89 (m, 2H), 7.71 (d, J = 2.8 Hz, 2H), 7.58 (d, J = 7.6 Hz, 1H), 7.54 (s, 1H), 7.33~7.37 (m, 2H), 7.13 (t, J = 8.4 Hz, 3H), 7.03 (t, J = 7.4 Hz, 1H), 5.93 (s, 1H), 3.08 (s, 3H), 2.88 (d, J = 4.8 Hz, 3H), 2.75 (s, 3H). | 570 |
| 136 | 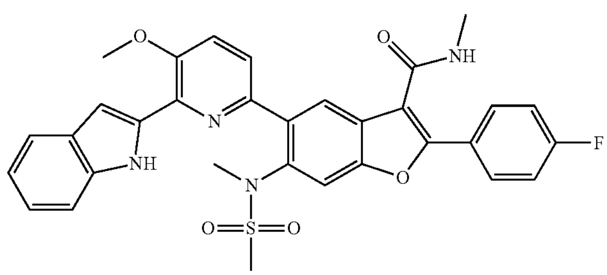 [SMILES: CNC(=O)c1c(-c2ccc(F)cc2)oc2cc(N(C)S(C)(=O)=O)c(-c3ccc(OC)c(-c4cc5ccccc5[nH]4)n3)cc12] | ¹H-NMR (CDCl₃, 400 MHz) δ 9.83 (s, 1H), 7.86~7.90 (m, 3H), 7.60 (d, J = 8.0 Hz, 1H), 7.52 (s, 1H), 7.28~7.40 (m, 3H), 7.10~7.14 (m, 4H), 7.02 (t, J = 7.2 Hz, 1H), 5.95 (d, J = 4.4 Hz, 1H), 4.00 (s, 3H), 3.07 (s, 3H), 2.88 (d, J = 4.8 Hz, 3H), 2.72 (s, 3H). | 599 |
| 137 | 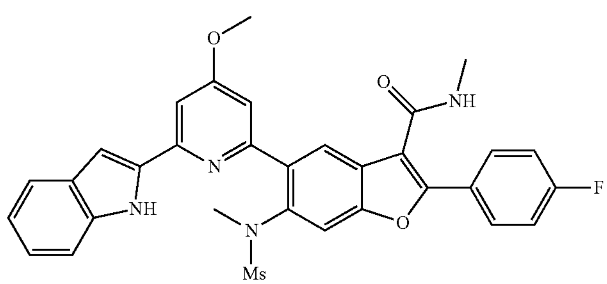 [SMILES: CNC(=O)c1c(-c2ccc(F)cc2)oc2cc(N(C)S(C)(=O)=O)c(-c3cc(OC)cc(-c4cc5ccccc5[nH]4)n3)cc12] | ¹H-NMR (CDCl₃, 400 MHz) δ 9.79 (d, J = 2.0 Hz, 1H), 8.06 (s, 1H), 7.99 (s, 2H), 7.65 (d, J = 8.0 Hz, 1H), 7.62 (s, 1H), 7.43 (d, J = 8.0 Hz, 1H), 7.34 (s, 1H), 7.19~7.23 (m, 3H), 7.11 (t, J = 7.6 Hz, 2H), 7.06 (s, 1H), 5.95 (s, 1H), 3.99 (s, 3H), 3.16 (s, 3H), 3.00 (d, J = 4.8 Hz, 3H), 2.92 (s, 3H). | 599 |
| 138 | 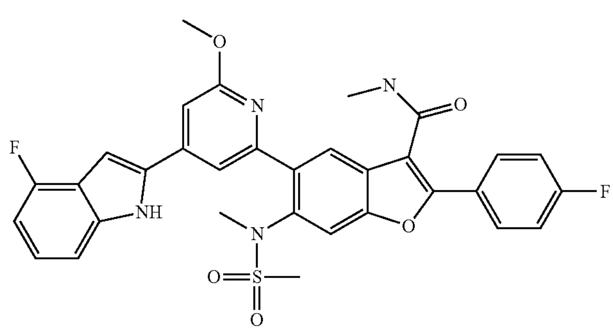 [SMILES: CNC(=O)c1c(-c2ccc(F)cc2)oc2cc(N(C)S(C)(=O)=O)c(-c3cc(-c4cc5c(F)cccc5[nH]4)cc(OC)n3)cc12] | ¹H-NMR (CDCl₃, 400 MHz) δ 9.48 (s, 1H), 8.10 (d, J = 8.0 Hz, 1H), 7.94 (s, 2H), 7.60 (s, 1H), 7.52 (d, J = 1.6 Hz, 1H), 7.20~7.11 (m, 4H), 6.97 (s, 2H), 6.78 (t, J = 8.8 Hz, 1H), 6.03 (s, 1H), 4.00 (d, J = 2.4 Hz, 3H), 3.16 (s, 3H), 3.04 (d, J = 2.4 Hz, 3H), 2.99 (t, J = 2.4 Hz, 3H). | 617 |

| No. | Structure | NMR | MS (M + H)+ |
|---|---|---|---|
| 139 | 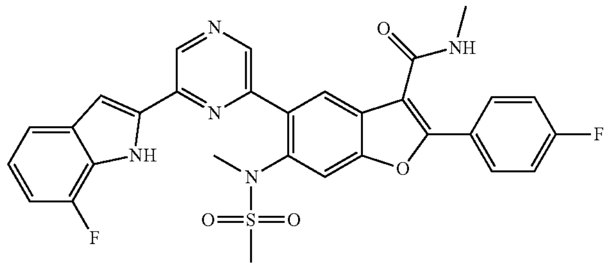 [SMILES: CNC(=O)c1c(-c2ccc(F)cc2)oc2cc(N(C)S(C)(=O)=O)c(-c3cncc(-c4cc5cccc(F)c5[nH]4)n3)cc12] | ¹H-NMR (CDCl₃, 400 MHz) δ 12.17 (s, 1H), 9.29 (s, 1H), 8.79 (s, 1H), 8.58 (d, J = 4.8 Hz, 1H), 8.18 (s, 1H), 8.10 (s, 1H), 8.06~8.03 (m, 2H), 7.49~7.42 (m, 4H), 7.05~7.02 (m, 2H), 3.36 (s, 3H), 3.02 (s, 3H), 2.85 (d, J = 4.8 Hz, 3H). | 588 |
| 140 | 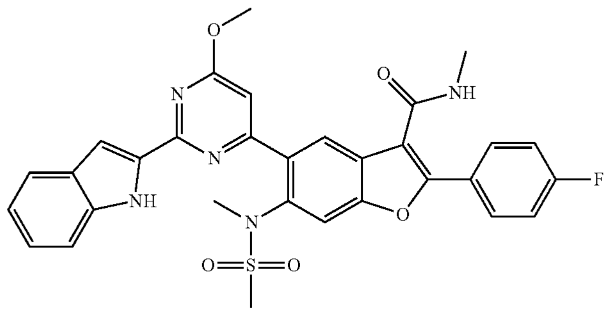 [SMILES: CNC(=O)c1c(-c2ccc(F)cc2)oc2cc(N(C)S(C)(=O)=O)c(-c3cc(OC)nc(-c4cc5ccccc5[nH]4)n3)cc12] | ¹H-NMR (CDCl₃, 400 MHz) δ 9.56 (s, 1H), 8.00 (s, 1H), 7.86~7.90 (m, 2H), 7.57~7.63 (m, 2H), 7.37~7.39 (m, 2H), 7.12~7.17 (m, 3H), 7.04~7.07 (m, 1H), 6.78 (s, 1H), 5.85 (s, 1H), 4.08 (s, 3H), 3.21 (s, 3H), 2.92 (d, J = 6.4 Hz, 3H), 2.82 (s, 3H). | 600 |
| 141 | 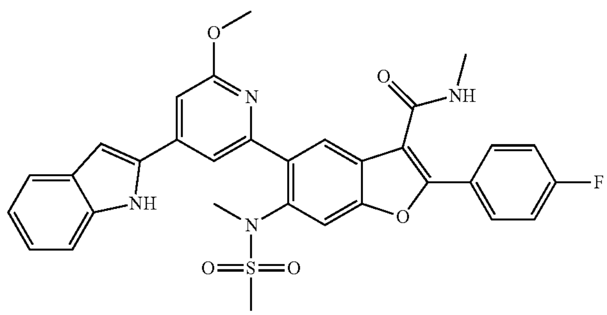 [SMILES: CNC(=O)c1c(-c2ccc(F)cc2)oc2cc(N(C)S(C)(=O)=O)c(-c3cc(-c4cc5ccccc5[nH]4)cc(OC)n3)cc12] | ¹H-NMR (CDCl₃, 400 MHz) δ 9.28 (s, 1H), 8.07 (d, J = 2.8 Hz, 1H), 7.92~7.95 (m, 2H), 7.59~7.64 (m, 2H), 7.53 (s, 1H), 7.40 (d, J = 8.0 Hz, 1H), 7.09~7.22 (m, 4H), 6.96 (d, J = 9.6 Hz, 2H), 6.05 (s, 1H), 3.99 (s, 3H), 3.17 (s, 3H), 2.97 (s, 6H). | 599 |
| 142 | 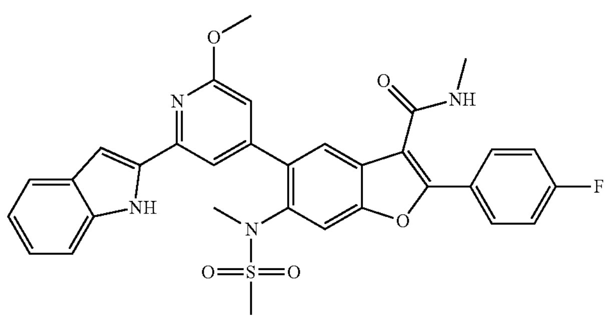 | ¹H-NMR (CDCl₃, 400 MHz) δ 9.38 (s, 1H), 7.92~7.96 (m, 2H), 7.86 (s, 1H), 7.64 (d, J = 7.6 Hz, 2H), 7.56 (s, 1H), 7.46 (d, J = 8.0 Hz, 1H), 7.21 (t, J = 4.8 Hz, 3H), 7.12 (t, J = 7.2 Hz, 1H), 7.04 (s, 1H), 6.75 (s, 1H), 5.86 (d, J = 4.0 Hz, 1H), 4.11 (s, 3H), 3.16 (s, 3H), 3.00 (d, J = 4.8 Hz, 3H), 2.86 (s, 3H). | 599 |
| 143 | 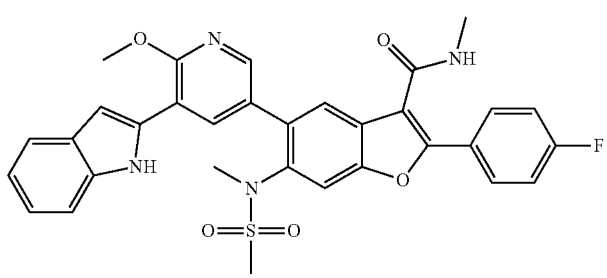 [SMILES: CNC(=O)c1c(-c2ccc(F)cc2)oc2cc(N(C)S(C)(=O)=O)c(-c3cnc(OC)c(-c4cc5ccccc5[nH]4)c3)cc12] | ¹H-NMR (CDCl₃, 400 MHz) δ 9.68 (s, 1H), 8.28 (t, J = 1.2 Hz, 1H), 8.14 (s, 1H), 7.90~7.95 (m, 2H), 7.82 (s, 1H), 7.62 (d, J = 8.0 Hz, 1H), 7.57 (s, 1H), 7.44 (d, J = 8.0 Hz, 1H), 7.08~7.22 (m, 4H), 7.03 (s, 1H), 5.98 (d, J = 4.4 Hz, 1H), 4.19 (s, 3H), 3.08 (s, 3H), 2.97 (d, J = 4.8 Hz, 3H), 2.89 (s, 3H). | 599 |

| No. | Structure | NMR | MS (M + H)+ |
|---|---|---|---|
| 144 | 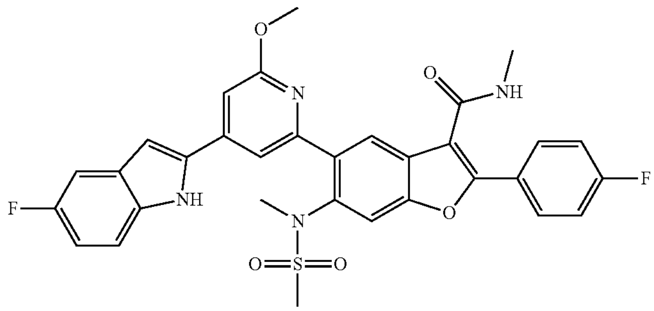 [SMILES: CNC(=O)c1c(-c2ccc(F)cc2)oc2cc(N(C)S(C)(=O)=O)c(-c3cc(-c4cc5cc(F)ccc5[nH]4)cc(OC)n3)cc12] | ¹H-NMR (CDCl₃, 400 MHz) δ 9.90 (s, 1H), 8.03 (s, 1H), 7.91~7.95 (m, 2H), 7.71 (s, 1H), 7.55 (s, 1H), 7.32~7.35 (m, 1H), 7.21~7.24 (m, 3H), 7.02 (s, 1H), 6.97~7.01 (m, 1H), 6.90 (s, 1H), 6.65 (s, 1H), 4.02 (s, 3H), 3.20 (s, 3H), 3.10 (s, 3H), 3.00 (d, J = 4.8 Hz, 3H). | 617 |
| 145 | 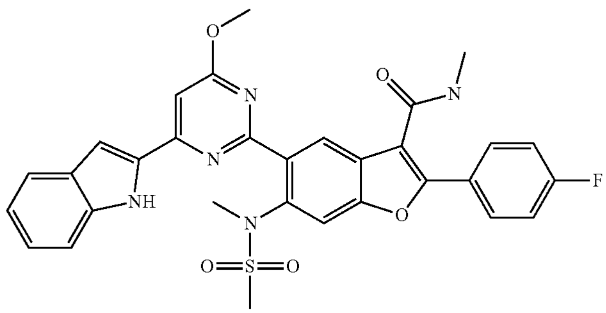 [SMILES: CNC(=O)c1c(-c2ccc(F)cc2)oc2cc(N(C)S(C)(=O)=O)c(-c3nc(OC)cc(-c4cc5ccccc5[nH]4)n3)cc12] | ¹H-NMR (CDCl₃, 400 MHz) δ 9.47 (s, 1H), 8.15 (s, 1H), 7.93~7.96 (m, 2H), 7.76 (s, 1H), 7.63~7.67 (m, 2H), 7.41~7.43 (m, 1H), 7.37~7.42 (m, 2H), 7.26~7.29 (m, 2H), 7.09~7.21 (m, 1H), 5.90 (s, 1H), 4.13 (s, 3H), 3.26 (s, 3H), 2.98 (d, J = 4.8 Hz, 3H), 2.94 (s, 3H). | 600 |
| 146 | 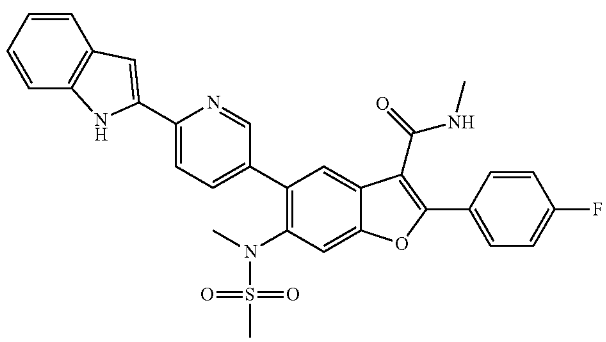 [SMILES: CNC(=O)c1c(-c2ccc(F)cc2)oc2cc(N(C)S(C)(=O)=O)c(-c3ccc(-c4cc5ccccc5[nH]4)nc3)cc12] | ¹H-NMR (DMSO-d6, 400 MHz) δ 11.71 (s, 1H), 8.67 (d, J = 1.6 Hz, 1H), 8.50 (d, J = 4.8 Hz, 1H), 8.08 (s, 1H), 7.98~8.03 (m, 3H), 7.90~7.93 (m, 1H), 7.70 (s, 1H), 7.55 (d, J = 7.6 Hz, 1H), 7.37~7.45 (m, 3H), 7.18 (s, 1H), 7.10 (t, J = 7.4 Hz, 1H), 6.98 (t, J = 7.4 Hz, 1H), 3.16 (s, 3H), 3.01 (s, 3H), 2.80 (d, J = 4.0 Hz, 3H). | 569 |
| 147 | 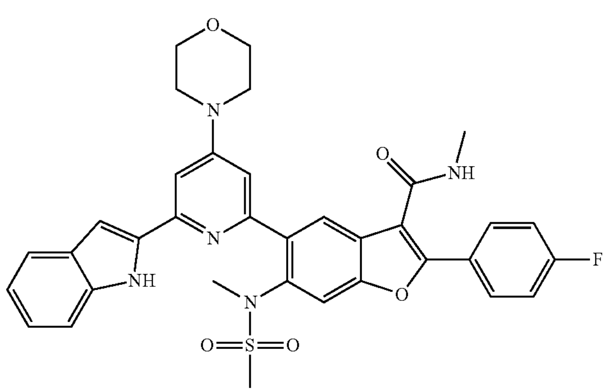 [SMILES: CNC(=O)c1c(-c2ccc(F)cc2)oc2cc(N(C)S(C)(=O)=O)c(-c3cc(N4CCOCC4)cc(-c4cc5ccccc5[nH]4)n3)cc12] | ¹H-NMR (CDCl₃, 400 MHz) δ 9.77 (s, 1H), 8.02 (s, 1H), 7.95~7.98 (m, 2H), 7.64 (d, J = 8.0 Hz, 1H), 7.59 (s, 1H), 7.40 (d, J = 8.0 Hz, 1H), 7.20 (t, J = 8.8 Hz, 4H), 7.10 (t, J = 7.2 Hz, 1H), 7.00 (d, J = 6.4 Hz, 2H), 5.98 (s, 1H), 3.87~3.90 (m, 4H), 3.44 (s, 4H), 3.13 (s, 3H), 2.98 (d, J = 4.8 Hz, 3H), 2.92 (s, 3H). | 654 |

| No. | Structure | NMR | MS (M + H)+ |
|---|---|---|---|
| 148 | 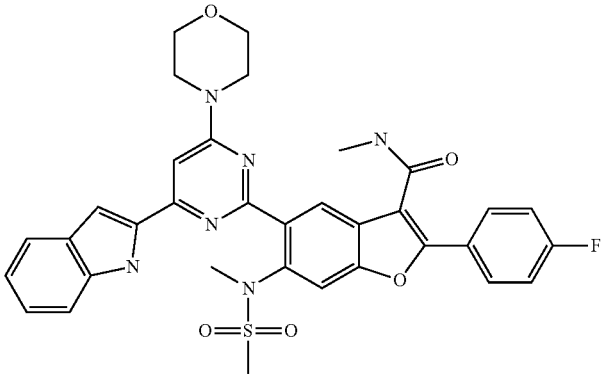 [SMILES: CNC(=O)c1c(-c2ccc(F)cc2)oc2cc(N(C)S(C)(=O)=O)c(-c3nc(-c4cc5ccccc5[nH]4)cc(N4CCOCC4)n3)cc12] | ¹H-NMR (Methanol-d4, 400 MHz) δ 8.21 (s, 1H), 8.06 (s, 1H), 7.94~7.97 (m, 2H), 7.66 (d, J = 8.0 Hz, 1H), 7.46~7.49 (m, 2H), 7.27~7.32 (m, 4H), 7.10~7.14 (m, 1H), 3.99 (s, 4H), 3.85 (s, 4H), 3.47 (s, 3H), 2.99 (s, 3H), 2.94 (s, 3H). | 655 |
| 149 | 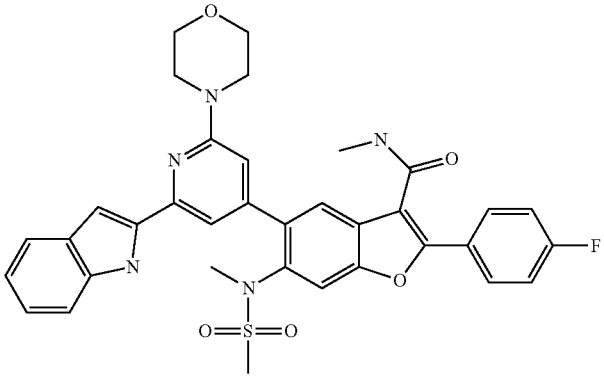 [SMILES: CNC(=O)c1c(-c2ccc(F)cc2)oc2cc(N(C)S(C)(=O)=O)c(-c3cc(-c4cc5ccccc5[nH]4)nc(N4CCOCC4)c3)cc12] | ¹H-NMR (CDCl₃, 400 MHz) δ 9.26 (s, 1H), 8.11 (s, 1H), 7.96~8.00 (m, 2H), 7.63 (d, J = 7.6 Hz, 1H), 7.53 (s, 1H), 7.43 (d, J = 6.4 Hz, 2H), 7.91~7.22 (m, 4H), 6.96 (d, J = 1.2 Hz, 1H), 6.91 (s, 1H), 5.94 (d, J = 3.6 Hz, 1H), 3.85~3.88 (m, 4H), 3.61~3.64 (m, 4H), 3.12 (s, 3H), 3.03 (s, 3H), 3.00 (d, J = 4.8 Hz, 3H). | 654 |

Compounds 189-248, depicted in the table below, were prepared using the method described in Example 13 and substituting the appropriate reactants and/or reagents.

| No. | Structure | NMR | MS (M + H)+ |
|---|---|---|---|
| 189 | 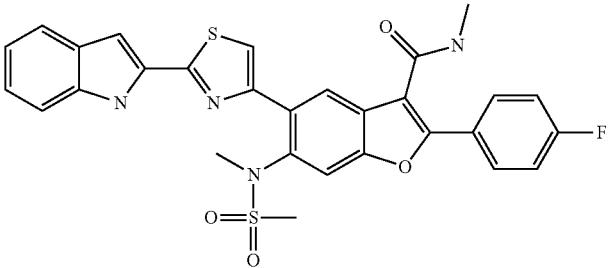 [SMILES: CNC(=O)c1c(-c2ccc(F)cc2)oc2cc(N(C)S(C)(=O)=O)c(-c3csc(-c4cc5ccccc5[nH]4)n3)cc12] | ¹H-NMR (CDCl₃, 400 MHz) δ 9.73 (s, 1H), 8.35 (s, 1H), 7.92~7.96 (m, 2H), 7.65 (t, J = 2.4 Hz, 2H), 7.59 (s, 1H), 7.46 (d, J = 8.0 Hz, 1H), 7.15~7.29 (m, 3H), 7.12 (t, J = 1.2 Hz, 1H), 7.04 (s, 1H), 5.93 (s, 1H), 3.21 (s, 3H), 3.03 (t, J = 4.8 Hz, 6H). | 575 |
| 190 | 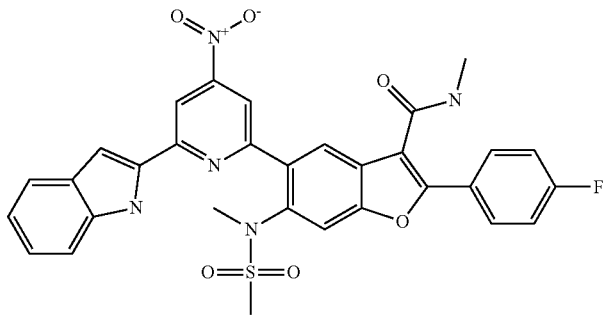 [SMILES: CNC(=O)c1c(-c2ccc(F)cc2)oc2cc(N(C)S(C)(=O)=O)c(-c3cc([N+](=O)[O-])cc(-c4cc5ccccc5[nH]4)n3)cc12] | ¹H-NMR (CDCl3, 400 MHz) δ 9.93 (s, 1H), 8.38 (d, J = 2.0 Hz, 1H), 8.15 (s, 1H), 8.08 (d, J = 1.6 Hz, 1H), 7.92~7.95 (m, 2H), 7.68 (t, J = 12.0 Hz, 1H), 7.64 (s, 1H), 7.43 (d, J = 8.0 Hz, 1H), 7.20~7.25 (m, 4H), 7.14 (t, J = 8.0 Hz, 1H), 5.95 (d, J = 4.8 Hz, 1H), 3.21 (s, 3H), 2.98 (d, J = 6.4 Hz, 6H). | 614 |

-continued
| No. | Structure | NMR | MS (M + H)+ |
|---|---|---|---|
| 191 | 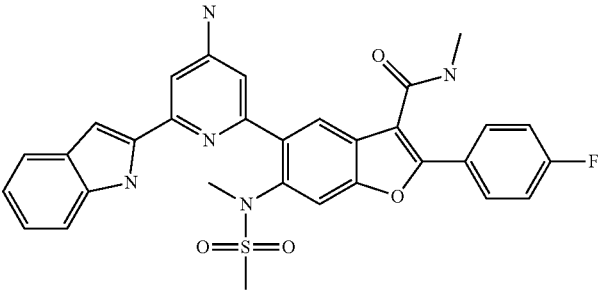 [SMILES: CNC(=O)c1c(-c2ccc(F)cc2)oc2cc(N(C)S(C)(=O)=O)c(-c3cc(N)cc(-c4cc5ccccc5[nH]4)n3)cc12] | ¹H-NMR (CDCl₃, 400 MHz) δ 9.82 (s, 1H), 7.92 (s, 3H), 7.59 (d, J = 7.6 Hz, 1H), 7.54 (s, 1H), 7.39 (d, J = 8.4 Hz, 1H), 7.14~7.20 (m, 3H), 7.09 (t, J = 8.0 Hz, 1H), 6.95 (d, J = 6.4 Hz, 1H), 6.86 (s, 1H), 6.63 (s, 1H), 6.08 (s, 1H), 4.39 (s, 2H), 3.11 (s, 3H), 2.91 (d, J = 4.8 Hz, 3H), 2.85 (s, 3H). | 584 |
| 192 | 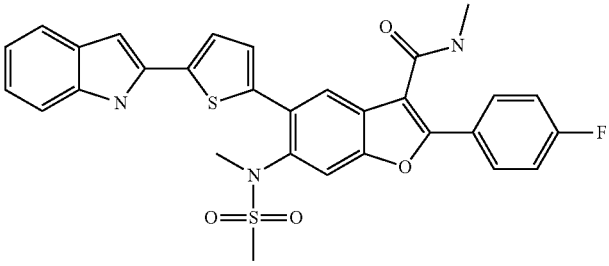 | ¹H-NMR (CDCl₃, 400 MHz) δ 8.59 (s, 1H), 8.03 (s, 1H), 7.89~7.92 (m, 2H), 7.64 (s, 1H), 7.56 (d, J = 7.6 Hz, 1H), 7.27~7.33 (m, 1H), 7.22 (d, J = 2.0 Hz, 1H), 7.10~7.20 (m, 4H), 7.06 (t, J = 7.6 Hz, 1H), 6.73 (s, 1H), 5.90 (d, J = 4.8 Hz, 1H), 3.29 (s, 3H), 2.99 (d, J = 4.8 Hz, 3H), 2.95 (s, 3H). | 574 |
| 193 | 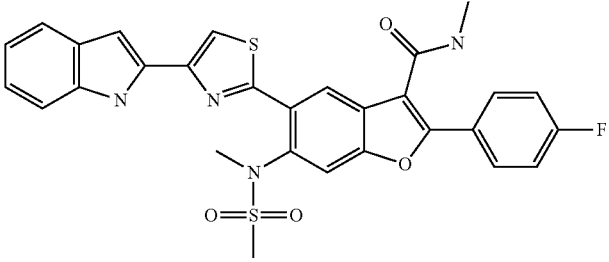 [SMILES: CNC(=O)c1c(-c2ccc(F)cc2)oc2cc(N(C)S(C)(=O)=O)c(-c3nc(-c4cc5ccccc5[nH]4)cs3)cc12] | ¹H-NMR (CDCl₃, 400 MHz) δ 9.49 (s, 1H), 8.66 (s, 1H), 7.84~7.87 (m, 2H), 7.60 (s, 1H), 7.55 (d, J = 8.0 Hz, 1H), 7.51 (s, 1H), 7.41 (d, J = 8.0 Hz, 1H), 7.12~7.16 (m, 3H), 7.03~7.06 (m, 1H), 6.81 (d, J = 1.2 Hz, 1H), 5.88 (d, J = 11.2 Hz, 1H), 3.26 (s, 3H), 3.00 (s, 3H), 2.98 (d, J = 5.2 Hz, 3H). | 575 |
| 194 | 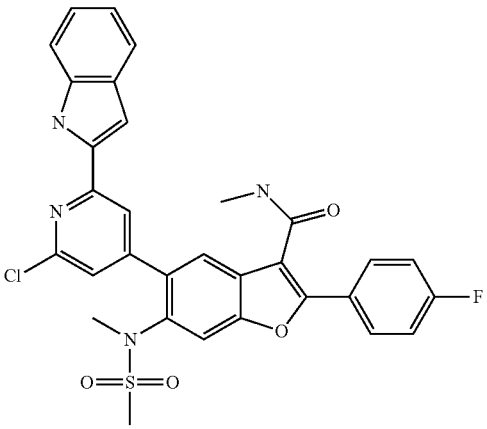 [SMILES: CNC(=O)c1c(-c2ccc(F)cc2)oc2cc(N(C)S(C)(=O)=O)c(-c3cc(Cl)nc(-c4cc5ccccc5[nH]4)c3)cc12] | ¹H-NMR (CDCl₃, 400 MHz) δ 9.46 (s, 1H), 7.89~7.96 (m, 4H), 7.64~7.66 (m, 2H), 7.45 (d, J = 8.4 Hz, 1H), 7.31 (s, 1H), 7.21~7.24 (m, 3H), 7.09~7.15 (m, 2H), 5.82 (br s, 1H), 3.16 (s, 3H), 3.01 (d, J = 4.8 Hz, 3H), 3.02 (s, 3H). | 603 |

| No. | Structure | NMR | MS (M + H)+ |
|---|---|---|---|
| 195 | 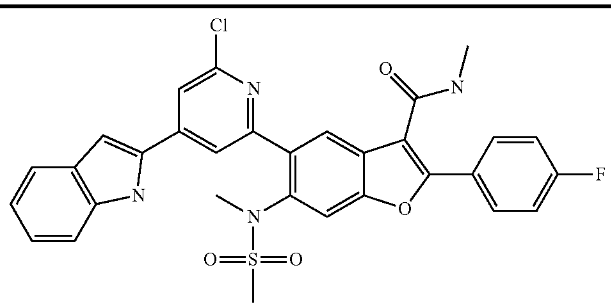 | ¹H-NMR (CDCl₃, 400 MHz) δ 11.91 (s, 1H), 8.57 (d, J = 4.8 Hz, 1H), 8.11 (t, J = 1.2 Hz, 1H), 7.98~8.03 (m, 1H), 7.90 (s, 3H), 7.61 (d, J = 8.0 Hz, 1H), 7.46 (d, J = 7.2 Hz, 1H), 7.42 (d, J = 8.8 Hz, 3H), 7.32 (d, J = 0.8 Hz, 1H), 7.21 (t, J = 8.0 Hz, 1H), 7.07 (t, J = 7.2 Hz, 1H), 3.31 (s, 3H), 3.16 (d, J = 5.2 Hz, 3H), 3.02 (s, 3H). | 603 |
| 196 | 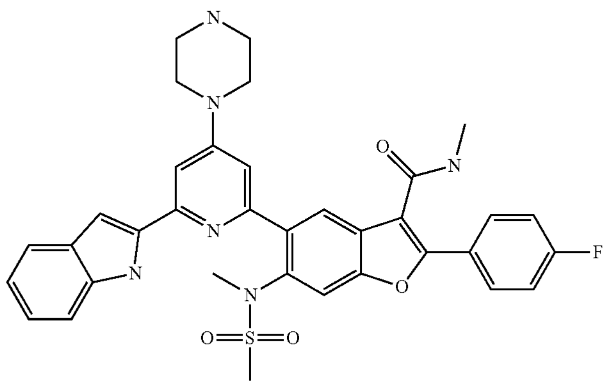 [SMILES: CNC(=O)c1c(-c2ccc(F)cc2)oc2cc(N(C)S(C)(=O)=O)c(-c3cc(N4CCNCC4)cc(-c4cc5ccccc5[nH]4)n3)cc12] | ¹H-NMR (CDCl₃, 400 MHz) δ 9.86 (s, 1H), 8.01 (s, 1H), 7.96~7.99 (m, 2H), 7.63 (d, J = 8.8 Hz, 1H), 7.60 (s, 1H), 7.41 (d, J = 8.0 Hz, 1H), 7.17~7.22 (m, 4H), 7.09 (t, J = 8.0 Hz, 1H), 6.99 (s, 1H), 6.93 (s, 1H), 6.07 (s, 1H), 3.43~3.47 (m, 4H), 3.14 (s, 3H), 3.04~3.06 (m, 4H), 2.99 (d, J = 4.8 Hz, 3H), 2.89 (s, 3H). | 653 |
| 197 | 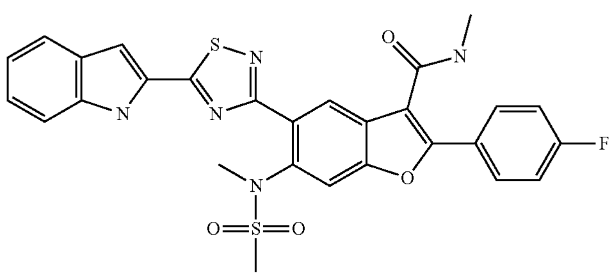 [SMILES: CNC(=O)c1c(-c2ccc(F)cc2)oc2cc(N(C)S(C)(=O)=O)c(-c3nsc(-c4cc5ccccc5[nH]4)n3)cc12] | ¹H-NMR (Methanol-d4, 400 MHz) δ 8.46 (s, 1H), 7.99 (t, J = 4.4 Hz, 2H), 7.88 (s, 1H), 7.64 (d, J = 7.6 Hz, 1H), 7.48 (d, J = 8.8 Hz, 1H), 7.24~7.32 (m, 4H), 7.09 (d, J = 7.2 Hz, 1H), 3.42 (s, 3H), 2.97 (s, 6H). | 576 |
| 198 | 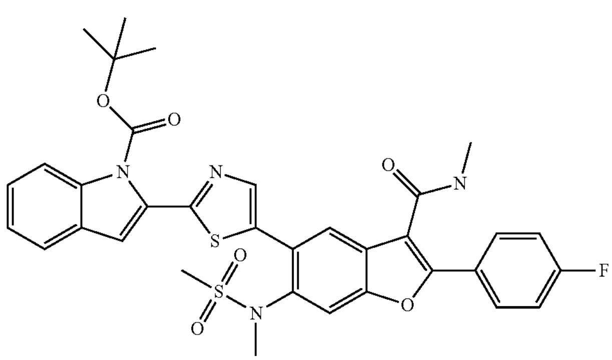 [SMILES: CNC(=O)c1c(-c2ccc(F)cc2)oc2cc(N(C)S(C)(=O)=O)c(-c3cnc(-c4cc5ccccc5n4C(=O)OC(C)(C)C)s3)cc12] | ¹H-NMR (CDCl₃, 400 MHz) δ 8.09~8.13 (m, 3H), 7.88~7.92 (m, 2H), 7.66 (s, 1H), 7.58 (d, J = 7.6 Hz, 1H), 7.33~7.37 (m, 1H), 7.27~7.29 (m, 1H), 7.18~7.25 (m, 2H), 6.92 (br s, 1H), 6.20 (br s, 1H), 3.26 (s, 3H), 3.04 (d, J = 4.8 Hz, 3H), 2.99 (s, 3H), 1.49 (s, 9H). | 675 |
| 199 | 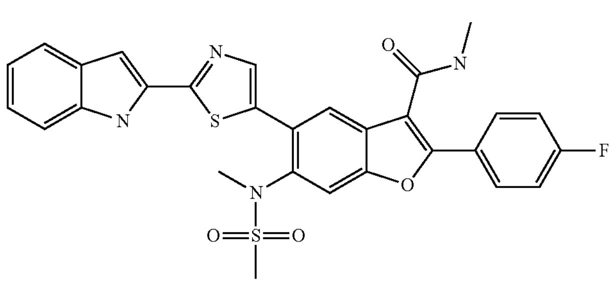 [SMILES: CNC(=O)c1c(-c2ccc(F)cc2)oc2cc(N(C)S(C)(=O)=O)c(-c3cnc(-c4cc5ccccc5[nH]4)s3)cc12] | ¹H-NMR (CDCl₃, 400 MHz) δ 9.25 (s, 1H), 8.09 (s, 1H), 8.00 (s, 1H), 7.89~7.92 (m, 2H), 7.66 (s, 1H), 7.60 (d, J = 8.0 Hz, 1H), 7.41 (d, J = 8.0 Hz, 1H), 7.19~7.28 (m, 3H), 7.13 (t, J = 8.0 Hz, 1H), 7.02 (s, 1H), 6.08 (d, J = 2.8 Hz, 1H), 3.27 (s, 3H), 3.05 (d, J = 5.6 Hz, 3H), 3.01 (s, 3H). | 575 |

| No. | Structure | NMR | MS (M + H)+ |
|---|---|---|---|
| 200 | 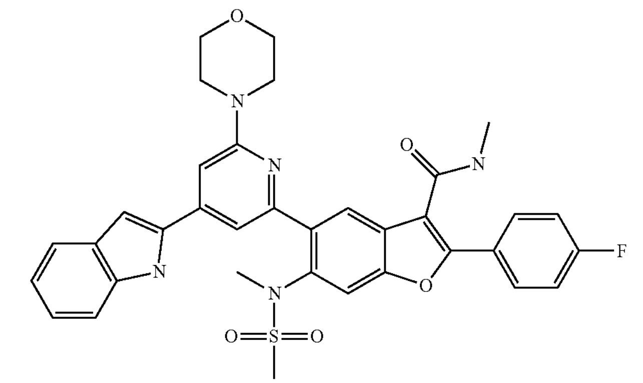 [SMILES: CNC(=O)c1c(-c2ccc(F)cc2)oc2cc(N(C)S(C)(=O)=O)c(-c3cc(-c4cc5ccccc5[nH]4)cc(N4CCOCC4)n3)cc12] | ¹H-NMR (CDCl₃, 400 MHz) δ 9.26 (s, 1H), 8.11 (s, 1H), 8.00~7.96 (m, 2H), 7.63 (d, J = 7.6 Hz, 1H), 7.53 (s, 1H), 7.43 (d, J = 6.4 Hz, 2H), 7.20 (t, J = 8.4 Hz, 3H), 7.12 (t, J = 7.6 Hz, 1H), 6.954 (d, J = 1.2 Hz, 1H), 6.91 (s, 1H), 5.95 (d, J = 3.6 Hz, 1H), 3.87 (t, J = 4.8 Hz, 4H), 3.62 (t, J = 4.4 Hz, 4H), 3.12 (s, 3H), 3.03 (s, 3H), 3.00 (d, J = 4.8 Hz, 3H). | 654 |
| 201 | 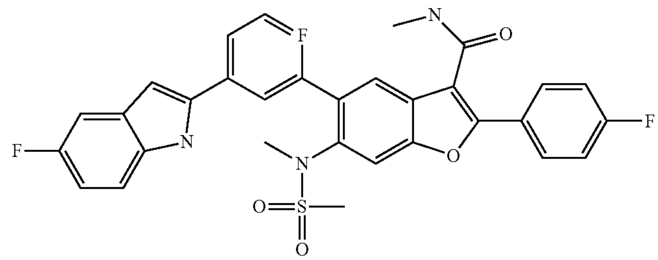 | ¹H-NMR (CDCl3, 400 MHz) δ 9.34 (s, 1H), 8.72 (d, J = 5.2 Hz, 1H), 8.18 (d, J = 8.8 Hz, 1H), 8.12 (s, 1H), 8.00~8.04 (m, 2H), 7.58 (d, J = 5.2 Hz, 1H), 7.53 (t, J = 6.0 Hz, 1H), 7.36~7.43 (m, 1H), 7.17~7.21 (m, 3H), 6.99 (s, 2H), 6.00 (brs, 1H), 3.20 (s, 3H), 3.02 (d, J = 4.0 Hz, 3H), 3.00 (s, 3H). | 587 |
| 202 | 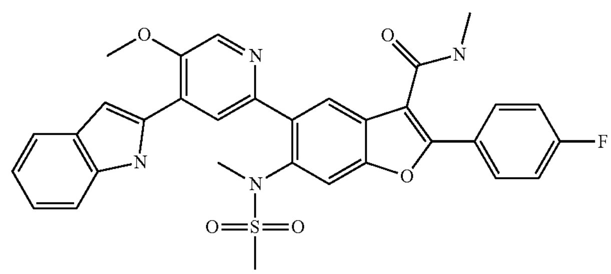 [SMILES: CNC(=O)c1c(-c2ccc(F)cc2)oc2cc(N(C)S(C)(=O)=O)c(-c3cc(-c4cc5ccccc5[nH]4)c(OC)cn3)cc12] | ¹H-NMR (CDCl₃, 400 MHz) δ 9.66 (s, 1H), 8.48 (s, 1H), 8.07 (s, 1H), 8.01 (s, 1H), 7.93~7.97 (m, 2H), 7.60 (d, J = 8.0 Hz, 1H), 7.55 (s, 1H), 7.39 (d, J = 8.0 Hz, 1H), 6.93~7.17 (m, 4H), 5.88 (d, J = 4.8 Hz, 1H), 4.13 (s, 3H), 3.08 (s, 3H), 2.95 (d, J = 5.2 Hz, 3H), 2.92 (s, 3H). | 599 |
| 203 | 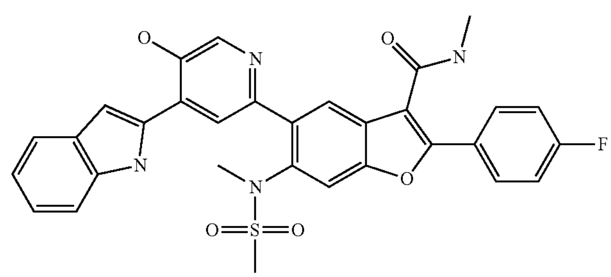 | ¹H-NMR (CDCl₃, 400 MHz) δ 8.64 (s, 1H), 8.28 (s, 1H), 8.04 (s, 1H), 7.93~7.97 (m, 2H), 7.58 (d, J = 7.6 Hz, 1H), 7.53 (s, 1H), 7.36 (d, J = 8.4 Hz, 1H), 7.32 (s, 1H), 7.23 (d, J = 7.6 Hz, 1H), 7.12 (t, J = 8.8 Hz, 2H), 7.06 (t, J = 7.6 Hz, 1H), 6.84 (d, J = 4.4 Hz, 1H), 3.21 (s, 3H), 2.92 (s, 6H). | 585 |
| 204 | 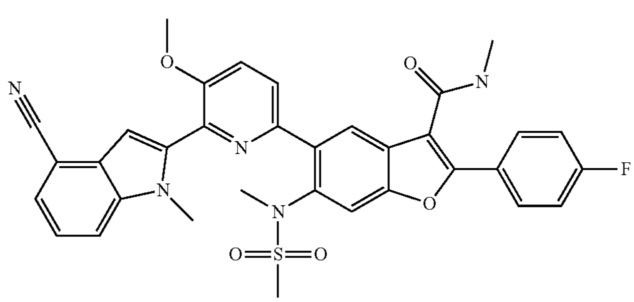 [SMILES: CNC(=O)c1c(-c2ccc(F)cc2)oc2cc(N(C)S(C)(=O)=O)c(-c3ccc(OC)c(-c4cc5c(C#N)cccc5n4C)n3)cc12] | ¹H-NMR (CDCl₃, 400 MHz) δ 8.05 (s, 1H), 7.95~7.98 (m, 2H), 7.73 (d, J = 8.8 Hz, 1H), 7.59 (d, J = 6.4 Hz, 2H), 7.55 (d, J = 8.8 Hz, 1H), 7.50 (d, J = 7.6 Hz, 1H), 7.29 (d, J = 8.4 Hz, 1H), 7.20 (s, 2H), 7.16 (s, 1H), 6.14 (br s, 1H), 3.99 (s, 3H), 3.86 (s, 3H), 3.23 (s, 3H), 3.00 (d, J = 4.8 Hz, 3H), 2.81 (s, 3H). | 638 |

| No. | Structure | NMR | MS (M + H)+ |
|---|---|---|---|
| 205 | 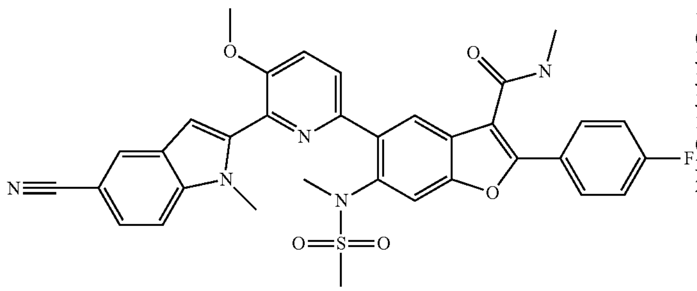 [SMILES: CNC(=O)c1c(-c2ccc(F)cc2)oc2cc(N(C)S(C)(=O)=O)c(-c3ccc(OC)c(-c4cc5cc(C#N)ccc5n4C)n3)cc12] | ¹H-NMR (CDCl₃, 400 MHz) δ 8.07 (s, 1H), 8.01 (s, 1H), 7.92~7.95 (dd, J₁ = 5.2 Hz, J₂ = 6.4 Hz, 2H), 7.68 (d, J = 8.4 Hz, 1H), 7.61 (s, 1H), 7.47 (d, J = 9.2 Hz, 2H), 7.42 (d, J = 8.4 Hz, 1H), 7.20 (t, 2H), 7.02 (s, 1H), 5.89 (s, 1H), 3.96 (s, 3H), 3.86 (s, 3H), 3.20 (s, 3H), 2.98 (d, J = 4.8 Hz, 3H), 2.79 (s, 3H). | 638 |
| 206 | 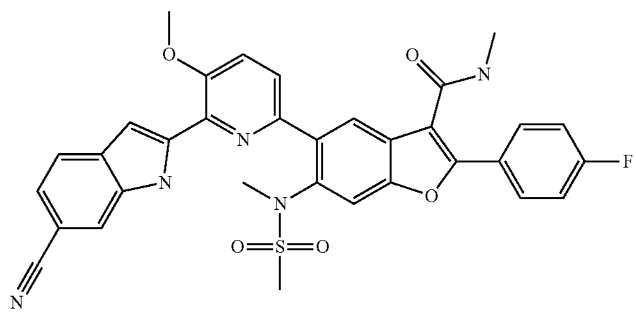 [SMILES: CNC(=O)c1c(-c2ccc(F)cc2)oc2cc(N(C)S(C)(=O)=O)c(-c3ccc(OC)c(-c4cc5ccc(C#N)cc5[nH]4)n3)cc12] | ¹H-NMR (CDCl₃, 400 MHz) δ 7.98 (s, 1H), 7.86~7.90 (m, 2H), 7.70 (s, 1H), 7.63 (d, J = 8.0 Hz, 1H), 7.50~7.53 (m, 2H), 7.36~7.40 (m, 2H), 7.19~7.21 (m, 1H), 7.11~7.15 (m, 2H), 4.03 (s, 3H), 3.09 (s, 3H), 2.87~2.89 (m, 6H). | 624 |
| 207 | 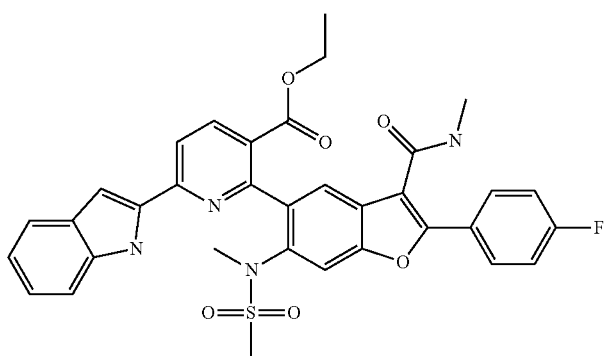 [SMILES: CCOC(=O)c1ccc(-c2cc3ccccc3[nH]2)nc1-c1cc2c(C(=O)NC)c(-c3ccc(F)cc3)oc2cc1N(C)S(C)(=O)=O] | ¹H-NMR (CDCl₃, 400 MHz) δ 9.95 (s, 1H), 8.37 (d, J = 8.2 Hz, 1H), 8.02 (t, J = 8.2 Hz, 2H), 7.82~7.88 (m, 2H), 7.66 (d, J = 6.4 Hz, 2H), 7.38 (d, J = 8.2 Hz, 1H), 7.18~7.22 (m, 3H), 7.12 (t, J = 7.6 Hz, 1H), 6.04 (d, J = 1.6 Hz, 1H), 4.18 (q, J = 7.2 Hz, 2H), 3.11 (s, 3H), 2.96 (d, J = 1.2 Hz, 3H), 2.81 (s, 3H), 1.15 (t, J = 7.2 Hz, 3H). | 641 |
| 208 | 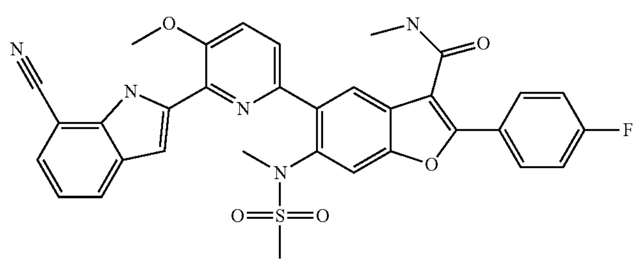 [SMILES: CNC(=O)c1c(-c2ccc(F)cc2)oc2cc(N(C)S(C)(=O)=O)c(-c3ccc(OC)c(-c4cc5cccc(C#N)c5[nH]4)n3)cc12] | ¹H-NMR (CDCl₃, 400 MHz) δ 10.14 (s, 1H), 7.97 (s, 1H), 7.90~7.94 (m, 2H), 7.82 (d, J = 8.0 Hz, 1H), 7.56 (s, 1H), 7.52 (d, J = 8.4 Hz, 1H), 7.44 (d, J = 4.0 Hz, 1H), 7.38 (d, J = 8.8 Hz, 1H), 7.12 (t, J = 8.4 Hz, 2H), 7.08 (t, J = 7.2 Hz, 1H), 5.87 (s, 1H), 4.05 (s, 3H), 3.22 (s, 3H), 2.96 (d, J = 4.8 Hz, 3H), 2.80 (s, 3H). | 624 |
| 209 | 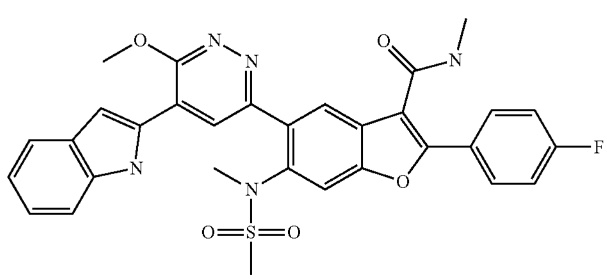 [SMILES: CNC(=O)c1c(-c2ccc(F)cc2)oc2cc(N(C)S(C)(=O)=O)c(-c3cc(-c4cc5ccccc5[nH]4)c(OC)nn3)cc12] | ¹H-NMR (CDCl₃, 400 MHz) δ 9.62 (s, 1H), 8.02 (s, 1H), 7.91 (s, 1H), 7.88~7.90 (m, 2H), 7.59 (d, J = 8.0 Hz, 1H), 7.50 (s, 1H), 7.38 (dd, J₁ = 8.4 Hz, J₂ = 4.8 Hz, 1H), 7.25 (s, 1H), 7.04~7.21 (m, 4H), 6.23 (brs, 1H), 4.27 (s, 3H), 3.03 (s, 3H), 3.00 (s, 3H), 2.93 (d, J = 4.8 Hz, 3H). | 600 |

-continued

| No. | Structure | NMR | MS (M + H)+ |
|---|---|---|---|
| 210 | 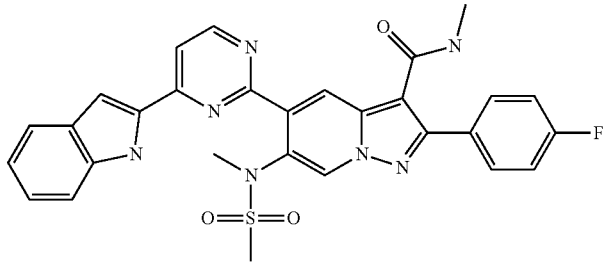 [SMILES: CNC(=O)c1c(-c2ccc(F)cc2)nn2cc(N(C)S(C)(=O)=O)c(-c3nccc(-c4cc5ccccc5[nH]4)n3)cc12] | ¹H-NMR (CDCl₃, 400 MHz) δ 10.56 (s, 1H), 9.21 (s, 1H), 8.82 (s, 1H), 8.67 (s, 1H), 7.66~7.76 (m, 4H), 7.52 (d, J = 8.8 Hz, 1H), 7.28~7.32 (m, 4H), 7.14 (t, J = 7.2 Hz, 1H), 5.77 (br s, 1H), 3.33 (s, 3H), 3.14 (s, 3H), 2.92 (s, 3H). | 570 |
| 211 | 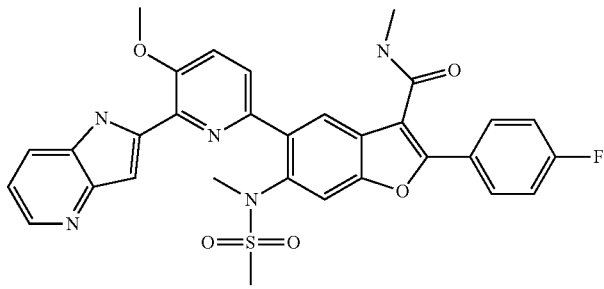 [SMILES: CNC(=O)c1c(-c2ccc(F)cc2)oc2cc(N(C)S(C)(=O)=O)c(-c3ccc(OC)c(-c4cc5ncccc5[nH]4)n3)cc12] | ¹H-NMR (Methanol-d₄, 400 MHz) δ 8.52 (s, 2H), 8.06-7.80 (m, 6H), 7.62 (s, 2H), 7.29 (s, 2H), 4.19 (s, 3H), 3.00 (s, 3H), 2.94 (s, 3H). | 600 |
| 212 | 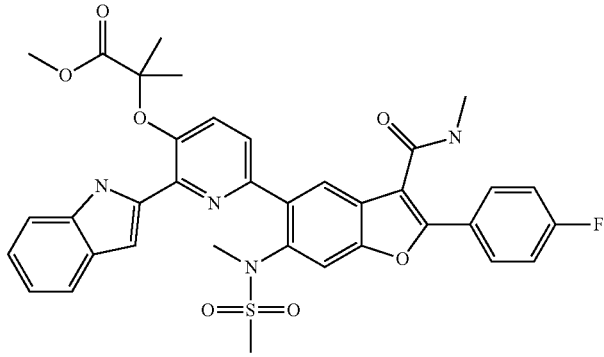 | ¹H-NMR (CDCl₃, 400 MHz) δ 10.55 (s, 1H), 7.96~8.00 (m, 3H), 7.66 (d, J = 8.0 Hz, 1H), 7.58 (s, 1H), 5.52 (d, J = 0.8 Hz, 1H), 7.42 (t, J = 8.0 Hz, 2H), 7.11~7.29 (m, 4H), 7.07 (t, J = 7.2 Hz, 1H), 6.56 (d, J = 4.0 Hz, 1H), 3.83 (s, 3H), 3.18 (s, 3H), 2.96 (d, J = 4.8 Hz, 3H), 2.80 (s, 3H), 1.83 (s, 6H). | 685 |
| 213 | 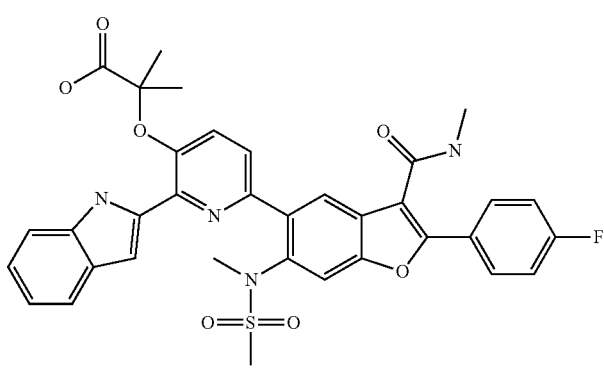 [SMILES: CNC(=O)c1c(-c2ccc(F)cc2)oc2cc(N(C)S(C)(=O)=O)c(-c3ccc(OC(C)(C)C(=O)O)c(-c4cc5ccccc5[nH]4)n3)cc12] | ¹H-NMR (Methanol-d₄, 400 MHz) δ 7.92~7.98 (m, 3H), 7.84 (s, 1H), 7.52~7.61 (m, 3H), 7.39~7.44 (m, 1H), 7.25 (t, J = 8.8 Hz, 2H), 7.16 (t, J = 7.2 Hz, 1H), 7.02 (t, J = 7.2 Hz, 1H). 3.26 (s, 3H), 2.91 (s, 3H), 2.88 (s, 3H), 1.78 (s, 6H). | 671 |
| 214 | 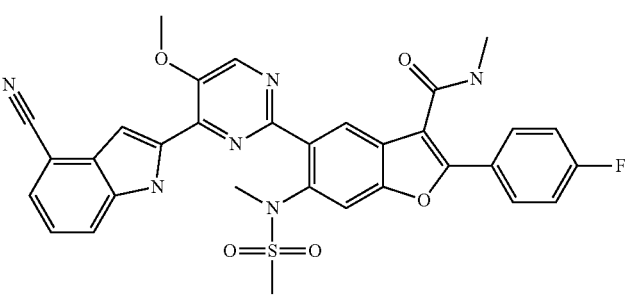 [SMILES: CNC(=O)c1c(-c2ccc(F)cc2)oc2cc(N(C)S(C)(=O)=O)c(-c3ncc(OC)c(-c4cc5c(C#N)cccc5[nH]4)n3)cc12] | ¹H-NMR (CDCl₃, 400 MHz) δ 10.97 (s, 1H), 8.59 (d, J = 12.8 Hz, 2H), 7.98 (dd, J₁ = 6.40 Hz, J₂ = 8.40 Hz, 2H), 7.72 (s, 1H), 7.60 (s, 1H), 7.48 (d, J = 7.20 Hz, 1H), 7.29 (t, J = 8.00 Hz, 1H), 7.19 (t, J = 8.40 Hz, 2H), 6.02 (brs, 1H), 4.22 (s, 3H), 3.22 (s, 3H), 3.15 (s, 3H), 3.03 (d, J = 7.20 Hz, 3H). | 625 |

| No. | Structure | NMR | MS (M + H)+ |
|---|---|---|---|
| 215 | 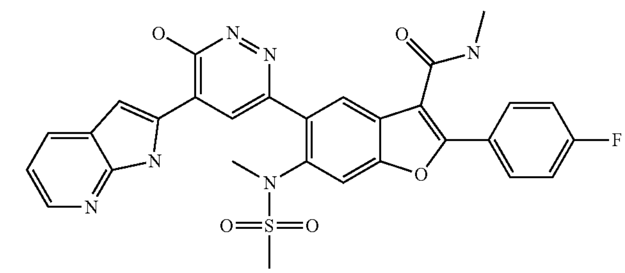 [SMILES: CNC(=O)c1c(-c2ccc(F)cc2)oc2cc(N(C)S(C)(=O)=O)c(-c3cc(-c4cc5cccnc5[nH]4)c(O)nn3)cc12] | ¹H-NMR (CDCl₃, 400 MHz) δ 13.51 (br s, 1H), 12.16 (br s, 1H), 8.59 (d, J = 4.8 Hz, 1H), 8.32 (d, J = 8.0 Hz, 1H), 8.17 (s, 1H), 8.14 (s, 1H), 8.08 (d, J = 7.2 Hz, 1H), 8.05~7.98 (m, 2H), 7.85 (s, 1H), 7.74 (s, 1H), 7.20 (t, J = 8.4 Hz, 2H), 7.13 (dd, J = 8.0, 4.8 Hz, 1H), 3.37 (s, 3H), 3.01 (s, 3H), 2.84 (d, J = 4.8 Hz, 3H). | 587 |
| 216 | 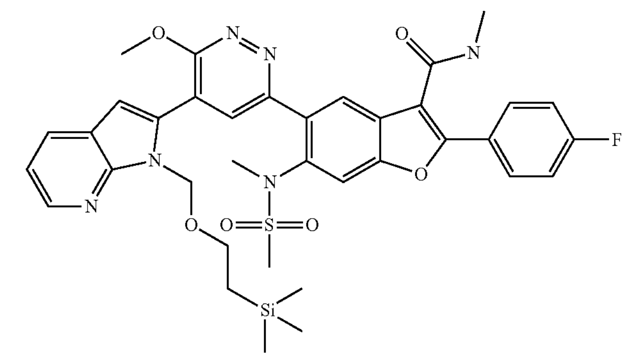 [SMILES: CNC(=O)c1c(-c2ccc(F)cc2)oc2cc(N(C)S(C)(=O)=O)c(-c3cc(-c4cc5cccnc5n4COCC[Si](C)(C)C)c(OC)nn3)cc12] | ¹H-NMR (CDCl₃, 400 MHz) δ 8.39 (d, J = 4.8 Hz, 1H), 8.15 (s, 1H), 8.09 (s, 1H), 8.05~7.95 (m, 3H), 7.65 (s, 1H), 7.21~7.10 (m, 3H), 7.01 (s, 1H), 6.29 (s, 1H), 5.76 (s, 2H), 4.62 (s, 3H), 3.50 (t, J = 8.4 Hz, 2H), 3.32 (s, 3H), 3.00 (d, J = 4.8 Hz, 3H), 2.87 (s, 3H), 0.76 (t, J = 8.4 Hz, 2H), −0.20 (s, 9H). | 731 |
| 217 | 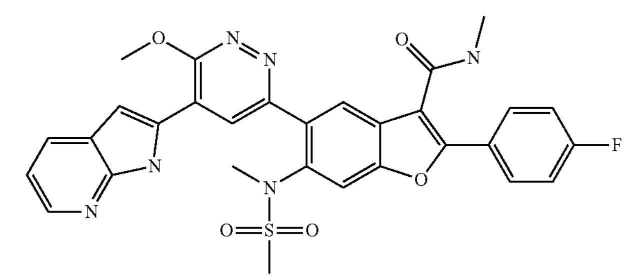 [SMILES: CNC(=O)c1c(-c2ccc(F)cc2)oc2cc(N(C)S(C)(=O)=O)c(-c3cc(-c4cc5cccnc5[nH]4)c(OC)nn3)cc12] | ¹H-NMR (CDCl₃, 400 MHz) δ 10.54 (br s, 1H), 8.36 (d, J = 4.8 Hz, 1H), 8.33 (s, 1H), 8.16 (s, 1H), 8.05~7.96 (m, 3H), 7.62 (s, 1H), 7.30 (s, 1H), 7.20 (t, J = 8.0 Hz, 2H), 7.09 (dd, J = 8.0, 4.8 Hz, 1H), 6.10~6.03 (m, 1H), 4.42 (s, 3H), 3.15 (s, 3H), 3.07 (s, 3H), 3.03 (d, J = 4.8 Hz, 3H). | 601 |
| 218 | 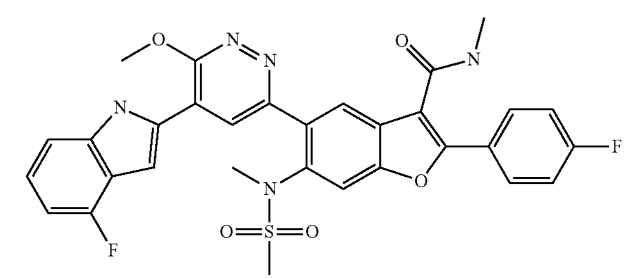 [SMILES: CNC(=O)c1c(-c2ccc(F)cc2)oc2cc(N(C)S(C)(=O)=O)c(-c3cc(-c4cc5c(F)cccc5[nH]4)c(OC)nn3)cc12] | ¹H-NMR (CDCl₃, 400 MHz) δ 9.72 (s, 1H), 8.21 (s, 1H), 8.12 (s, 1H), 7.94~7.98 (m, 2H), 7.55 (s, 1H), 7.36 (s, 1H), 7.11~7.15 (m, 4H), 6.74 (t, J = 8.8 Hz, 1H), 6.06 (s, 1H), 4.35 (s, 3H), 3.08 (s, 3H), 3.05 (s, 3H), 2.97 (t, J = 4.8 Hz, 3H). | 618 |
| 219 | 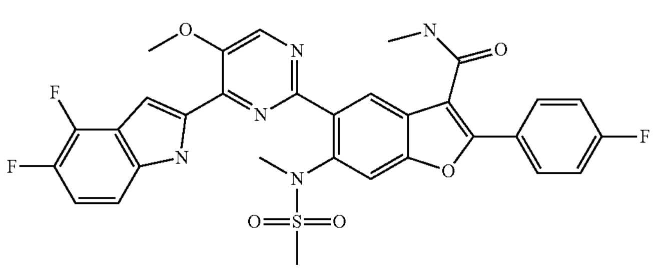 [SMILES: CNC(=O)c1c(-c2ccc(F)cc2)oc2cc(N(C)S(C)(=O)=O)c(-c3ncc(OC)c(-c4cc5c(F)c(F)ccc5[nH]4)n3)cc12] | ¹H-NMR (CDCl₃, 400 MHz) δ 10.57 (s, 1H), 8.50 (s, 1H), 8.47 (s, 1H), 7.92~7.95 (m, 2H), 7.56 (s, 1H), 7.11~7.16 (m, 3H), 6.99~7.05 (m, 1H), 5.90 (d, J = 4.4 Hz, 1H), 4.14 (s, 3H), 3.16 (s, 3H), 3.04 (s, 3H), 2.96 (d, J = 4.8 Hz, 3H). | 636 |

| No. | Structure | NMR | MS (M + H)+ |
|---|---|---|---|
| 220 | 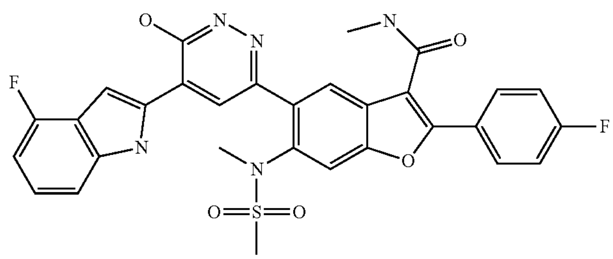 [SMILES: CNC(=O)c1c(-c2ccc(F)cc2)oc2cc(N(C)S(C)(=O)=O)c(-c3cc(-c4cc5c(F)cccc5[nH]4)c(O)nn3)cc12] | $^1$H-NMR (CDCl$_3$, 400 MHz) δ 11.11 (s, 1H), 10.53 (s, 1H), 8.08 (s, 1H), 8.04 (s, 1H), 7.89~7.91 (m, 2H), 7.56 (s, 1H), 7.05~7.16 (m, 5H), 6.70~6.74 (m, 1H), 5.79 (d, J = 4.8 Hz, 1H), 3.22 (s, 3H), 2.96 (s, 3H), 2.95 (s, 3H). | 604 |
| 221 | 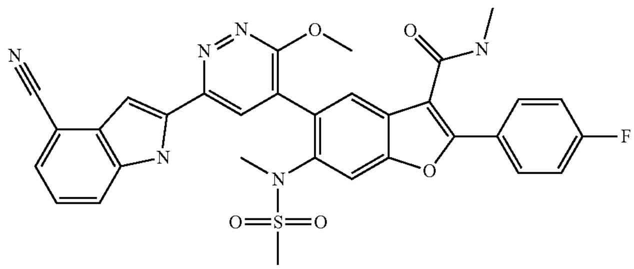 [SMILES: CNC(=O)c1c(-c2ccc(F)cc2)oc2cc(N(C)S(C)(=O)=O)c(-c3cc(-c4cc5c(C#N)cccc5[nH]4)nnc3OC)cc12] | $^1$H-NMR (CDCl$_3$, 400 MHz) δ 10.32 (s, 1H), 7.93 (m, 4H), 7.63 (d, J = 11.2 Hz, 2H), 7.44 (d, J = 7.6 Hz, 1H), 7.23 (m, 3H), 7.13 (s, 1H), 6.00 (bs, 1H), 3.30 (s, 3H), 2.99 (d, J = 4.8 Hz, 3H), 2.80 (s, 3H). | 625 |
| 222 | 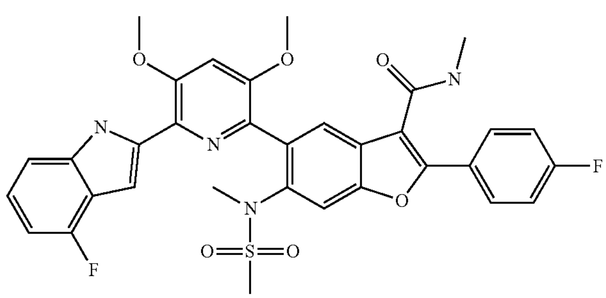 [SMILES: CNC(=O)c1c(-c2ccc(F)cc2)oc2cc(N(C)S(C)(=O)=O)c(-c3nc(-c4cc5c(F)cccc5[nH]4)c(OC)cc3OC)cc12] | $^1$H-NMR (CDCl$_3$, 400 MHz) δ 9.77 (br s, 1H), 7.99~7.92 (m, 2H), 7.87 (s, 1H), 7.66 (s, 1H), 7.29 (d, J = 0.8 Hz, 1H), 7.22~7.13 (m, 2H), 7.11 (d, J = 8.0 Hz, 1H). 7.08~7.01 (m, 1H), 6.96 (s, 1H), 6.73 (dd, J = 10.0, 8.0 Hz, 1H), 5.99 (d, J = 4.8 Hz, 1H), 4.12 (s, 3H) 3.85 (s, 3H), 3.13 (s, 3H), 2.94 (d, J = 4.8 Hz, 3H), 2.72 (s, 3H). | 647 |
| 223 | 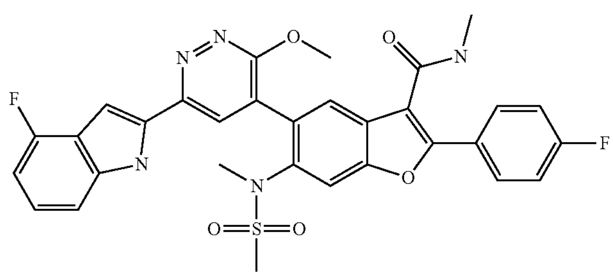 [SMILES: CNC(=O)c1c(-c2ccc(F)cc2)oc2cc(N(C)S(C)(=O)=O)c(-c3cc(-c4cc5c(F)cccc5[nH]4)nnc3OC)cc12] | $^1$H-NMR (CDCl$_3$, 400 MHz) δ 9.70 (s, 1H), 7.9~7.96 (m, 3H), 7.88 (s, 1H), 7.63 (s, 1H), 7.18~7.22 (m, 3H), 7.15~7.17 (m, 1H), 7.06 (s, 1H), 6.78 (t, J = 8.0 Hz, 1H), 5.86 (s, 1H), 4.15 (s, 3H), 3.27 (s, 3H), 2.99 (d, J = 4.8 Hz, 3H), 2.76 (s, 3H). | 618 |
| 224 | 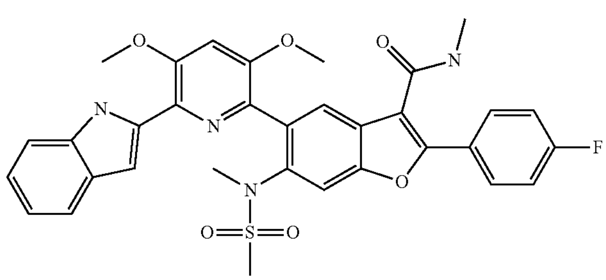 [SMILES: CNC(=O)c1c(-c2ccc(F)cc2)oc2cc(N(C)S(C)(=O)=O)c(-c3nc(-c4cc5ccccc5[nH]4)c(OC)cc3OC)cc12] | $^1$H-NMR (CDCl$_3$, 400 MHz) δ 10.18 (br s, 1H), 8.05~8.00 (m, 2H), 7.88 (s, 1H), 7.67 (s, 1H), 7.65 (d, J = 8.4 Hz, 1H), 7.39~7.35 (m, 2H), 7.24~7.15 (m, 3H), 7.10~7.05 (m, 2H), 6.59 (br s, 1H), 4.17 (s, 3H) 3.90 (s, 3H), 3.21 (s, 3H), 2.99 (d, J = 4.8 Hz, 3H), 2.75 (s, 3H). | 629 |

| No. | Structure | NMR | MS (M + H)+ |
|---|---|---|---|
| 225 | 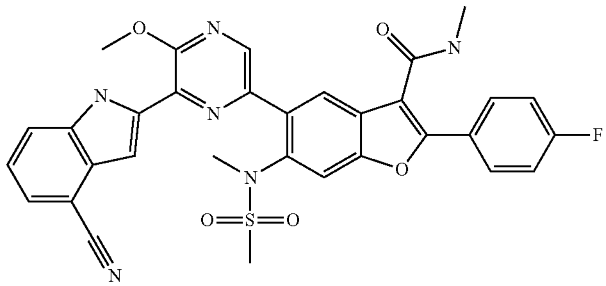 [SMILES: CNC(=O)c1c(-c2ccc(F)cc2)oc2cc(N(C)S(C)(=O)=O)c(-c3cnc(OC)c(-c4cc5c(C#N)cccc5[nH]4)n3)cc12] | ¹H-NMR (CDCl₃, 400 MHz) δ 10.43 (s, 1H), 8.35 (s, 1H), 8.11 (s, 1H), 7.95 (t, J = 8.0 Hz, 2H), 7.64~7.68 (m, 3H), 7.48 (d, J = 7.6 Hz, 2H), 7.22~7.26 (m, 2H), 5.86 (s, 1H), 4.27 (s, 3H), 3.14 (s, 3H), 3.06 (s, 3H), 3.00 (d, J = 4.8 Hz, 3H). | 625 |
| 226 | 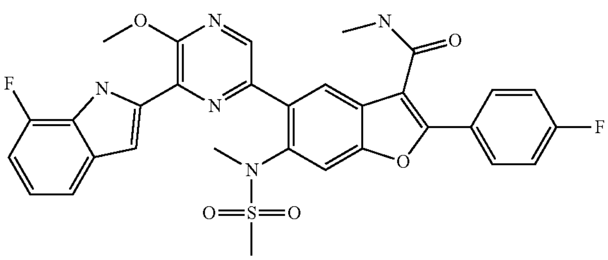 [SMILES: CNC(=O)c1c(-c2ccc(F)cc2)oc2cc(N(C)S(C)(=O)=O)c(-c3cnc(OC)c(-c4cc5cccc(F)c5[nH]4)n3)cc12] | ¹H-NMR (CDCl₃, 400 MHz) δ 10.08 (s, 1H), 8.29 (s, 1H), 8.09 (s, 1H), 7.96 (t, J = 9.2 Hz, 2H), 7.65 (s, 1H), 7.56 (s, 1H), 7.19~7.24 (m, 3H), 7.13~7.17 (m, 1H), 6.77 (t, J = 8.4 Hz, 1H), 5.88 (s, 1H), 4.25 (s, 3H), 3.18 (s, 3H), 3.00 (d, J = 4.8 Hz, 3H), 2.98 (s, 3H). | 618 |
| 227 | 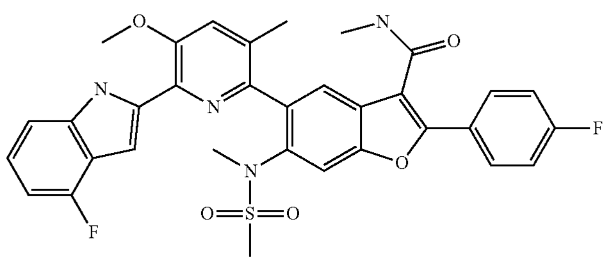 | ¹H-NMR (DMSO-d₆, 400 MHz) δ 9.69 (s, 1H), 7.91~7.88 (m, 2H), 7.71 (s, 1H), 7.61 (s, 1H), 7.32 (d, J = 1.2 Hz, 1H), 7.17~7.12 (m, 3H), 7.05~ 6.97 (m, 2H), 6.67 (d, J = 8.0 Hz, 1H), 5.77 (d, J = 4.0 Hz, 1H), 4.03 (s, 3H), 3.05 (s, 3H), 2.89 (d, J = 4.8 Hz, 3H), 2.63 (s, 3H), 2.23 (s, 3H). | 631 |
| 228 | 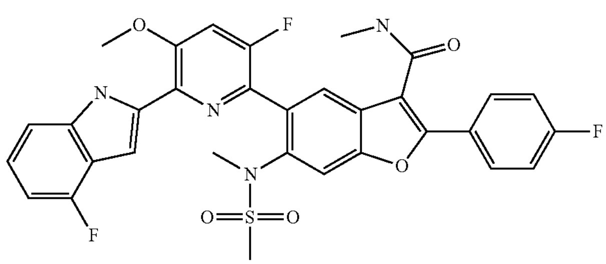 [SMILES: CNC(=O)c1c(-c2ccc(F)cc2)oc2cc(N(C)S(C)(=O)=O)c(-c3nc(-c4cc5c(F)cccc5[nH]4)c(OC)cc3F)cc12] | ¹H-NMR (DMSO-d₆, 400 MHz) δ 11.46 (s, 1H), 8.49 (d, J = 4.4 Hz, 1H), 8.09 (s, 1H), 7.97 (d, J = 5.6 Hz, 2H), 7.81 (s, 1H), 7.72 (d, J = 8.0 Hz, 1H), 7.39 (t, J = 4.4 Hz, 2H), 7.29 (d, J = 8.0 Hz, 1H), 7.23 (s, 1H), 7.06~7.01 (m, 1H), 6.73 (d, J = 8.0 Hz, 1H), 4.08 (s, 3H), 3.26 (s, 3H), 2.86 (s, 3H), 2.78 (d, J = 4.8 Hz, 3H). | 635 |
| 229 | 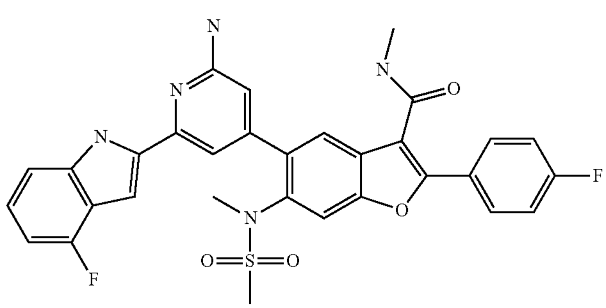 [SMILES: CNC(=O)c1c(-c2ccc(F)cc2)oc2cc(N(C)S(C)(=O)=O)c(-c3cc(N)nc(-c4cc5c(F)cccc5[nH]4)c3)cc12] | ¹H-NMR (CDCl₃, 400 MHz) δ 9.58 (s, 1H), 7.93~7.96 (m, 2H), 7.88 (s, 1H), 7.62 (s, 1H), 7.32 (s, 1H), 7.20~7.24 (m, 3H), 7.11~7.13 (m, 1H), 7.04 (s, 1H), 6.75~6.79 (m, 1H), 6.58 (s, 1H), 5.84 (s, 1H), 4.60 (s, 1H), 3.18 (s, 3H), 3.00 (d, J = 4.80 Hz, 3H), 2.88 (s, 3H). | 602 |

| No. | Structure | NMR | MS (M + H)+ |
|---|---|---|---|
| 230 | 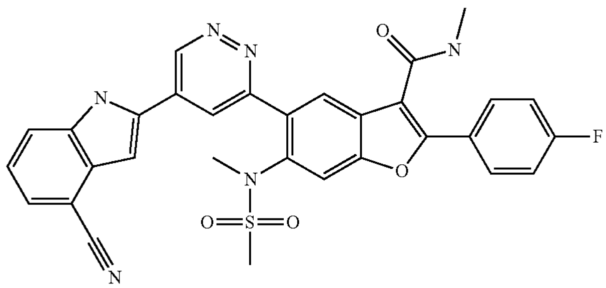 [SMILES: CNC(=O)c1c(-c2ccc(F)cc2)oc2cc(N(C)S(C)(=O)=O)c(-c3cc(-c4cc5c(C#N)cccc5[nH]4)cnn3)cc12] | ¹H-NMR (CDCl₃, 400 MHz) δ 10.00 (s, 1H), 9.41 (s, 1H), 8.17 (s, 1H), 8.12 (s, 1H), 7.87~7.90 (m, 2H), 7.62 (d, J = 8.8 Hz, 1H), 7.47 (d, J = 7.2 Hz, 2H), 7.25 (t, J = 8.0 Hz, 1H), 7.16 (s, 1H), 7.08~7.12 (m, 2H), 6.02~6.04 (m, 1H), 3.18 (s, 3H), 2.99 (s, 3H), 2.97 (d, J = 4.8 Hz, 3H). | 595 |
| 231 | 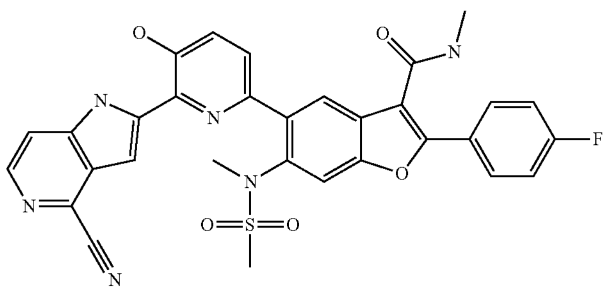 [SMILES: CNC(=O)c1c(-c2ccc(F)cc2)oc2cc(N(C)S(C)(=O)=O)c(-c3ccc(O)c(-c4cc5c(C#N)nccc5[nH]4)n3)cc12] | ¹H-NMR (Methanol-d₄, 400 MHz) δ 8.25 (d, J = 5.6 Hz, 1H), 7.95~7.99 (m, 3H), 7.83 (s, 1H), 7.68 (d, J = 5.6 Hz, 1H), 7.58~7.61 (m, 2H), 7.44 (d, J = 8.4 Hz, 1H), 7.26 (t, J = 8.8 Hz, 2H), 3.23 (s, 3H), 2.94 (s, 3H), 2.92 (s, 3H). | 611 |
| 232 | 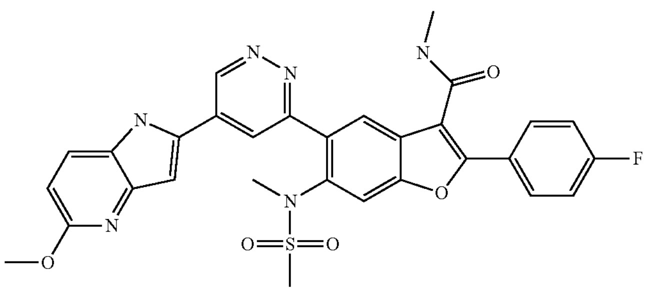 [SMILES: CNC(=O)c1c(-c2ccc(F)cc2)oc2cc(N(C)S(C)(=O)=O)c(-c3cc(-c4cc5nc(OC)ccc5[nH]4)cnn3)cc12] | ¹H-NMR (CDCl₃, 400 MHz) δ 9.51 (s, 1H), 9.39 (d, J = 1.6 Hz, 1H), 8.19 (s, 1H), 8.10 (s, 1H), 7.91~7.94 (m, 2H), 7.59 (d, J = 9.2 Hz, 1H), 7.48 (s, 1H), 7.09~7.14 (m, 4H), 6.63 (d, J = 8.8 Hz, 1H), 6.03 (d, J = 4.8 Hz, 1H), 3.95 (s, 3H), 3.15 (s, 3H), 2.94 (d, J = 4.4 Hz, 6H). | 601 |
| 233 | 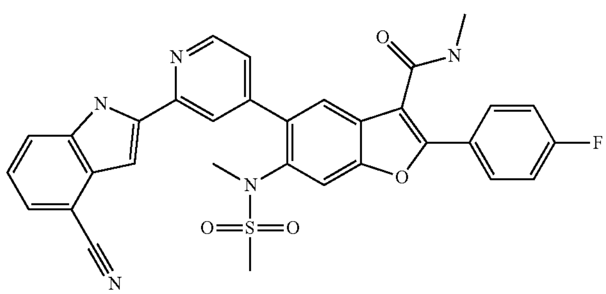 [SMILES: CNC(=O)c1c(-c2ccc(F)cc2)oc2cc(N(C)S(C)(=O)=O)c(-c3ccnc(-c4cc5c(C#N)cccc5[nH]4)c3)cc12] | ¹H-NMR (CDCl₃, 400 MHz) δ 10.02 (s, 1H), 8.61 (d, J = 4.8 Hz, 1H), 7.88~7.94 (m, 4H), 7.59~7.61 (m, 2H), 7.44 (d, J = 7.6 Hz, 1H), 7.34~7.36 (m, 1H), 7.17~7.25 (m, 4H), 6.02 (br s, 1H), 3.19 (s, 3H), 3.00 (d, J = 4.8 Hz, 3H), 2.87 (s, 3H). | 594 |
| 234 | 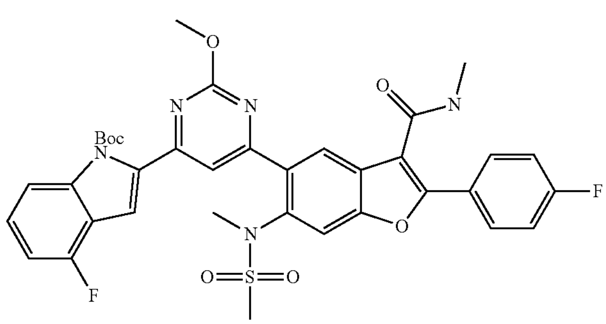 [SMILES: CNC(=O)c1c(-c2ccc(F)cc2)oc2cc(N(C)S(C)(=O)=O)c(-c3cc(-c4cc5c(F)cccc5n4C(=O)OC(C)(C)C)nc(OC)n3)cc12] | ¹H-NMR (CDCl₃, 400 MHz) δ 8.15 (s, 1H), 7.90~7.94 (m, 2H), 7.73~7.76 (m, 1H), 7.63 (s, 1H), 7.55 (s, 1H), 7.13~7.22 (m, 3H), 6.88~6.93 (m, 2H), 6.69 (br s, 1H), 4.12 (s, 3H), 3.32 (s, 3H), 3.09 (d, J = 4.8 Hz, 3H), 2.96 (s, 3H), 1.46 (s, 9H). | 718 |

| No. | Structure | NMR | MS (M + H)+ |
|---|---|---|---|
| 235 | 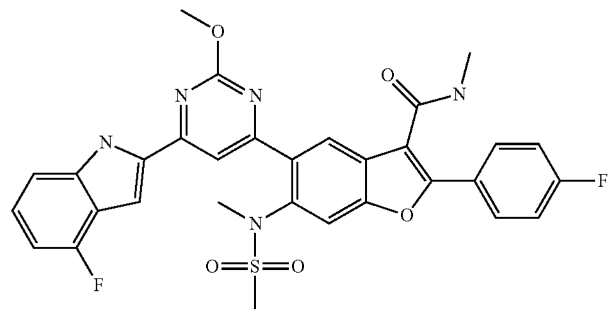 [SMILES: CNC(=O)c1c(-c2ccc(F)cc2)oc2cc(N(C)S(C)(=O)=O)c(-c3cc(-c4cc5c(F)cccc5[nH]4)nc(OC)n3)cc12] | ¹H-NMR (CDCl₃, 400 MHz) δ 9.60 (br s, 1H), 8.15 (s, 1H), 7.92~7.97 (m, 2H), 7.76 (s, 1H), 7.62 (s, 1H), 7.31 (s, 1H), 7.17~7.22 (m, 4H), 6.76~6.82 (m, 1H), 6.04 (br s, 1H), 4.14 (s, 3H), 3.29 (s, 3H), 3.02 (d, J = 4.8 Hz, 3H), 2.97 (s, 3H). | 618 |
| 236 | 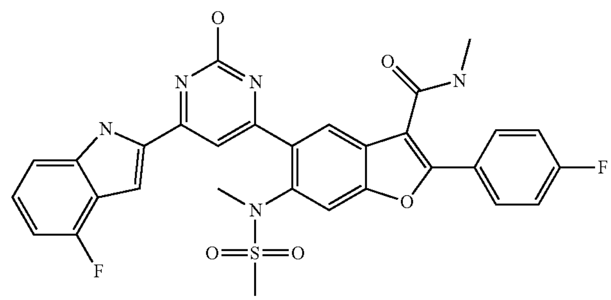 [SMILES: CNC(=O)c1c(-c2ccc(F)cc2)oc2cc(N(C)S(C)(=O)=O)c(-c3cc(-c4cc5c(F)cccc5[nH]4)nc(O)n3)cc12] | ¹H-NMR (DMSO-d₆, 400 MHz) δ 12.26 (br s, 1H), 11.84 (br s, 1H), 8.46 (br s, 1H), 8.19 (s, 1H), 8.00~8.04 (m, 2H), 7.92 (s, 1H), 7.41~7.47 (m, 3H), 7.35 (d, J = 8.0 Hz, 1H), 7.17~7.23 (m, 2H), 6.81~6.86 (m, 1H), 3.40 (s, 3H), 3.06 (s, 3H), 2.86 (d, J = 4.4 Hz, 3H). | 604 |
| 237 | 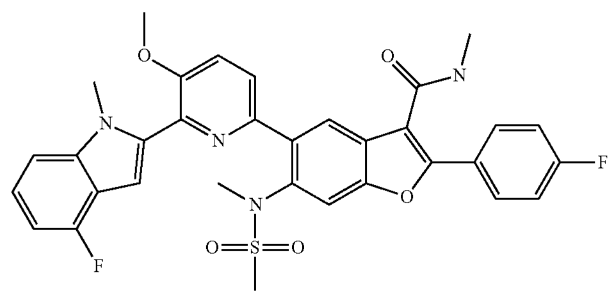 [SMILES: CNC(=O)c1c(-c2ccc(F)cc2)oc2cc(N(C)S(C)(=O)=O)c(-c3ccc(OC)c(-c4cc5c(F)cccc5n4C)n3)cc12] | ¹H-NMR (CDCl₃, 400 MHz) δ 8.04 (s, 1H), 7.94~7.96 (m, 2H), 7.67~7.59 (m, 2H), 7.45 (d, J = 8.6 Hz, 1H), 7.24~7.11 (m, 4H), 7.03 (s, 1H), 6.83~6.75 (m, 1H), 5.92 (d, J = 3.9 Hz, 1H), 3.96 (s, 3H), 3.82 (s, 3H), 3.18 (s, 3H), 2.99 (d, J = 4.7 Hz, 3H), 2.74 (s, 3H) | 631 |
| 238 | 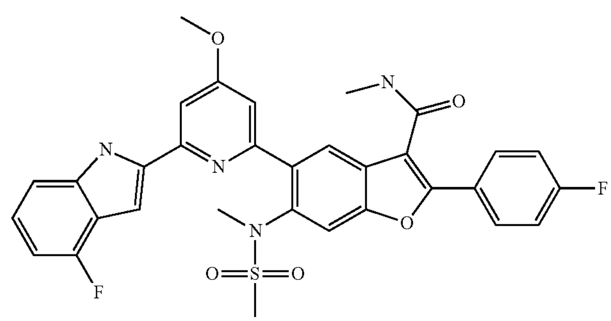 [SMILES: CNC(=O)c1c(-c2ccc(F)cc2)oc2cc(N(C)S(C)(=O)=O)c(-c3cc(OC)cc(-c4cc5c(F)cccc5[nH]4)n3)cc12] | ¹H-NMR (CDCl₃, 400 MHz) δ 9.96 (s, 1H), 8.05 (s, 1H), 7.95~7.99 (m, 2H), 7.62 (s, 1H), 7.33 (d, J = 2.4 Hz, 1H), 7.18~7.34 (m, 3H), 7.08~7.13 (m, 3H), 7.75~7.79 (m, 1H), 5.87 (d, J = 8.0 Hz, 1H), 3.99 (s, 3H), 3.12 (s, 3H), 3.00 (d, J = 4.2 Hz, 3H), 2.96 (s, 3H). | 617 |
| 239 | 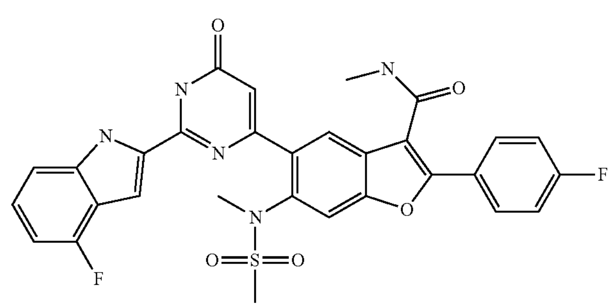 [SMILES: CNC(=O)c1c(-c2ccc(F)cc2)oc2cc(N(C)S(C)(=O)=O)c(-c3cc(=O)[nH]c(-c4cc5c(F)cccc5[nH]4)n3)cc12] | ¹H-NMR (Methanol-d₄, 400 MHz) δ 8.00 (d, J = 5.2 Hz, 2H), 7.85 (s, 1H), 7.79 (s, 1H), 7.23~7.30 (m, 4H), 7.06~7.11 (m, 3H), 6.68 (d, J = 8.0 Hz, 2H), 6.42 (s, 1H), 3.37 (s, 3H), 2.97 (s, 3H), 2.86 (s, 3H). | 604 |

-continued

| No. | Structure | NMR | MS (M + H)+ |
|---|---|---|---|
| 240 | 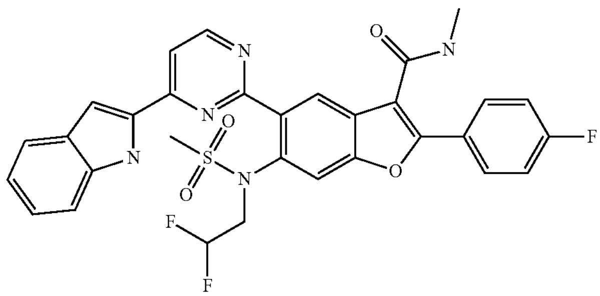 [SMILES: CNC(=O)c1c(-c2ccc(F)cc2)oc2cc(N(CC(F)F)S(C)(=O)=O)c(-c3nccc(-c4cc5ccccc5[nH]4)n3)cc12] | ¹H-NMR (CDCl₃, 400 MHz) δ 10.49 (s, 1H), 8.67 (s, 2H), 7.86~7.90 (m, 2H), 7.60~7.62 (m, 2H), 7.55~7.56 (m, 1H), 7.41~7.43 (m, 1H), 7.17~7.23 (m, 2H), 7.05~7.13 (m, 3H), 5.74~6.03 (m, 2H), 4.18~4.30 (m, 1H), 3.55~3.66 (m, 1H), 3.10 (s, 3H), 2.91 (d, J = 4.8 Hz, 3H). | 620 |
| 241 | 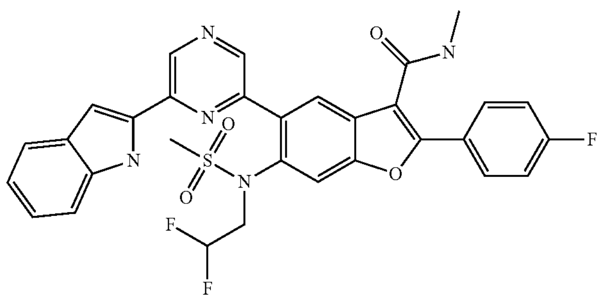 [SMILES: CNC(=O)c1c(-c2ccc(F)cc2)oc2cc(N(CC(F)F)S(C)(=O)=O)c(-c3cncc(-c4cc5ccccc5[nH]4)n3)cc12] | ¹H-NMR (CDCl₃, 400 MHz) δ 8.92 (s, 1H), 8.53 (s, 1H), 7.97 (s, 1H), 7.77~7.80 (m, 2H), 7.58~7.59 (m, 2H), 7.36~7.39 (m, 1H), 7.02~7.16 (m, 5H), 6.11~6.12 (m, 1H), 5.62~5.90 (m, 1H), 3.90~4.05 (m, 1H), 3.32~3.45 (m, 1H), 3.06 (s, 3H), 2.87 (d, J = 4.8 Hz, 3H). | 620 |
| 242 | 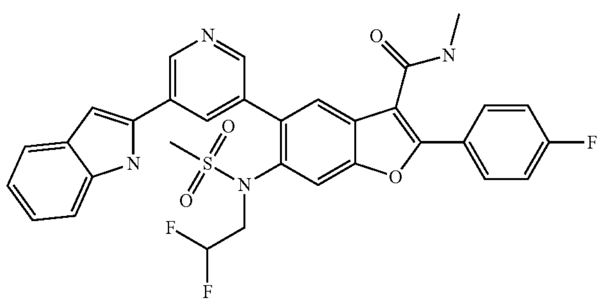 [SMILES: CNC(=O)c1c(-c2ccc(F)cc2)oc2cc(N(CC(F)F)S(C)(=O)=O)c(-c3cncc(-c4cc5ccccc5[nH]4)c3)cc12] | ¹H-NMR (CDCl₃, 400 MHz) δ 9.99 (s, 1H), 9.05 (s, 1H), 8.72 (s, 1H), 8.56 (s, 1H), 7.94 (s, 1H), 7.86~7.90 (m, 2H), 7.59~7.60 (m, 2H), 7.38~7.40 (m, 1H), 7.16~7.23 (m, 3H), 7.08~7.12 (m, 1H), 6.96 (s, 1H), 6.31 (d, J = 4.4 Hz, 1H), 5.71 (t, J = 5.5 Hz, 1H), 3.82~3.92 (m, 1H), 3.28~3.36 (m, 1H), 3.22 (s, 3H), 2.98 (d, J = 4.8 Hz, 3H). | 619 |
| 243 | 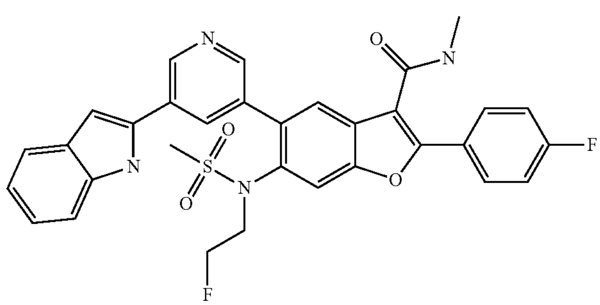 [SMILES: CNC(=O)c1c(-c2ccc(F)cc2)oc2cc(N(CCF)S(C)(=O)=O)c(-c3cncc(-c4cc5ccccc5[nH]4)c3)cc12] | ¹H-NMR (CDCl₃, 400 MHz) δ 9.34 (s, 1H), 8.96 (d, J = 1.6 Hz, 1H), 8.49 (d, J = 1.6 Hz, 1H), 8.40 (s, 1H), 7.88~7.92 (m, 3H), 7.62 (d, J = 8.0 Hz, 1H), 7.54 (s, 1H), 7.42 (d, J = 8.0 Hz, 1H), 7.08~7.20 (m, 4H), 6.89 (s, 1H), 6.07 (d, J = 3.6 Hz, 1H), 4.12~4.36 (m, 3H), 3.27 (s, 3H), 2.95 (d, J = 4.8 Hz, 3H), 2.71~2.85 (m, 1H). | 601 |
| 244 | 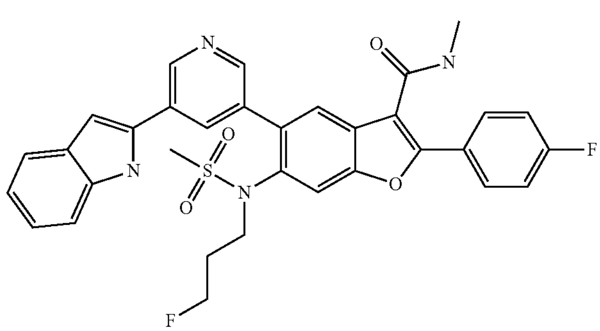 [SMILES: CNC(=O)c1c(-c2ccc(F)cc2)oc2cc(N(CCCF)S(C)(=O)=O)c(-c3cncc(-c4cc5ccccc5[nH]4)c3)cc12] | ¹H-NMR (CDCl₃, 400 MHz) δ 9.55 (s, 1H), 8.95 (s, 1H), 8.44 (d, J = 1.6 Hz, 1H), 8.26 (t, J = 1.6 Hz, 1H), 7.80~7.87 (m, 3H), 7.61 (d, J = 8.0 Hz, 1H), 7.48 (s, 1H), 7.42 (d, J = 2.0 Hz, 1H), 7.08~7.24 (m, 4H), 6.86 (d, J = 1.2 Hz, 1H), 6.17 (br s, 1H), 4.02~4.26 (m, 2H), 3.45~3.52 (m, 1H). 3.18~3.22 (m, 1H), 3.10 (s, 3H), 2.90 (d, J = 4.8 Hz, 3H), 1.50~1.63 (m, 2H). | 615 |

| No. | Structure | NMR | MS (M + H)+ |
|---|---|---|---|
| 245 | 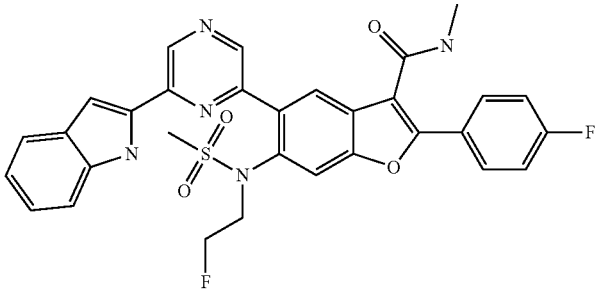 [SMILES: CNC(=O)c1c(-c2ccc(F)cc2)oc2cc(N(CCF)S(C)(=O)=O)c(-c3cncc(-c4cc5ccccc5[nH]4)n3)cc12] | ¹H-NMR (Methanol-d₄, 400 MHz) δ 9.11 (s, 1H), 8.81 (s, 1H), 8.01 (s, 1H), 7.95~8.00 (m, 2H), 7.93 (s, 1H), 7.61 (d, J = 8.0 Hz, 1H), 7.42 (d, J = 8.0 Hz, 1H), 7.26~7.30 (m, 3H), 7.04 (d, J = 8.0 Hz, 1H), 7.02 (d, J = 8.0 Hz, 1H), 4.57 (br. s, 1H), 4.44 (br. s, 1H), 4.06 (br, s, 1H), 3.79 (br. s, 1H), 3.12 (s, 3H), 2.94 (s, J = 4.8 Hz, 3H). | 602 |
| 246 | 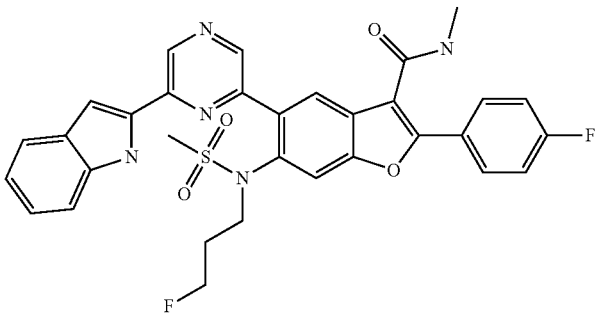 [SMILES: CNC(=O)c1c(-c2ccc(F)cc2)oc2cc(N(CCCF)S(C)(=O)=O)c(-c3cncc(-c4cc5ccccc5[nH]4)n3)cc12] | ¹H-NMR (Methanol-d₄, 400 MHz) δ 9.11 (s, 1H), 8.80 (s, 1H), 8.00 (s, 1H), 7.90~8.00 (m, 3H), 7.61 (d, J = 8.0 Hz, 1H), 7.43 (m, 1H), 7.30 (m, 3H), 7.11 (m, 1H), 7.01 (m, 1H), 4.29 (br s, 1H), 4.17 (br s, 1H), 3.70 (m, 2H), 3.09 (s, 3H,), 2.93 (d, J = 4.8 Hz, 3H), 1.88 (m, 1H), 1.78 (m, 1H). | 616 |
| 247 | 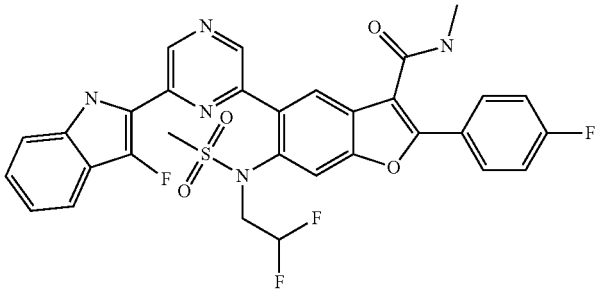 [SMILES: CNC(=O)c1c(-c2ccc(F)cc2)oc2cc(N(CC(F)F)S(C)(=O)=O)c(-c3cncc(-c4[nH]c5ccccc5c4F)n3)cc12] | ¹H-NMR (DMSO-d₆, 400 MHz) δ 11.49 (s, 1H), 9.08 (s, 1H), 8.79 (s, 1H), 8.53 (d, J = 4.8 Hz, 1H), 8.11 (s, 1H), 7.98~8.03 (m, 3H), 7.61 (d, J = 8.0 Hz, 1H), 7.38~7.44 (m, 3H), 7.23 (t, J = 7.6 Hz, 1H), 7.09 (t, J = 7.6 Hz, 1H), 6.08~6.36 (m, 1H), 4.02~1.09 (m, 2H), 3.10 (s, 3H), 2.80 (d, J = 4.4 Hz, 3H). | 638 |
| 248 | 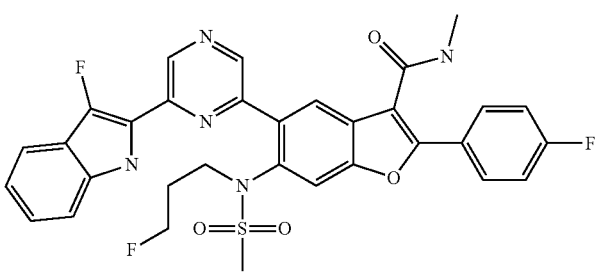 [SMILES: CNC(=O)c1c(-c2ccc(F)cc2)oc2cc(N(CCCF)S(C)(=O)=O)c(-c3cncc(-c4[nH]c5ccccc5c4F)n3)cc12] | ¹H-NMR (CDCl₃, 400 MHz) δ 9.61 (s, 1H), 9.20 (s, 1H), 8.69 (s, 1H), 8.12 (s, 1H), 7.90~7.93 (m, 2H), 7.66~7.67 (d, J = 5.2 Hz, 2H), 7.36 (d, J = 8.8 Hz, 1H), 7.11~7.28 (m, 4H), 5.92 (br s, 1H), 4.23~4.36 (m, 2H), 3.68 (s, 1H), 3.46 (s, 1H), 3.07 (s, 3H), 2.98 (d, J = 5.2 Hz, 3H), 1.73~1.83 (m, 2H). | 634 |

Compounds 258 to 296, depicted in the table below, were prepared using the method described in Example 13 and substituting the appropriate reactants and/or reagents.

| No. | Structure | MS (M + H)+ |
|---|---|---|
| 258 | 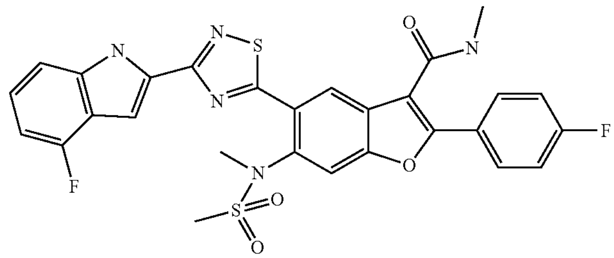 [SMILES: CNC(=O)c1c(-c2ccc(F)cc2)oc2cc(N(C)S(C)(=O)=O)c(-c3nc(-c4cc5c(F)cccc5[nH]4)ns3)cc12] | 594 |
| 259 | 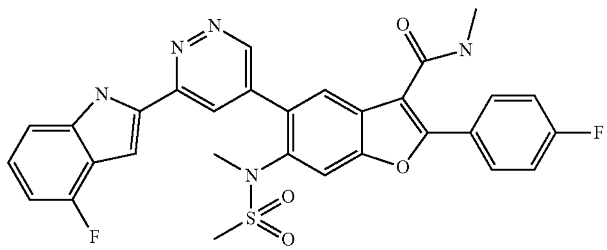 [SMILES: CNC(=O)c1c(-c2ccc(F)cc2)oc2cc(N(C)S(C)(=O)=O)c(-c3cnnc(-c4cc5c(F)cccc5[nH]4)c3)cc12] | 588 |
| 260 | 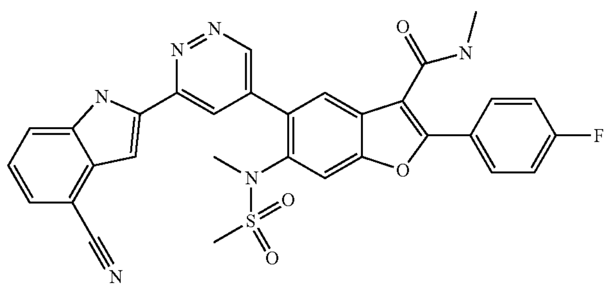 [SMILES: CNC(=O)c1c(-c2ccc(F)cc2)oc2cc(N(C)S(C)(=O)=O)c(-c3cnnc(-c4cc5c(C#N)cccc5[nH]4)c3)cc12] | 595 |
| 261 | 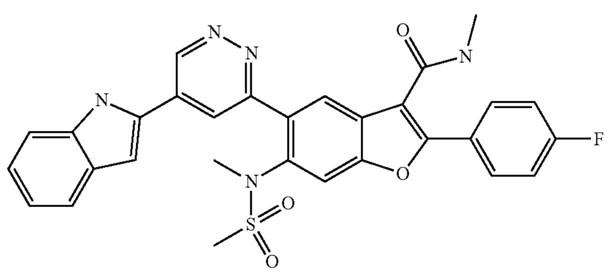 [SMILES: CNC(=O)c1c(-c2ccc(F)cc2)oc2cc(N(C)S(C)(=O)=O)c(-c3cc(-c4cc5ccccc5[nH]4)cnn3)cc12] | 570 |
| 262 | 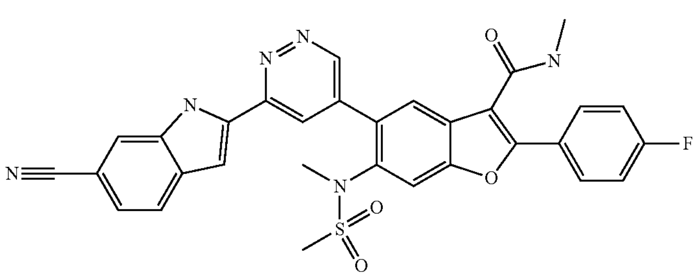 [SMILES: CNC(=O)c1c(-c2ccc(F)cc2)oc2cc(N(C)S(C)(=O)=O)c(-c3cnnc(-c4cc5ccc(C#N)cc5[nH]4)c3)cc12] | 595 |

| No. | Structure | MS (M + H)+ |
|---|---|---|
| 263 | 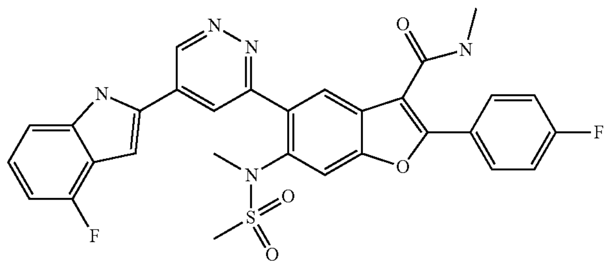 [SMILES: CNC(=O)c1c(-c2ccc(F)cc2)oc2cc(N(C)S(C)(=O)=O)c(-c3cc(-c4cc5c(F)cccc5[nH]4)cnn3)cc12] | 588 |
| 264 | 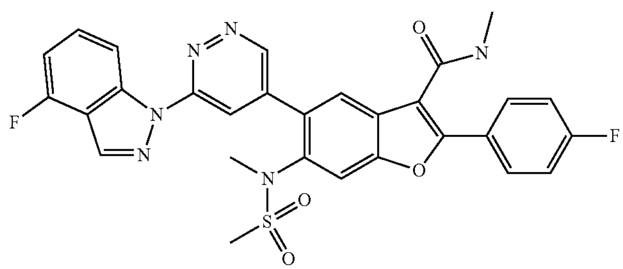 [SMILES: CNC(=O)c1c(-c2ccc(F)cc2)oc2cc(N(C)S(C)(=O)=O)c(-c3cnnc(-n4ncc5c(F)cccc54)c3)cc12] | 589 |
| 265 | 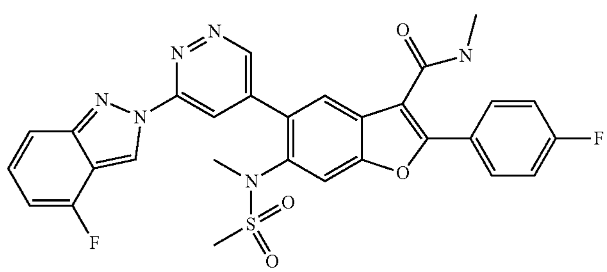 [SMILES: CNC(=O)c1c(-c2ccc(F)cc2)oc2cc(N(C)S(C)(=O)=O)c(-c3cnnc(-n4cc5c(F)cccc5n4)c3)cc12] | 589 |
| 266 | 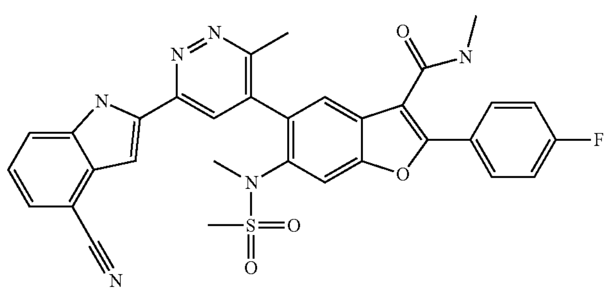 [SMILES: CNC(=O)c1c(-c2ccc(F)cc2)oc2cc(N(C)S(C)(=O)=O)c(-c3cc(-c4cc5c(C#N)cccc5[nH]4)nnc3C)cc12] | 609 |
| 267 | 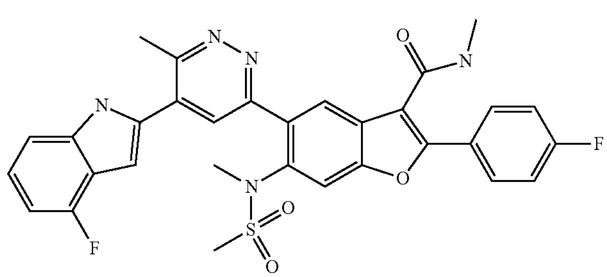 [SMILES: CNC(=O)c1c(-c2ccc(F)cc2)oc2cc(N(C)S(C)(=O)=O)c(-c3cc(-c4cc5c(F)cccc5[nH]4)c(C)nn3)cc12] | 602 |

-continued
| No. | Structure | MS (M + H)+ |
|---|---|---|
| 268 | 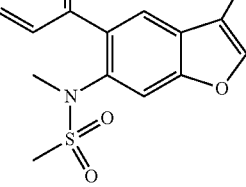 | 602 |
| 269 | 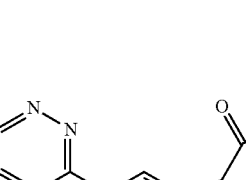 | 609 |
| 270 | 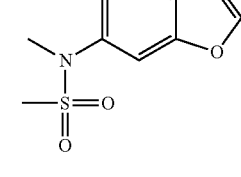 | 495 |
| 271 | 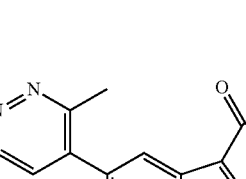 | 572 |
| 272 | 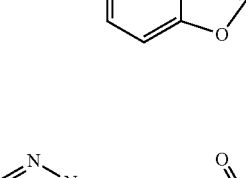 | 603 |

-continued

| No. | Structure | MS (M + H)+ |
|---|---|---|
| 273 | 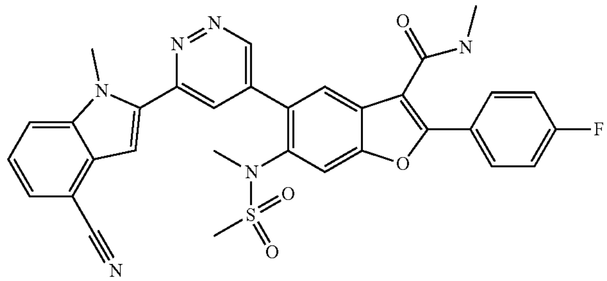 [SMILES: CNC(=O)c1c(-c2ccc(F)cc2)oc2cc(N(C)S(C)(=O)=O)c(-c3cnnc(-c4cc5c(C#N)cccc5n4C)c3)cc12] | 609 |
| 274 | 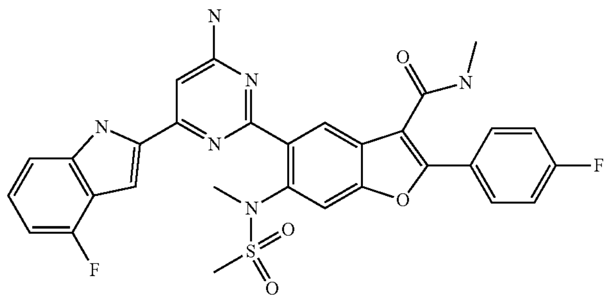 [SMILES: CNC(=O)c1c(-c2ccc(F)cc2)oc2cc(N(C)S(C)(=O)=O)c(-c3nc(N)cc(-c4cc5c(F)cccc5[nH]4)n3)cc12] | 603 |
| 275 | 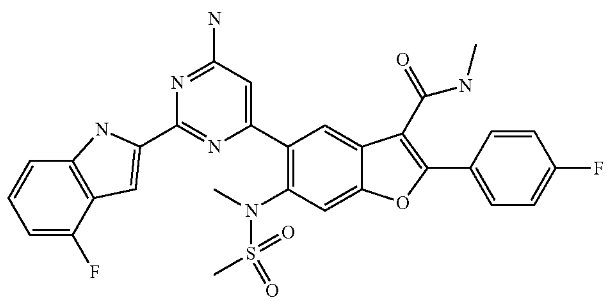 [SMILES: CNC(=O)c1c(-c2ccc(F)cc2)oc2cc(N(C)S(C)(=O)=O)c(-c3cc(N)nc(-c4cc5c(F)cccc5[nH]4)n3)cc12] | 603 |
| 276 | 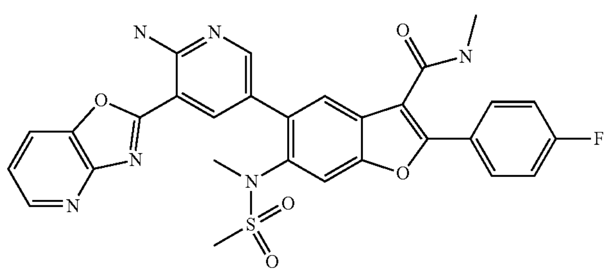 [SMILES: CNC(=O)c1c(-c2ccc(F)cc2)oc2cc(N(C)S(C)(=O)=O)c(-c3cnc(N)c(-c4nc5ncccc5o4)c3)cc12] | 587 |
| 277 | 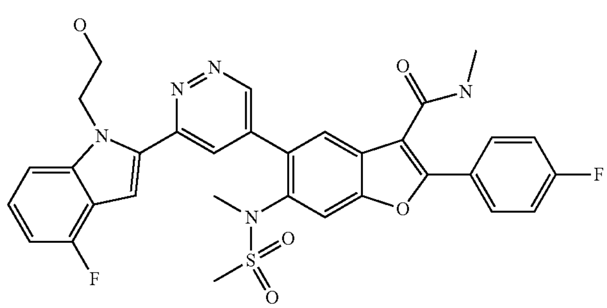 [SMILES: CNC(=O)c1c(-c2ccc(F)cc2)oc2cc(N(C)S(C)(=O)=O)c(-c3cnnc(-c4cc5c(F)cccc5n4CCO)c3)cc12] | 632 |

-continued

| No. | Structure | MS (M + H)+ |
|---|---|---|
| 278 | 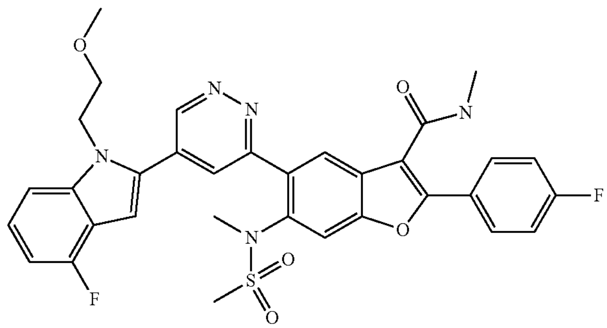 [SMILES: CNC(=O)c1c(-c2ccc(F)cc2)oc2cc(N(C)S(C)(=O)=O)c(-c3cc(-c4cc5c(F)cccc5n4CCOC)cnn3)cc12] | 646 |
| 279 | 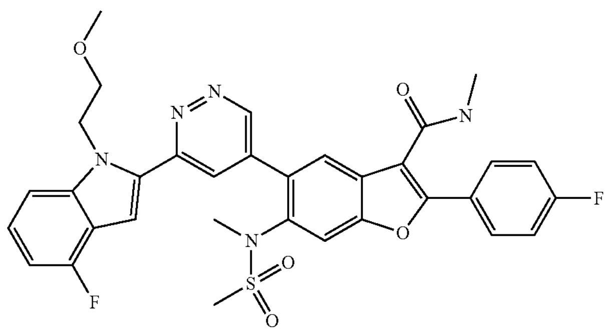 [SMILES: CNC(=O)c1c(-c2ccc(F)cc2)oc2cc(N(C)S(C)(=O)=O)c(-c3cnnc(-c4cc5c(F)cccc5n4CCOC)c3)cc12] | 646 |
| 280 | 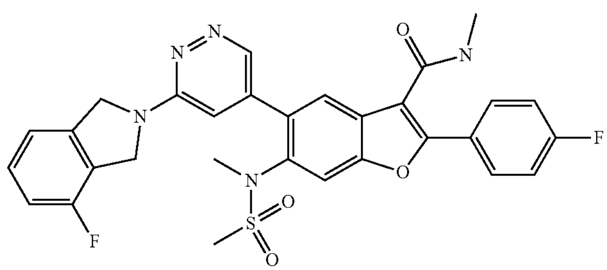 [SMILES: CNC(=O)c1c(-c2ccc(F)cc2)oc2cc(N(C)S(C)(=O)=O)c(-c3cnnc(N4Cc5cccc(F)c5C4)c3)cc12] | 590 |
| 281 | 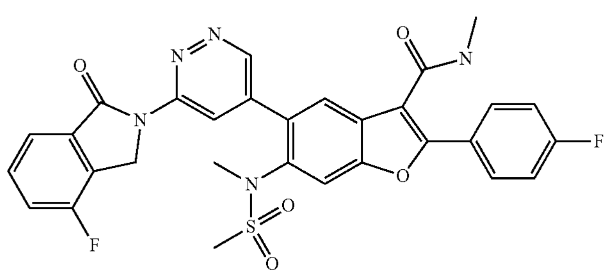 [SMILES: CNC(=O)c1c(-c2ccc(F)cc2)oc2cc(N(C)S(C)(=O)=O)c(-c3cnnc(N4Cc5c(F)cccc5C4=O)c3)cc12] | 604 |
| 282 | 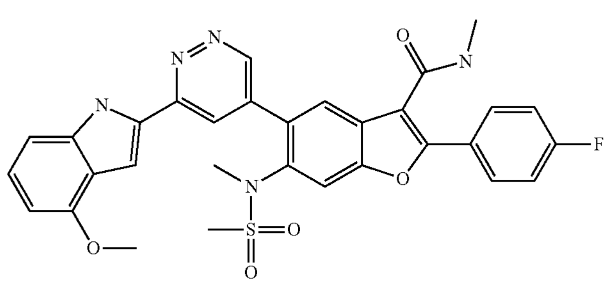 [SMILES: CNC(=O)c1c(-c2ccc(F)cc2)oc2cc(N(C)S(C)(=O)=O)c(-c3cnnc(-c4cc5c(OC)cccc5[nH]4)c3)cc12] | 600 |

-continued

| No. | Structure | MS (M + H)+ |
|---|---|---|
| 283 | 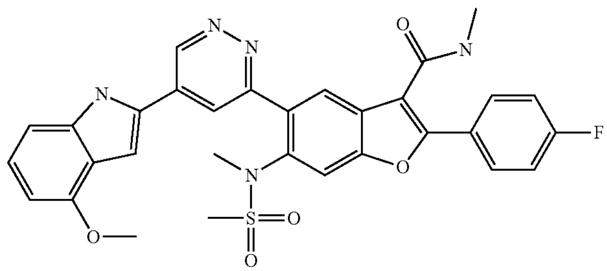 | 600 |
| 284 | 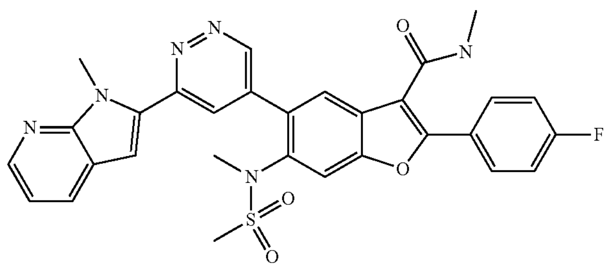 | 585 |
| 285 | 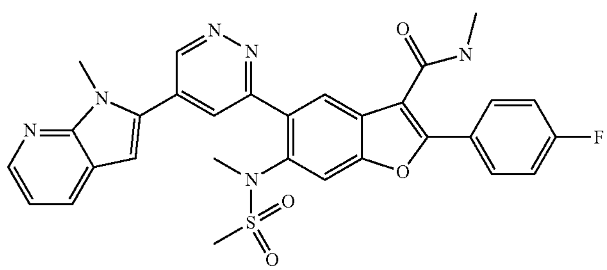 [SMILES: CNC(=O)c1c(-c2ccc(F)cc2)oc2cc(N(C)S(C)(=O)=O)c(-c3cc(-c4cc5cccnc5n4C)cnn3)cc12] | 585 |
| 286 | 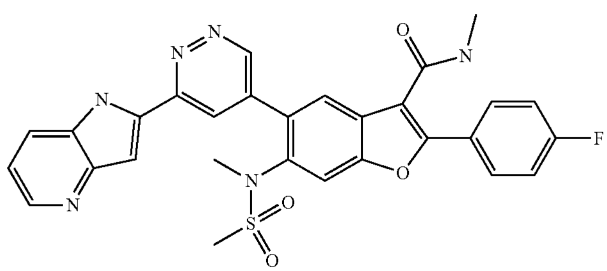 [SMILES: CNC(=O)c1c(-c2ccc(F)cc2)oc2cc(N(C)S(C)(=O)=O)c(-c3cnnc(-c4cc5ncccc5[nH]4)c3)cc12] | 571 |
| 287 | 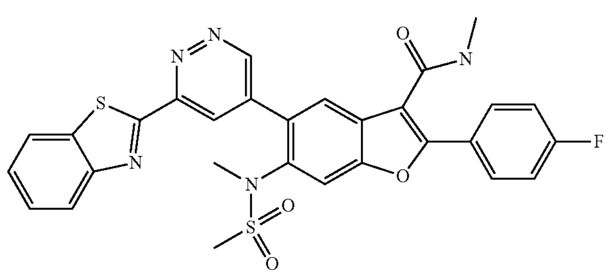 [SMILES: CNC(=O)c1c(-c2ccc(F)cc2)oc2cc(N(C)S(C)(=O)=O)c(-c3cnnc(-c4nc5ccccc5s4)c3)cc12] | 588 |

-continued

| No. | Structure | MS (M + H)+ |
|---|---|---|
| 288 | 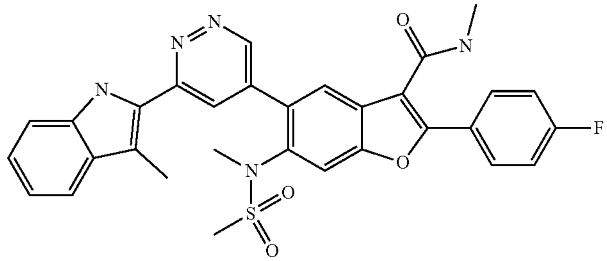 [SMILES: CNC(=O)c1c(-c2ccc(F)cc2)oc2cc(N(C)S(C)(=O)=O)c(-c3cnnc(-c4[nH]c5ccccc5c4C)c3)cc12] | 584 |
| 289 | 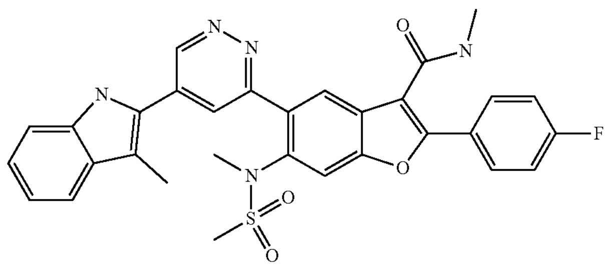 [SMILES: CNC(=O)c1c(-c2ccc(F)cc2)oc2cc(N(C)S(C)(=O)=O)c(-c3cc(-c4[nH]c5ccccc5c4C)cnn3)cc12] | 584 |
| 290 | 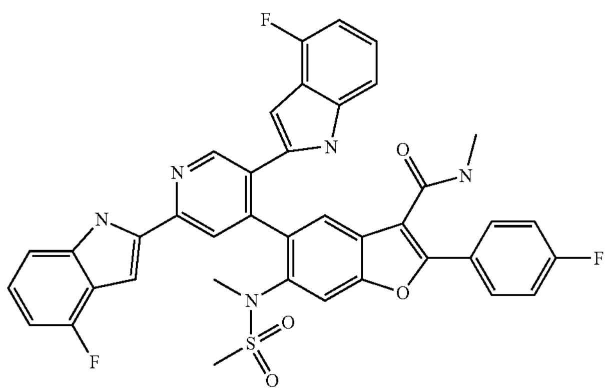 [SMILES: CNC(=O)c1c(-c2ccc(F)cc2)oc2cc(N(C)S(C)(=O)=O)c(-c3cc(-c4cc5c(F)cccc5[nH]4)ncc3-c3cc4c(F)cccc4[nH]3)cc12] | 720 |
| 291 | 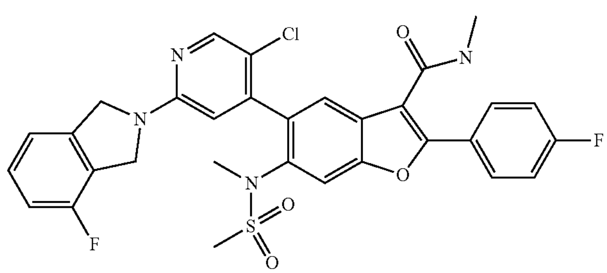 [SMILES: CNC(=O)c1c(-c2ccc(F)cc2)oc2cc(N(C)S(C)(=O)=O)c(-c3cc(N4Cc5cccc(F)c5C4)ncc3Cl)cc12] | 624 |
| 292 | 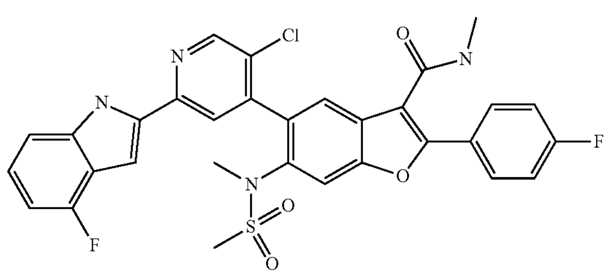 [SMILES: CNC(=O)c1c(-c2ccc(F)cc2)oc2cc(N(C)S(C)(=O)=O)c(-c3cc(-c4cc5c(F)cccc5[nH]4)ncc3Cl)cc12] | 622 |

| No. | Structure | MS (M + H)+ |
|---|---|---|
| 293 | 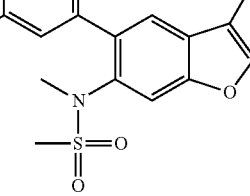 | 617 |
| 294 | 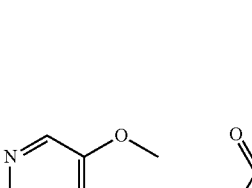 | 619 |
| 295 | 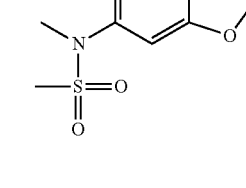 | 602 |
| 296 | 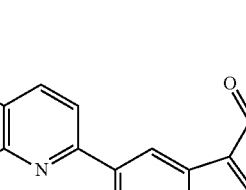 | 604 |

Example 14

Preparation of Compound 150

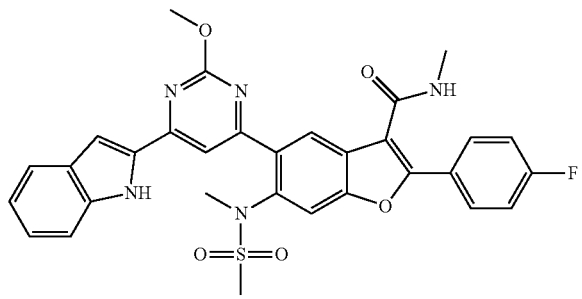

150

Step A—Synthesis of tert-butyl 2-(2,6-dichloropyrimidin-4-yl)-1H-indole-1-carboxylate

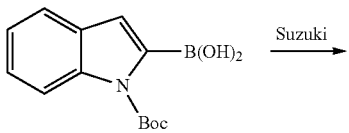

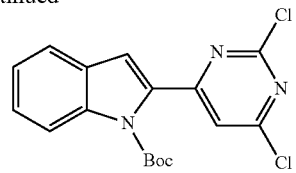

To a mixture of 1-(tert-butoxycarbonyl)-1H-indol-2-ylboronic acid (200 mg, 0.78 mmol), 2,4,6-trichloropyrimidine (436 mg, 2.4 mmol) and $K_3PO_4 \cdot 3H_2O$ (620 mg, 2.4 mmol) in DMF (4 mL), under $N_2$ atmosphere, was added Pd(dppf)Cl$_2$ (56 mg, 0.08 mmol). The reaction was heated to 80° C. and allowed to stir at this temperature for 12 hours. Water was added, and the resulting solution was extracted with EtOAc. The organic extract was washed with brine, dried over $Na_2SO_4$, filtered and concentrated in vacuo and the resulting residue was purified using prep-TLC (eluted with PE:EtOAc=5:1) to provide tert-butyl 2-(2,6-dichloropyrimidin-4-yl)-1H-indole-1-carboxylate (142 mg, yield: 50%). $^1$H-NMR (Methanol-d$_4$, 400 MHz) δ 8.09 (d, J=7.6 Hz, 1H), 7.55~7.58 (m, 1H), 7.40 (s, 1H), 7.21~7.25 (m, 1H), 7.09 (s, 1H), 7.01 (s, 1H), 1.43 (s, 9H).

Step B—Synthesis of tert-butyl 2-(2-chloro-6-(2-(4-fluorophenyl)-3-(methylcarbamoyl)-6-(N-methylmethylsulfonamido)benzofuran-5-yl)pyrimidin-4-yl)-1H-indole-1-carboxylate

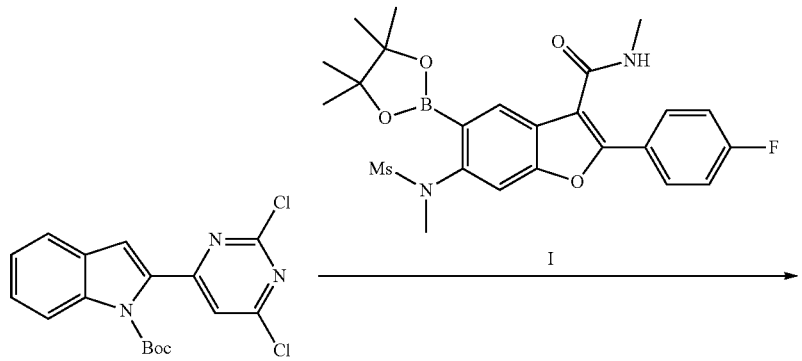

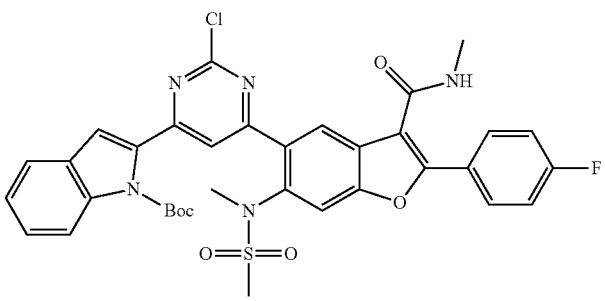

To a mixture of tert-butyl 2-(2,6-dichloropyrimidin-4-yl)-1H-indole-1-carboxylate (110 mg, 0.3 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 151 mg, 0.3 mmol) and $K_3PO_4 \cdot 3H_2O$ (310 mg, 1.2 mmol) in DMF (4 mL), under $N_2$ atmosphere, was added Pd(dppf)Cl$_2$ (28 mg, 0.04 mmol). The reaction was heated to 80° C. and allowed to stir at this temperature for 12 hours. Water was added, and the aqueous solution was extracted with EtOAc. The combined organic layers were washed with brine, dried over $Na_2SO_4$, filtered and concentrated in vacuo and the resulting residue was purified using prep-TLC (eluted with PE:EtOAc=4:1) to provide tert-butyl 2-(2-chloro-6-(2-(4-fluorophenyl)-3-(methylcarbamoyl)-6-(N-methylmethylsulfonamido)benzofuran-5-yl)pyrimidin-4-yl)-1H-indole-1-carboxylate (115 mg, yield: 55%).

Step C—Synthesis of 5-(6-(1H-indol-2-yl)-2-methoxypyrimidin-4-yl)-2-(4-fluorophenyl)-N-methyl-6-(N-methylmethylsulfonamido)benzofuran-3-carboxamide (Compound 150)

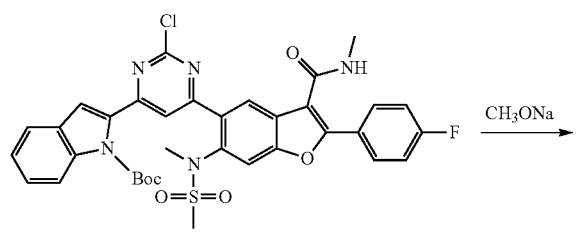

CH$_3$ONa

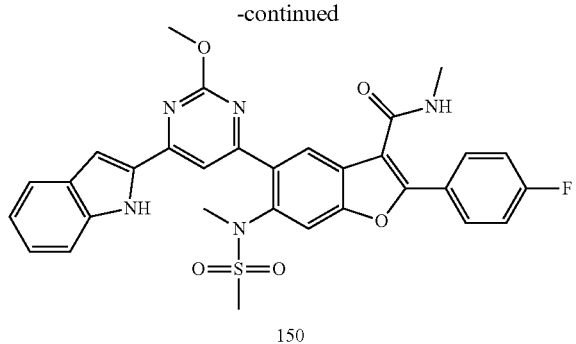

150

To a solution of tert-butyl 2-(2-chloro-6-(2-(4-fluorophenyl)-3-(methylcarbamoyl)-6-(N-methylmethylsulfonamido)benzofuran-5-yl)pyrimidin-4-yl)-1H-indole-1-carboxylate (35 mg, 0.05 mmol) in MeOH (2 mL), NaOCH$_3$ (8 mg, 0.15 mmol) in MeOH (0.1 mL) was added by dropwise at 25° C. The mixture was allowed to stir at 60° C. for 3 hours, Then cooled to 25° C. and H$_2$O (5 mL) was added to the mixture. Then the mixture was extracted with ethyl acetate and washed with brine, dried over Na$_2$SO$_4$. After being concentrated in vacuo, the resulting residue was purified using prep-HPLC to provide Compound 150 (20 mg, yield: 70%). $^1$H-NMR (CDCl$_3$, 400 MHz) δ 9.50 (s, 1H), 8.16 (s, 1H), 7.94~7.98 (m, 2H), 7.78 (s, 1H), 7.64~7.68 (m, 2H), 7.44~7.46 (m, 1H), 7.28~7.31 (m, 2H), 7.12~7.23 (m, 3H), 5.96 (s, 1H), 4.15 (s, 3H), 3.28 (s, 3H), 3.01 (d, J=4.8 Hz, 3H), 2.96 (s, 3H). MS (M+H)$^+$: 600.

Compounds 151-152, depicted in the table below, were prepared using the method described in Example 14 and substituting the appropriate reactants and/or reagents.

| No. | Structure | NMR | MS (M + H)$^+$ |
|---|---|---|---|
| 151 | 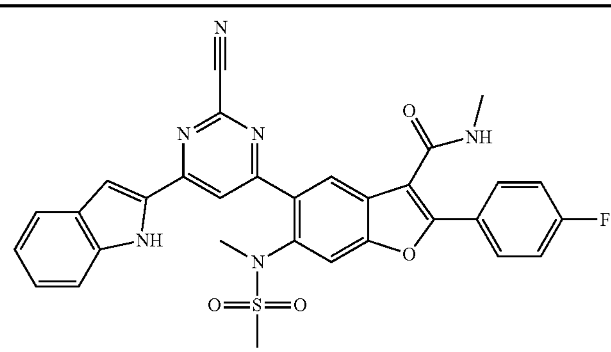 | $^1$H-NMR (CDCl$_3$, 400 MHz) δ 9.49 (s, 1H), 8.25~8.29 (m, 2H), 7.94~7.98 (m, 2H), 7.65~7.71 (m, 2H), 7.48~7.50 (m, 1H), 7.33~7.39 (m, 2H), 7.15~7.24 (m, 3H), 5.89 (s, 1H), 3.31 (s, 3H), 3.03~3.04 (m, 6H). | 595 |
| 152 | 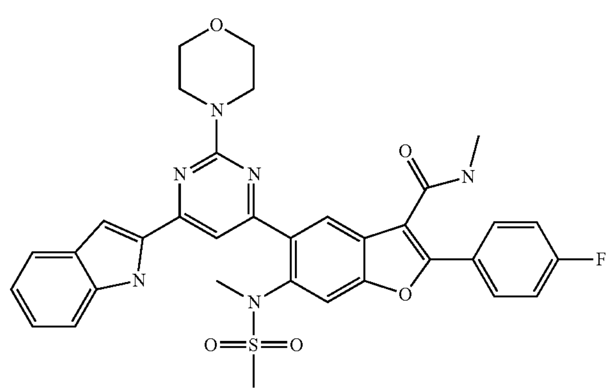 [SMILES: CNC(=O)c1c(-c2ccc(F)cc2)oc2cc(N(C)S(C)(=O)=O)c(-c3cc(-c4cc5ccccc5[nH]4)nc(N4CCOCC4)n3)cc12] | $^1$H-NMR (CDCl$_3$, 400 MHz) δ 9.34 (s, 1H), 8.10 (s, 1H), 7.94~7.98 (m, 2H), 7.64~7.68 (m, 2H), 7.46 (d, J = 8.0 Hz, 1H), 7.36 (s, 1H), 7.11~7.24 (m, 4H), 5.85 (s, 1H), 3.96~3.98 (m, 4H), 3.83~3.86 (m, 4H), 3.29 (s, 3H), 3.01 (d, J = 4.8 Hz, 3H), 2.89 (s, 3H). | 655 |

Example 15

Preparation of Compound 153 and 154

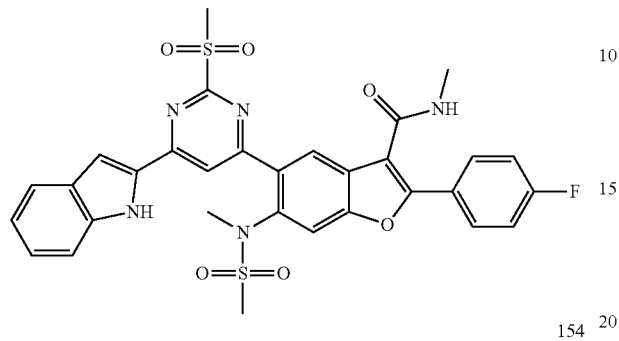

Step A—Synthesis of 5-(6-(1H-indol-2-yl)-2-(methylthio)pyrimidin-4-yl)-2-(4-fluorophenyl)-N-methyl-6-(N-methylmethylsulfonamido)benzofuran-3-carboxamide

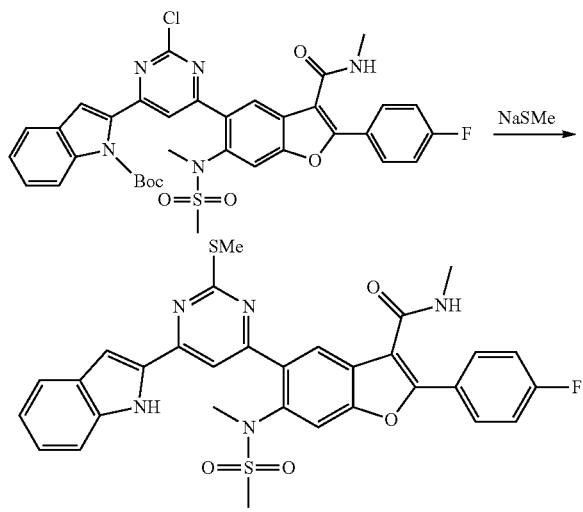

To a solution of tert-butyl 2-(2-chloro-6-(2-(4-fluorophenyl)-3-(methylcarbamoyl)-6-(N-methylmethylsulfonamido)benzofuran-5-yl)pyrimidin-4-yl)-1H-indole-1-carboxylate (57 mg, 0.08 mmol) in CH$_3$CN (2 mL), was added NaSMe (70 mg, 1 mmol). The reaction was allowed to stir at reflux for about 15 hours, then the reaction mixture was directly purified using prep-TLC (eluted with PE:EtOAc=1:1) to provide 5-(6-(1H-indol-2-yl)-2-(methylthio)pyrimidin-4-yl)-2-(4-fluorophenyl)-N-methyl-6-(N-methylmethylsulfonamido)benzofuran-3-carboxamide (40 mg, yield: 80%). $^1$H-NMR (CDCl$_3$, 400 MHz) δ 9.37 (s, 1H), 8.09 (s, 1H), 7.88~7.92 (m, 2H), 7.71 (s, 1H), 7.60~7.63 (m, 2H), 7.40-7.42 (m, 1H), 7.21~7.28 (m, 2H), 7.06~7.15 (m, 3H), 5.81~5.82 (m, 1H), 3.21 (s, 3H), 2.95 (d, J=4.8 Hz, 3H), 2.87 (s, 3H), 2.64 (s, 3H).

Step B—Synthesis of 5-(6-(1H-indol-2-yl)-2-(methylsulfonyl)pyrimidin-4-yl)-2-(4-fluorophenyl)-N-methyl-6-(N-methylmethylsulfonamido)benzofuran-3-carboxamide (Compound 153) and 5-(6-(1H-indol-2-yl)-2-(methylsulfinyl)pyrimidin-4-yl)-2-(4-fluorophenyl)-N-methyl-6-(N-methylmethylsulfonamido)benzofuran-3-carboxamide (Compound 154)

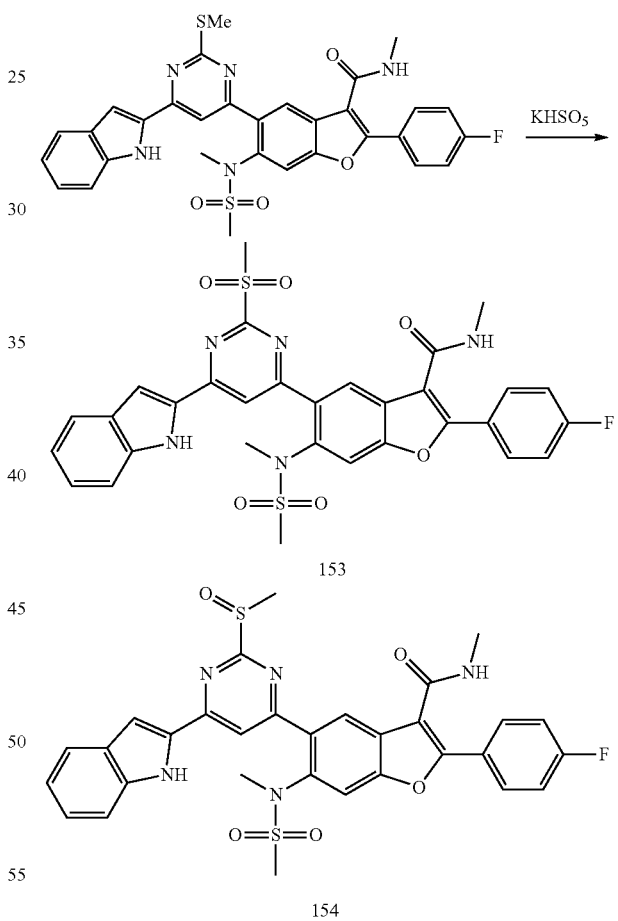

To a mixture of 5-(6-(1H-indol-2-yl)-2-(methylthio)pyrimidin-4-yl)-2-(4-fluorophenyl)-N-methyl-6-(N-methylmethylsulfonamido)benzofuran-3-carboxamide (20 mg, 0.033 mmol) in DCM (2 mL), was added KHSO$_5$ (0.02 mL, 0.13 mmol). The reaction was allowed to stir at 25° C. for 12 hours, then the reaction mixture was poured into water and extracted with ethyl acetate. The organic extract was washed with brine, dried over Na$_2$SO$_4$, filtered and concentrated in vacuo, and the resulting residue was purified using prep- TLC (eluted with PE:EtOAc=1:1) to provide Compound 153 (10 mg, yield: 50%) and Compound 154 (5 mg, yield: 25%).

Compound 153: ¹H-NMR (CDCl₃, 400 MHz) δ 9.73 (s, 1H), 8.24 (d, J=6.4 Hz, 2H), 7.91~7.95 (m, 2H), 7.65~7.71 (m, 2H), 7.31~7.49 (m, 3H), 7.14~7.24 (m, 3H), 5.90 (s, 1H), 3.43 (s, 3H), 3.36 (s, 3H), 3.01 (d, J=4.8 Hz, 3H), 2.97 (s, 3H). MS (M+H)⁺: 647.

Compound 154: ¹H-NMR (CDCl₃, 400 MHz) δ 10.18 (s, 1H), 8.25 (s, 1H), 8.12 (s, 1H), 7.93~7.97 (m, 2H), 7.65~7.71 (m, 2H), 7.47~7.49 (m, 1H), 7.38 (s, 1H), 7.30~7.34 (m, 1H), 7.14~7.24 (m, 3H), 5.94 (s, 1H), 3.36 (s, 3H), 3.06 (s, 3H), 3.02 (d, J=4.8 Hz, 3H), 2.98 (s, 3H). MS (M+H)⁺: 632.

Example 16

Preparation of Compound 155

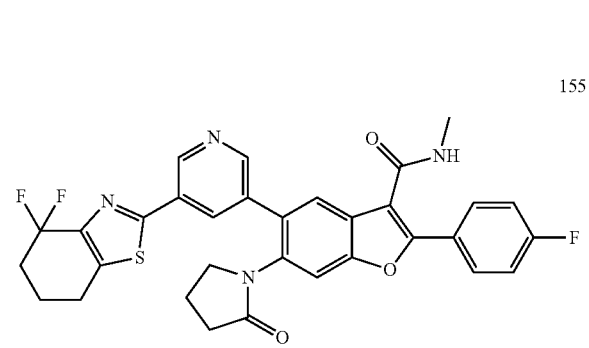 [SMILES: CNC(=O)c1c(-c2ccc(F)cc2)oc2cc(N3CCCC3=O)c(-c3cncc(-c4nc5c(s4)CCCC5(F)F)c3)cc12]

Step A—Synthesis of ethyl 5-bromo-2-(4-fluorophenyl)-6-(2-oxopyrrolidin-1-yl)benzofuran-3-carboxylate

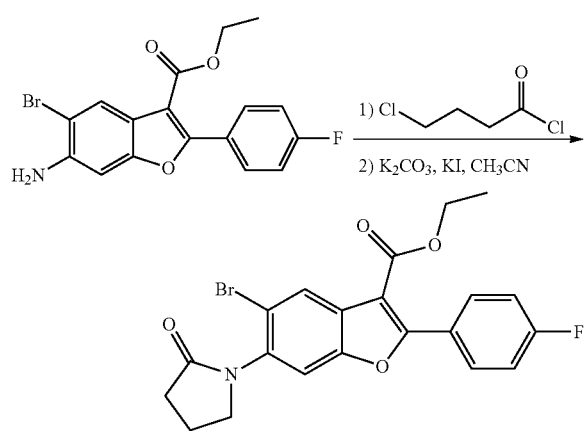

4-chlorobutanoyl chloride (670 mg, 4.76 mmol) was added dropwise to a 0° C. solution of ethyl 6-amino-5-bromo-2-(4-fluorophenyl)benzofuran-3-carboxylate and Et₃N (1.0 mL) in CH₂Cl₂ (10 mL) under N₂ atmosphere. The resulting reaction was allowed to stir at room temperature for 16 hours, then the reaction mixture was concentrated in vacuo. The resulting residue was dissolved in CH₃CN (10 mL), and then K₂CO₃ (658 mg, 4.76 mmol) and KI (263 mg, 1.59 mmol) was added and the mixture was heated to reflux and allowed to stir at this temperature for 16 hours. After being cooled to room temperature, the mixture was diluted with water and extracted with EtOAc. The organic extract was washed with brine, dried over Na₂SO₄, filtered and concentrated in vacuo. The residue obtained was purified using column chromatography (eluted with PE:EtOAc=2:1) to provide ethyl 5-bromo-2-(4-fluorophenyl)-6-(2-oxopyrrolidin-1-yl)benzofuran-3-carboxylate (280 mg, yield: 40%). ¹H-NMR (CDCl₃, 400 MHz) δ 8.32 (s, 1H), 8.04~8.07 (m, 2H), 7.48 (s, 1H), 7.17~7.21 (m, 2H), 4.42~4.43 (m, 2H), 3.82-3.86 (m, 2H), 2.61~2.65 (m, 2H), 2.27~2.31 (m, 2H), 1.40~1.44 (m, 3H).

Step B—Synthesis of 5-bromo-2-(4-fluorophenyl)-6-(2-oxopyrrolidin-yl)benzofuran-3-carboxylic acid

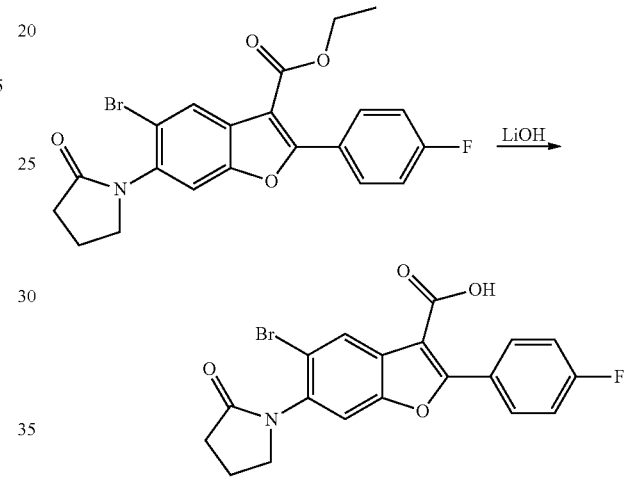

A solution of ethyl 5-bromo-2-(4-fluorophenyl)-6-(2-oxopyrrolidin-1-yl)benzofuran-3-carboxylate (2.5 g, 5.8 mmol) and LiOH (0.5 g, 21.0 mmol) in dioxane (30 mL) and water (10 mL) was allowed to stir at 90° C. for 1 hour. The mixture was cooled to room temperature and extracted with DCM, the organic extract was washed with brine, dried over Na₂SO₄ and concentrated to provide 5-bromo-2-(4-fluorophenyl)-6-(2-oxopyrrolidin-1-yl)benzofuran-3-carboxylic acid (2.2 g, yield: 91%). ¹H-NMR (CDCl₃, 400 MHz) δ 8.08 (s, 1H), 7.81-7.84 (m, 2H), 7.34 (s, 1H), 6.89~6.93 (m, 2H), 3.79~3.82 (m, 2H), 2.66~2.70 (m, 2H), 2.26-2.31 (m, 2H).

Step C—Synthesis of 5-bromo-2-(4-fluorophenyl)-N-methyl-6-(2-oxopyrrolidin-1-yl)benzofuran-3-carboxamide (Compound W)

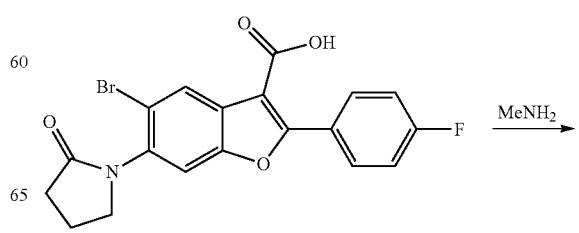

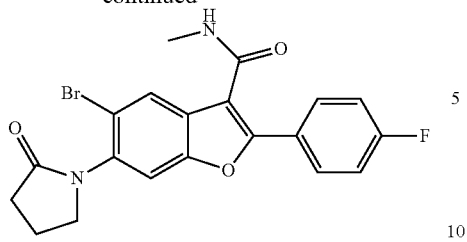

A solution of 5-bromo-2-(4-fluorophenyl)-6-(2-oxopyrrolidin-1-yl)benzofuran-3-carboxylic acid (280 mg, 0.67 mmol), HOBT (150 mg, 1.11 mmol) and EDCI (280 mg, 1.47 mmol) in dry DMF (2 mL) was allowed to stir at room temperature for 1 hour. Then $Et_3N$ (0.2 mL) and $CH_3NH_2$ (HCl salt, 100 mg, 1.48 mmol) was added to the mixture, and the reaction was allowed to stir for about 15 hours. After being concentrated in vacuo, water was added and the mixture was extracted with ethyl acetate. The organic extract was washed with brine, dried and concentrated in vacuo and the resulting residue was purified using column chromatography (eluted with PE:EtOAc=1:1) to provide 5-bromo-2-(4-fluorophenyl-N-methyl-6-(2-oxopyrrolidin-1-yl)benzofuran-3-carboxamide (Compound W, 220 mg, yield: 73%). $^1$H-NMR (CDCl$_3$, 400 MHz) δ 7.94 (s, 1H), 7.82~7.86 (m, 2H), 7.32 (s, 1H), 7.09-7.14 (m, 2H), 6.29 (s, 1H), 3.75~3.78 (m, 2H), 2.97 (d, J=4.8 Hz, 3H), 2.56~2.60 (m, 2H), 2.24-2.26 (m, 2H).

Step D—Synthesis of 4,4-difluoro-2-(5-(4,4,5,5-tetramethyl-1,3,2-dioxaborolan-2-yl)pyridin-3-yl)-4,5,6,7-tetrahydrobenzo[d]thiazole

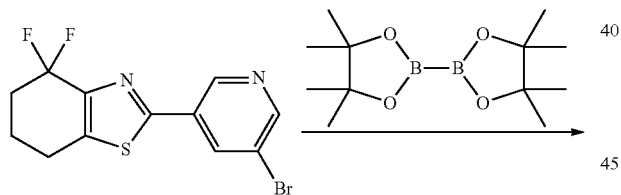

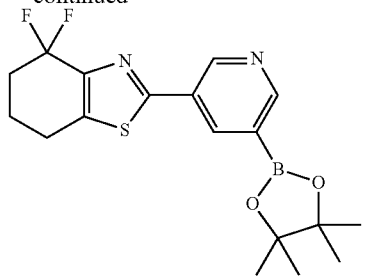

To a solution of 2-(5-bromopyridin-3-yl)-4,4-difluoro-4,5,6,7-tetrahydrobenzo[d]thiazole (intermediate of Compound 92, described in step 2 of Example 9, 270 mg, 0.82 mmol), 4,4,4',4',5,5,5',5'-octamethyl-2,2'-bis(1,3,2-dioxaborolane) (625 mg, 2.46 mmol) and KOAc (322 mg, 3.28 mmol) in dioxane (15 mL), under $N_2$ atmosphere, was added Pd(dppf)Cl$_2$ (30 mg, 0.04 mmol). The reaction was heated to 80~90° C. and allowed to stir at this temperature for about 15 hours. The reaction mixture was filtered and the filtrated was concentrated in vacuo. The resulting residue was purified using column chromatography on silica gel (eluted with PE:EtOAc=5:1~2:1) to provide 4,4-difluoro-2-(5-(4,4,5,5-tetramethyl-1,3,2-dioxaborolan-2-yl)pyridin-3-yl)-4,5,6,7-tetrahydrobenzo[d]thiazole as light yellow solid (100 mg, yield: 32.2%). $^1$H-NMR (CDCl$_3$, 400 MHz) δ 9.20 (s, 1H), 8.97 (s, 1H), 8.16 (s, 1H), 2.93~2.98 (m, 2H), 2.33~2.44 (m, 2H), 2.07~2.19 (m, 2H), 1.35 (s, 12H).

Step E—Synthesis of 5-(5-(4,4-difluoro-4,5,6,7-tetrahydrobenzo[d]thiazol-2-yl)pyridin-3-yl)-2-(4-fluorophenyl)-N-methyl-6-(2-oxopyrrolidin-1-yl)benzofuran-3-carboxamide (Compound 155)

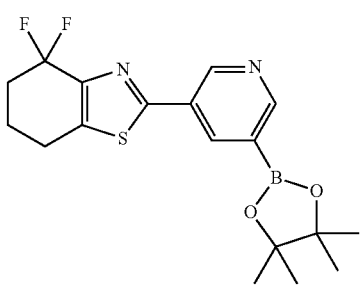 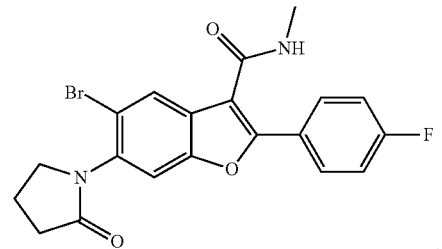

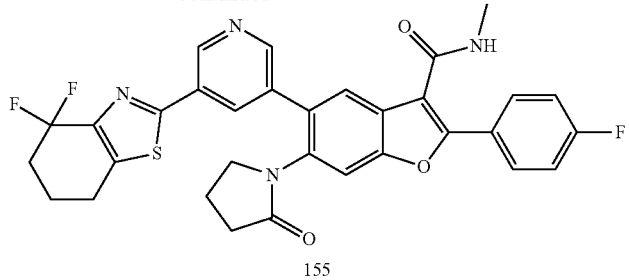

155

Compound 155 was made from the indicated starting material using methods described in Example 1. $^1$H-NMR (CDCl$_3$, 400 MHz) δ 9.20 (s, 1H), 8.79 (s, 1H), 8.63 (s, 1H), 7.91-7.96 (m, 3H), 7.54 (s, 1H), 7.22 (t, J=8.8 Hz, 2H), 5.98 (d, J=4.0 Hz, 1H), 3.68 (t, J=6.8 Hz, 2H), 2.99~3.03 (m, 5H), 2.38~2.44 (m, 4H), 2.09~2.19 (m, 4H). MS (M+H)$^+$: 603.

Compound 156, depicted in the table below, were prepared using the method described in Example 16 and substituting the appropriate reactants and/or reagents.

| No. | Structure | NMR | MS (M + H)$^+$ |
|---|---|---|---|
| 156 | 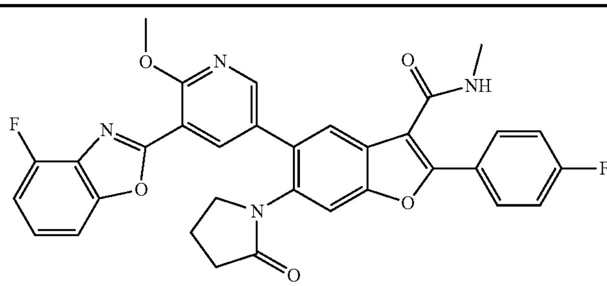 | $^1$H-NMR (CDCl$_3$, 400 MHz) δ 8.57 (d, J = 2.4 Hz, 1H), 8.43 (d, J = 2.4 Hz, 1H), 7.96~8.00 (m, 2H), 7.93 (s, 1H), 7.57 (s, 1H), 7.47 (d, J = 8.4 Hz, 1H), 7.34~7.39 (m, 1H), 7.24 (t, J = 8.4 Hz, 2H), 7.13 (t, J = 8.8 Hz, 1H), 5.93 (s, 1H), 4.25 (s, 3H), 3.51 (t, J = 6.8 Hz, 2H), 3.05 (d, J = 5.2 Hz, 3H), 2.52 (t, J = 7.6 Hz, 2H), 2.06 (t, J = 7.2 Hz, 2H). | 595 |

Compounds 249 and 250, depicted in the table below, were prepared using the method described in Example 16 and substituting the appropriate reactants and/or reagents.

| No. | Structure | NMR | MS (M + H)$^+$ |
|---|---|---|---|
| 249 | 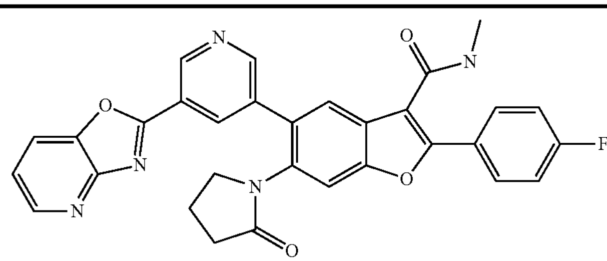 | $^1$H-NMR (CDCl$_3$, 400 MHz) δ 9.46 (d, J = 1.6 Hz, 1H), 8.80 (s, 1H), 8.68 (s, 1H), 8.60 (d, J = 4.4 Hz, 1H), 7.93 (s, 1H), 7.89 (d, J = 7.2 Hz, 1H), 7.86 (t, J = 3.2 Hz, 2H), 7.49 (s, 1H), 7.34~7.37 (m, 1H), 7.16 (t, J = 8.4 Hz, 2H), 5.85 (t, J = 2.8 Hz, 1H), 3.58 (t, J = 6.8 Hz, 2H), 2.94 (d, J = 5.2 Hz, 3H), 2.35 (t, J = 8.0 Hz, 2H), 2.01 (t, J = 7.2 Hz, 2H). | 548 |
| 250 | 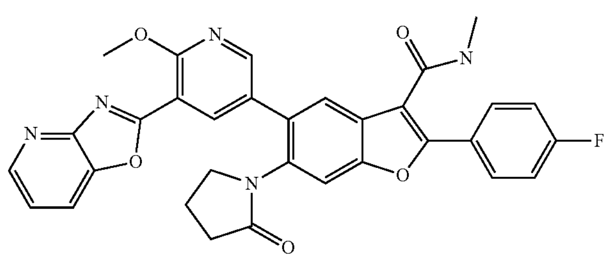 [SMILES: CNC(=O)c1c(-c2ccc(F)cc2)oc2cc(N3CCCC3=O)c(-c3cnc(OC)c(-c4nc5ncccc5o4)c3)cc12] | $^1$H-NMR (CDCl$_3$, 400 MHz) δ 8.56 (d, J = 3.6 Hz, 1H), 8.52 (s, 1H), 8.38 (d, J = 2.4 Hz, 1H), 7.86~7.90 (m, 3H), 7.84 (s, 1H), 7.46 (d, J = 8.4 Hz, 1H), 7.28~7.31 (m, 1H), 7.14 (t, J = 8.8 Hz, 2H), 5.79 (s, 1H), 4.15 (s, 3H), 3.47 (t, J = 7.2 Hz, 2H), 2.94 (d, J = 4.8 Hz, 3H), 2.41 (d, J = 8.0 Hz, 2H), 1.96~2.01 (m, 2H). | 578 |

Example 17

Preparation of Compound 251

251

Step A—Synthesis of 1-(4-iodopyridin-2-yl)-1H-indazole

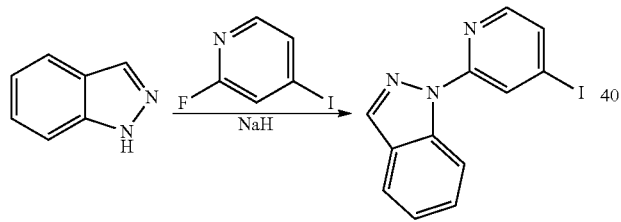

NaH in oil (120 mg, 3.1 mmol) was added to a solution of 1H-indazole (300 mg, 2.5 mmol) in THF (10 mL) at 0° C. in portions. The mixture was stirred at 0° C. for 10 min, and then 2-fluoro-4-iodopyridine (680 mg, 3.1 mmol) was added to the mixture. The mixture was stirred at 80° C. for 6 h. After concentrated, the mixture was diluted with water and extracted with EtOAc. The combined organic layers were washed with brine, dried over $Na_2SO_4$, filtered and concentrated. The residue was purified by column chromatography (PE:EA=100:1) to give 1-(4-iodopyridin-2-yl)-1H-indazole (280 mg, yield: 34.4%) as a white solid. $^1$H-NMR (CDCl$_3$, 400 MHz) δ 8.97 (s, 1H), 8.64 (s, 1H), 8.06 (d, J=5.2 Hz, 1H), 7.61~7.67 (m, 2H), 7.57 (d, J=5.2 Hz, 1H), 7.23~7.27 (m, 1H), 7.00~7.04 (m, 1H). MS (M+H)$^+$: 119.

Step B—Synthesis of 5-(2-(1H-indazol-1-yl)pyridin-4-yl)-2-(4-fluorophenyl)-N-methyl-6-(N-methylmethylsulfonamido)benzofuran-3-carboxamide (Compound 251)

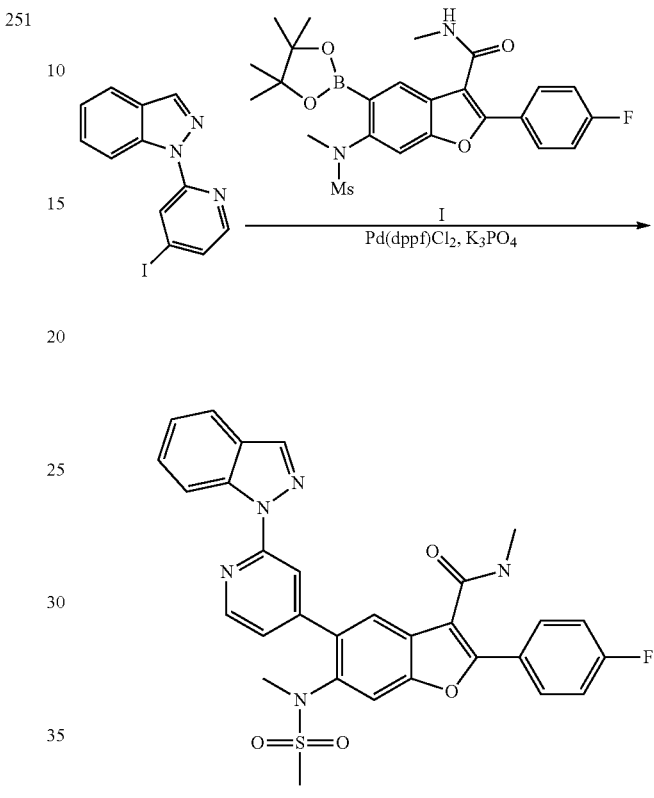

251

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 80 mg, 0.2 mmol) and 2-(5-bromo-2-methoxypyridin-3-yl)-4-fluorobenzo[d]oxazole (50 mg, 0.2 mmol) in dry DMF (3 mL) were added Pd(dppf)Cl$_2$ (10 mg) and K$_3$PO$_4$ (120 mg, 0.4 mmol) under N$_2$ protection. The mixture was heated to 100° C. and allowed to stir at this temperature for about 2 hours and then it was cooled to room temperature and filtered. The filtrate was washed with H$_2$O, brine, dried over Na$_2$SO$_4$. After concentrated in vacuo, the resulting residue was purified using prep-HPLC to provide Compound 251 (60 mg, yield: 65.9%). $^1$H-NMR (CDCl$_3$, 400 MHz) δ 9.15 (s, 1H), 8.31 (d, J=8.4 Hz, 1H), 8.11 (s, 1H), 7.94-7.98 (m, 3H), 7.75~7.77 (m, 1H), 7.71 (d, J=8.8 Hz, 1H), 7.67 (s, 1H), 7.61 (d, J=8.8 Hz, 1H), 7.35 (t, J=6.0 Hz, 1H), 7.32~7.33 (m, 2H), 7.08~7.22 (m, 1H), 5.92 (d, J=4.4 Hz, 1H), 3.30 (s, 3H), 3.00 (d, J=4.8 Hz, 3H), 2.73 (s, 3H). MS (M+H)$^+$: 570.

Compounds 252 and 253, depicted in the table below, were prepared using the method described in Example 17 and substituting the appropriate reactants and/or reagents.

| No. | Structure | NMR | MS (M + H)+ |
|---|---|---|---|
| 252 | 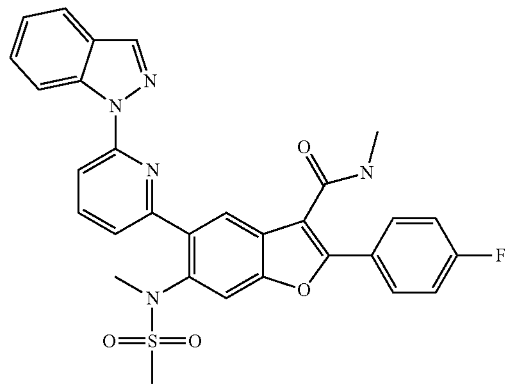 [SMILES: CNC(=O)c1c(-c2ccc(F)cc2)oc2cc(N(C)S(C)(=O)=O)c(-c3cccc(-n4ncc5ccccc54)n3)cc12] | ¹H-NMR (CDCl₃, 400 MHz) δ 9.08 (s, 1H), 8.50 (d, J = 4.8 Hz, 1H), 8.29 (s, 1H), 7.84~7.88 (m, 3H), 7.62~7.69 (m, 2H), 7.59 (s, 1H), 7.41~7.43 (m, 1H), 7.23~7.27 (m, 1H), 7.11~7.16 (m, 2H), 7.02~7.06 (m, 1H), 5.92 (d, J = 4.4 Hz, 1H), 3.13 (s, 3H), 2.95 (d, J = 5.2 Hz, 3H), 2.83 (s, 3H). | 570 |
| 253 | 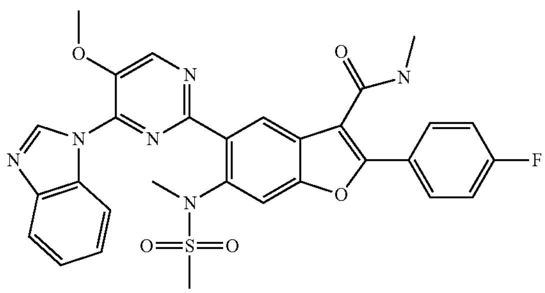 [SMILES: CNC(=O)c1c(-c2ccc(F)cc2)oc2cc(N(C)S(C)(=O)=O)c(-c3ncc(OC)c(-n4cnc5ccccc54)n3)cc12] | ¹H-NMR (Methanol-d₄, 400 MHz) δ 9.36 (s, 1H), 8.98 (s, 1H), 8.29~8.27 (m, 2H), 8.23 (s, 1H), 8.02~7.98 (s, 2H), 7.94 (s, 1H), 7.86~7.84 (m, 1H), 7.53~7.51 (m, 2H), 7.30 (t, J = 8.8 Hz, 2H), 4.22 (s, 3H), 3.44 (s, 3H), 2.97 (s, 6H). | 601 |

Example 18

Preparation of Compound 254

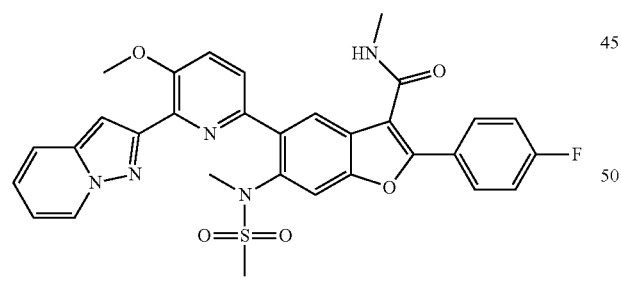

254

Step A—Synthesis of 2-(6-chloro-3-methoxypyridin-2-yl)pyrazolo[1,5-a]pyridine

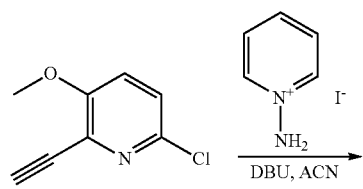

-continued

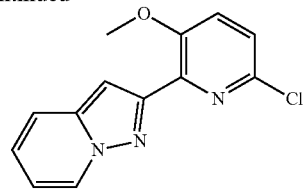

A mixture of 6-chloro-2-ethynyl-3-methoxypyridine (38 mg, 0.2 mmol), 1-aminopyridinium iodide (50 mg, 0.2 mmol) and DBU (67 mg, 0.4 mmol) in MeCN (2 mL) was stirred at 80° C. for 2 h. Then, water (10 mL) was added and the mixture was extracted with ethyl acetate. The organic layer was washed with brine and dried over Na₂SO₄. After concentrated, the residue was purified by prep-TLC (PE: EA=2:1) to give the product of 2-(6-chloro-3-methoxypyridin-2-yl)pyrazolo[1,5-a]pyridine (25 mg, yield: 45%). ¹H-NMR (Methanol-d₄, 400 MHz) δ 8.67 (d, J=9.2 Hz, 2H), 8.57 (d, J=7.2 Hz, 1H), 7.45 (d, J=8.4 Hz, 1H), 7.38~7.45 (m, 1H), 7.15 (d, J=8.4 Hz, 1H), 7.00~7.04 (m, 1H), 4.01 (s, 3H). MS (M+H)⁺: 260.

Step B—Synthesis of 2-(4-fluorophenyl)-5-(5-methoxy-6-(pyrazolo[1,5-a]pyridin-2-yl)pyridin-2-yl)-N-methyl-6-(N-methylmethylsulfonamido)benzofuran-3-carboxamide (Compound 254)

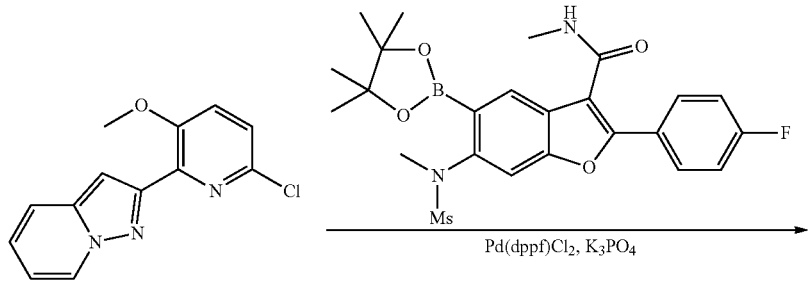

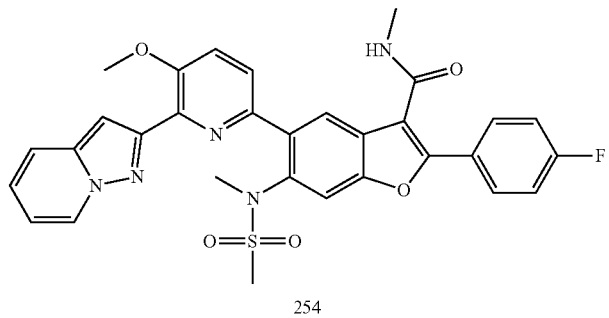

254

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (Compound I, 140 mg, 0.3 mmol) and 2-(6-chloro-3-methoxypyridin-2-yl)pyrazolo[1,5-a]pyridine (60 mg, 0.2 mmol) in dioxane/$H_2O$ (2 mL/0.5 mL) were added $Pd_2(dba)_3$ (21 mg), X-Phos (22 mg) and $K_3PO_4$ (180 mg, 0.7 mmol) under $N_2$ protection. The mixture was heated to 100° C. and allowed to stir at this temperature for about 2 hours and then it was cooled to room temperature and filtered. The filtrate was washed with $H_2O$, brine, dried over $Na_2SO_4$.

After concentrated in vacuo, the resulting residue was purified using prep-HPLC to provide Compound 254 (70 mg, yield: 50.0%). $^1$H-NMR (DMSO-$d_6$, 400 MHz) δ 8.69 (d, J=7.2 Hz, 1H), 8.55 (s, 1H), 8.11~8.07 (m, 3H), 8.03 (s, 1H), 7.96 (dd, J=8.8, 5.2 Hz, 2H), 7.82 (d, J=8.8 Hz, 1H), 7.48 (t, J=7.6 Hz, 1H), 7.30 (t, J=8.8 Hz, 2H), 7.11 (t, J=6.8 Hz, 1H), 4.12 (s, 3H), 3.43 (s, 3H), 2.98 (s, 3H), 2.93 (s, 3H). MS (M+H)$^+$: 600.

Compound 255, depicted in the table below, were prepared using the method described in Example 18 and substituting the appropriate reactants and/or reagents.

| No. | Structure | NMR | MS (M + H)$^+$ |
|---|---|---|---|
| 255 | 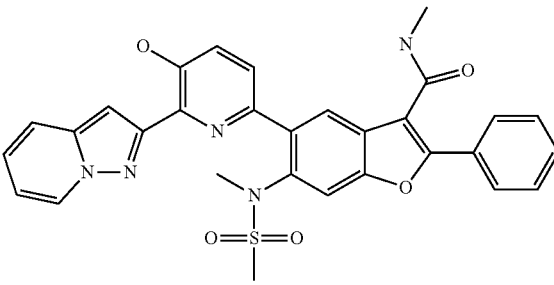 | $^1$H-NMR (CDCl$_3$, 400 MHz) δ 8.66 (s, 1H), 8.43 (d, J = 9.2 Hz, 1H), 8.36 (d, J = 6.8 Hz, 1H), 8.00 (s, 1H), 7.85 (dd, J = 8.8, 5.2 Hz, 2H), 7.60 (s, 1H), 7.34 (d, J = 8.0 Hz, 1H), 7.16 (t, J = 8.8 Hz, 2H), 7.08 (t, J = 8.0 Hz, 1H), 7.04 (s, 1H), 6.74 (t, J = 6.8 Hz, 1H), 6.50 (d, J = 4.4 Hz, 1H), 3.11 (s, 3H), 2.96 (d, J = 4.8 Hz, 3H), 2.54 (s, 3H). | 586 |

Example 19

Preparation of Compound 256

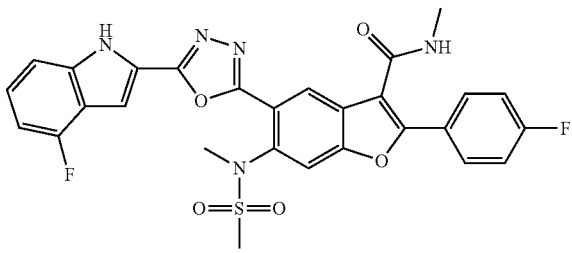

Step A—Synthesis of 2-(4-fluorophenyl)-3-(methyl-carbamoyl)-6-(N-methylmethylsulfonamido)benzo-furan-5-carboxylic acid

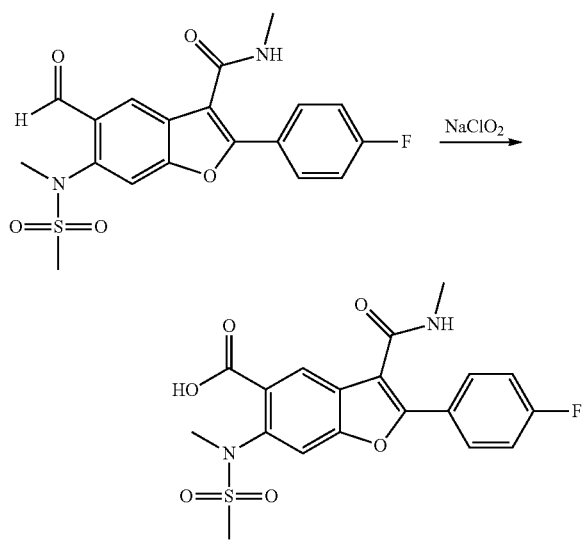

To a solution of 2-(4-fluorophenyl)-5-formyl-N-methyl-6-(N-methylmethylsulfonamido)benzofuran-3-carboxamide (100 mg, 0.3 mmol) in THF/H$_2$O (2:1, mL), NaH$_2$PO$_4$.3H$_2$O (200 mg, 1.2 mmol) and sulfamic acid (50 mg, 0.5 mmol) were added at room temperature and the resulting mixture was stirred at 0° C. for 10 mins. Then a solution of NaClO$_2$ (30 mg, 0.3 mmol) in H$_2$O was added dropwise and the mixture was stirred at 0° C. for 2 hours. After NaHSO$_3$ (aq) was added, the mixture was stirred at room temperature for 10 mins and extracted with EtOAc. The combined organic phases were washed with brine, dried over Na$_2$SO$_4$, filtered and evaporated to give 2-(4-fluorophenyl)-3-(methylcarbamoyl)-6-(N-methylmethylsulfonamido)benzofuran-5-carboxylic acid (100 mg, yield: 96%). $^1$H-NMR (DMSO-d$_6$, 400 MHz) δ 13.02 (br s, 1H), 8.58 (br s, 1H), 7.96~8.01 (m, 4H), 7.39~7.45 (m, 2H), 3.28 (s, 3H), 3.04 (s, 3H), 2.85 (d, J=4.4 Hz, 3H). MS (M+H)$^+$: 421.

Step B—Synthesis of 5-(2-(4-fluoro-1H-indole-2-carbonyl)hydrazinecarbonyl)-2-(4-fluorophenyl)-N-methyl-6-(N-methylmethylsulfonamido)benzofuran-3-carboxamide

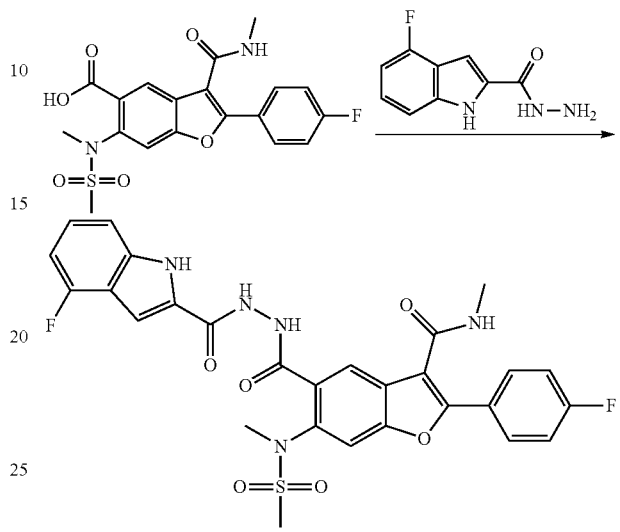

2-(4-fluorophenyl)-3-(methylcarbamoyl)-6-(N-methylmethylsulfonamido)benzofuran-5-carboxylic acid (50 mg, 0.1 mmol), HOBT (20 mg, 0.2 mmol) and EDCI (50 mg, 0.3 mmol) were dissolved in dry DMF (2 mL). The resulting solution was stirred for 2 hours. And then 4-fluoro-1H-indole-2-carbohydrazide (25 mg, 0.1 mmol) and Et$_3$N (0.1 mL) were added to the mixture. The mixture was stirred at RT overnight. Then H$_2$O was added, and the mixture was extracted with EtOAc. The combined organic phases were washed with brine, dried over Na$_2$SO$_4$, filtered and evaporated. The crude product was purified by prep-HPLC to give the product 5-(2-(4-fluoro-1H-indole-2-carbonyl)hydrazinecarbonyl)-2-(4-fluorophenyl)-N-methyl-6-(N-methylmethylsulfonamido)benzofuran-3-carboxamide (60 mg, yield: 82%). $^1$H-NMR (DMSO-d$_6$, 400 MHz) δ 12.16 (s, 1H), 10.77 (br s, 1H), 10.44 (br s, 1H), 8.62 (d, J=4.8 Hz, 1H), 7.99~8.03 (m, 2H), 7.92 (s, 2H), 7.40~7.46 (m, 3H), 7.32 (d, J=8.4 Hz, 1H), 7.18~7.24 (m, 1H), 6.84~6.89 (m, 1H), 3.33 (s, 3H), 3.17 (s, 3H), 2.88 (d, J=4.4 Hz, 3H). MS (M+H)$^+$: 596.

Step C—Synthesis of 5-(5-(4-fluoro-1H-indol-2-yl)-1,3,4-oxadiazol-2-yl)-2-(4-fluorophenyl)-N-methyl-6-(N-methylmethylsulfonamido)benzofuran-3-carboxamide (Compound 256)

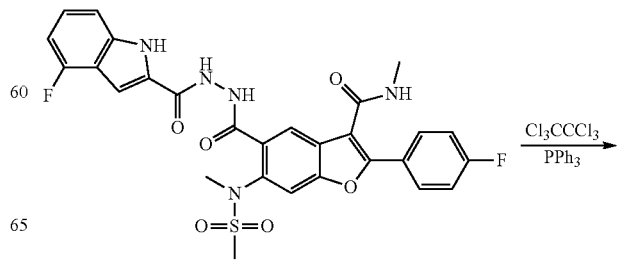

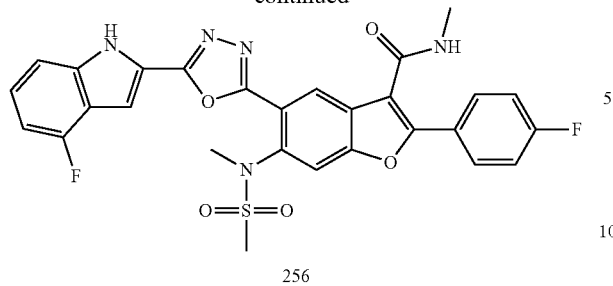

256

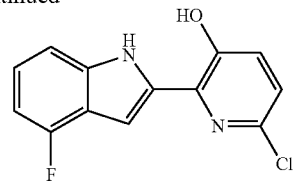

To a solution of 5-(2-(4-fluoro-1H-indole-2-carbonyl)hydrazinecarbonyl)-2-(4-fluorophenyl)-N-methyl-6-(N-methylmethylsulfonamido)benzofuran-3-carboxamide (90 mg, 0.2 mmol) in ACN (5 mL), PPh$_3$ (80 mg, 0.3 mmol) and DIPEA (150 mg, 1.2 mmol) were added. The reaction mixture was stirred at RT for 2 mins. Then Cl$_3$CCCl$_3$ (70 mg, 0.3 mmol) was added and the mixture was stirred at RT overnight. After concentrated, the residue was suspended in water and extracted with EtOAc. The combined organic phases were washed with brine, dried over Na$_2$SO$_4$, filtered and evaporated. The residue was purified by prep-HPLC to give the product of Compound 256 (10 mg, yield: 11%). $^1$H-NMR (DMSO-d$_6$, 400 MHz) δ 12.72 (s, 1H), 8.66 (d, J=4.4 Hz, 1H), 8.39 (s, 1H), 8.25 (s, 1H), 7.99~8.03 (m, 2H), 7.42~7.47 (m, 2H), 7.35~7.37 (m, 2H), 7.24~7.29 (m, 1H), 6.89~6.94 (m, 1H), 3.43 (s, 3H), 3.14 (s, 3H), 2.88 (d, J=4.4 Hz, 3H). MS (M+H)$^+$: 578.

To a solution of (1-(tert-butoxycarbonyl)-4-fluoro-1H-indol-2-yl) boronic acid (126 g, 0.45 mol, 1.2 eq) and 6-chloro-2-iodopyridin-3-ol (96 g, 0.37 mmol, 1 eq) in 1,4-dioxane (1.8 L) and water (0.2 L) were added Pd(PPh$_3$)$_2$Cl$_2$ (13.2 g, 18.6 mmol, 0.05 eq) and NaHCO$_3$ (94.8 g, 1.13 mol, 3 eq) under nitrogen atmosphere, and the mixture was heated at 90° C. under N$_2$ for 16 h. The reaction mixture was cooled to room temperature, diluted with EtOAc (900 mL), filtered and concentrated. The residue was diluted with H$_2$O (400 mL) and EtOAc (800 mL), and the layer was separated, the aqueous layer was extracted with EtOAc (3×400 mL). The combined organic layers were washed with brine (800 mL), dried over Na$_2$SO$_4$, filtered and concentrated. The residue was purified by column chromatography (PE:EtOAc=20:1~3:1) to give 6-chloro-2-(4-fluoro-1H-indol-2-yl)pyridin-3-ol (70 g, yield: 70.1%). $^1$H-NMR (Methanol-d$_4$, 400 MHz) δ 7.36 (s, 1H), 7.23~7.27 (m, 2H), 7.03~7.11 (m, 2H), 6.63~6.68 (m, 1H). MS (M+H)$^+$: 263.

Step B—Synthesis of 6-chloro-2-(4-fluoroindolin-2-yl)pyridin-3-ol

Example 20

Preparation of Compound 257

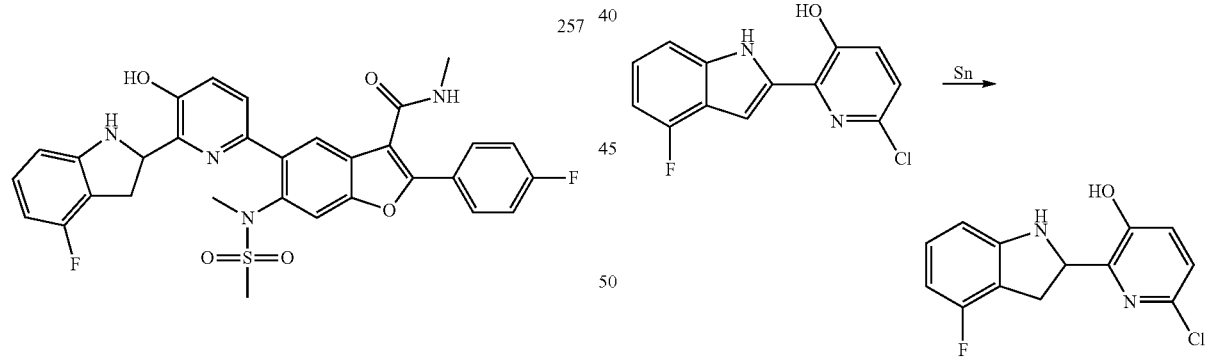

257

Step A—Synthesis of 6-chloro-2-(4-fluoro-1H-indol-2-yl)pyridin-3-ol

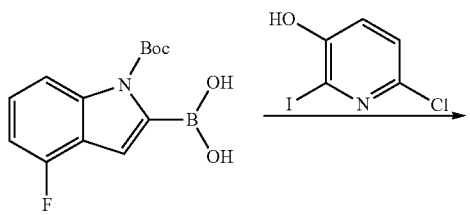

A solution of 6-chloro-2-(4-fluoro-1H-indol-2-yl)pyridin-3-ol (10 g, 38 mmol) and Sn (23 g, 190 mmol) in CH$_3$CH$_2$OH/con. HCl (60 mL/40 mL) was stirred under reflux for 3 h. The mixture was cooled to room temperature and adjusted to pH=7 by saturated NaOH and filtered though a Celit pad. The filtrate was extracted with EtOAc, washed by brine, dried over Na$_2$SO$_4$ and concentrated. The residue was purified by silica gel chromatography (PE:EA=10:1) to get 6-chloro-2-(4-fluoroindolin-2-yl)pyridin-3-ol (8 g, yield: 80%). $^1$H-NMR (CDCl$_3$, 400 MHz) δ 9.86 (s, 1H), 7.10~7.20 (m, 3H), 6.33~6.91 (m, 2H), 5.15~5.21 (m, 1H), 4.61 (s, 1H), 3.65~3.71 (m, 1H), 3.04~3.11 (m, 1H). MS (M+H)$^+$: 265.

Step C—Synthesis of 5-(6-(4-fluoroindolin-2-yl)-5-hydroxypyridin-2-yl)-2-(4-fluorophenyl)-N-methyl-6-(N-methylmethylsulfonamido)benzofuran-3-carboxamide (Compound 257)

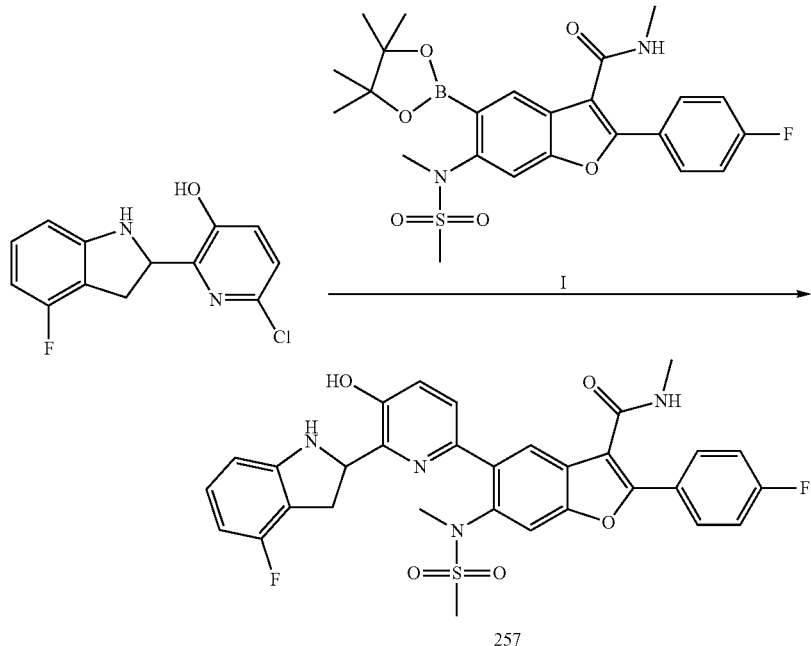

The procedure of Compound 257 (50 mg, yield: 57%) was similar to step 3 of Example 1. $^1$H-NMR (CDCl$_3$, 400 MHz) δ 7.93~7.98 (m, 3H), 7.62 (s, 1H), 7.42 (d, J=8.4 Hz, 1H), 7.29 (d, J=8.4 Hz, 1H), 7.17~7.23 (m, 2H), 7.09~7.15 (m, 1H), 6.61~6.69 (m, 2H), 5.94 (br s, 1H), 5.28 (dd, J=9.2 Hz, 11.6 Hz 1H), 3.68 (dd, J=9.2 Hz, 15.6 Hz 1H), 3.29 (s, 3H), 3.16 (dd, J=15.6, 11.6 Hz, 1H), 2.99 (d, J=4.8 Hz, 3H), 2.78 (s, 3H). (M+H)$^+$: 605.

Example 21

Preparation of Compound 297

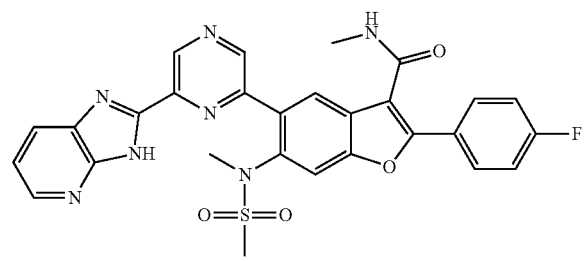

Step A—Synthesis of Intermediate Compound Int-21a

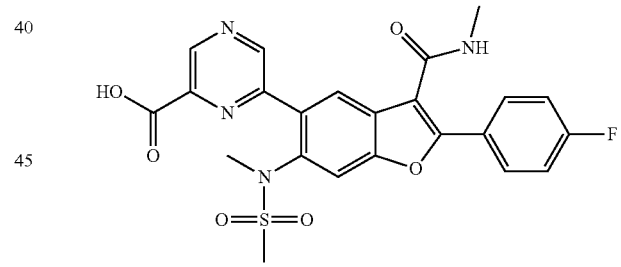

A mixture of 6-bromopyrazine-2-carboxylic acid (404 mg, 1.99 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (1 g, 1.99 mmol), 2M sodium carbonate (4 ml, 8 mmol), Bis(triphenylphosphine)palladium(II) dichloride (70 mg, 0.1 mmol) was suspended in DME (7 ml), DMf (2 ml), water (3 ml) and EtOH (2 ml) in a sealed tube and heated in a microwave oven at 120° C. for 20 min. Then concentrated under vacuum, applied onto Prep HPLC and eluted with H$_2$O (0.1% TFA) and Acetonitrile (0.1% TFA). This resulted in 0.96 g (95%) of 6-(2-(4-fluorophenyl)-3-(methylcarbamoyl)-6-(N-methylmethylsulfonamido)benzofuran-5-yl)pyrazine-2-carboxylic acid as a white solid. LC-MS (ES, m/z) C23H19FN4O6S: 498. Found: 499 [M+H]+.

Step B—Synthesis of Compound 297

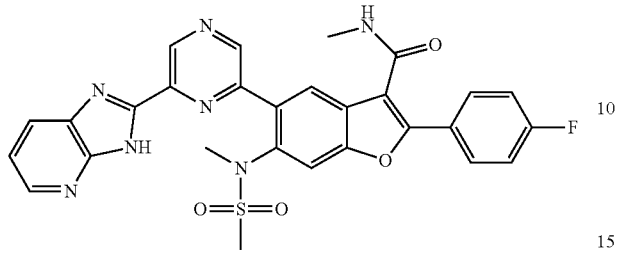

A mixture of Int-21a (10.95 mg, 0.100 mmol), diethyl cyanophosphonate (18.00 mg, 0.110 mmol) and triethylamine (0.042 ml, 0.301 mmol) was dissolved in DME (2 ml) in a sealed tube and heated in a microwave oven at 170° C. for 1 hour. The reaction mixture was then concentrated under vacuum and the residue obtained was purified using Prep HPLC and eluting with $H_2O$ (0.1% TFA) and acetonitrile (0.1% TFA) to provide 14 mg (20.4%) of Compound 297 as a white solid. LC-MS (ES, m/z) C28H22FN7O4S:571. Found: 572 [M+H]+.

Example 22

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. Virological Methods 201 (2003); Steven S. Carroll et al., *Inhibition of Hepatitis C Virus RNA Replication by 2'-Modified Nucleoside Analogs*, 278(14) J. Biological Chemistry 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was determined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. $IC_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

| Compound No. | 1a $IC_{50}$ (nM) | 1b $IC_{50}$ (nM) |
|---|---|---|
| 1 | 0.9 | 0.6 |
| 2 | 0.3 | 0.8 |
| 9 | 0.6 | 1.3 |
| 13 | 0.7 | 1.4 |
| 62 | 2.0 | 1.2 |
| 82 | 0.8 | 1.1 |
| 94 | 0.8 | 1.9 |
| 95 | 0.9 | 1.1 |
| 108 | 0.7 | 1.2 |
| 109 | 0.4 | 1.0 |
| 113 | 0.3 | 0.8 |
| 119 | 0.7 | 1.5 |
| 121 | 0.8 | 1.2 |
| 139 | 0.8 | 0.8 |
| 150 | 3.2 | 5.1 |
| 151 | 7.7 | 3.7 |
| 155 | 2.9 | 1.0 |
| 157 | 0.9 | 1.5 |
| 159 | 0.8 | 1.3 |
| 170 | 27 | 5.1 |
| 179 | 8.2 | 5.1 |
| 180 | 5.4 | 2.3 |
| 182 | 4.4 | 4.3 |
| 202 | 8.4 | 7.6 |
| 208 | 27 | 7.2 |
| 209 | 8.9 | 4.7 |
| 210 | 11 | 4.7 |
| 211 | 8.8 | 2.5 |
| 214 | 33 | 9.9 |
| 218 | 4.2 | 9.2 |
| 223 | 2.8 | 4.5 |
| 224 | 99 | 31 |
| 225 | 4.7 | 7.0 |
| 226 | 3.4 | 7.2 |
| 230 | 1.4 | 1.9 |
| 231 | 339 | 47 |
| 233 | 0.1 | 0.4 |
| 244 | 2.7 | 4.7 |
| 254 | 214 | 26 |
| 255 | 1451 | 104 |
| 256 | 0.4 | 0.7 |
| 257 | 13 | 10 |
| 258 | 2.6 | 2.5 |
| 259 | 1.1 | 2.6 |
| 260 | 0.7 | 1.1 |
| 263 | 3.2 | 2.4 |
| 264 | 25 | 10 |
| 265 | 4.5 | 4.1 |
| 266 | 3.2 | 3.0 |
| 268 | 5.3 | 6.1 |
| 270 | 42 | 36 |
| 271 | 14 | 10 |
| 272 | 4.2 | 4.4 |
| 273 | 0.3 | 0.2 |
| 277 | 7.4 | 6.7 |
| 278 | 37 | 14 |
| 279 | 2.5 | 3.2 |
| 280 | 1.2 | 1.4 |
| 281 | 22.3 | 4.8 |
| 282 | 3.3 | 1.8 |
| 284 | 6.0 | 2.7 |
| 286 | 17 | 5.0 |
| 287 | 3.2 | 5.1 |
| 288 | 75 | 25 |
| 289 | 54 | 22 |
| 290 | 9.8 | 10 |
| 291 | 4.8 | 8.0 |
| 292 | 12 | 13 |
| 293 | 131 | 41 |
| 294 | 54 | 22 |

Uses of the Heterocyclic-Substituted Benzofuran Derivatives

The Heterocyclic-Substituted Benzofuran Derivatives are useful in human and veterinary medicine for treating or preventing a viral infection in a patient. In one embodiment, the Heterocyclic-Substituted Benzofuran Derivatives can be inhibitors of viral replication. In another embodiment, the Heterocyclic-Substituted Benzofuran Derivatives can be inhibitors of HCV replication. Accordingly, the Heterocyclic-Substituted Benzofuran Derivatives are useful for treating viral infections, such as HCV. In accordance with the invention, the Heterocyclic-Substituted Benzofuran Derivatives can be administered to a patient in need of treatment or prevention of a viral infection.

Accordingly, in one embodiment, the invention provides methods for treating a viral infection in a patient comprising administering to the patient an effective amount of at least one Heterocyclic-Substituted Benzofuran Derivative or a pharmaceutically acceptable salt thereof.

Treatment or Prevention of a Flaviviridae Virus

The Heterocyclic-Substituted Benzofuran Derivatives may be useful for treating or preventing a viral infection caused by the Flaviviridae family of viruses.

Examples of Flaviviridae infections include but are not limited to, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Heterocyclic-Substituted Benzofuran Derivatives are useful in the inhibition of HCV (e.g., HCV NS5B), the treatment of HCV infection and/or reduction of the likelihood or severity of symptoms of HCV infection and the inhibition of HCV viral replication and/or HCV viral production in a cell-based system. For example, the Heterocyclic-Substituted Benzofuran Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Heterocyclic-Substituted Benzofuran Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Heterocyclic-Substituted Benzofuran Derivatives are also useful in the preparation and execution of screening assays for antiviral compounds. For example the Heterocyclic-Substituted Benzofuran Derivatives are useful for identifying resistant HCV replicon cell lines harboring mutations within NS5B, which are excellent screening tools for more powerful antiviral compounds. Furthermore, the Heterocyclic-Substituted Benzofuran Derivatives are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Heterocyclic-Substituted Benzofuran Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Heterocyclic-Substituted Benzofuran Derivative, or a pharmaceutically acceptable salt thereof, and (ii) at least one additional therapeutic agent that is other than a Heterocyclic-Substituted Benzofuran Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Heterocyclic-Substituted Benzofuran Derivative and an additional therapeutic agent may be present in fixed amounts (dosage amounts) in a single dosage unit (e.g., a capsule, a tablet and the like).

In one embodiment, the at least one Heterocyclic-Substituted Benzofuran Derivative is administered during a time when the additional therapeutic agent(s) exert their prophylactic or therapeutic effect, or vice versa.

In another embodiment, the at least one Heterocyclic-Substituted Benzofuran Derivative and the additional therapeutic agent(s) are administered in doses commonly employed when such agents are used as monotherapy for treating a viral infection.

In another embodiment, the at least one Heterocyclic-Substituted Benzofuran Derivative and the additional therapeutic agent(s) are administered in doses lower than the doses commonly employed when such agents are used as monotherapy for treating a viral infection.

In still another embodiment, the at least one Heterocyclic-Substituted Benzofuran Derivative and the additional therapeutic agent(s) act synergistically and are administered in doses lower than the doses commonly employed when such agents are used as monotherapy for treating a viral infection.

In one embodiment, the at least one Heterocyclic-Substituted Benzofuran Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Heterocyclic-Substituted Benzofuran Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Heterocyclic-Substituted Benzofuran Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin. HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/ViroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature*

*Reviews*, 1:867 (2002); and Beaulieu et al., *Current Opinion in Investigational Drugs*, 5:838 (2004).

Additional HCV polymerase inhibitors useful in the present compositions and methods include, but are not limited to, nucleoside compounds such as those disclosed in International Application Nos. PCT/US12/032,991, PCT/US12/033,017 and PCT/US12/033,028.

Other HCV polymerase inhibitors useful in the present compositions and methods include, but are not limited to, those disclosed in International Publication Nos. WO 08/082,484, WO 08/082,488, WO 08/083,351, WO 08/136,815, WO 09/032,116, WO 09/032,123, WO 09/032,124 and WO 09/032,125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™ from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™ Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

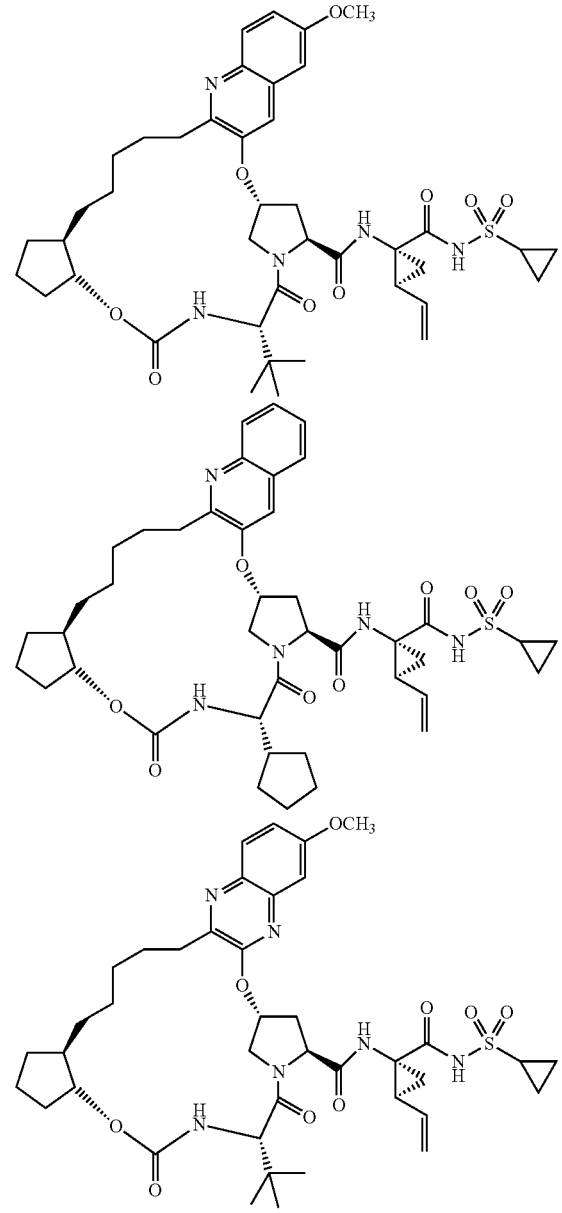

207
-continued
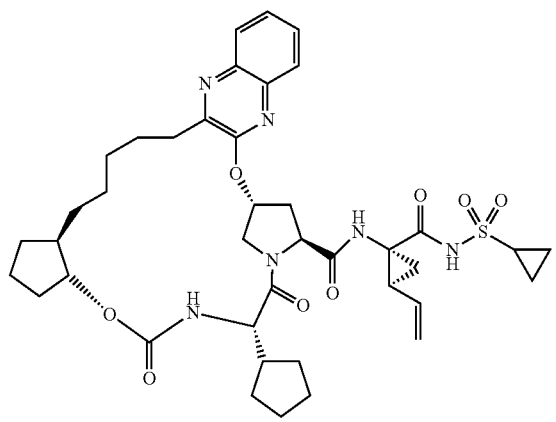
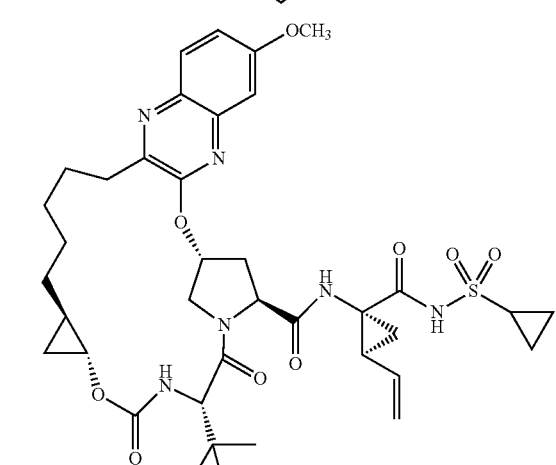
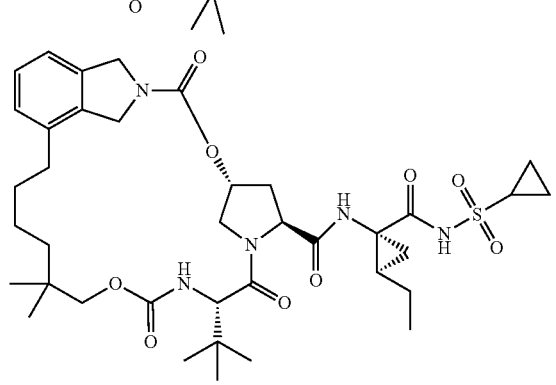
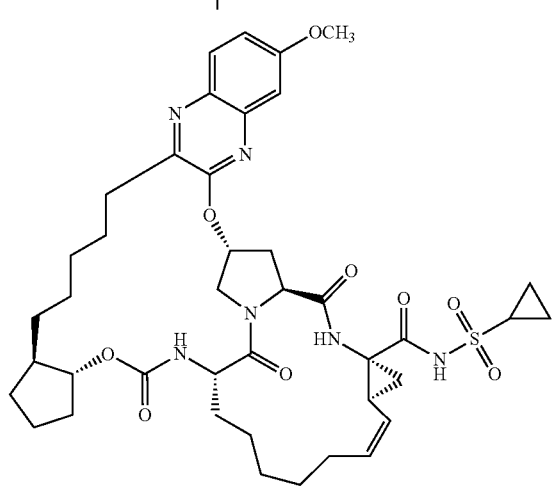
208
-continued
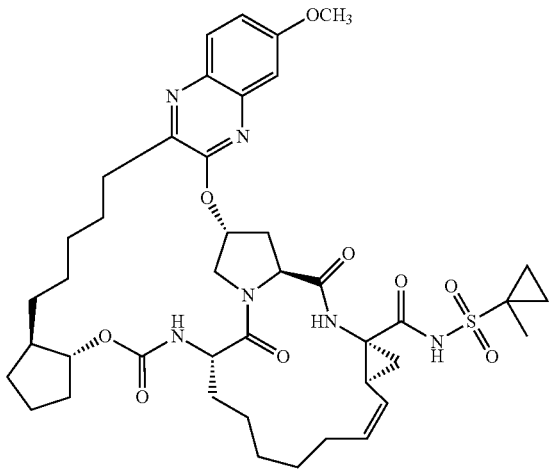
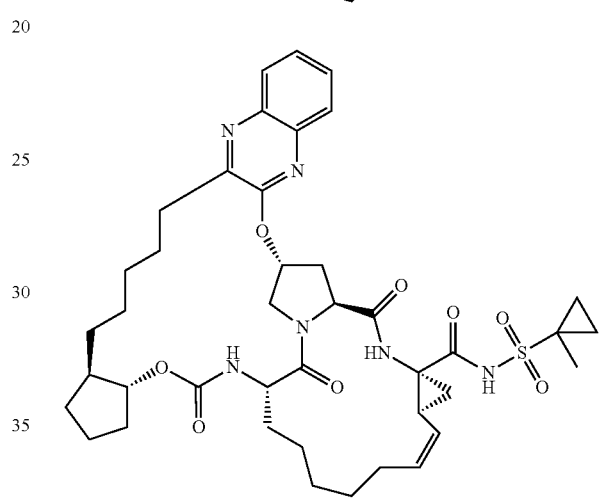
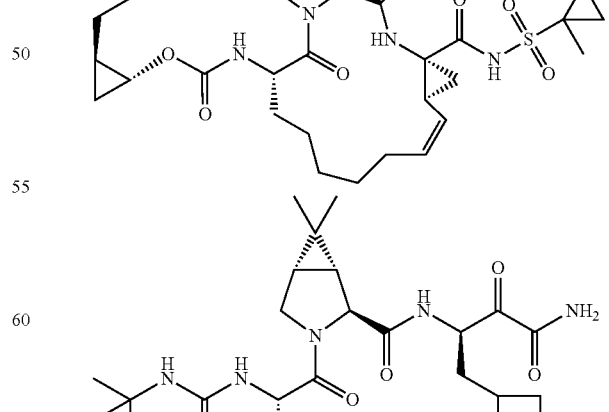
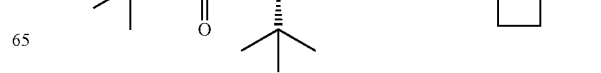

209
-continued
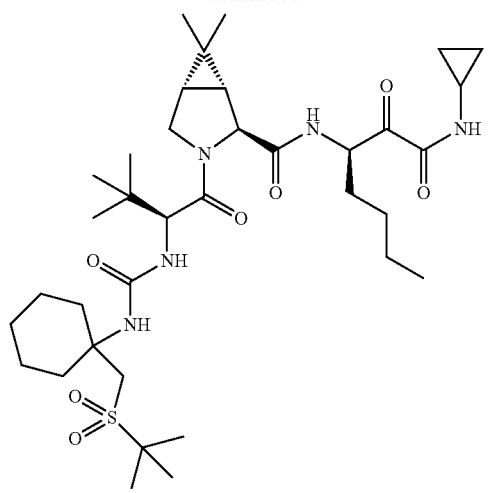
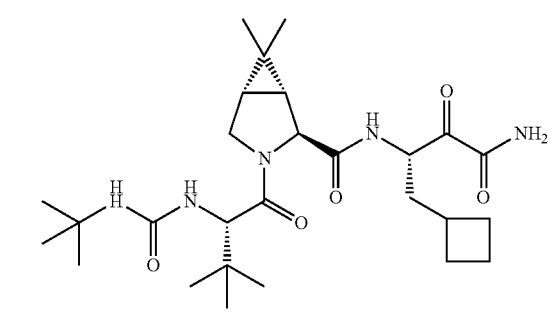
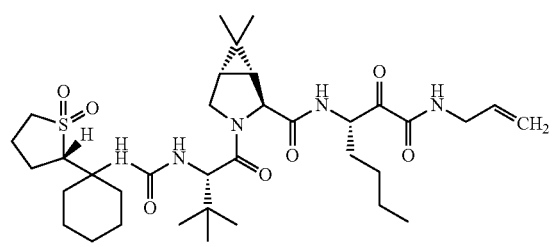
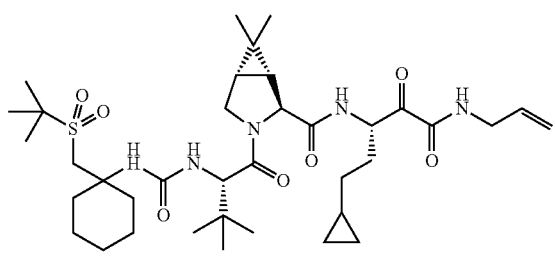
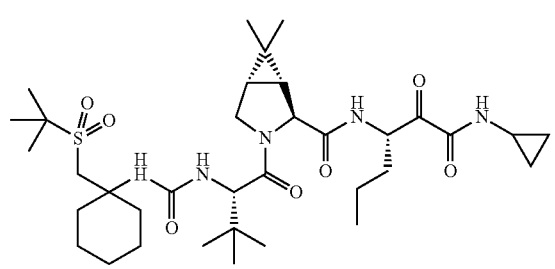
210
-continued
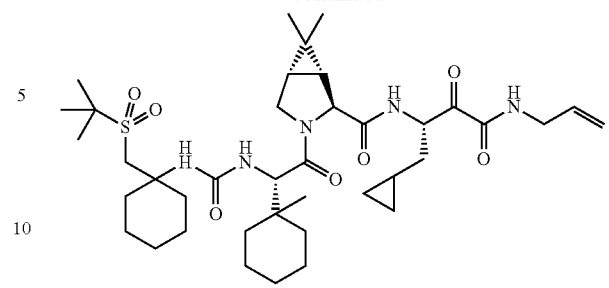
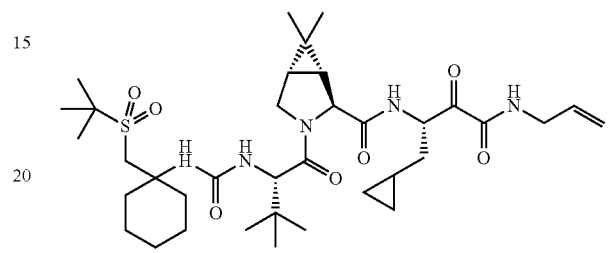
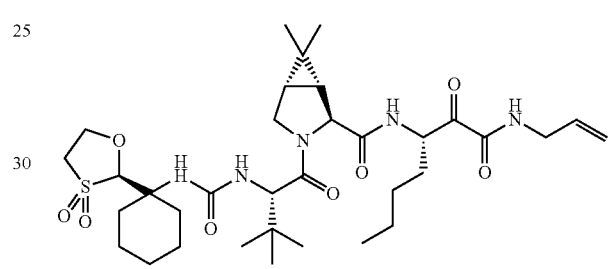
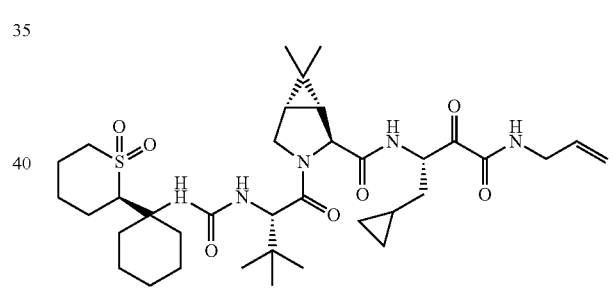
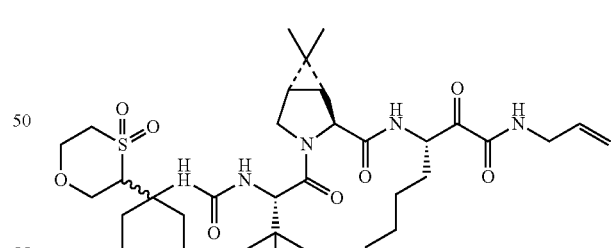
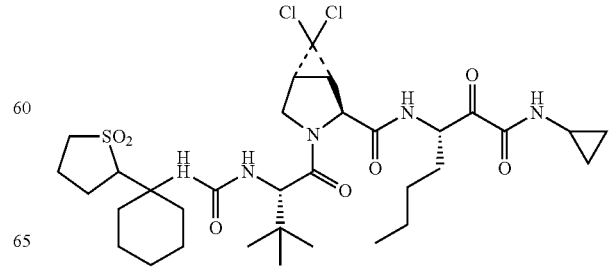

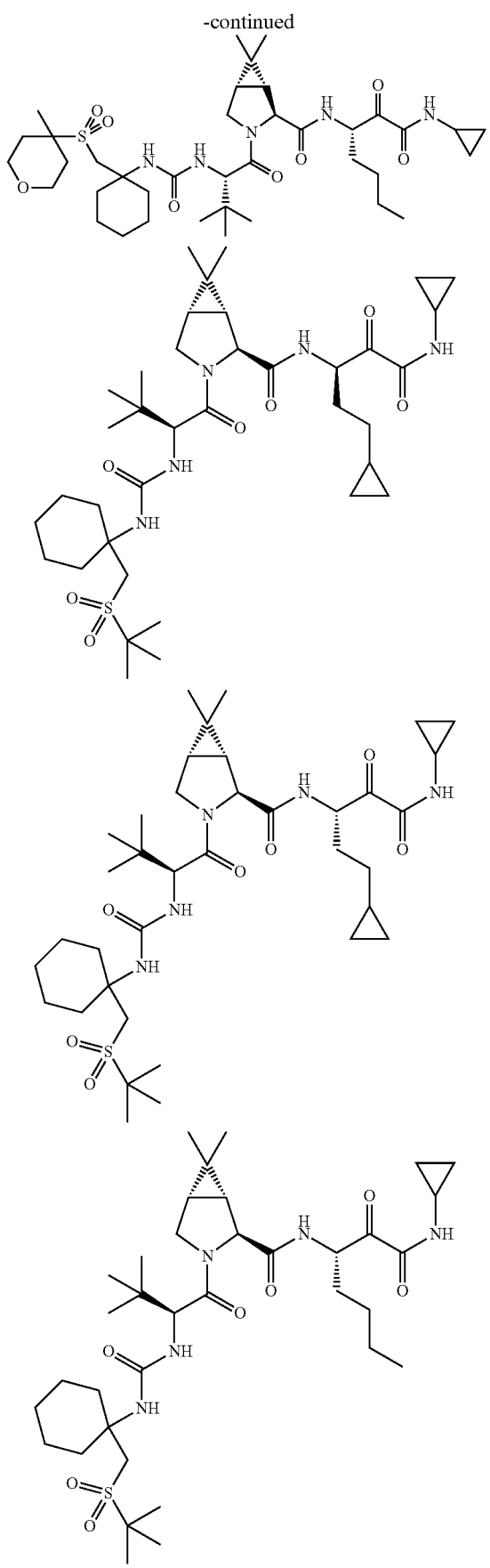

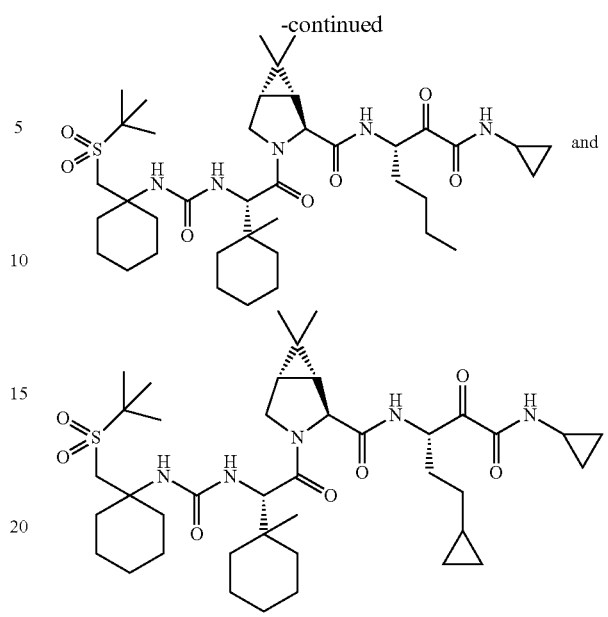

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenics), REP-9C (REPICor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, ACH-2928 (Achillon), AZD-7295 (Astra Zeneca), A-832 (Arrow Therpeutics), PPI-461 (Presidio), PPI-1301 (Presidio), GS-5885 (Gilead) and BMS-790052 (Bristol-Myers Squibb).

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPROTM (Pevion Biotect), HCV/MF59 (Chiron/Novartis), MBL-HCV1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT0-33 (Benitec/Tacere Bio/

Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Heterocyclic-Substituted Benzofuran Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Heterocyclic-Substituted Benzofuran Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the Heterocyclic-Substituted Benzofuran Derivatives are useful in veterinary and human medicine. As described above, the Heterocyclic-Substituted Benzofuran Derivatives are useful for treating or preventing HCV infection in a patient in need thereof.

When administered to a patient, the Heterocyclic-Substituted Benzofuran Derivatives can be administered as a component of a composition that comprises a pharmaceutically acceptable carrier or vehicle. The present invention provides pharmaceutical compositions comprising an effective amount of at least one Heterocyclic-Substituted Benzofuran Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Heterocyclic-Substituted Benzofuran Derivatives are administered orally.

In another embodiment, the one or more Heterocyclic-Substituted Benzofuran Derivatives are administered intravenously.

In one embodiment, a pharmaceutical preparation comprising at least one Heterocyclic-Substituted Benzofuran Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Heterocyclic-Substituted Benzofuran Derivative(s) by weight or volume. In various embodiments, the present compositions can contain, in one embodiment, from about 1% to about 70% or from about 5% to about 60% of the Heterocyclic-Substituted Benzofuran Derivative(s) by weight or volume.

The quantity of Heterocyclic-Substituted Benzofuran Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Heterocyclic-Substituted Benzofuran Derivatives will be regulated according to the judgment of the attending clinician considering such factors as age, condition and size of the patient as well as severity of the symptoms being treated. Generally, a total daily dosage of the Heterocyclic-Substituted Benzofuran Derivatives range from about 0.1 to about 2000 mg per day, although variations will necessarily occur depending on the target of therapy, the patient and the route of administration.

In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Heterocyclic-Substituted Benzofuran Derivative or a pharmaceutically acceptable salt thereof; (ii) one or more additional therapeutic agents that are not a Heterocyclic-Substituted Benzofuran Derivative; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Kits

In one aspect, the present invention provides a kit comprising a therapeutically effective amount of at least one Heterocyclic-Substituted Benzofuran Derivative, or a pharmaceutically acceptable salt, solvate, ester or prodrug of said compound and a pharmaceutically acceptable carrier, vehicle or diluent.

In another aspect the present invention provides a kit comprising an amount of at least one Heterocyclic-Substituted Benzofuran Derivative, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Heterocyclic-Substituted Benzofuran Derivatives and the one or more additional therapeutic agents are provided in the same container. In one embodiment, the one or more Heterocyclic-Substituted Benzofuran Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

The invention claimed is:

1. A compound having the formula:

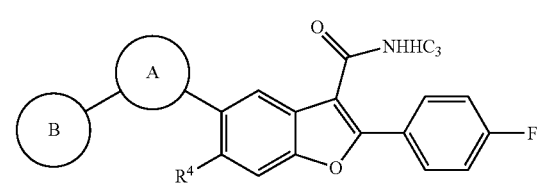

or a pharmaceutically acceptable salt thereof, wherein:

the group

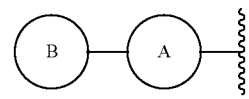

is selected from:

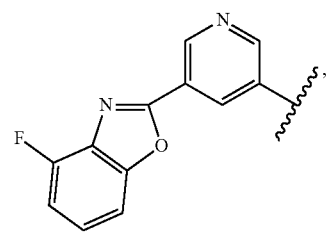

-continued
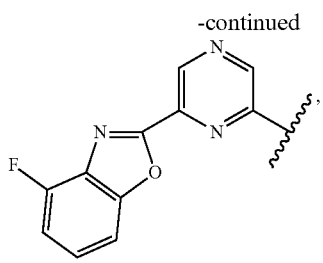
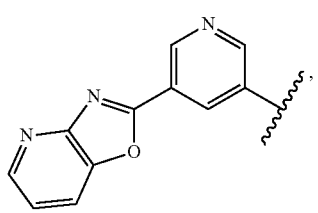
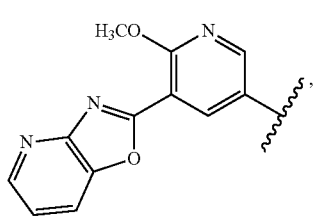
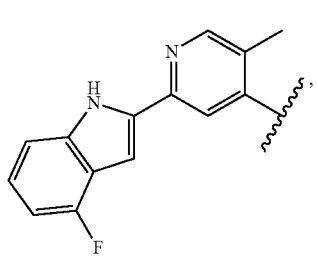
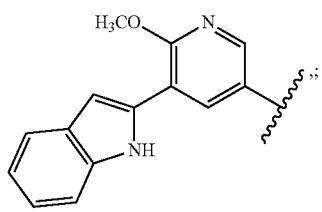
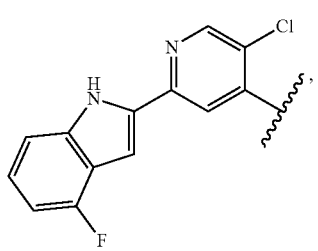
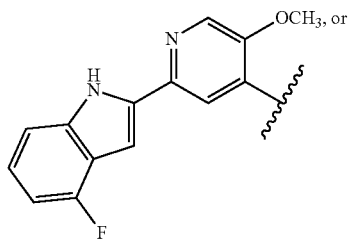
-continued
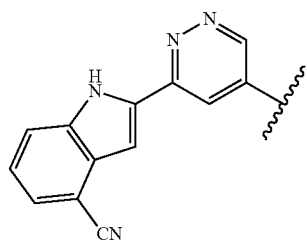
$R^4$ is H, $-N(R^6)SO_2R^7$ or
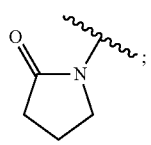 [SMILES: *N1CCCC1=O ; ";"]
$R^6$ is $C_1$-$C_6$ alkyl or $C_1$-$C_6$ haloalkyl; and
$R^7$ is independently $C_1$-$C_6$ alkyl.
2. The compound of claim 1, wherein $R^4$ is $-N(CH_3)SO_2CH_3$.
3. The compound of claim 1, wherein the group
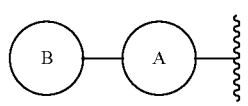
is selected from:
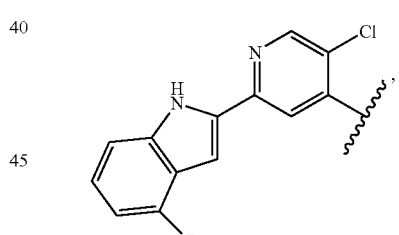
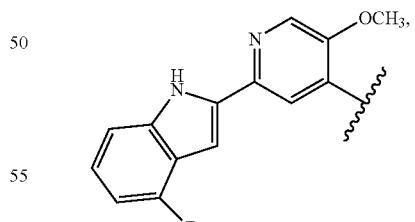
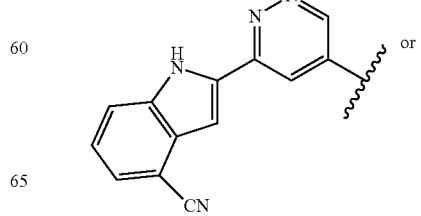

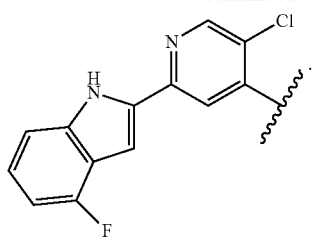
4. A compound having the structure:
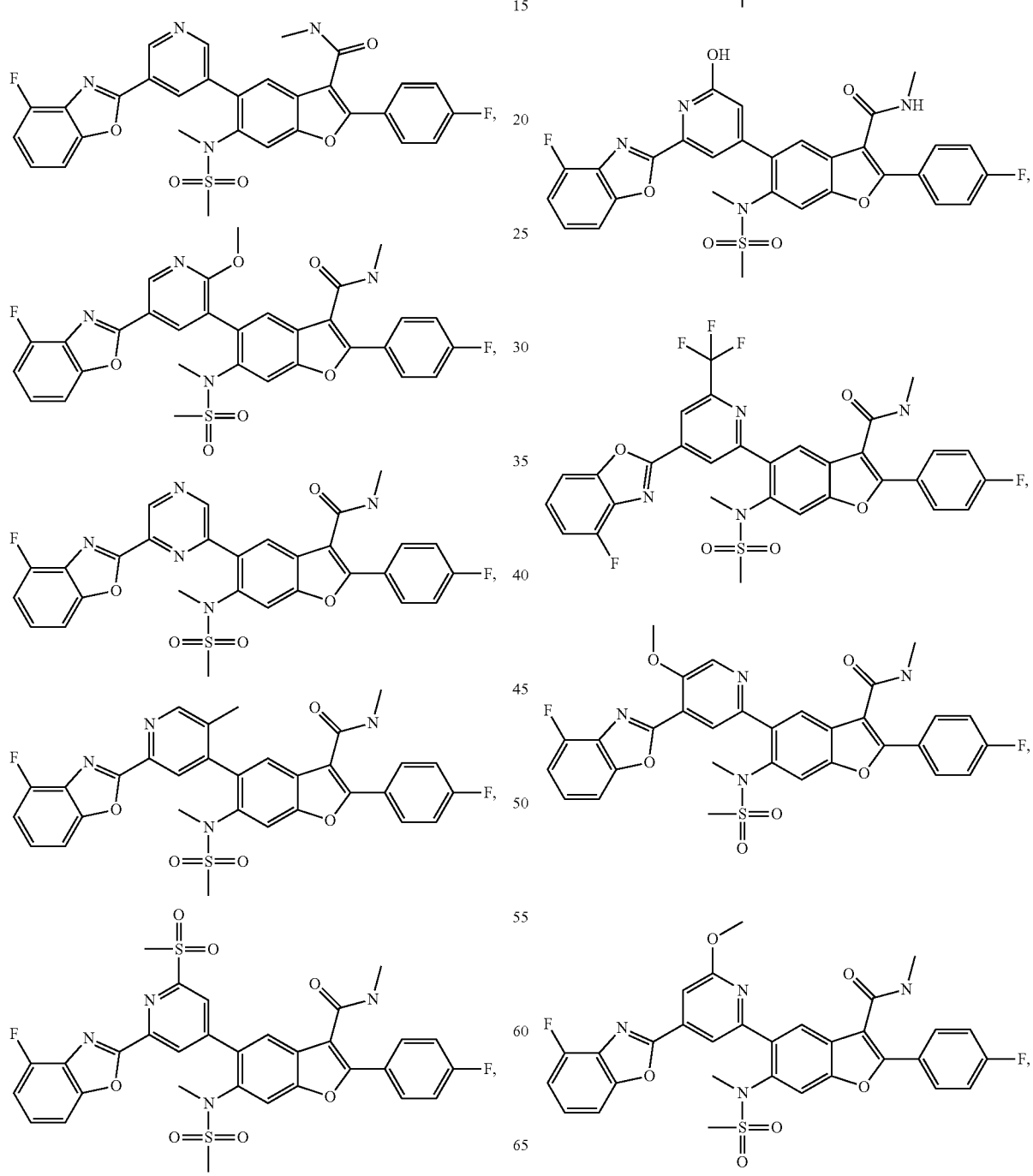
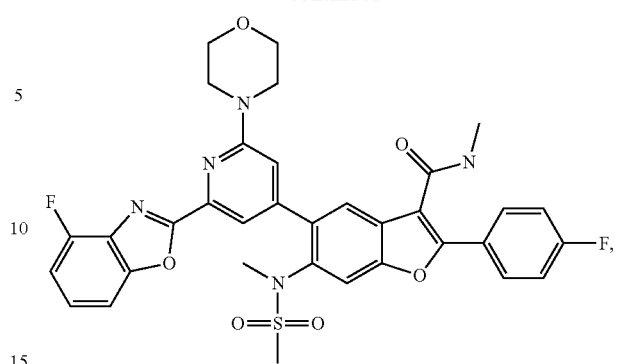

223
-continued
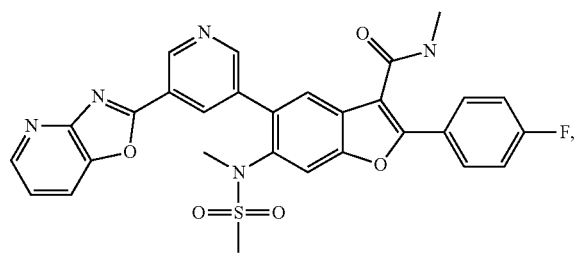
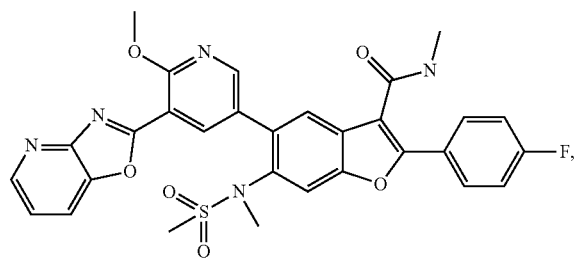
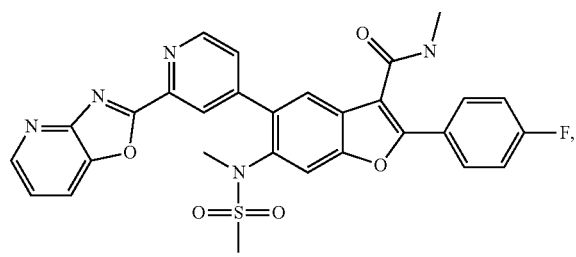
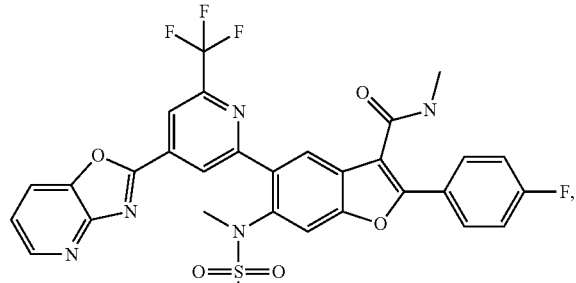
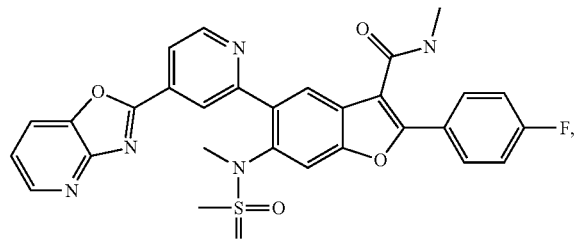
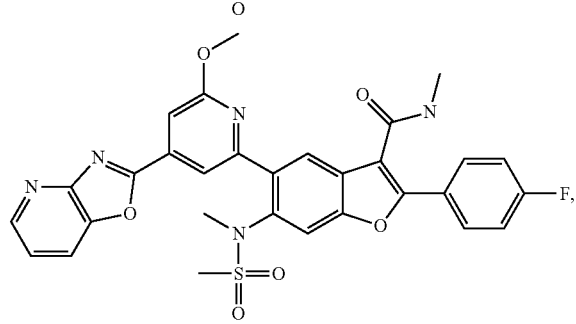
224
-continued
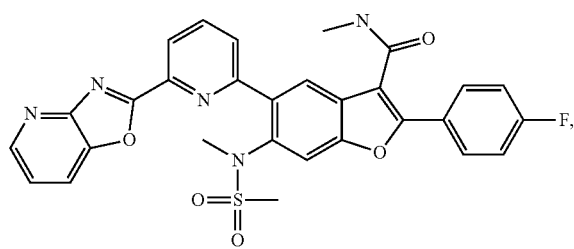
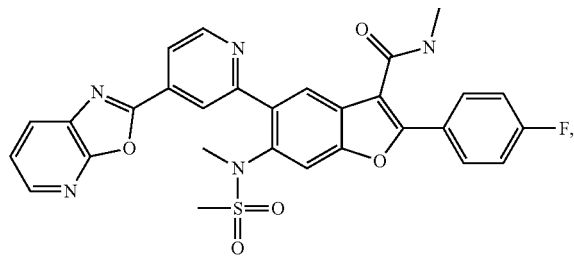
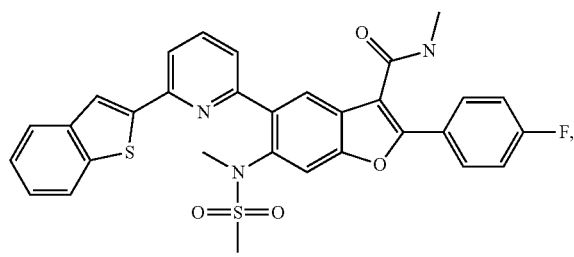
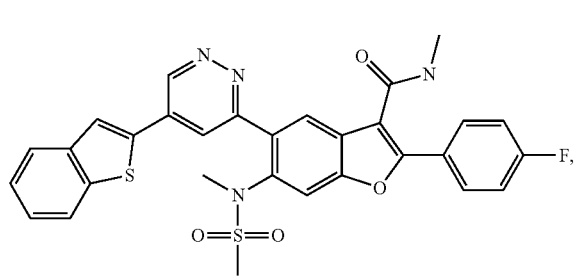
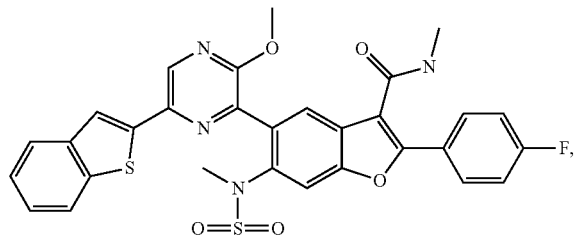
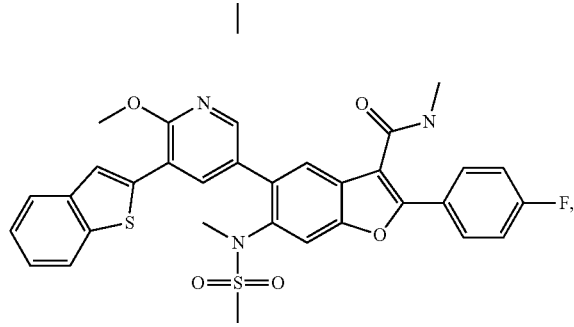

225
-continued
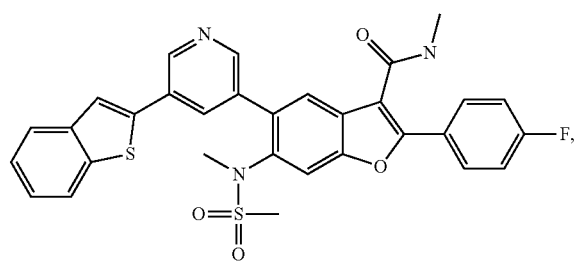
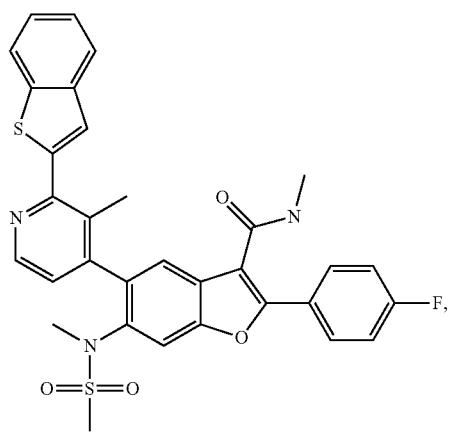
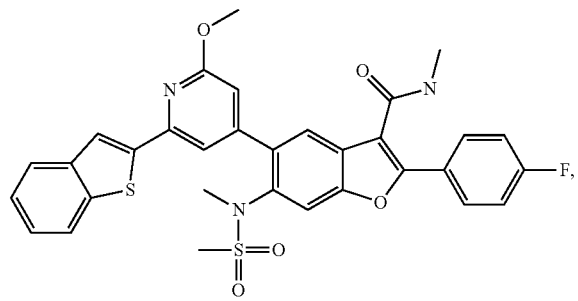
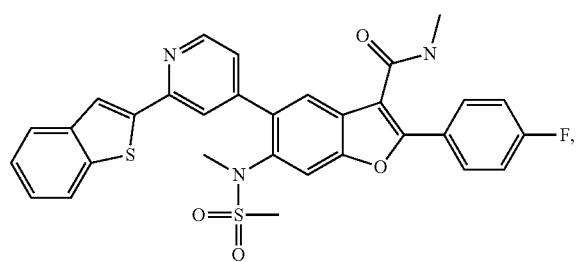
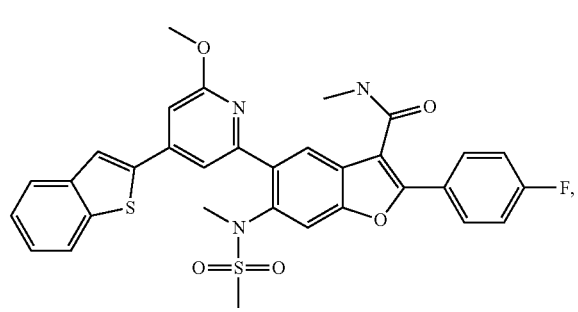
226
-continued
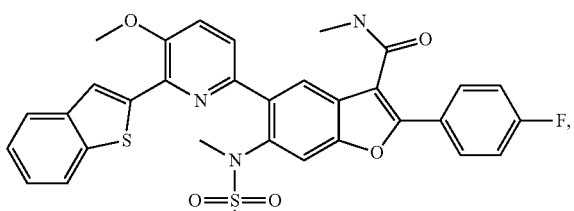
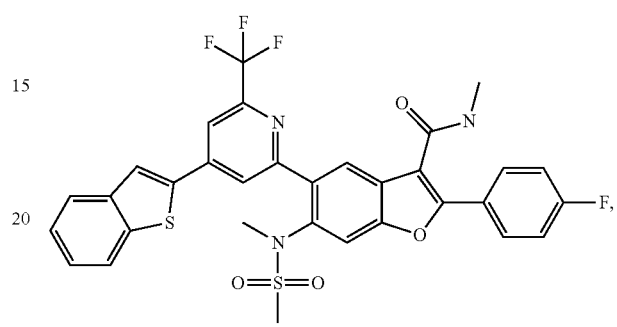
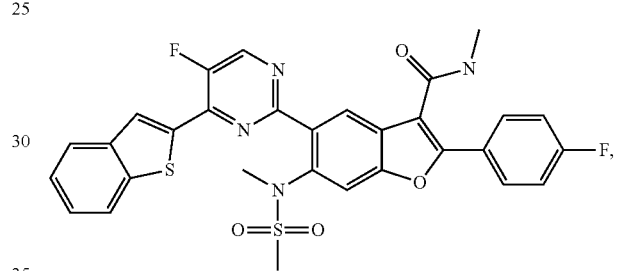
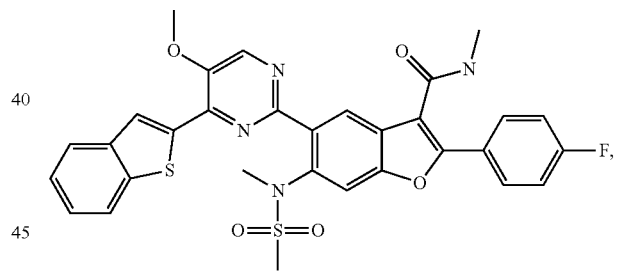
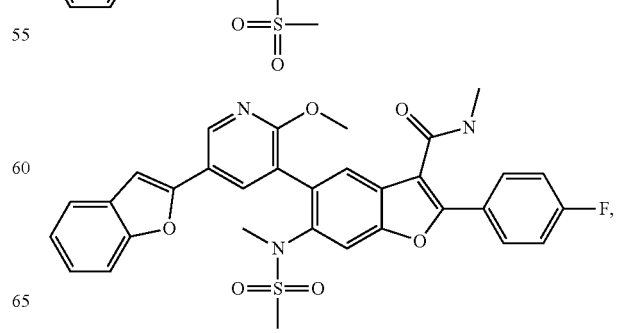

227
-continued
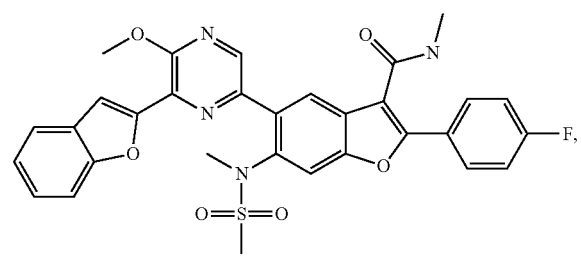
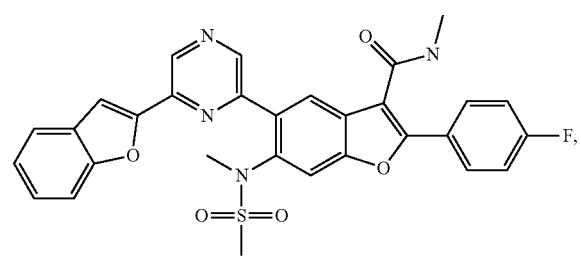
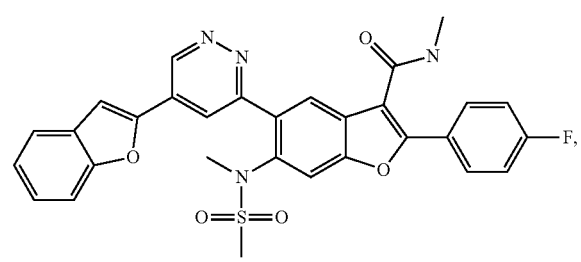
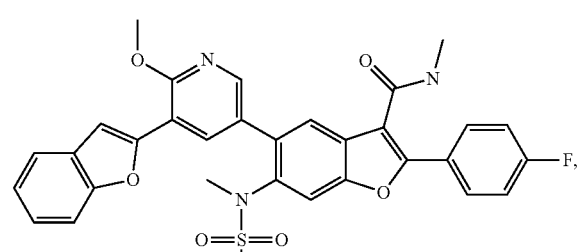
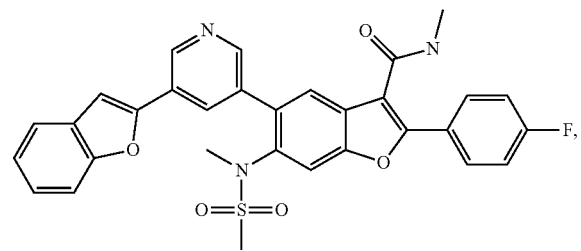
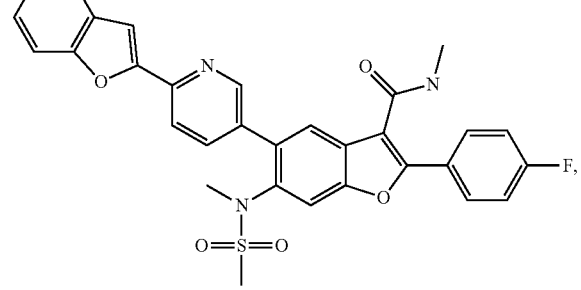
228
-continued
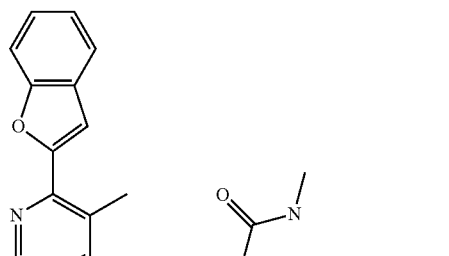
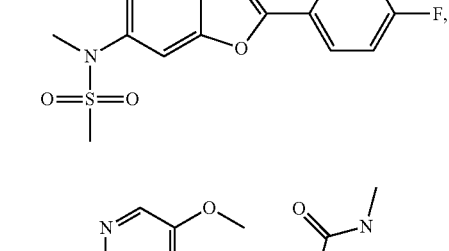
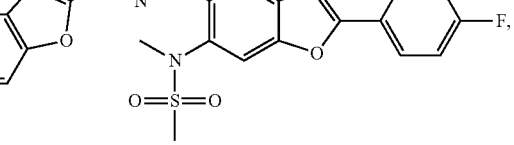
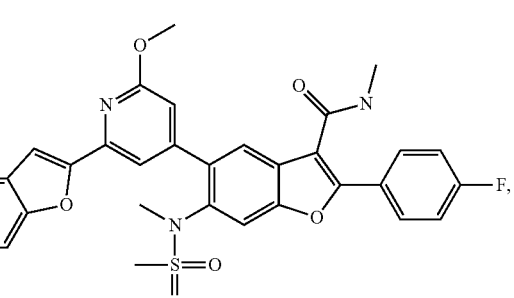
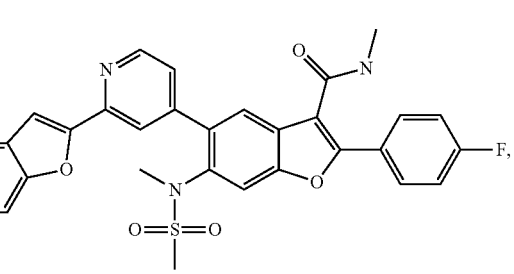
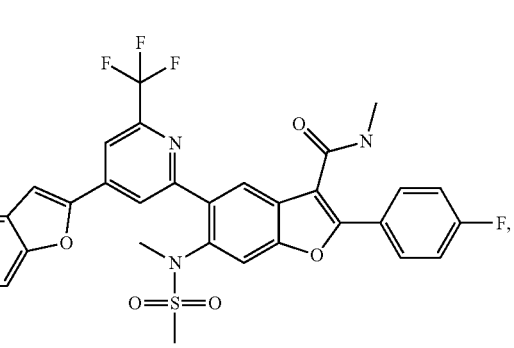

229
-continued
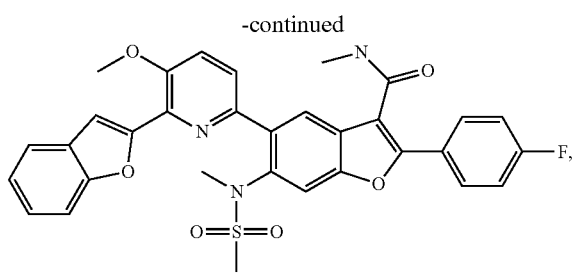
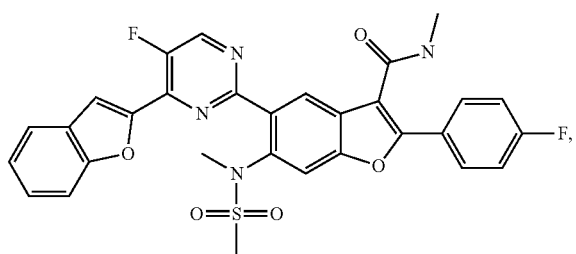
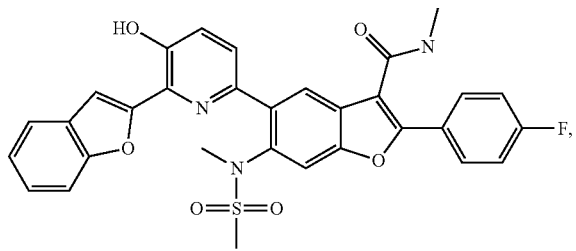
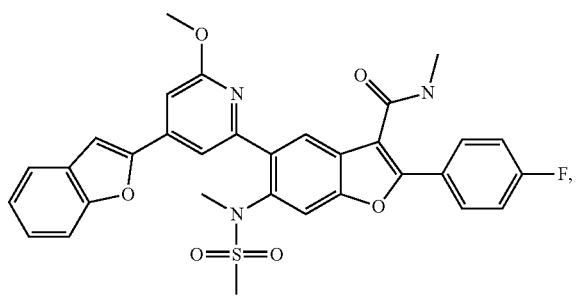
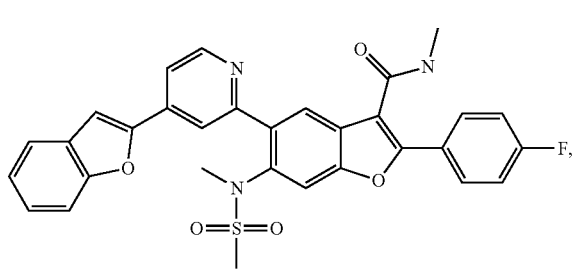
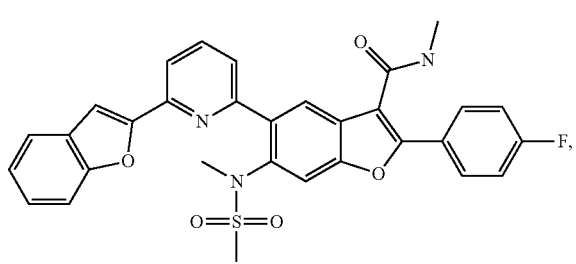
230
-continued
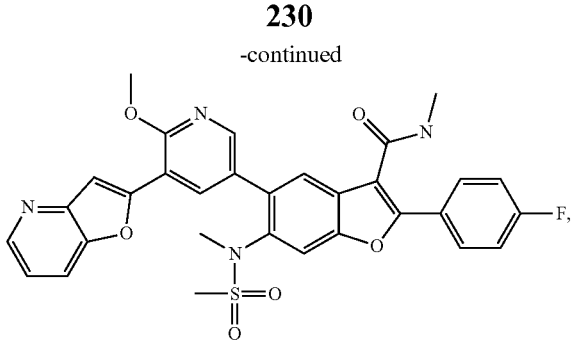
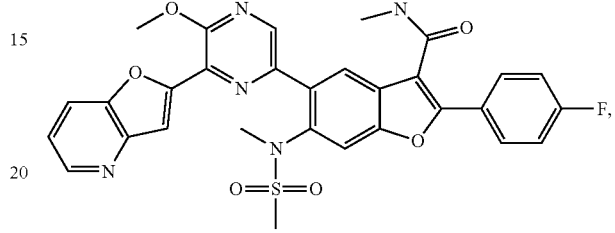
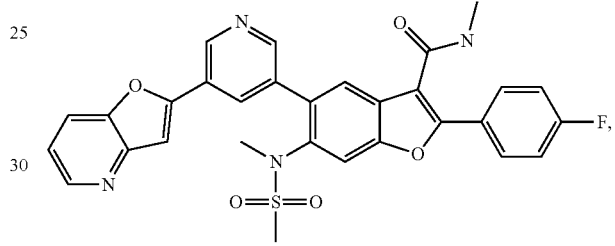
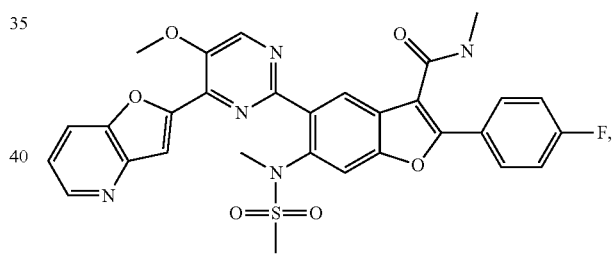
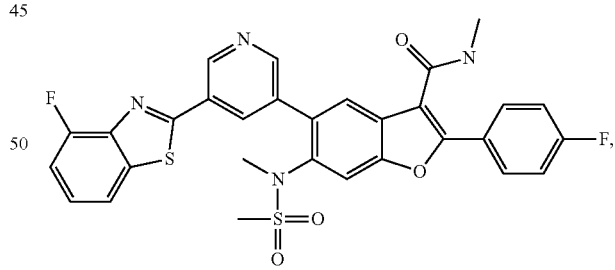
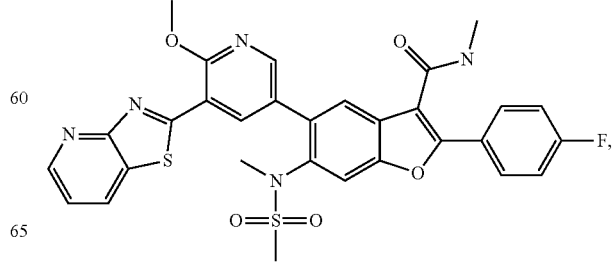

231
-continued
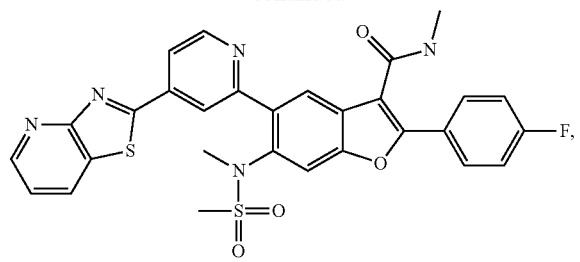
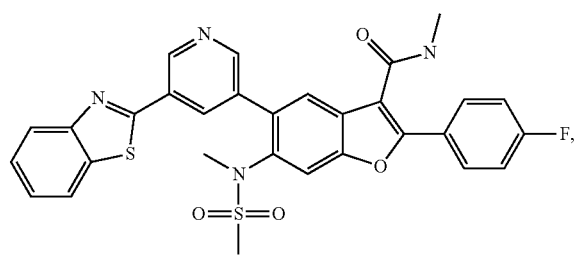
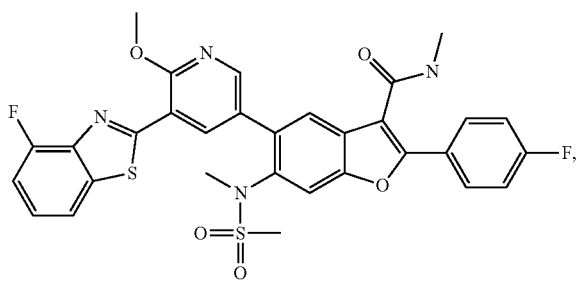
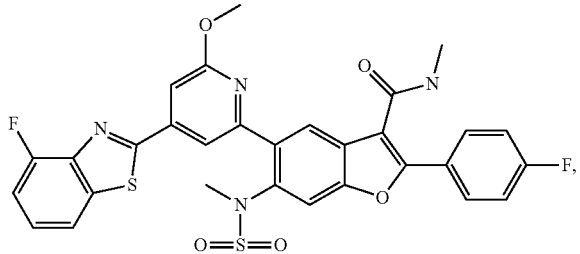
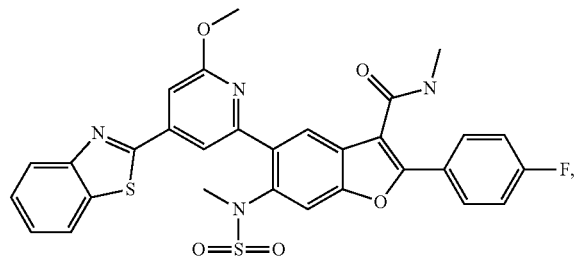
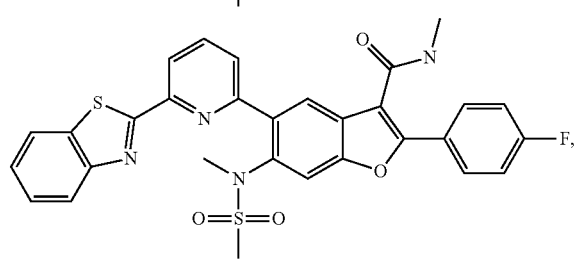
232
-continued
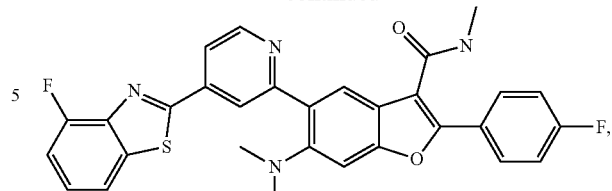
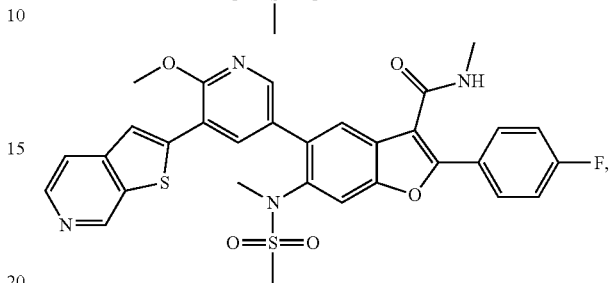
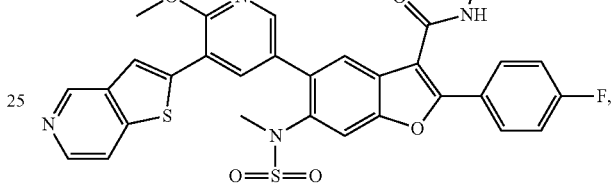
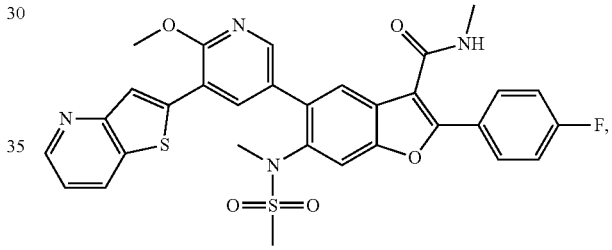
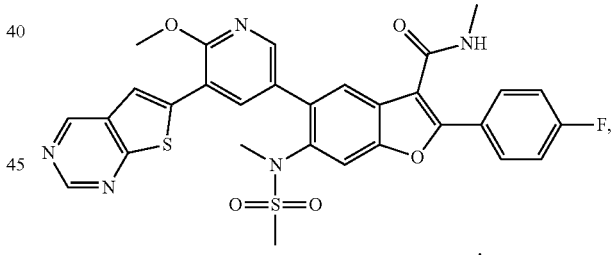
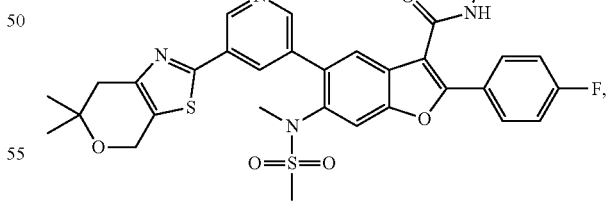
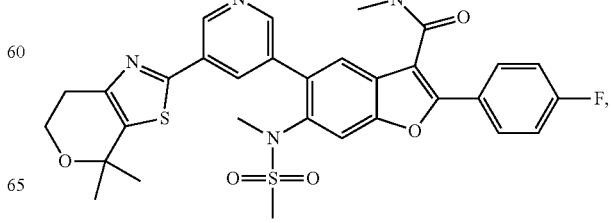

233 -continued
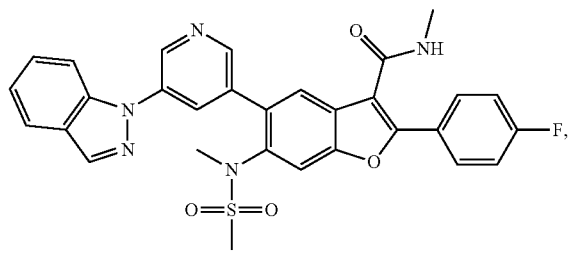
234 -continued
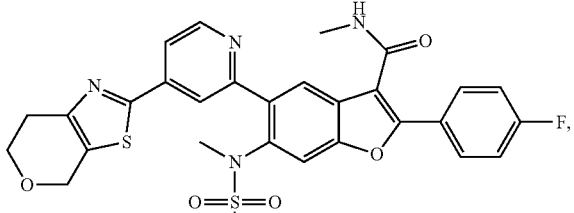
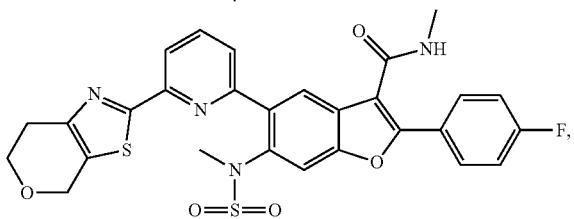
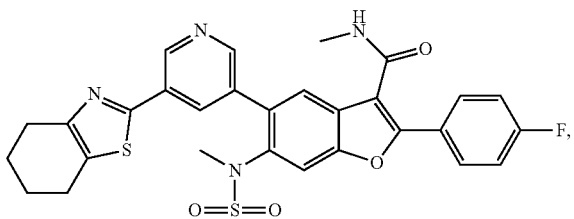
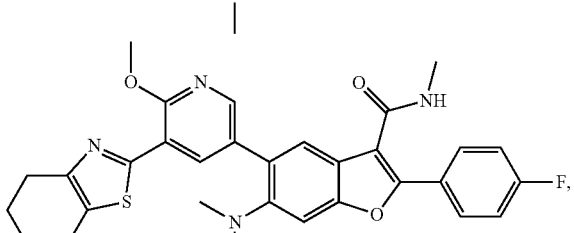
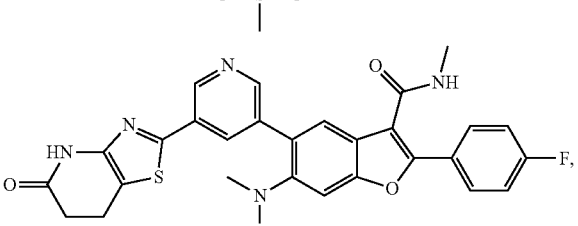
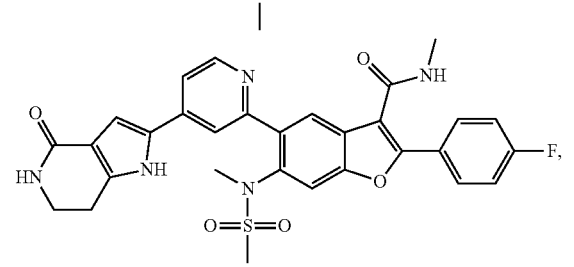

235
-continued
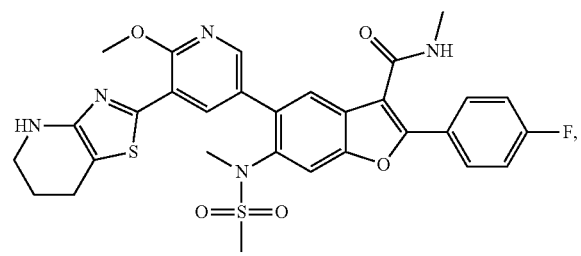
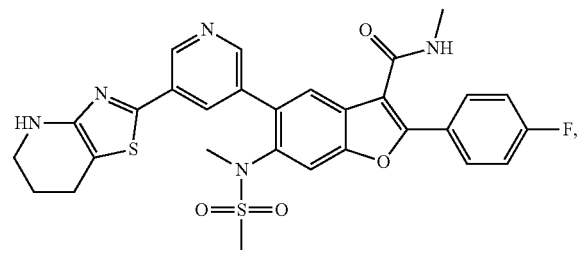
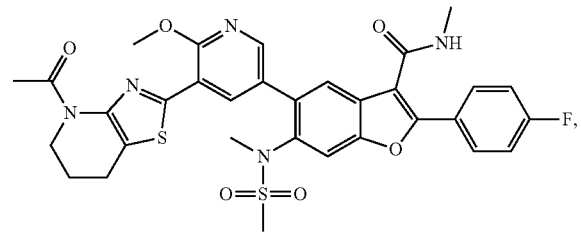
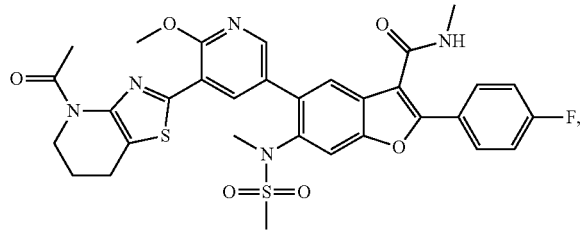
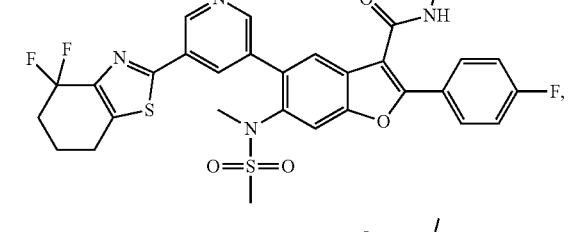
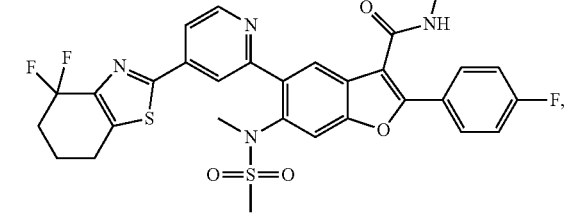
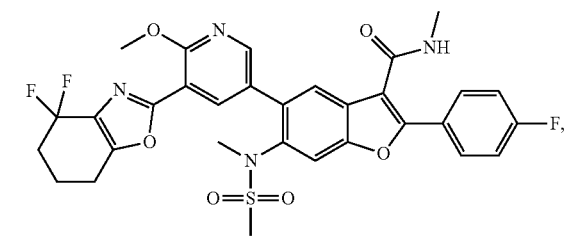
236
-continued
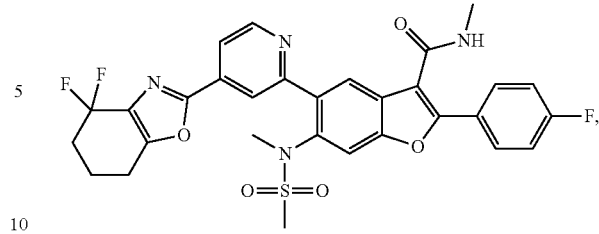
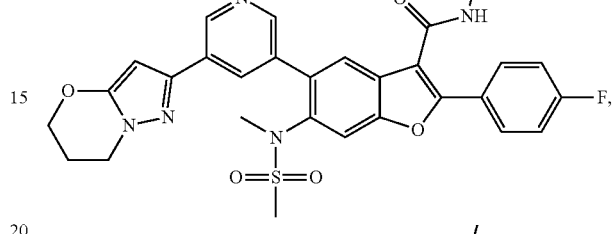
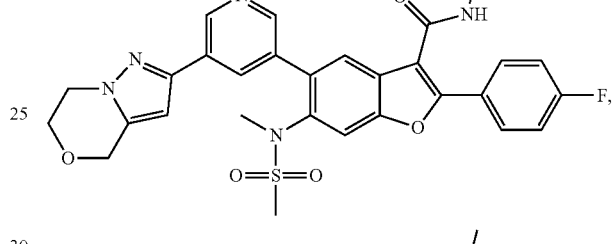
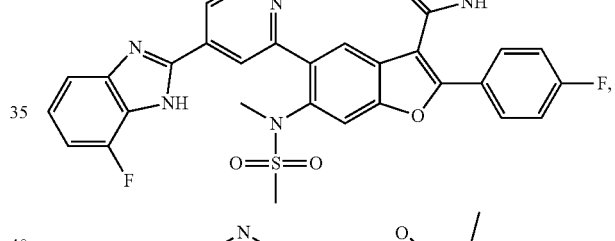
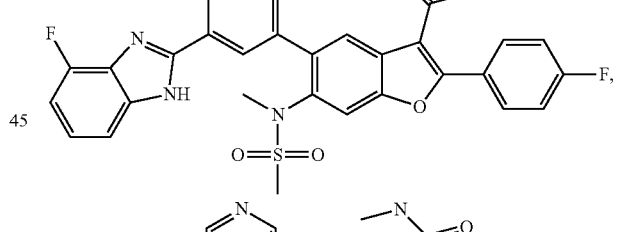
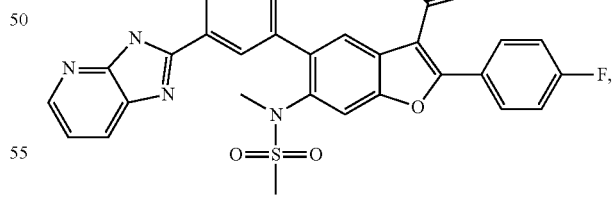
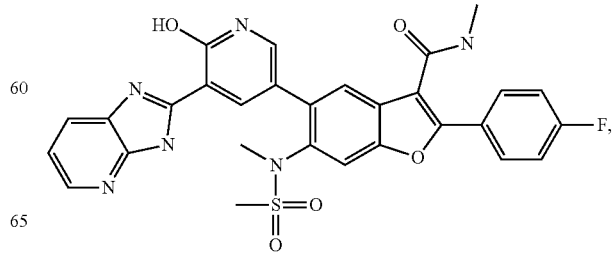

237
-continued
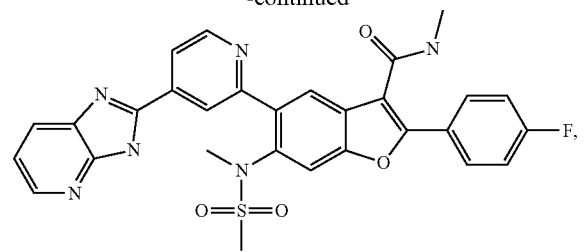
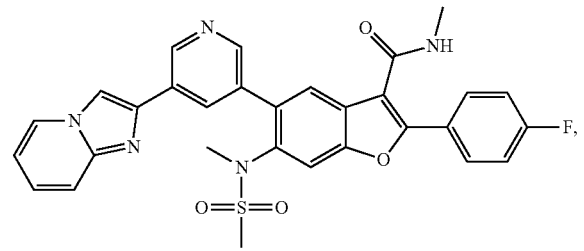
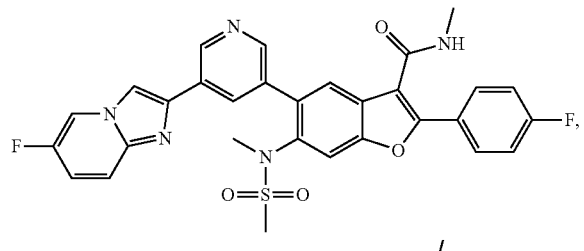
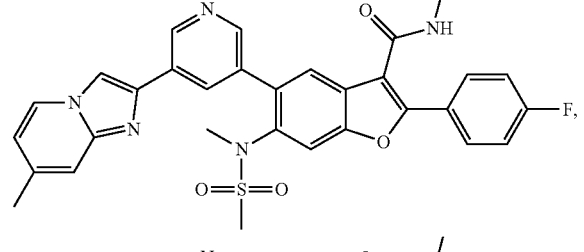
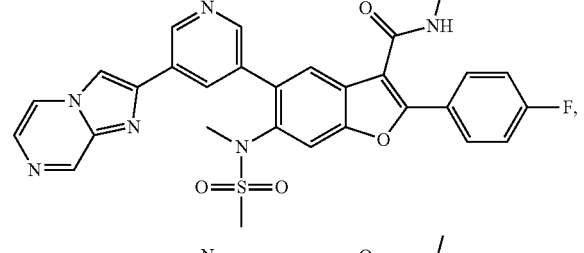
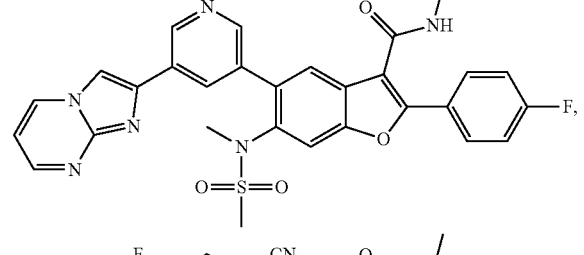
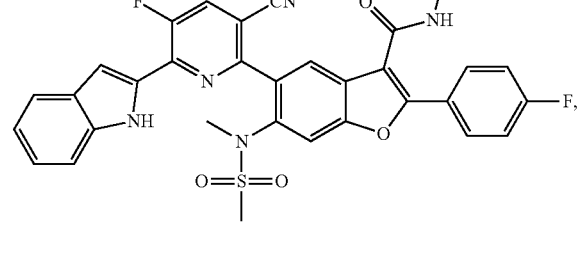
238
-continued
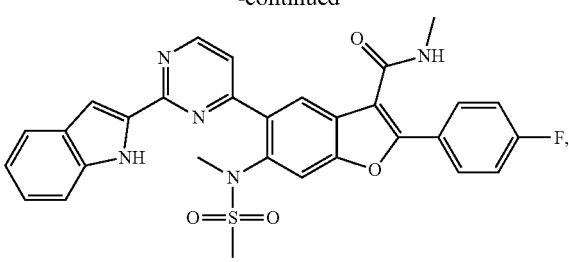
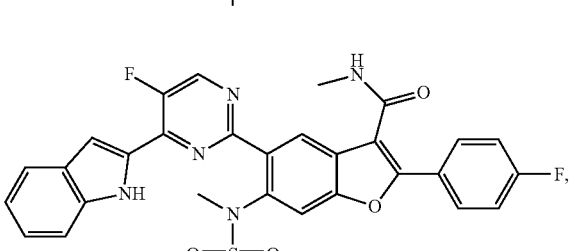
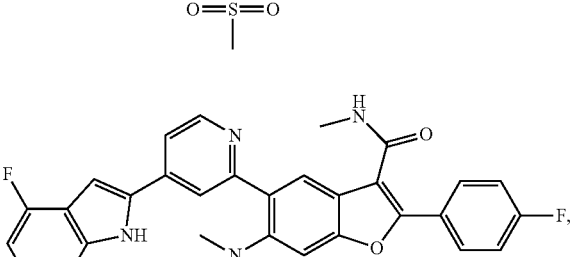
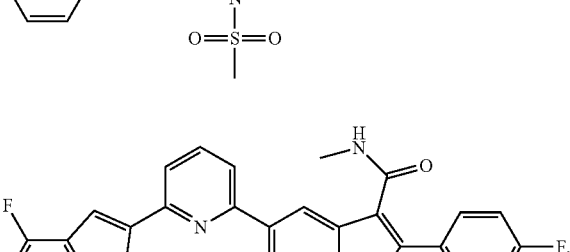
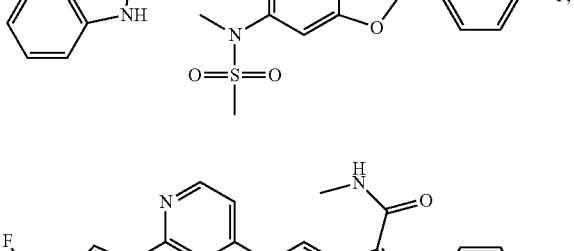
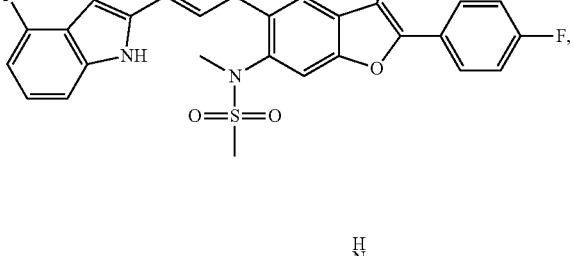
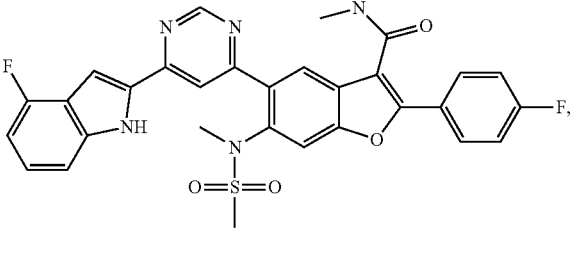

239
-continued
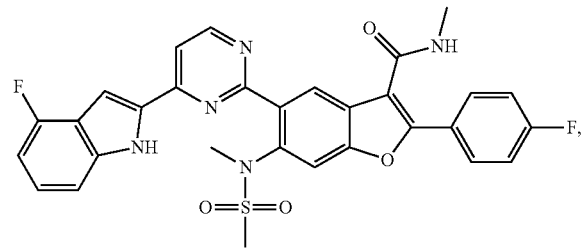
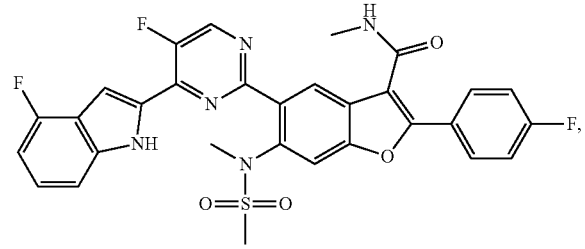
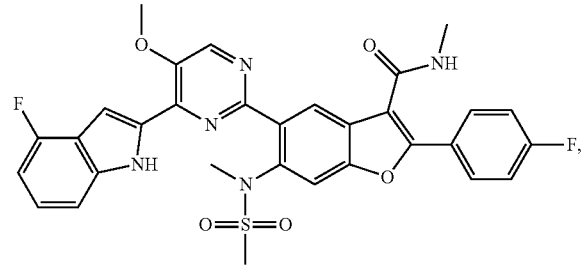
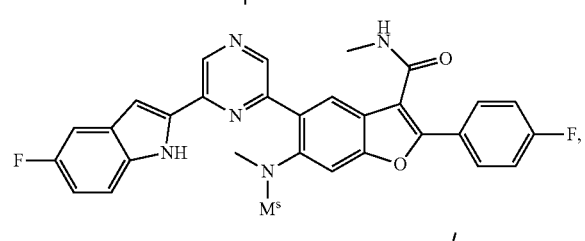
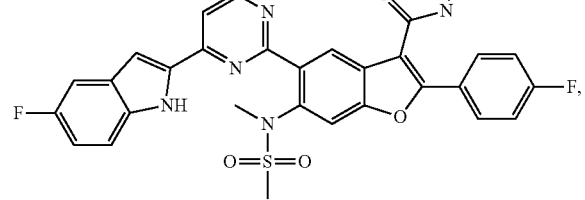
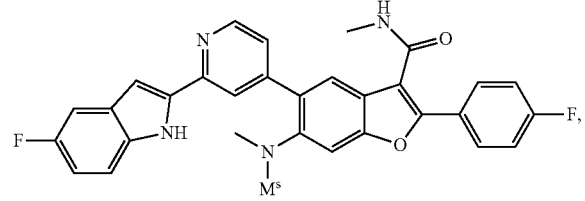
240
-continued
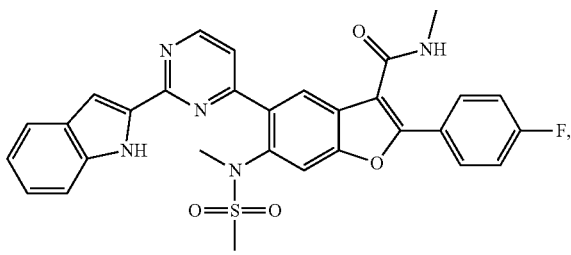
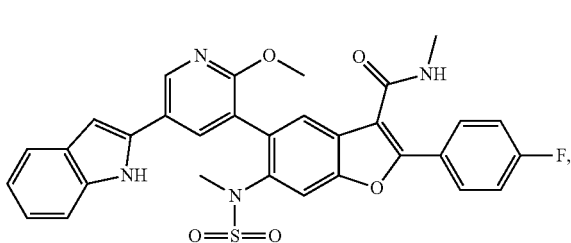
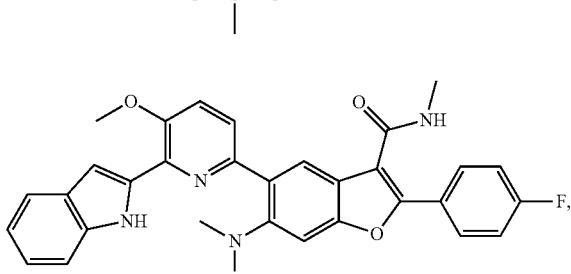
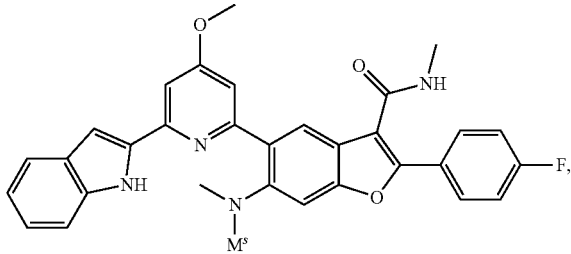
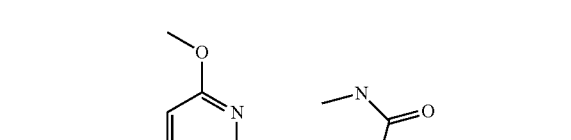
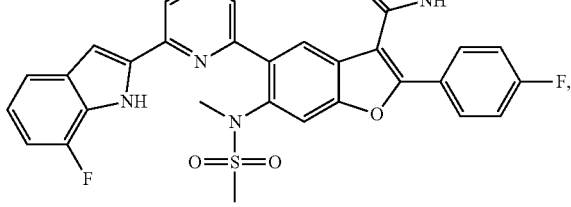

241
-continued
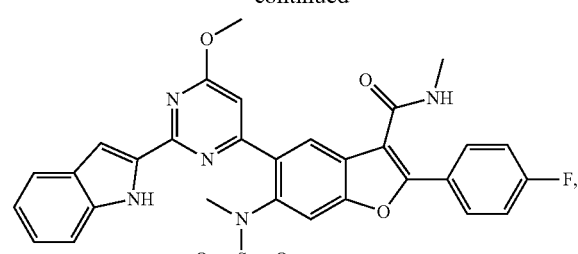
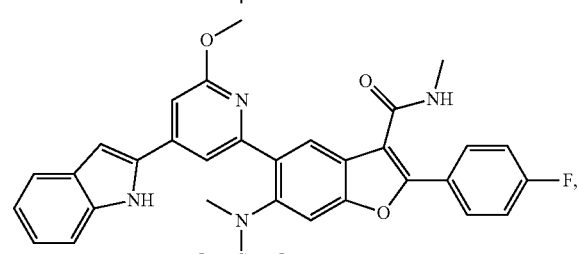
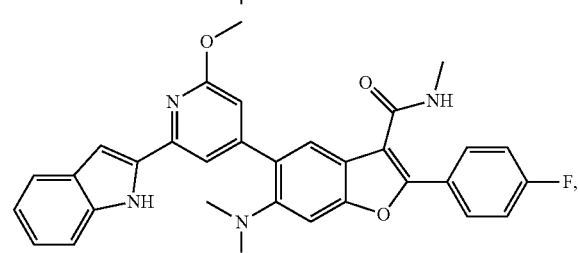
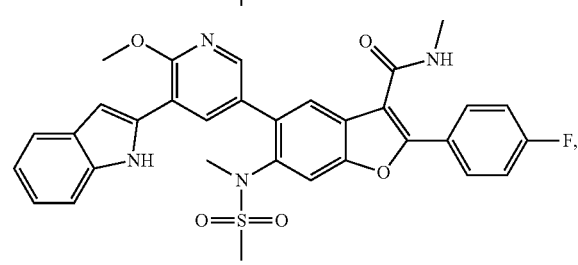
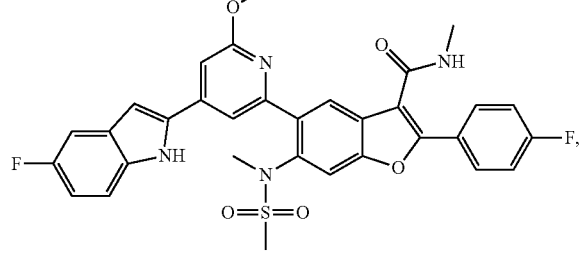
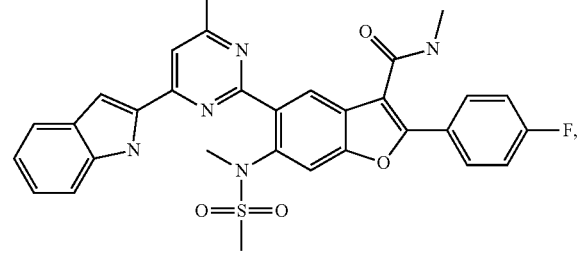
242
-continued
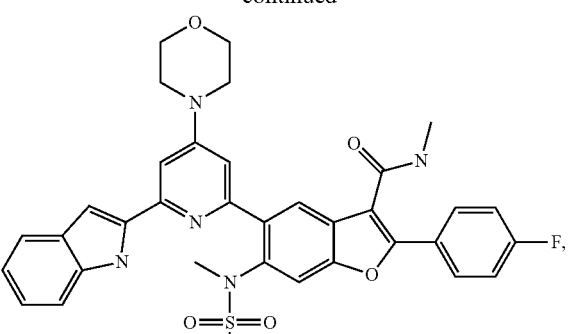
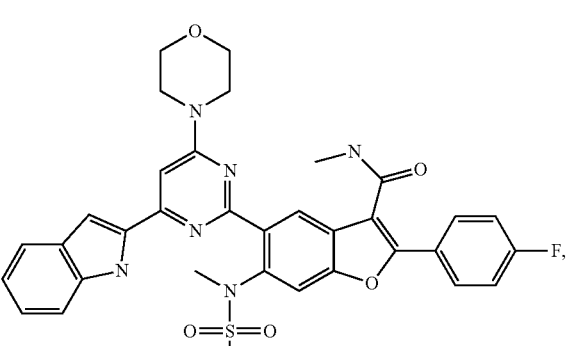
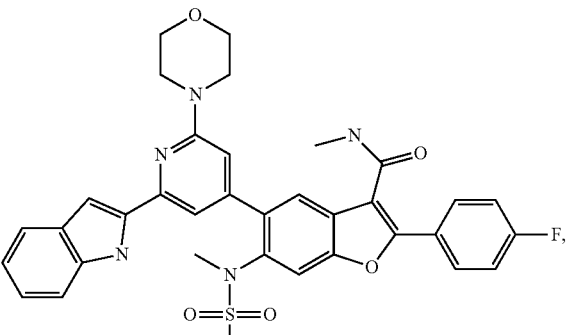
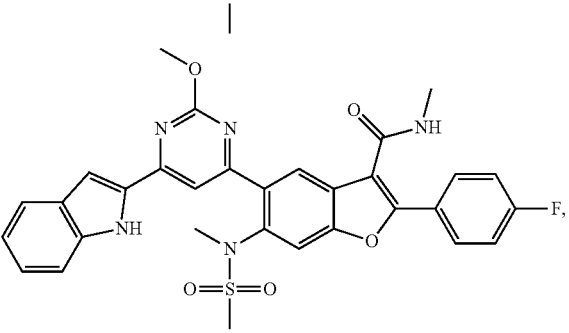
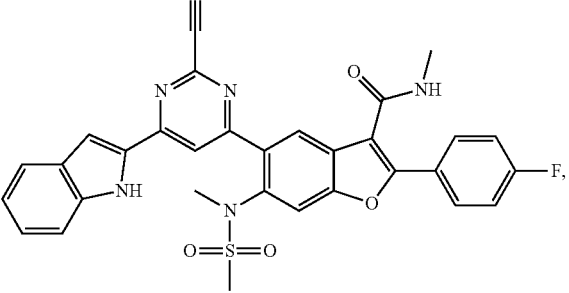

-continued
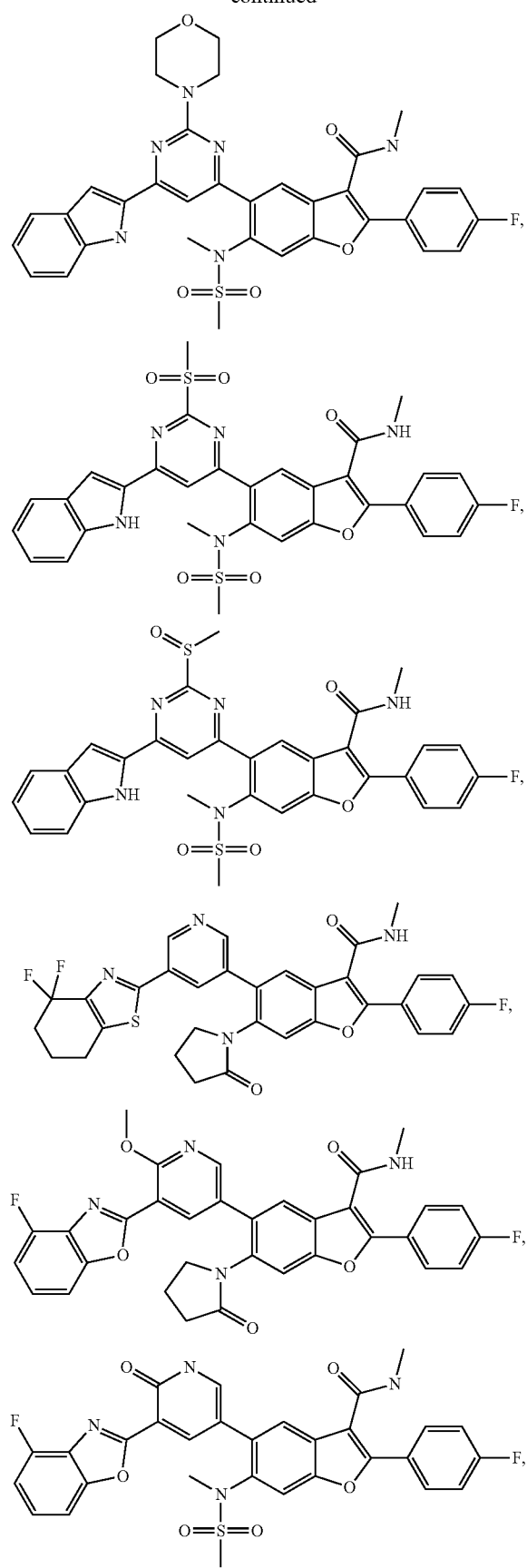
-continued
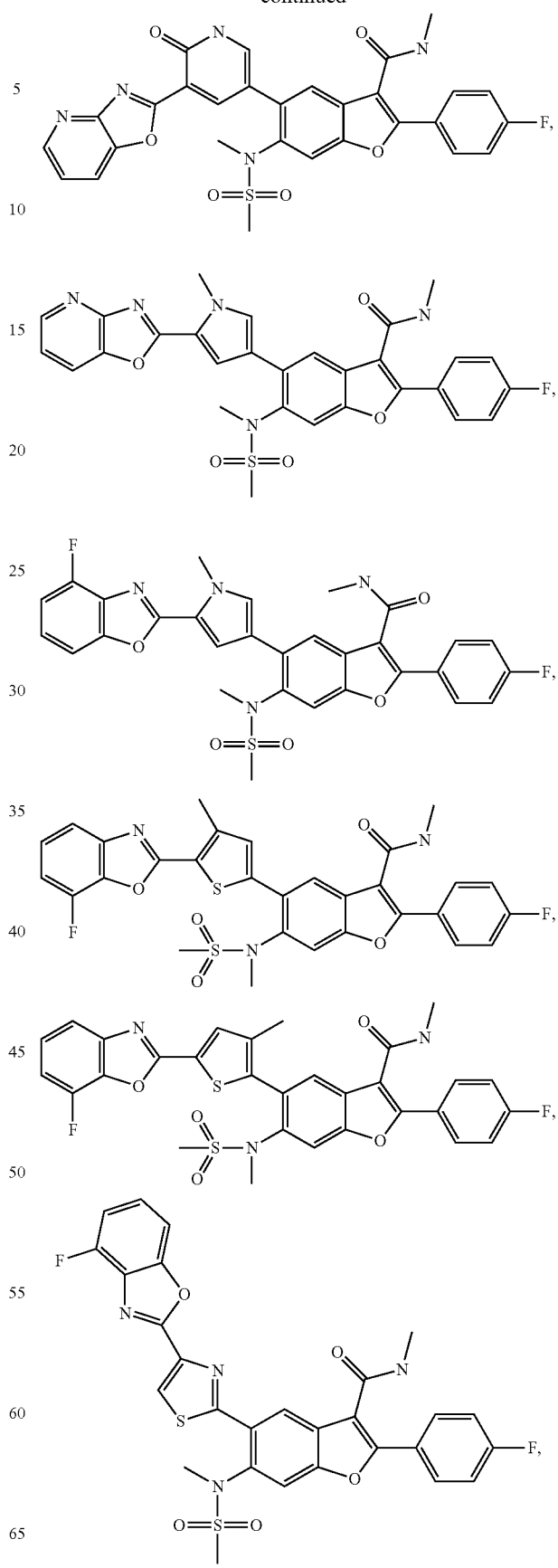

245
-continued
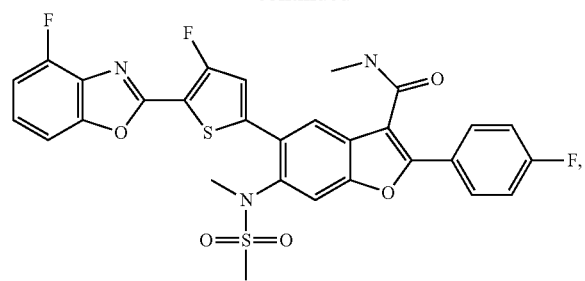
246
-continued
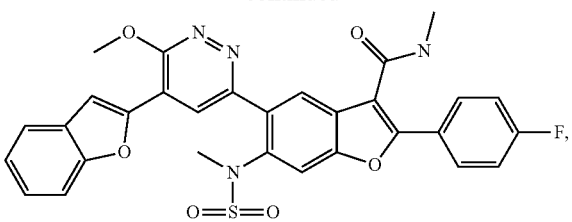
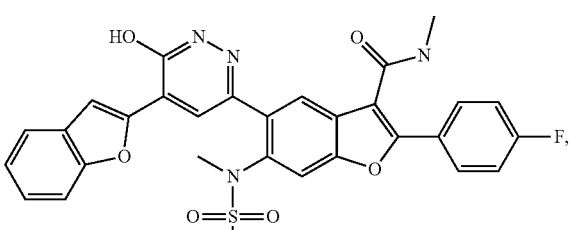
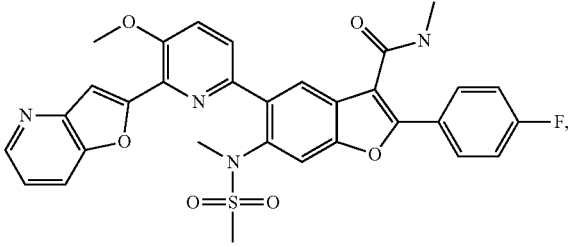
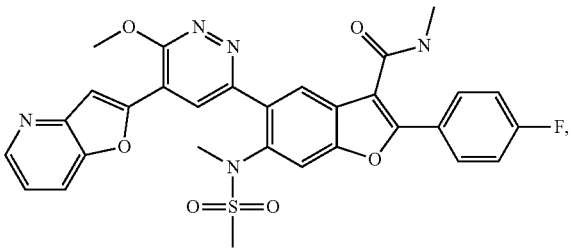
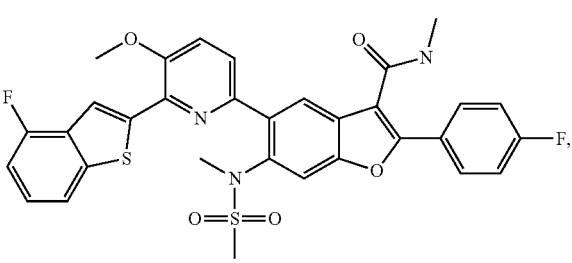
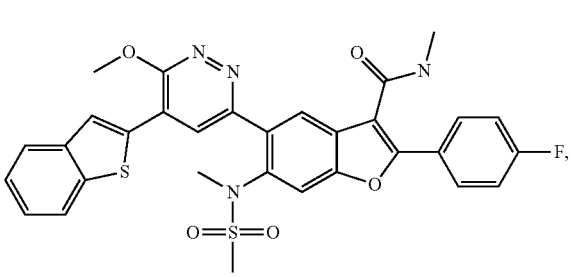

247
-continued
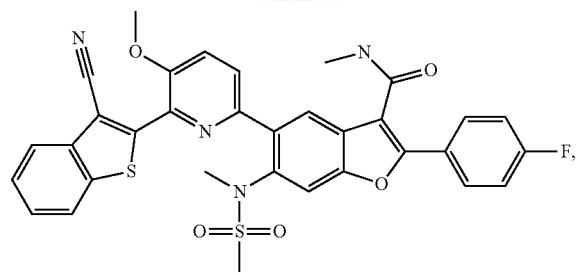
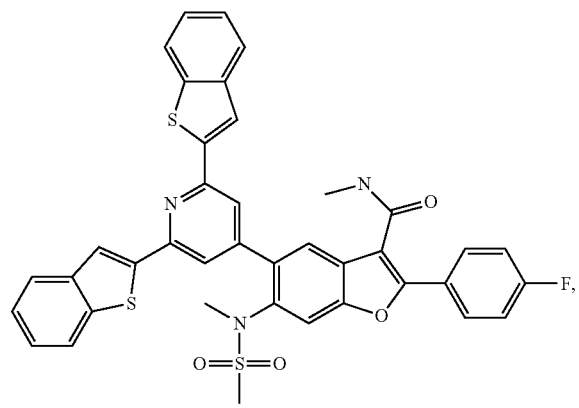
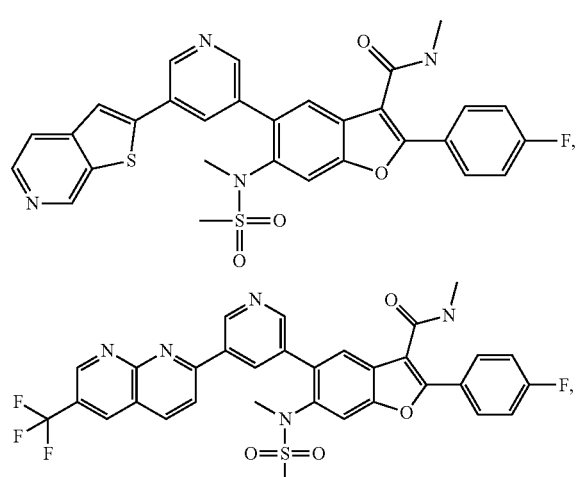
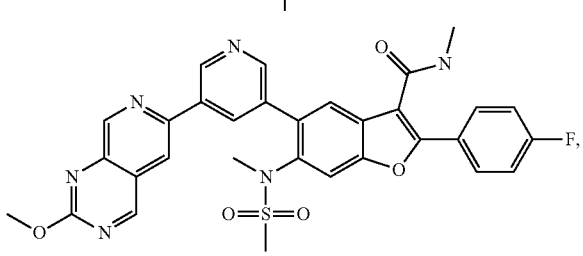
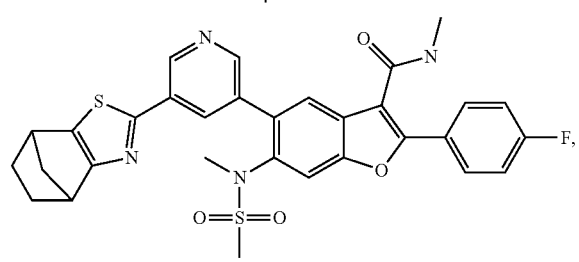
248
-continued
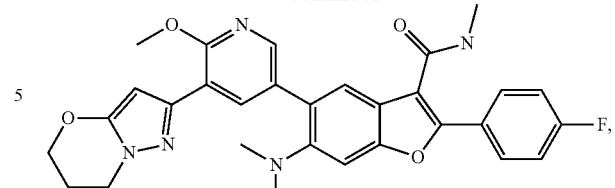
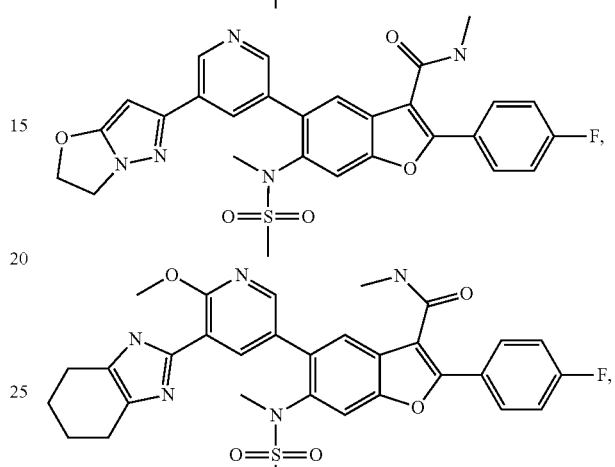
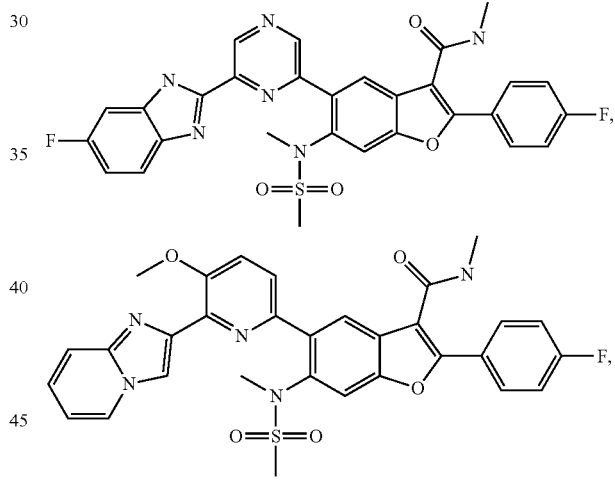
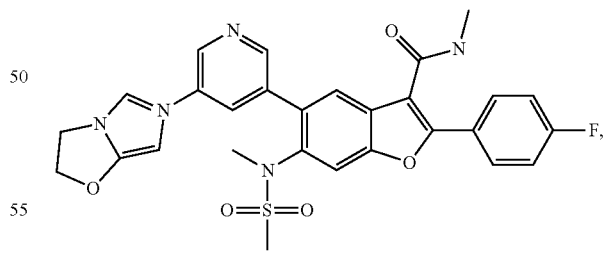
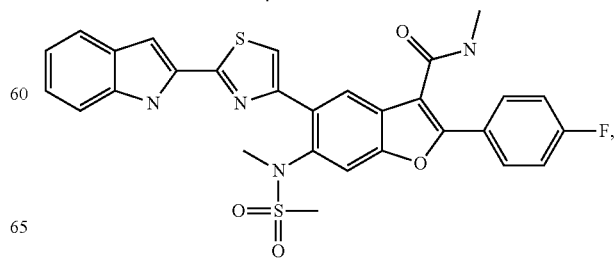

249
-continued

250
-continued

251
-continued
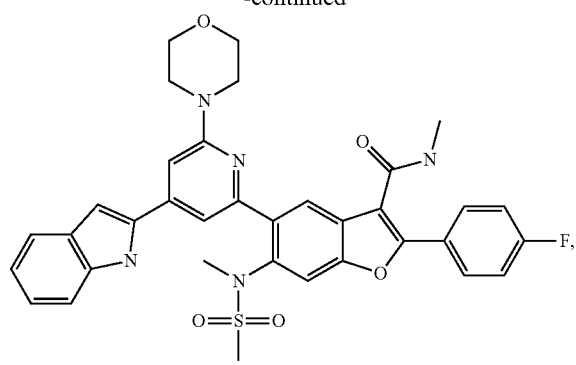
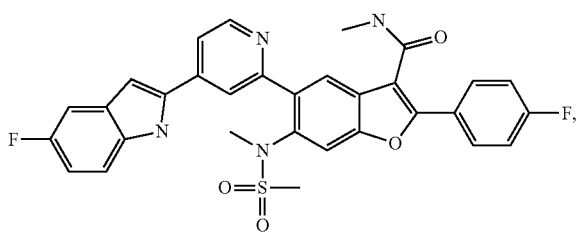
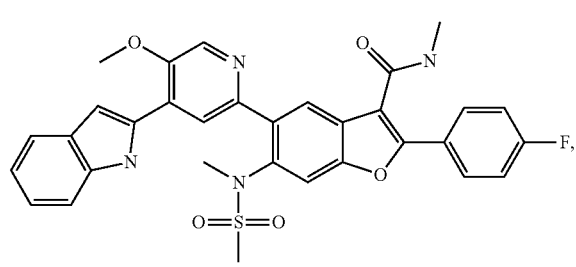
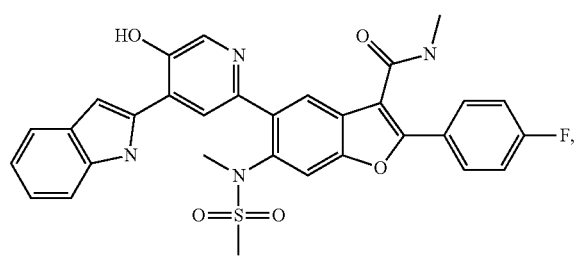
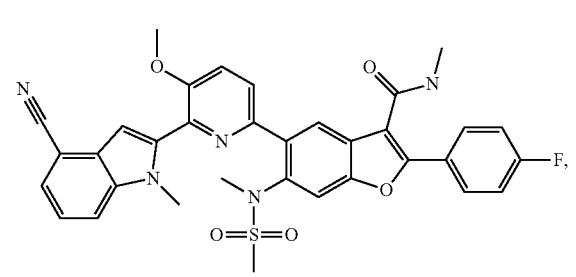
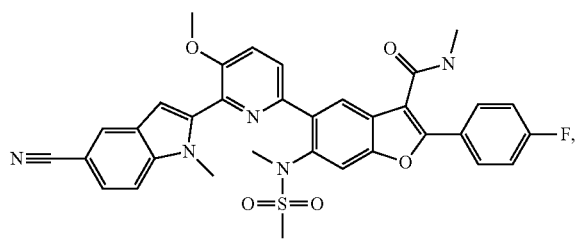
252
-continued
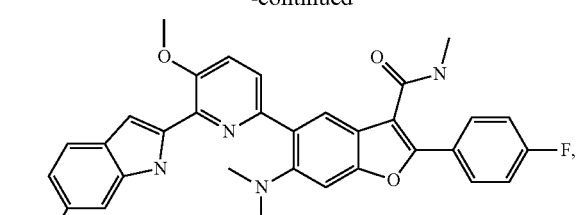
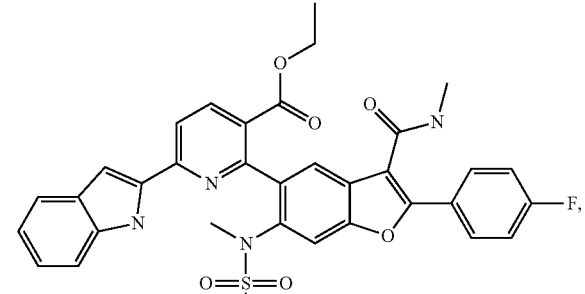
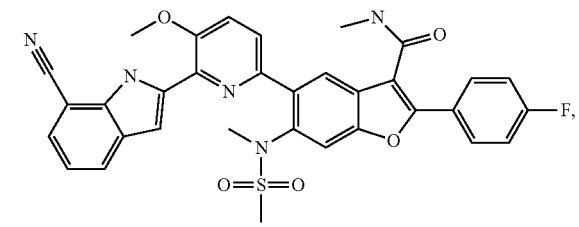
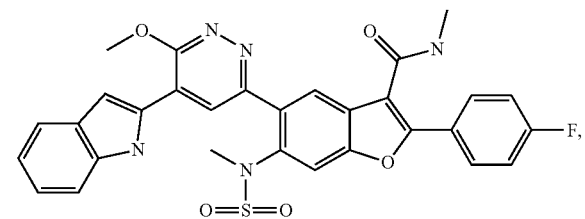
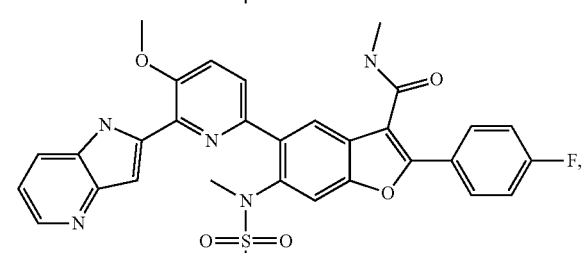
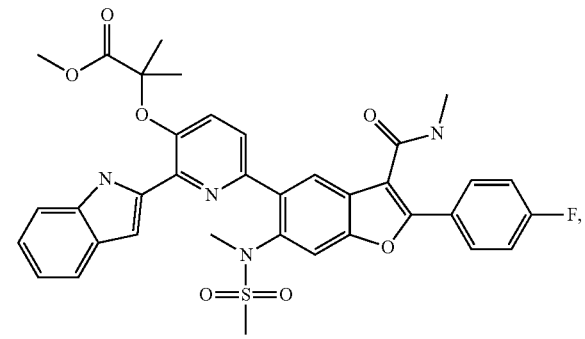

253
-continued
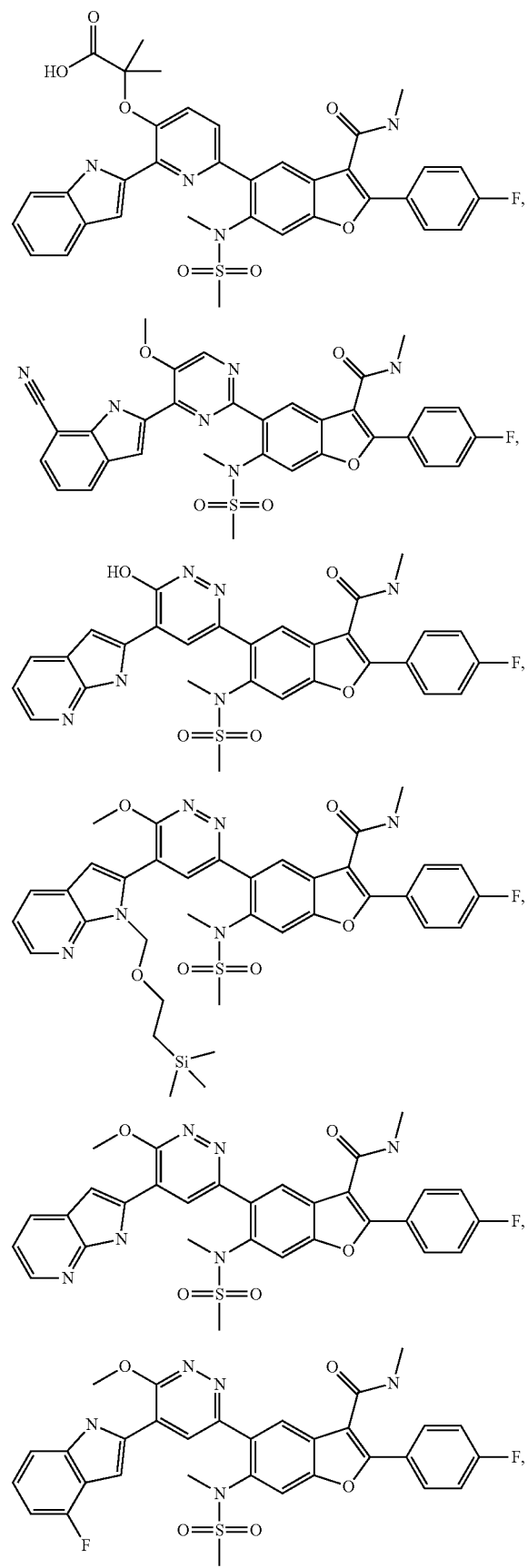
254
-continued
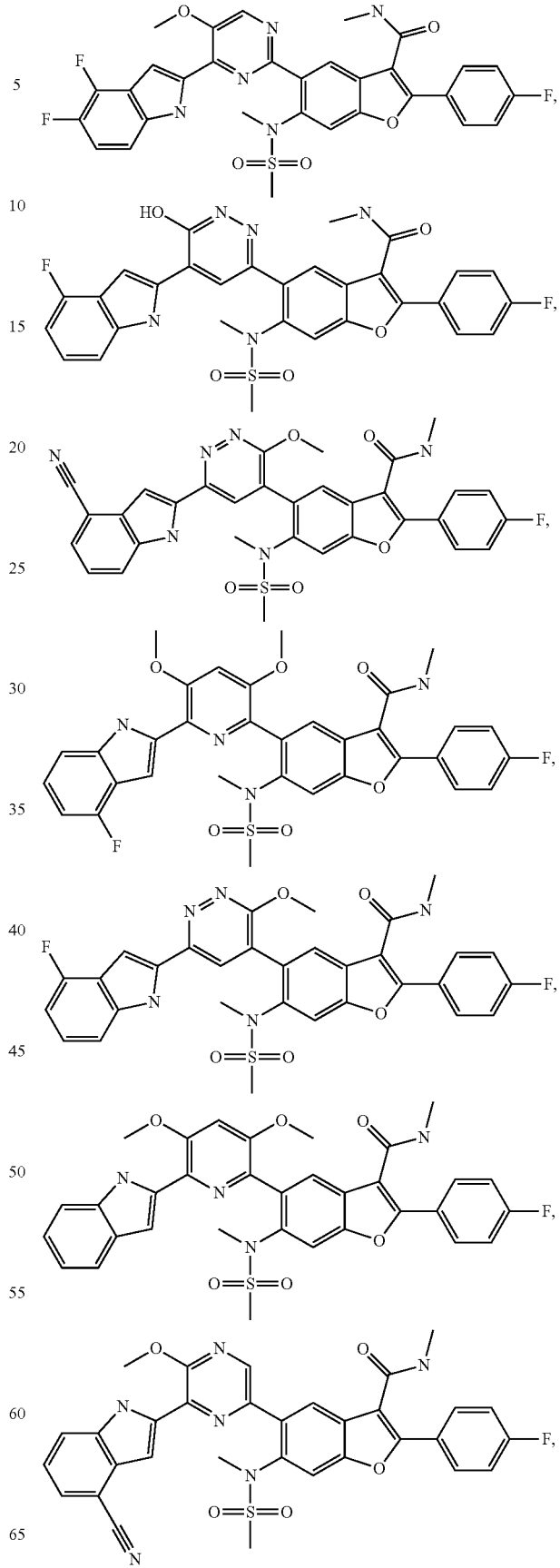

255
-continued
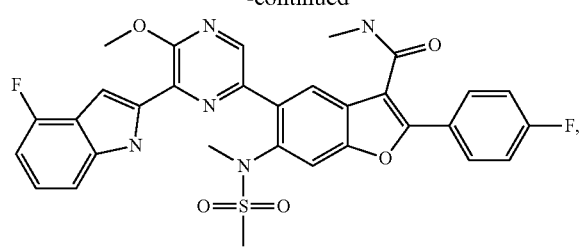
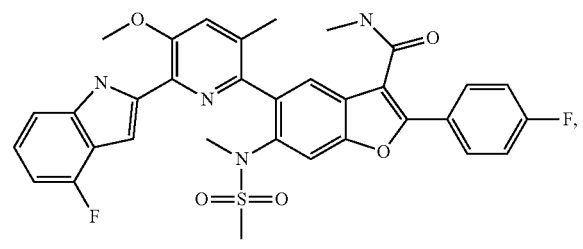
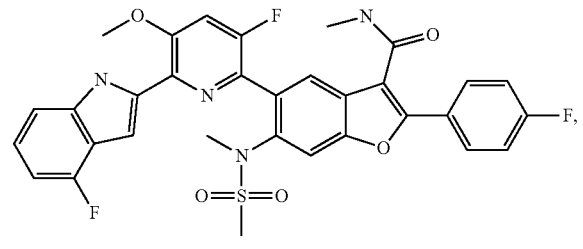
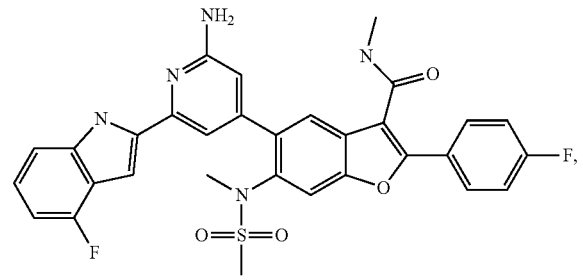
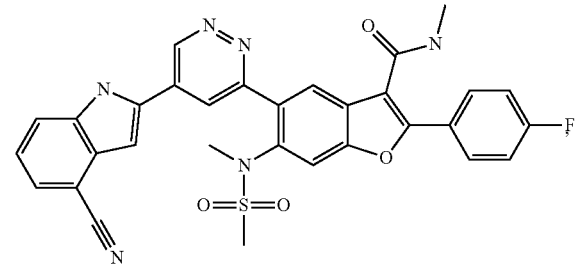
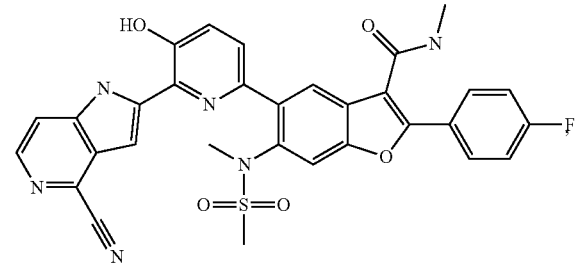
256
-continued
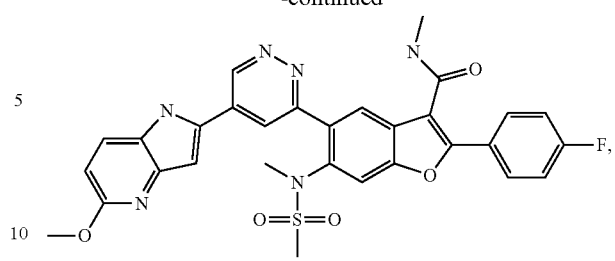
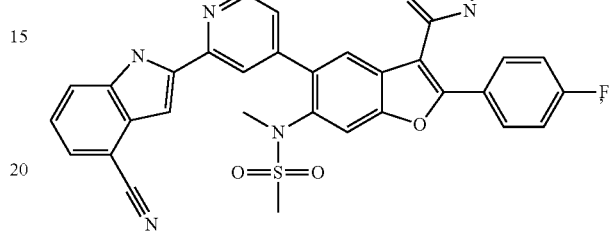
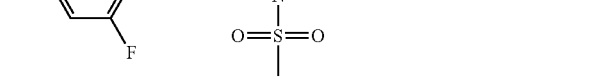
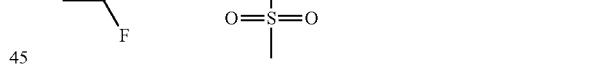
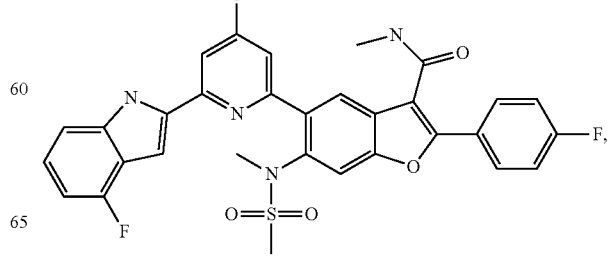

257
-continued
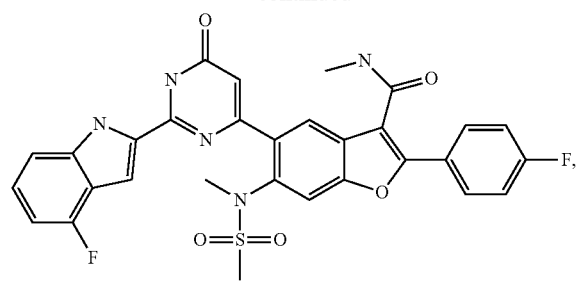
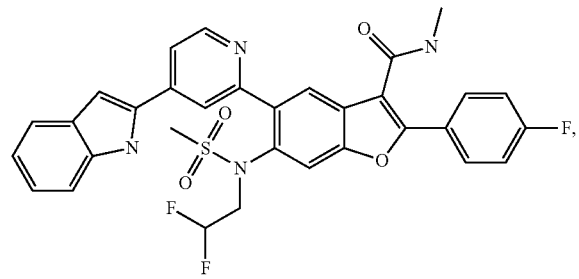
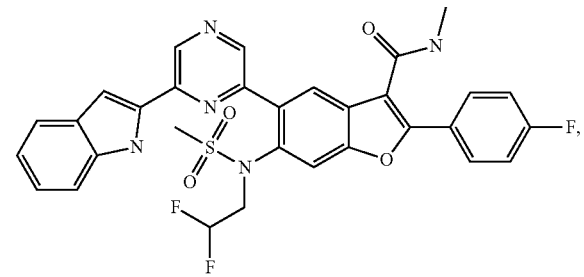
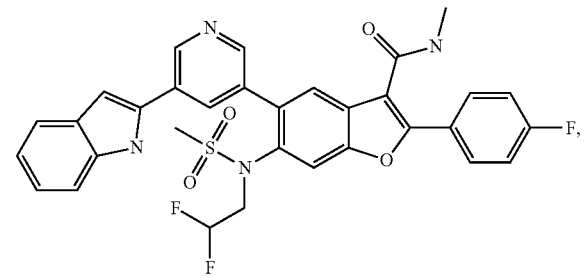
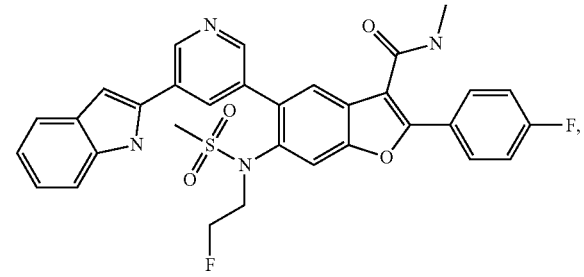
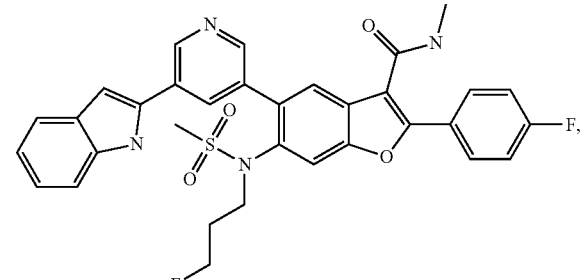
258
-continued
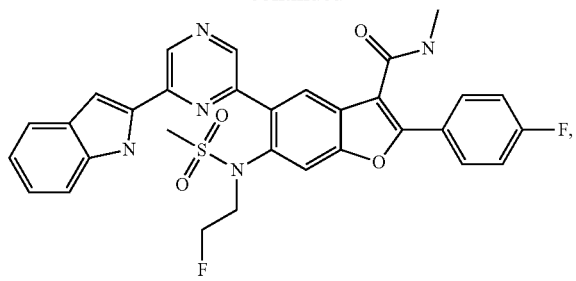
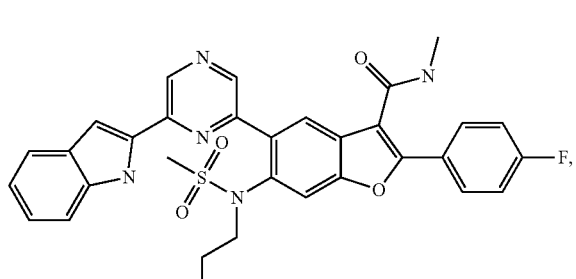
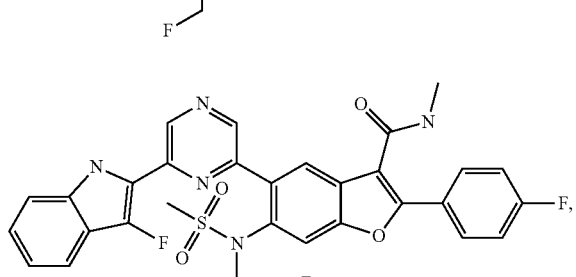
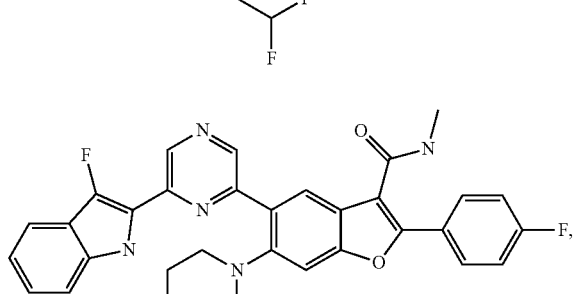
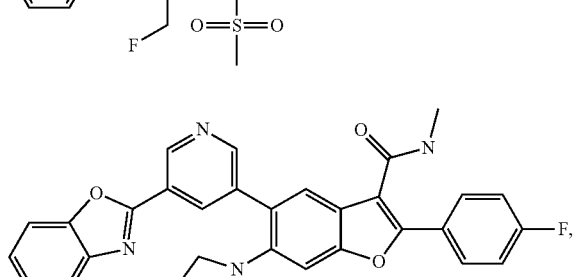
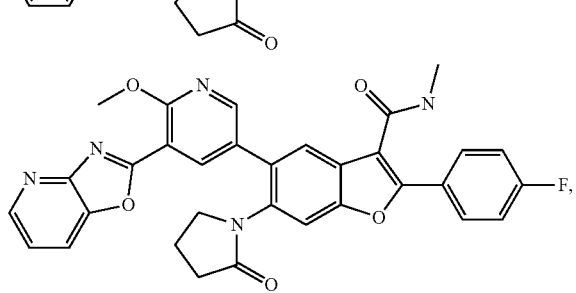

259
-continued
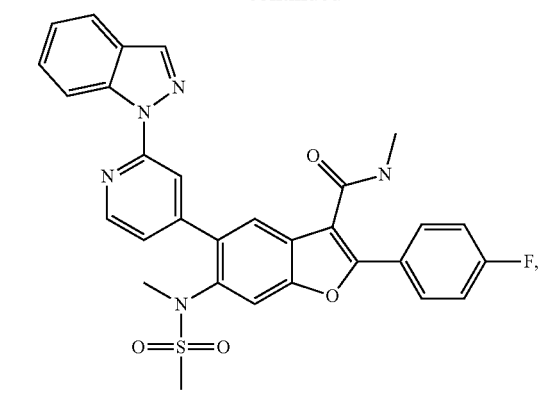
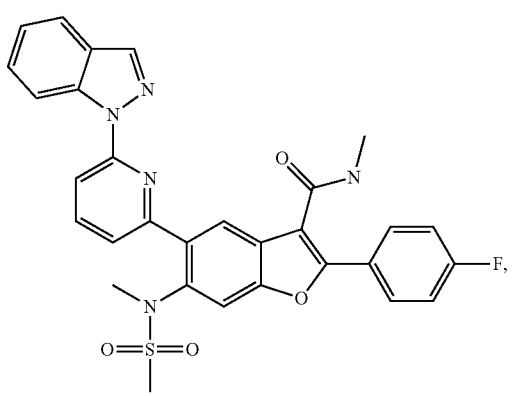
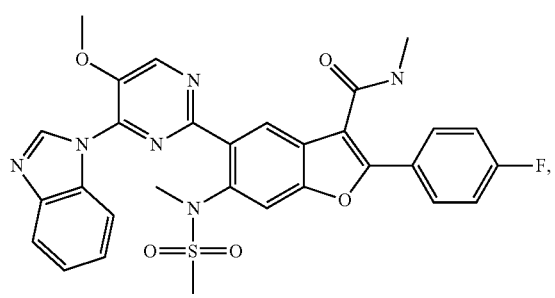
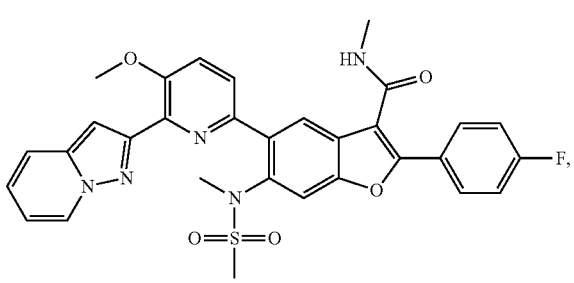
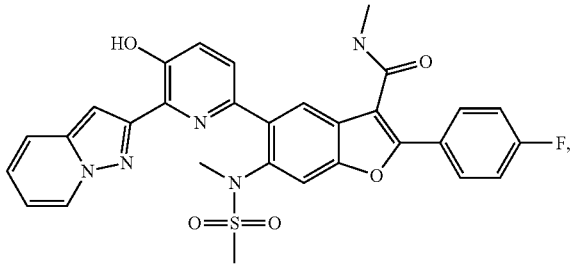
260
-continued
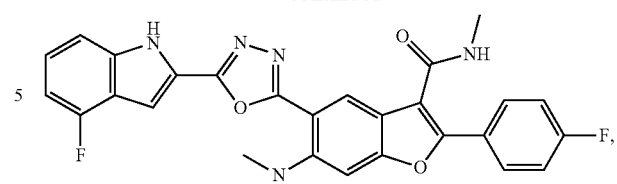
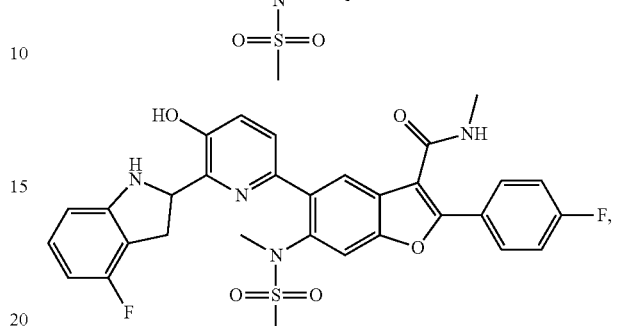
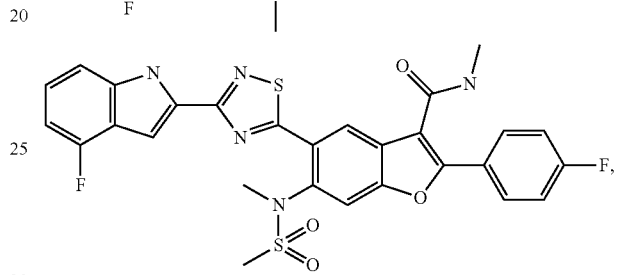
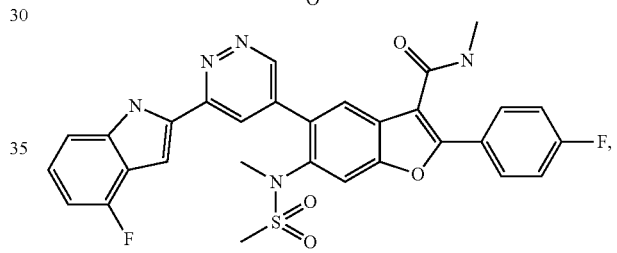
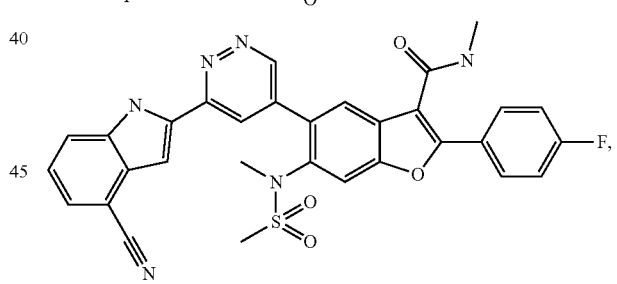
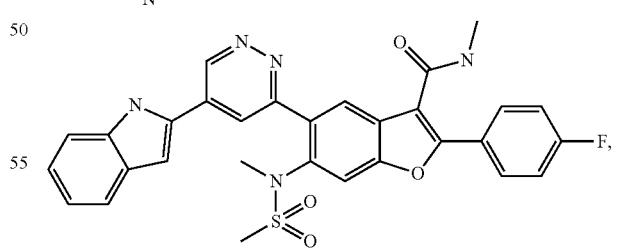
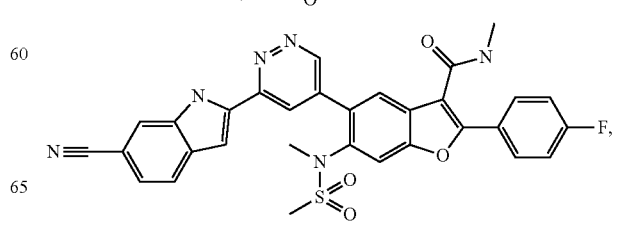

261
-continued
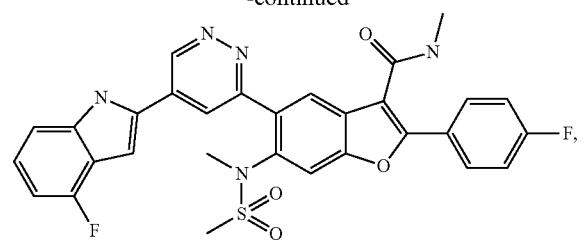
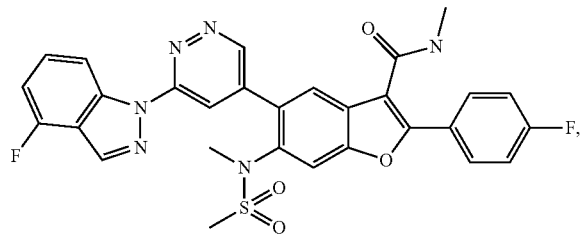
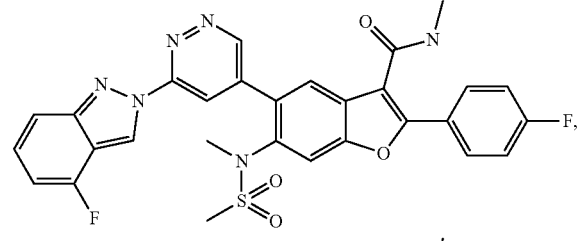
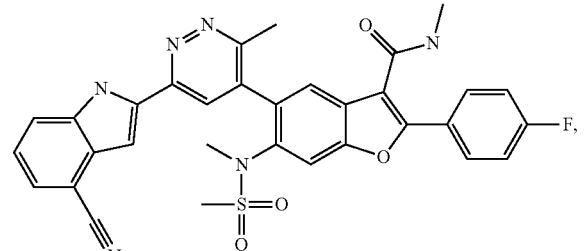
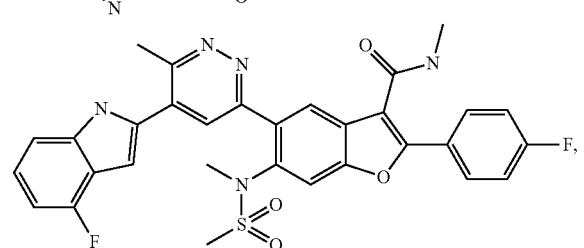
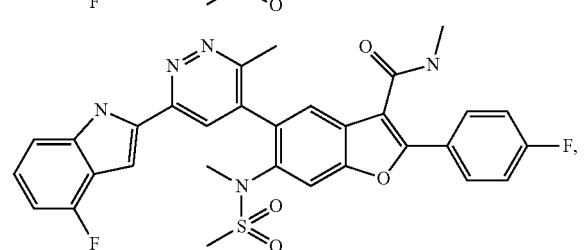
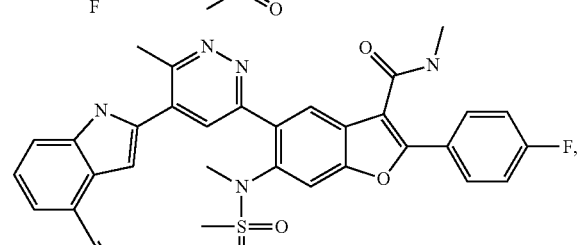
262
-continued
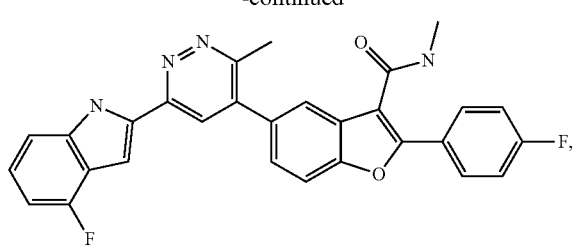
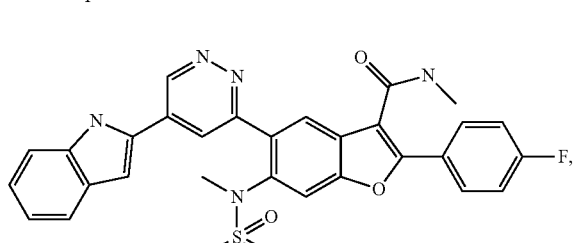
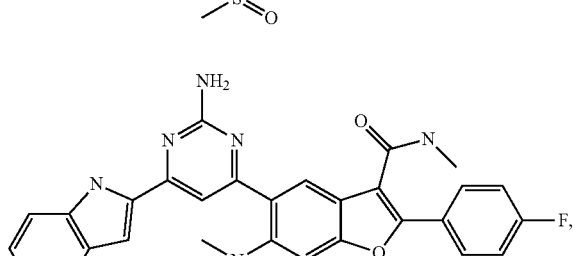
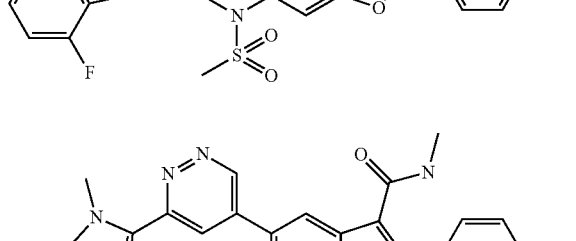
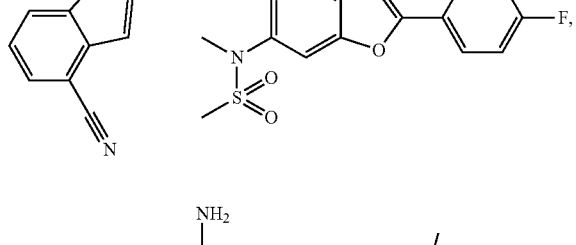
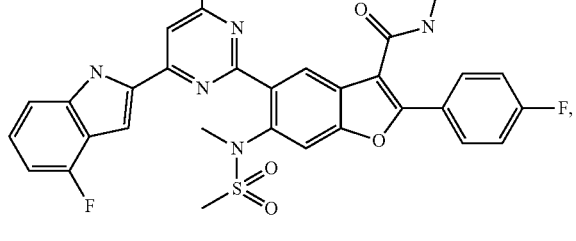
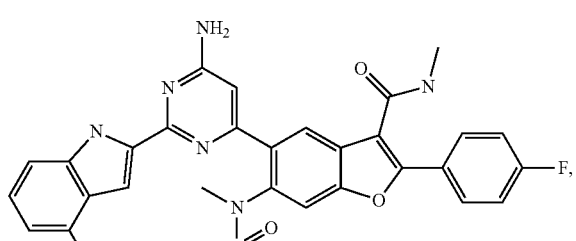

263
-continued
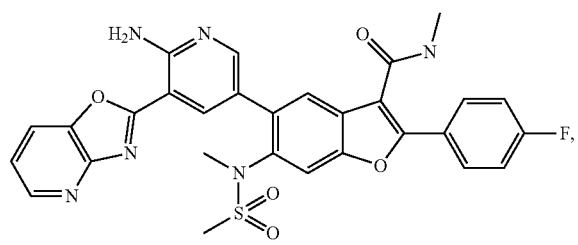
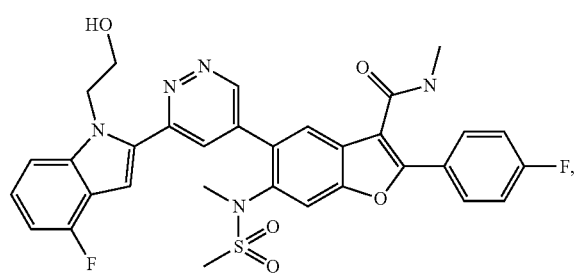
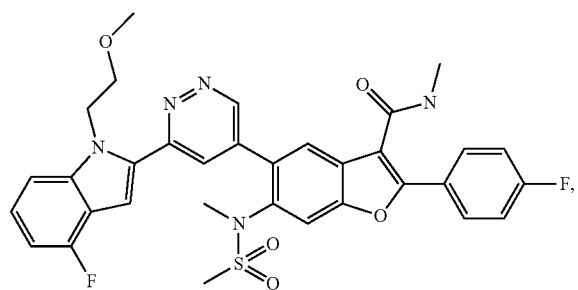
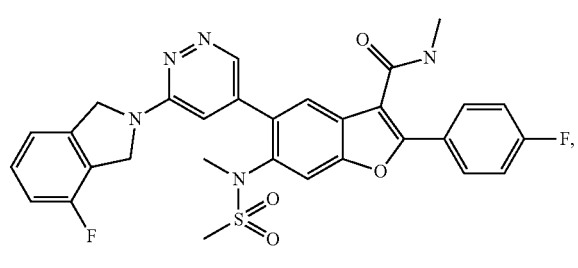
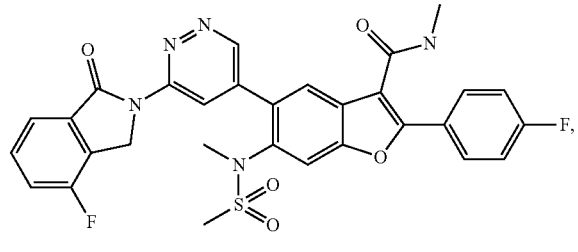
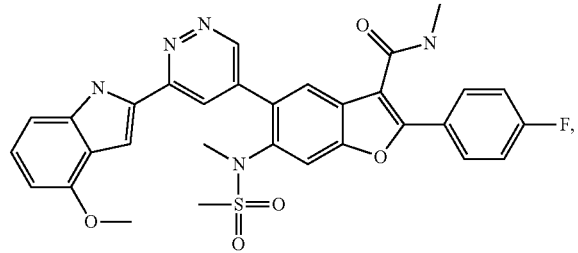
264
-continued
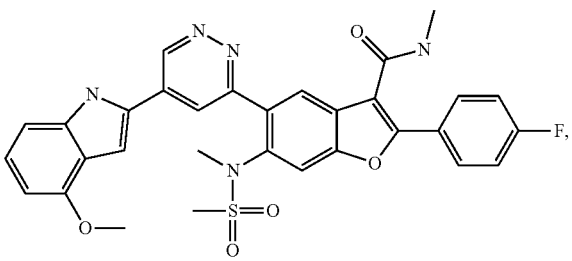
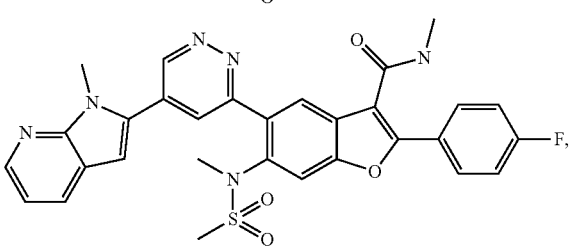
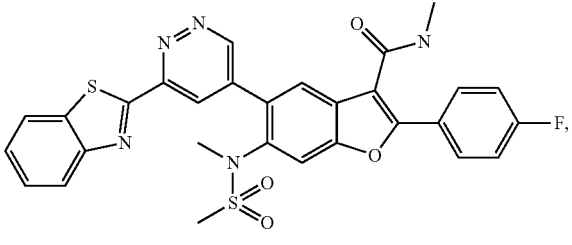
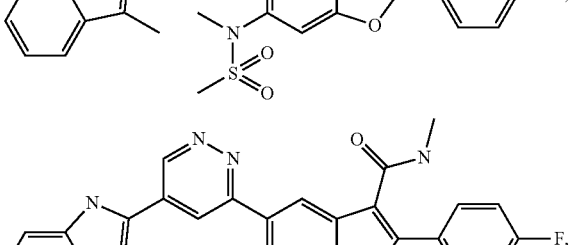
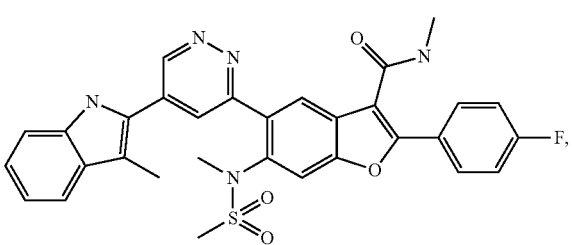

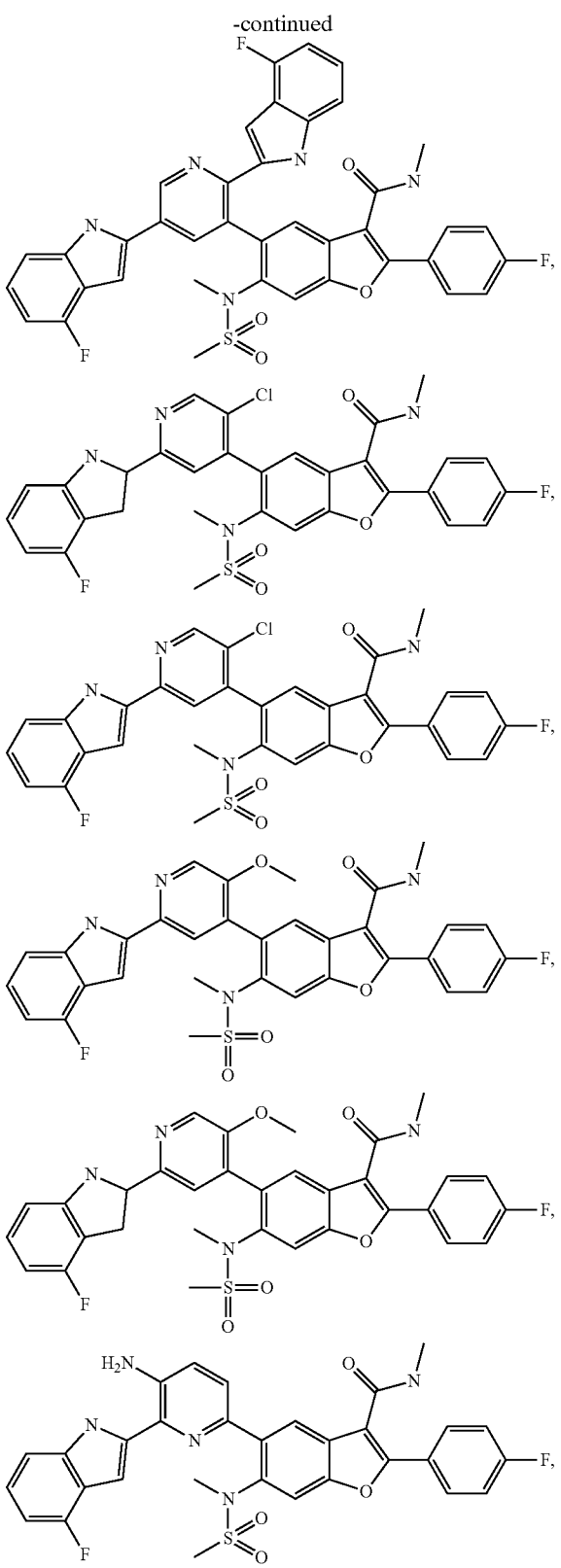

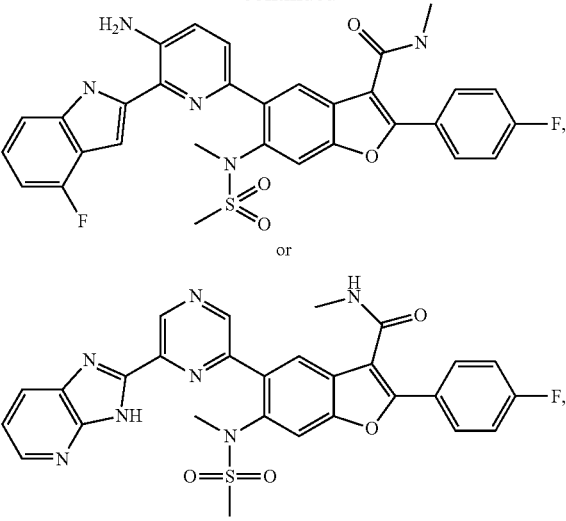

or a pharmaceutically acceptable salt thereof.

5. A pharmaceutical composition comprising a pharmaceutically acceptable carrier and a compound of claim 1 or a pharmaceutically acceptable salt thereof.

6. The pharmaceutical composition of claim 5, further comprising a second therapeutic agent selected from the group consisting of HCV antiviral agents, immunomodulators, and anti-infective agents.

7. The pharmaceutical composition of claim 6, wherein the second therapeutic agent is selected from the group consisting of HCV protease inhibitors, HCV NS5A inhibitors and HCV NS5B polymerase inhibitors.

8. A method of treating a patient infected with HCV, the method comprising administering to the patient the compound of claim 1, or a pharmaceutically acceptable salt thereof, in an amount effective to treat infection by HCV in the patient.

9. The method of claim 8, further comprising the step of administering pegylated-interferon alpha and ribovirin to the patient.

10. A pharmaceutical composition comprising a pharmaceutically acceptable carrier and a compound of claim 4 or a pharmaceutically acceptable salt thereof.

11. The pharmaceutical composition of claim 10, further comprising a second therapeutic agent selected from the group consisting of HCV antiviral agents, immunomodulators, and anti-infective agents.

12. The pharmaceutical composition of claim 11, wherein the second therapeutic agent is selected from the group consisting of HCV protease inhibitors, HCV NS5A inhibitors and HCV NS5B polymerase inhibitors.

13. A method of treating a patient infected with HCV, the method comprising administering to the patient the compound of claim 4, or a pharmaceutically acceptable salt thereof, in an amount effective to treat infection by HCV in the patient.

14. The method of claim 13, further comprising the step of administering pegylated-interferon alpha and ribovirin to the patient.

* * * * *

UNITED STATES PATENT AND TRADEMARK OFFICE
CERTIFICATE OF CORRECTION

PATENT NO. : 9,549,917 B2
APPLICATION NO. : 14/343448
DATED : January 24, 2017
INVENTOR(S) : Casey C. McComas et al.

Page 1 of 1

It is certified that error appears in the above-identified patent and that said Letters Patent is hereby corrected as shown below:

On the Title Page

Please amend (73) Assignee to read as follows:
(73) Assignee:  Merck Sharp & Dohme Corp.
                  Rahway, NJ (US)
                  MSD Italia S.R.L.
                  Rome (IT)

Signed and Sealed this
Eleventh Day of December, 2018

Andrei Iancu
*Director of the United States Patent and Trademark Office*